United States Patent [19]
Ishikawa et al.

[11] Patent Number: 5,444,152
[45] Date of Patent: Aug. 22, 1995

[54] ENDOTHELIN ANTAGONISTIC PEPTIDE DERIVATIVES

[75] Inventors: Kiyofumi Ishikawa; Takehiro Fukami; Takashi Hayama; Kenji Niiyama; Toshio Nagase; Toshiaki Mase; Kagari Fujita; Masaki Ihara; Fumihiko Ikemoto; Mitsuo Yano, all of Tokyo, Japan

[73] Assignee: Banyu Pharmaceutical Co., Ltd., Tokyo, Japan

[21] Appl. No.: 214,679

[22] Filed: Mar. 21, 1994

Related U.S. Application Data

[60] Continuation of Ser. No. 884,642, May 18, 1992, abandoned, which is a division of Ser. No. 712,095, Jun. 7, 1991, abandoned.

[30] Foreign Application Priority Data

Jun. 7, 1990 [JP] Japan .................................. 2-149105

[51] Int. Cl.$^6$ .............................................. A61K 38/06
[52] U.S. Cl. ..................................... 530/331; 546/184; 548/496; 562/30
[58] Field of Search ............... 514/18, 7, 19; 530/331; 546/184; 548/496; 562/30

[56] References Cited

U.S. PATENT DOCUMENTS 3,872,074  3/1975  König et al. ........................ 530/333

FOREIGN PATENT DOCUMENTS

76446/91  11/1991  Australia ..................... C07K 05/08
0333174   9/1989   European Pat. Off. ........ C07K 5/00
0460679   12/1991  European Pat. Off. ........ C07K 5/02
WO93/10144 5/1993  WIPO .......................... C07K 5/06

OTHER PUBLICATIONS

Biochemical and Biophysical Research Communications, vol. 156, No. 3, Nov. 15, 1988, pp. 1182–1186, S. Kimura, et al., "Structure–Activity Relationships of Endothelin: Importance of the C–Terminal Moiety".
Journal of the American Chemical Society, vol. 83, No. 1, Jan. 16, 1961, & Jan. 5, 1961, pp. 1, 145–149.
Bulletin of the Chemical Society of Japan, vol. 43, No. 4, Apr. 1970, pp. 1197–1202, S. Matsuura, et al., "Studies of Peptide Antibiotics. XVI. Analogs of Gramicidin S Containing Beta–Alanine in Place of L–Proline".

Primary Examiner—Jill Warden
Assistant Examiner—David Lukton
Attorney, Agent, or Firm—Oblon, Spivak, McClelland, Maier & Neustadt

[57]  ABSTRACT

Peptides having the formula $$A^1\underset{B}{\overset{R^3}{\diagdown}}\underset{\underset{O}{\|}}{\overset{H}{\diagup}}\underset{R^5}{\overset{R^4}{\underset{|}{N}}}\overset{X^2}{\underset{H}{\overset{\|}{\diagdown}}}A^2 \quad (I)$$

inhibit the binding of endothelin to its receptor and are useful in treating diseases associated with excess production or secretion of endothelin.

14 Claims, 8 Drawing Sheets

ENDOTHELIN ANTAGONISTIC PEPTIDE DERIVATIVES

This application is a Continuation of application Ser. No. 07/884,642, filed on May 18, 1992, now abandoned, which is a Divisional of Ser. No. 07/712,095, filed Jun. 7, 1991, abandoned.

The present invention relates to novel compounds having antagonism against a physiologically highly active endogenous peptide, endothelin, processes for their preparation and their use as a drug.

The compounds of the present invention have antagonism against endothelin, and thereby providing a new therapeutic potential, particularly for the treatment of hypertension, pulmonary hypertension, Raynaud's disease, myocardial infarction, angina pectoris, acute renal failure, cerebral infarction, cerebral vasospasm, arteriosclerosis, asthma, endotoxin shock, endotoxin-induced multiple organ failure or disseminated intravascular coagulation, and/or cyclosporin-induced renal failure or hypertension.

Endothelin is a polypeptide composed of 21 amino acids, and it is produced by vascular endothelial cells of human or pig. It is known that endothelin has a potent vasoconstrictor effect and a sustained and potent pressor action. It is also known that such a vasoconstriction is caused by binding of endothelin to its receptors on the vascular smooth muscles (Nature, 332, 411–415 (1988), FEBS Letters, 231, 440–444 (1988) and Biochem. Biophys. Res. Commun., 154, 868–875 (1988)).

As reported, the endothelin levels are clearly elevated in the blood of patients with essential hypertension, acute myocardial infarction, pulmonary hypertension, Raynaud's disease or atherosclerosis, or in the washing fluids of the respiratory tract of patients with asthmaticus as compared with normal levels (Japan. J. Hypertension, 12, 79 (1989), J. Vascular Medicine Biology, 2, 207 (1990), J. Am. Med. Association, 264, 2868 (1990), and The Lancet, ii, 207 (1990) and ii, 747–748 (1989)).

Further, an increased sensitivity of the cerebral blood vessel to endothelin in an experimental model of cerebral vasospasm (Japan. Soc. Cereb. Blood Flow & Metabol., 1, 73 (1989)) and an improved renal function by the endothelin antibody in an acute renal failure model have been reported (J. Clin. Invest., 83, 1762–1767 (1989)). Therefore, endothelin is assumed to be one of mediators causing acute renal failure or cerebral vasospasm following subarachnoid hemorrhage.

Further, endothelin is secreted not only by endothelial cells but also by tracheal epithelial cells or from kidney cells (FEBS Letters, 255, 129–132 (1989), and FEBS Letters, 249, 42–46 (1989)).

Endothelin was also found to control the release of physiologically active substances such as renin, atrial natriuretic peptide, endothelium-derived relaxing factor (EDRF), thromboxane $A_2$, prostacyclin, noradrenaline, angiotensin II and substance P (Biochem. Biophys. Res. Commun., 157, 1164–1168 (1988); Biochem. Biophys. Res. Commun., 155, 167–172 (1989); Proc. Natl. Acad. Sci. USA, 85, 9797–9800 (1989); J. Cardiovasc. Pharmacol., 13, S89–S92 (1989); Japan. J. Hypertension, 12, 76 (1989) and Neuroscience Letters, 102, 179–184 (1989)). Further, endothelin causes contraction of the smooth muscle of gastrointestinal tract and the uterine smooth muscle (FEBS Letters, 247, 337–340 (1989); Eur. J. Pharmacol., 154, 227–228 (1988); and Biochem. Biophys. Res. Commun., 159, 317–323 (1989)). Further, endothelin was found to promote proliferation of rat vascular smooth muscle cells, suggesting a possible relevance to the arterial hypertrophy (Atherosclerosis, 78, 225–228 (1989)). Furthermore, since the endothelin receptors are present in a high concentration not only in the peripheral tissues but also in the central nervous system, and the cerebral administration of endothelin induces a behavioral change in animals, endothelin is likely to play an important role for controlling nerval functions (Neuroscience Letters, 97, 276–279 (1989)).

On the other hand, endotoxin is one of potential candidates to promote the release of endothelin. Remarkable elevation of the endothelin levels in the blood or in the culture supernatant of endothelial cells was observed when endotoxin was exogenously administered to animals or added to the culture endothelial cells, respectively. These findings suggest that endothelin is one of important mediators for endotoxin-induced diseases (Biochem. Biophys. Res. Commun., 161, 1220–1227 (1989); and Acta Physiol. Scand., 137, 317–318 (1989)).

Further, cyctosporin, when added to the renal cell culture (LLC-PK1 cells), remarkably increased endothelin secretion (Eur. J. Pharmacol., 180, 191–192 (1990)). Further, when cyclosporin was administered to rats, a decrease in the glomerular filtration rate and an increase in the blood pressure were observed, in association with a remarkable increase in the circulating endothelin in level. This cyclosporin-induced renal failure can be suppressed by the administration of endothelin antibody (Kidney Int., 37, 1487–1491 (1990)). Thus, it is assumed that endothelin is significantly involved in the pathogenesis of the cyclosporin-induced diseases.

Accordingly, substances which specifically inhibit the binding of endothelin to its receptor are believed to antagonize the above-mentioned various physiological activities of endothelin and thereby being useful as a medicine in a wide range of fields. However, such a highly potent endothelin antagonist has never been reported yet.

Endothelin is an endogenous substance which directly or indirectly (by controlling liberation of various endogenous substances) induces sustained contraction of vascular or non-vascular smooth muscles, and its excess production or excess secretion is believed to be one of pathogeneses for hypertension, pulmonary hypertension, Raynaud's disease, bronchial asthma, acute renal failure, myocardial infarction, angina pectoris, arteriosclerosis, cerebral vasospasm and cerebral infarction. Further, it is suggested that endothelin serves as an important mediator involved in diseases such as endotoxin shock, endotoxin-induced multiple organ failure or disseminated intravascular coagulation, and/or cyctosporin-induced renal failure or hypertension. Accordingly, the objective of the present invention is to provide a novel therapeutics for the treatment of the above-mentioned various diseases by an invention of an endothelin antagonist.

In order to solve the above-mentioned problems, the present inventors have synthesized various peptide derivatives and have investigated their endothelin antagonistic activities, and as a result have found that novel peptide derivatives represented by the following formula (I) have strong endothelin antagonistic activities. The present invention has been accomplished on the basis of this discovery.

Thus, the present invention provides a peptide derivative of the formula:

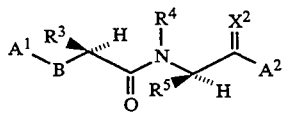

wherein $A^1$ is a group of the formula $R^{11}$—CO— {wherein $R^{11}$ is a lower alkyl group, a cycloalkyl group, a cycloalky lower alkyl group, a group of the formula $Ar^1$—$(CH_2)_p$— wherein $Ar^1$ is a phenyl group, a furyl group or a thienyl group, and p is 0, 1 or 2), a 1,3-dithiol-2-ylidenemethyl group, or a 1,3-dithiol-2-ylidene(lower alkoxycarbonyl)methyl group}, a group of the formula $R^{12}O$—CO— {wherein $R^{12}$ is a lower alkyl group, a cycloalkyl group, a cycloalkyl lower alkyl group or a phenyl group}, or a group of the formula $R^{13}R^{14}N$—$C(=X^1)$- {wherein $X^1$ is an oxygen atom or a sulfur atom, $R^{13}$ is a lower alkyl group which may be substituted by a lower alkoxycarbonyl group, a cycloalkyl group, a lower alkynyl group, a 1-adamantyl group, a pyrrolidino group, a piperidino group, a perhydroazepin-1-yl group, a perhydroazocin-1-yl group, a perhydroazonin-1-yl group, or a group of the formula $Ar^2$—$(CH_2)_q$— (wherein $Ar^2$ is a phenyl group wherein one or two optional hydrogen atoms on the benzene ring may independently be replaced by a halogen atom, a lower alkyl group or a lower alkoxy group, a furyl group, or a thienyl group, and q is 0,1 or 2), $R^{14}$ is a hydrogen atom, a lower alkyl group which may be substituted by a hydroxyl group, a cycloalkyl group, or a group of the formula $Ar^3$—$(CH_2)_r$— (wherein $Ar^3$ is a phenyl group, a furyl group or a thienyl group, and r is 1 or 2), or $R^{13}$ and $R^{14}$ form, together with the adjacent nitrogen atom, a 5- to 9- membered nitrogen-containing saturated heterocyclic ring having 4 to 8 carbon atoms {wherein among methylene groups forming the ring, one optional methylene group not adjacent to the above nitrogen atom may be replaced by an oxy group, a thio group or a group of the formula —$NR^{15}$— (wherein $R^{15}$ is a lower alkyl group), and one to four optional hydrogen atoms on the carbon atoms of the heterocyclic ring may independently be replaced by a hydroxyl group or a lower alkyl group which may be substituted by a hydroxyl group, and further two adjacent carbon atoms in the heterocyclic ring may form a double bond or a benzo-fused ring}, or together with B represents a group of the following formula(II)

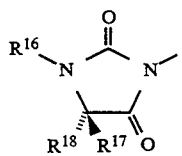

wherein $R^{16}$ is a hydrogen atom, a lower alkyl group or a cycloalkyl group, and each of $R^{17}$ and $R^{18}$ which are independent from each other, is a hydrogen atom or a lower alkyl group; B is an oxygen atom or a group of the formula —$NR^2$— (wherein $R^2$ is a hydrogen atom or a methyl group), or together with $A^1$ represents a group of the above formula (II); $R^3$ is a lower alkyl group having 3 to 5 carbon atoms; $R^4$ is a hydrogen atom or a methyl group; $R^5$ is a 3-indolylmethyl group, a (2,3-dihydro-2-oxo-3-indolyl)methyl group, a 3-indolylmethyl group wherein the indole ring is substituted at the 1-position by a group of the formula $R^{51}$—CO—$(CH_2)_s$— (wherein $R^{51}$ is a hydrogen atom, a lower alkyl group, a hydroxyl group, a lower alkoxy group, a benzyloxy group, an amino group or a mono lower alkylamino group, s is an integer of from 0 to 6, provided that when s=0, $R^{51}$ is other than a hydroxyl group) or a group of the formula $(R^{52}O)_2P(=O)$—$(CH_2)_t$— (wherein $R^{52}$ is a hydrogen atom, a lower alkyl group or a benzyl group, and t is an integer of from 0 to 6), a benzyl group wherein an optional hydrogen atom on the benzene ring may be replaced by a group of the formula $R^{53}O$—CO—$(CH_2)_u$— (wherein $R^{53}$ is a hydrogen atom or a lower alkyl group, and u is an integer of from 0 to 6), a benzyl group wherein one or two optional hydrogen atoms on the benzene ring are replaced by a hydroxyl group(s), or two optional hydrogen atoms on the benzene ring are replaced by a hydroxyl group and a sulfo group, a 3-benzothienytmethyl group, a (1-oxo-3-benzothienyl)methyl group, or a (1,1-dioxo-3-benzothienyl)methyl group; $X^2$ is an oxygen atom or a sulfur atom; $A^2$ is an optional group selected from the class consisting of groups of the following formulas (III), (IV), (V), (VI), (VII) and (VIII):

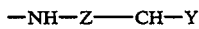

wherein Y is a sulfo group, a phosphono group, a group of the formula —$CO_2R^{91}$ (wherein $R^{91}$ is a hydrogen atom, a lower alkyl group or a benzyl group), or a group of the formula —$CONR^{92}R^{93}$ (wherein $R^{92}$ is a hydrogen atom, a lower alkyl group, a lower alkylsulfonyl group, a phenylsulphonyl group wherein one to five optional hydrogen atoms on the benzene ring may independently be replaced by a lower alkyl group or a halogen atom, or a carboxymethyl group, and $R^{93}$ is a hydrogen atom or a lower alkyl group), $R^{61}$ is a hydrogen atom or a lower alkyl group, or together with $R^{71}$ represents a methylene group, $R^{71}$ is a hydrogen atom, a lower alkyl group which may be substituted by a hydroxyl group, a phenyl group, a thienyl group, a phenyl lower alkyl group wherein an optional hydrogen atom on the benzene ring may be replaced by a hydroxyl group or a benzyloxy group, a thienyl lower alkyl group, a thiazolyl lower alkyl group, a 4-imidazolylmethyl group, a (lower alkyl-substituted 4-imidazolyl)methylthiomethyl group, a 3-indolylmethyl group, a carbamoyl lower alkyl group or an N-benzyloxycarbonyl-ω-amino lower liner alkyl group, or together with $R^{61}$ represents a methylene group, provided than when $R^{61}$ is a lower alkyl group, $R^{71}$ is a group other than a hydrogen atom, $R^{62}$ is a hydrogen atom, a phenyl group, a benzyl group, a carboxy group, a carbamoyl group or an N-phenylcarbamoyl group, or together with $R^8$ represents a single bond, $R^{72}$ is a hydrogen atom, a lower alkyl group, a phenyl group, a benzyl group, a 3-indolylmethyl group, a carbamoyl group or an N-phenylcarbamoyl group, provided that when $R^{62}$ is a group other than a hydrogen atom, $R^{72}$ is a hydrogen atom or a lower alkyl group, $R^8$ is a hydrogen atom, a lower alkyl group, a lower alkoxy group or a hydroxyl group, or together with $R^{62}$ represents a single bond, v is 3, 4 or 5, $R^{63}$ is a hydrogen atom, a lower alkyl group, a carboxy lower alkyl group, a group of the formula $Ar^4$—$(CH_2)_w$— (wherein $Ar^4$ is a phenyl group, a furyl group or a thienyl group, and w is 1 or 2), Z is CH or N, and x is 1,2 or 3; or a pharmaceutically acceptable salt thereof.

The present invention also provides a process for producing a peptide derivative as defined in claim 1, which comprises reacting a compound of the formula (IX) or its protected compound:

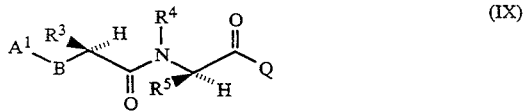

wherein $A^1, B, R^3, R^4$ and $R^5$ are as defined above, and Q is a hydroxyl group or a leaving group, with a compound of formula (X), its protected compound or its salt:

wherein $A^2$ is as defined above, using, if necessary, a condensing agent, or reacting a compound of the formula (XI) or its protected compound:

wherein $A^1$, B, $R^3$ and Q are as defined above, with a compound of the formula (XII), its protected compound or its salt:

wherein $A^2, R^4, R^5$ and $X^2$ are as defined above, using, if necessary, a condensing agent, to obtain a peptide derivative wherein an N-terminal amino group, a sidechain functional group(s) and/or a C-terminal carboxyl group may be protected; subjecting, if necessary, the resulting peptide derivative to at least one reaction selected from the group consisting of 1) removal of a sidechain and/or a C-terminal protective group(s), 2) acylation, alkoxycarbonylation, aryloxycarbonylation, carbamoylation or thiocarbamoylation of an N-terminal α-amino group after removal of an N-terminal α-amino-protecting group, 3) formylation at the 1-position or oxidation at the 2-position of the indole ring in a tryptophanyl residue, 4) conversion of a seryl residue to a dehydroalanyl residue, and 5) condensation of a C-terminal carboxyl group with ammonia, a primary or secondary amine, or an alkane- or arene-sulfonamide, and furthermore optionally conducting the conversion to a pharmaceutically acceptable salt.

Further, the present invention provides a drug for treating hypertension, pulmonary hypertension, Raynaud's disease, acute renal failure, myocardial infarction, angina pectoris, cerebral infarction, cerebral vasospasm, arteriosclerosis, asthma, endotoxin shock, endotoxin-induced multiple organ failure or disseminated intravascular coagulation, and/or cyclosporin-induced renal failure or hypertension, which contains a peptide derivative of the formula (I) or a pharmaceutically acceptable salt thereof.

In the accompanying drawings:

Figure 1:
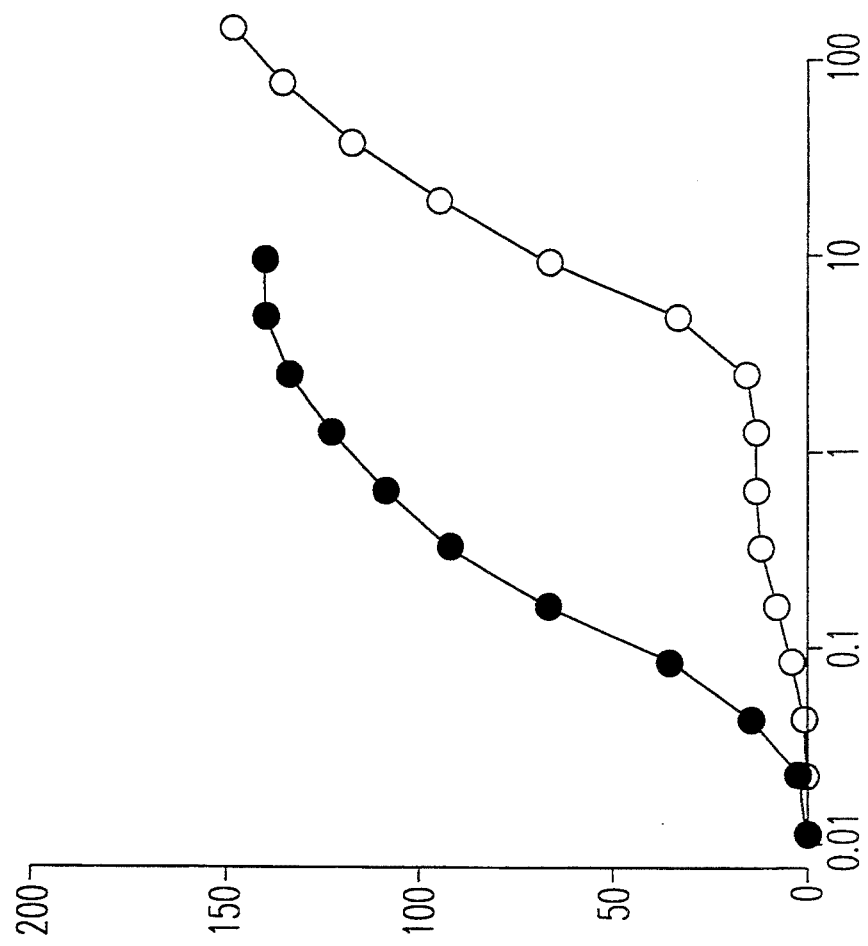
FIG. 1 shows the activities of Compound 50 (o) against endothelin-induced contraction of isolated porcine coronary artery as compared with the case in which no drug is present ( ).

Now, the present invention will be described in further detail with reference to the preferred embodiments.

Now, the definitions of the various terms mentioned in this specification will be explained.

In this specification, the lower alkyl group means a linear or branched alkyl group having 1 to 6 carbon atoms such as a methyl, ethyl, propyl, isopropyl, butyl, isobutyl, sec-butyl, tert-butyl, pentyl, isopentyl, neopentyl, tert-pentyl, 1-methytbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl or 1-ethyl-1-methylpropyl group.

The cycloalkyl group means a cyclopropyl, cyclobutyl, cyclopentyl, cyclohexyt, cycloheptyl, cyclooctyl or cyclononyl group.

The lower alkoxycarbonyl group means an atkyloxycarbonyl group having a linear or branched alkyl group having 1 to 6 carbon atoms such as a methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl or hexyloxycarbonyl group.

The lower alkynyl group means a linear or branched alkynyl group having 3 to 6 carbon atoms such as a 1-propynyl, 2-propynyl, 1-butynyl, 2-butynyl, 3butynyl, 1-methyl-2-propynyl, 1-pentynyl, 2-pentynyl, 3pentynyl, 4-pentynyl, 3-methyl-t-butynyl, 2-methyl-3-butynyl, 1-methyl-2-butynyl, 1-methyl-3-butynyl, 1,1-dimethyl-2-propynyl, 1-hexynyl, 2-hexynyl, 3-hexynyl, 4-hexynyl or 5-hexynyl group.

The halogen atom means a fluorine, chlorine, bromine or iodine atom.

The lower alkoxy group means an alkyloxy group having a linear or branched alkyl group having 1 to 6 carbon atoms such as a methoxy, ethoxy, propoxy, isomropoxy, butoxy, isobutoxy, sec-butoxy, tert-butoxy, pentyloxy, isopentyloxy, neopentyloxy, tert-pentyloxy, hexyloxy or isohexyloxy group.

To disclose this invention more specifically, the various symbols used in formula (I) will be explained in detail by citing examples.

In $A^1$, $R^{11}$ means a lower alkyl goup, a cycloalkyl goup, a lower alkyl group substituted by a cycloalkyl goup, a group of the formula $Ar^1$—$(CH_2)_p$— (wherein $Ar^1$ and p are as defined above), a 1,3-dithiol-2-ylidenemethyl goup or a 1,3-dithiol-2-ylidene(lower alkoxycarbonyl)methyl group. Examples of the lower alkyl group are methyl, ethyl, propyl, isopropyl, butyl, isobutyl, sec-butyl, tert-butyl, pentyl, isopentyl, neopentyl, tert-pentyl, 1,1-dimethylbutyl and 1-ethyl-l-methyl-propyl groups. Examples of the cycloalkyl group are cyclopropyl, cyclobutyl, cyclopentyl, cyclohexyl, cycloheptyl, cyclooctyl and cyclononyl groups. Examples of the lower alkyl group substituted by a cycloalkyl group are cyclopropylmethyl, 1-cyclopropylethyl, 2-cyclopropylethyl, 1-cyclopropylpropyl, 2-cyctopropylpropyl, 3-cyclopropylpropyl, cyclopentylmethyl, 1-cyclopentylethyl, 2-cyclopentylethyl, 1-cyclopentylpropyl, 2-cyclopentylpropyl, 3-cyclopentylpropyl, cyclohexylmethyl, lcyclohexylethyl, 2-cyclohexylethyl, 1-cyclohexylpropyl, 2-cyclohexylpropyl, 3-cyclohexylpropyl, cycloheptylmethyl, 1-cycloheptylethyl, 1-cycloheptylpropyl, 1-cyclopropyl-1-methylethyl, 1-cyclobutyl-1-methylethyl, 1-cyclomentyl-1-methylethyl and 1-cyclohexyl-1-methylethyl groups. Examples of the group represented by the formula $Ar^1$—$(CH_2)_p$— are phenyl, 2-furyl, 3-furyl, 2-thienyl, 3-thienyl, benzyl, 2-furylmethyl, 3-furylmethyl, 2-thienylmethyl, 3-thienylmethyl, 2-phenylethyl, 2-(2-furyl)ethyl, 2-(3-furyl)ethyl, 2-(2-thienyl)ethyl and 2-(3-thienyl)ethyl groups. Examples of the 1,3-dithiol-2-ylidene(lower alkoxycarbonyl)methyl group are 1,3-dithiol-2-ylidene(methoxycarbonyl)methyl, 1,3-di-thiol-2-ylidene(ethoxycarbonyl)methyl, 1,3-dithiol-2-ylidene(propoxycarbonyl)methyl, 1,3-dithiol-2-ylidene-(isopropoxycarbonyl)methyl, 1,3-dithiol-2-ylidene(-butoxycarbonyl)methyl and 1,3-dithiol-2-ylidene(tert-butoxycarbonyl)methyl groups.

In $A^1$, $R^{12}$ means a lower alkyl group, a cycloalkyl group, a cycloalkyl lower alkyl group or a phenyl group. Examples of the lower alkyl group are methyl, ethyl, propyl, isopropyl, butyl, isobutyl, sec-butyl, tert-butyl, pentyl, isopentyl, neopentyl, tert-pentyl, 1,1-dimethylbutyl, 1-ethyl-1-methylpropyl and 1,1,2-trimethylpropyl groups. Examples of the cycloalkyl group are cyclopropyl, cyclobutyl, cyclopentyl, cyclohexyl, cycloheptyl, cyclooctyl and cyclononyl groups. Examples of the cycloalkyl lower alkyl group are cyclopropylmethyl, 1-cyclopropylethyl, 2-cyclopropylethyl, 1-cyclopropyl-1-methylethyl, cyclobutylmethyl, 1-cyclobutylethyl, 2-cyclobutylethyl, 1-cyclobutyl-1-methylethyl, cyclopentylmethyl, 1-cyclopentylethyl, 2cyclopentylethyl, 1-cyclopentyl-1-methylethyl, 1-cyclohexylmethyl, 1-cyclohexylethyl, 1-cyclohexyl-1-methyl-ethyl, 1-cycloheptylmethyl, 1-cycloheptylethyl, 1-cyclooctylmethyl and 1-cyclooctylethyl groups.

In $A^1$, $R^{13}$ means a lower alkyl group which may be substituted by a lower alkoxycarbonyl group, a cycloalkyl group, a lower alkynyl group, a 1-adamantyl group, a pyrrolidino group, a piperidino group, a perhydroazepin-1-yl group, a perhydroazonin-1-yl group, or a group of the formula $Ar^2$—$(CH_2)_q$— (wherein $Ar^2$ and q are as defined above); or a group which forms, together with $R^{14}$ and the adjacent nitrogen atom, one of the heterocyclic groups mentioned below. Examples of the lower alkyl group which may be substituted by a lower alkoxycarbonyl group are methyl, ethyl, propyl, isopropyl, butyl, isobutyl, sec-butyl, tert-butyl, pentyl, isopentyl, neopentyl, tert-pentyl, 1,1-dimethylbutyl, 1-ethyl-1-methylpropyl, 1,1,2-trimethylpropyl, methoxycarbonylmethyl, 1-(methoxyocarbonyl)ethyl, 2-(methoxycarbonyl)ethyl, 1-(methoxycarbonyl)propyl, 2-(methoxycarbonyl)propyl, 3-(methoxycarbonyl)propyl, 1-methoxycarbonyl-1-methylethyl, 2-methoxycarbonyl-1-methylethyl, 1,1-dimethyl-2-(methoxycarbonyl)ethyl, 1-methoxycarbonylmethyl-1-methylpropyl, ethoxycarbonylmethyl, 1-(ethoxycarbonyl)ethyl, 2-(ethoxycarbonyl)ethyl, 1-ethoxycarbonyl-1-methylethyl and 1-ethoxycarbonyl- 1-methylpropyl groups. Examples of the cycloalkyl group are cyclopropyl, cyclobutyl, cyclopentyl, cyclohexyl and cycloheptyl groups. Examples of the lower alkynyl group are 1-propynyl, 2-propynyl, 1,1-dimethyl-2-propynyl, 1-butynyl, 2-butynyl, 3-butynyl, 1,1-dimethyl-2-butynyl, 1,1-dimethyl-3-butynyl and 1-ethyl-1-methyl-2-propynyl groups. Examples of the group represented by the formula $Ar^2$—$(CH_2)_q$— are phenyl, 2chlorophenyl, 2-bromophenyl, 2-methylphenyl, 2-ethylphenyl, 2-propylphenyl, 2-isopropylphenyl, 2-methoxyphenyl, 2-ethoxyphenyl, 2-propoxyphenyl, 2-isopropoxyphenyl, 2-tert-butoxyphenyl, 3-chlorophenyl, 3-bromophenyl, 3-methylphenyl, 3-ethylphenyl, 3-propylphenyl, 3-isopropylphenyl, 3-methoxyphenyl, 3-ethoxyphenyl, 3propoxyphenyl, 3-isopropoxyphenyl, 3-tert-butoxyphenyl, 4-chlorophenyl, 4-bromophenyl, 4-methylphenyl, 4-ethylphenol, 4-propylphenyl, 4-isopropylphenyl, 4-methoxyphenyl, 4-ethoxyphenyl, 4-propoxyphenyl, 4-isopropoxyphenyl, 4-tert-butoxyphenyl, 2,6-dichlorophenyl, 2,6-dibromophenyl, 2,6-dimethylphenyl, 2,6-diethylphenyl, 2,6-dipropylphenyl, 2,6-diisopropylphenyl, 2,6-dimethoxyphenyl, 2,6-diethoxyphenyl, 2,6-dipropoxyphenyl, 2,6diisopromoxyphenyl, 2-chloro-6-isopropylphenyl, 2-methoxy-6-methylphenyl, 2-methoxy-6-isopropytphenyl, 2-isopropoxy-6-isopropylphenyl, 2-furyl, 3-furyl, 2-thienyl, 3-thienyl, benzyl, 2-furylmethyl, 3-furylmethyl, 2-thienylmethyl, 3-thienylmethyl, 2-phenylethyl, 2-(2-furyl)ethyl, 2-(3-furyl)ethyl, 2-(2-thienyl)ethyl and 2-(3-thienyl)ethyl groups.

In $A^1$, $R^{14}$ means a hydrogen atom, a lower alkyl group which may be substituted by a hydroxyl group, a cycloalkyl group or a group of the formula $Ar^1$—$(CH_2)_r$— (wherein $A^3$ and r are as defined above); or a group which forms, together with $R^{13}$ and the adjacent nitrogen atom, one of the heterocyclic groups mentioned below. Examples of the lower alkyl group which may be substituted by a hydroxyl group are methyl, ethyl, propyl, isopropyl, butyl, isobutyl, sec-butyl, tert-butyl, pentyl, isopentyl, neopentyl, tert-pentyl, 2hydroxyethyl, 2-hydroxypropyl, 3-hydroxypropyl, 2-hydroxy-1-methylethyl, 2-hydroxybutyl, 3-hydroxybutyl, 4hydroxybutyl and 1,1-dimethyl-2-hydroxyethyl groups. Examples of the cycloalkyl group are cyclopropyl, cyclobutyl, cyclopentyl, cyclohexyl and cycloheptyl groups. Examples of the group represented by the formula $Ar^3$—$(CH_2)_r$— are benzyl, 2-furylmethyl, 3-furylmethyl, 2-thienylmethyl, 3-thienylmethyl, 2-phenylethyl, 2-(2-furyl)ethyl, 2-(3-furyl)ethyl, 2-(2-thienyl)ethyl and 2-(3-thienyl)ethyl groups.

In $A^1$, $R^{13}$ and $R^{14}$ may also form, together with the adjacent nitrogen atom, a 5- to 9- membered nitrogen-containing saturated heterocyclic group having 4 to 8 carbon atoms. Among methylene groups forming the heterocycle, one optional methylene group not adjacent to the above nitrogen atom may be replaced by an oxy group, a thio group or a group of the formula —$NR^{15}$— (wherein $R^{15}$ is a lower alkyl group), and one to four optional hydrogen atoms on the carbon atoms of the heterocycle may independently be replaced by a hydroxyl group and/or a lower alkyl group which may be substituted by a hydroxyl group, and further two adjacent carbon atoms in the heterocycle may form a double bond or fused-benzene ring. Examples of the heterocyclic group are pyrrolidino, piperidino, perhydroazepin-1-yl, perhydroazocin-1-yl, perhydroazonin-1-yl, 1,3-thiazolidin-1-yl, indolin-1-yl, isoindolin-2-yl, 3-pyrolin-1-yl, 1,5-dihydro-2H-pyrrol-1-yl, morpholino, perhydro-1,4-thiadin-4-yl, perhydro-4-lower alkyl-1,4-diadin-1-yl, 1,2,3,4-tetrahydroquinolin-1-yl, 1,2,3,4-tetrahydroisoquinolin-2-yl, 1,2,3,4-tetrahydropyridin-1-yl, 1,2,3,6-tetrahydropyridin-1-yl, perhydro-1,4-oxazepin-4-yl, perhydro-1,4-thiazepin-4-yl, perhydro-4-lower alkyl-1,4-diazepin-1-yl, 2,3,4,5-tetrahydro-1-benzazepin-1-yl, 2,3,4,5-tetrahydro-2-benzazepin-2-yl, 1,2,4,5-tetrahydro-3-benzazepin-3-yl, 2,3,4,5-tetrahydro-1H-azepin-1-yl, 2,3,6,7-tetrahydro1H-azepin-1-yl, 1,3,4,7-tetrahydro-2H-azepin-1-yl, perhydro-1,4-oxazocin-4-yl, perhydro-1,4-thiazocin-4-yl, perhydro-4-1lower alkyl-1,4-diazocin-1-yl, 1,2,3,4,5,6-hexahydro-1-benzazocin-1-yl, 1,2,3,4,5,6-hexahydro-2-benzazocin-2-yl, 1,2,3,4,5,6-hexahydro-3-benzazocin-3-yl, 1,2,3,4,5,6-hexahydroazocin-1-yl, 1,2,3,4,7,8-hexaylhydroazocin-1-yl and 1,2,3,4,5,8-hexahydroazocin-1-yl groups, or the above mentioned heterocyclic groups wherein one to four optional hydrogen atoms on the carbon atoms of the heterocycle may independently be replaced by a hydroxyl group and/or a lower alkyl group optionally substituted by a hydroxyl group. Examples of the lower alkyl group optionally substituted by a hydroxyl group are methyl, ethyl, propyl, isopropyl, butyl, isobutyl, sec-butyl, tert-butyl, hydroxymethyl, 1-hydroxyethyl, 2-hydroxyethyl, 1-hydroxypropyl, 2hydroxypropyl, 3-hydroxypropyl, 1-hydroxy-1-methylethyl, 1-hydroxybutyl, 2-hydroxybutyl, 3-hydroxybutyl, 4-hydroxybutyl, 1-hydroxy-1-methylpropyl, 1-hydroxy-2-methylpropyl, 2-hydroxy-2-methylpropyl, 2-hydroxy-1-methylpropyl, 1,1-dimethyl-2-hydroxyethyl, 3-hydroxy-2methylpropyl, methylpropyl and 3-hydroxy-1-methylpropyl groups. $R^{13}$ means a lower alkyl group such as a methyl, ethyl, propyl, isopropyl, butyl, isobutyl, sec-butyl or tert-butyl group. $R^{16}$ in the formula (II) means a hydrogen atom, a lower alkyl group or a cycloalkyl group. Examples of the lower alkyl group are methyl, ethyl, propyl, isopropyl, butyl, isobutyl, sec-butyl and tert-butyl groups. Examples of the cycloalkyl group are cyclopropyl, cyclobutyl, cyclopentyl and cyclohexyl groups. Examples of the lower alkyl group represented by and $R^{17}$ and $R^{18}$ in the formula (II) are methyl, ethyl, propyl, isopropyl, butyl, isobutyl, sec-butyl and tert-butyl groups.

$R^2$ means a hydrogen atom or a methyl group.

$R^3$ means a lower alkyl group having 3 to 5 carbon atoms such as a propyl, isopropyl, butyl, isobutyl, sec-butyl, tert-butyl, pentyl, isopentyl, neopentyl or tert-pentyl group.

$R^4$ means a hydrogen atom or a methyl group.

In $R^5$, examples of the indolylmethyl group wherein the indole ring is substituted at the 1-position by a group of the formula $R^{51}$—CO—$(CH_2)_s$— (wherein $R^{51}$ and s are as defined above) or by a group of the formula $(R^{52}O)_2P(=O)$—$(CH_2)_t$— (wherein $R^{52}$ and t are as defined above), are (1-formyl-3-indolyl)methyl, (1-acetyl-3-indolyl)methyl, (1-methoxycarbonyl-3-indolyl)methyl, (1-ethoxycarbonyl-3-indolyl)methyl, (1-propoxycarbonyl-3indolyl)methyl, (1-tert-butoxycarbonyl-3-indolyl)methyl, (1-benzyloxycarbonyl-3-indolyl)methyl, (1-carbamoyl-3indolyl)methyl, (1-methylcarbamoyl-3-indolyl)methyl, (1-ethylcarbamoyl-3-indolyl)methyl, (1-formylmethyl-3-indolyl)methyl, {(1-(2-oxopropyl)-3-indolyl}methyl, (1-carboxymethyl-3-indolyl)methyl, (1-methoxycarbonylmethyl-3indolyl)methyl, (1-ethoxycarbonylmethyl-3-indolyl)methyl, (1-tert-butoxycarbonylmethyl-3-indolyl)methyl, (1-benzyloxycarbonylmethyl-3-indolyl)methyl, (1-carbamoylmethyl-3-indolyl)methyl, (1-methylcarbamoylmethyl-3-indolyl)methyl, (1-ethylcarbamoylmethyl-3-indolyl)methyl, {1-(2-formylethyl)-3-indolyl}methyl, {1-(2-carboxyethyl)-3-indolyl}methyl, (1-phosphono-3-indolyl)methyl, (1-dimethoxyphosphoryl-3-indolyl)methyl, (1-diethoxyphosphoryl-3-indolyl)methyl, (1-phosphonomethyl-3-indolyl)methyl, (1-dimethoxyphosphorylmethyl-3-indolyl)methyl, (1-diethoxyphosphorylmethyl-3-indolyl)methyl and {1-(2-phosphonoethyl)-3-indolyl}methyl groups. In $R^5$, examples of the benzyl group wherein an optional hydrogen atom on the benzene ring may be replaced by a group of the formula $R^{53}O$—CO—$(CH_2)_u$—(wherein $R^{53}$ and u are as defined above) are benzyl, 2-carboxyphenylmethyl, 3carboxyphenylmethyl, 4-carboxyphenylmethyl, 2-methoxycarbonylphenylmethyl, 3-methoxycarbonylphenylmethyl, 4methoxycarbonylphenylmethyl, 2-ethoxycarbonyphenylmethyl, 3-ethoxycarbonytphenylmethyl, 4-ethoxycarbonylphenylmethyl groups, and examples of the benzyl group wherein one or two optional hydrogen atoms on the benzene ring are replaced by a hydroxyl group(s) or two optional hydrogen atoms on the benzene ring are replaced by a hydroxyl group and a sulfo group are 2hydroxyphenylmethyl, 3-hydroxyphenylmethyl, 4-hydroxyphenylmethyl, 2-hydroxy-3-sulfophenylmethyl, 3-hydroxy-2-sulfophenylmethyl, 4-hydroxy-3-sulfophenylmethyl, 2,3- dihydroxyphenylmethyl, 2,4-dihydroxyphenylmethyl, 2,5dihydroxyphenylmethyl, 2,6-dihydroxyphenylmethyl, 3,4-dihydroxyphenylmethyl and 3,5-dihydroxyphenylmethyl groups.

$R^{61}$ means a hydrogen atom or a lower alkyl group, or together with $R^{71}$ represents a methylene group. Examples of the lower alkyl group are methyl and ethyl groups.

$R^{71}$ means a hydrogen atom, a lower alkyl group which may be substituted by a hydroxyl group, a phenyl group, a thienyl group, a phenyl lower alkyl group wherein an optional hydrogen atom on the benzene ring may be replaced by a hydroxyl group or a benzyloxy group, a thienyl lower alkyl group, a thiazolyl lower alkyl group, a 4-imidazolylmethyl group, a (lower alkyl-substituted 4-imidazolyl)methylthiomethyl group, a 3-indolylmethyl group, a carbamoyl lower alkyl group, or an N-benzyloxycarbonyl-ω-amino lower liner alkyl group; or together with $R^{61}$ represents a methylene group. Examples of the lower alkyl group which may be substituted by a hydroxyl group are methyl, ethyl, propyl, isopropyl, butyl, isobutyl, sec-butyl, tert-butyl, pentyl, isopentyl, neopentyl, tert-pentyl, hexyl, hydroxymethyl, 1-hydroxyethyl, 2-hydroxyethyl, 1-hydroxypropyl, 2-hydroxypropyl, 3-hydroxypropyl, 1-hydroxy-1methylethyl, 2-hydroxy-1-methylethyl, 1-hydroxybutyl, 2hydroxybutyl, 3-hydroxybutyl, 4-hydroxybutyl, 1-hydroxy-1-methylpropyl and 2-hydroxy-1-methylpropyl groups. Examples of the phenyl lower alkyl group wherein an optional hydrogen atom on the benzene ring may be replaced by a hydroxyl group or a benzyloxy group are benzyl, 1-phenylethyl, 2-phenylethyl, 1-phenylpropyl, 2phenylpropyl, 3-phenylpropyl, 1-methyl-2-phenylethyl, lphenylbutyl, 2-phenylbutyl, 3-phenylbutyl, 4-phenylbutyl, 1-phenyl-2-methytpropyl, 2-phenyl-1-methylpropyl, 2-hydroxyphenylmethyl, 3-hydroxyphenylmethyl, 4-hydroxyphenylmethyl, 2-benzyloxyphenylmethyl, 3-benzyloxyphenylmethyl, 4-benzyloxyphenylmethyl, 1-(2-hydroxyphenyl)ethyl, 1-(3-hydroxyphenyl)ethyl, 1-(4-hydroxyphenyl)ethyl, 1-(2-benzyloxyphenyl)ethyl, 1-(3-benzyloxyphenyl)ethyl, 1-(4-benzyloxyphenyl)ethyl, 2-(2-hydroxyphenyl)ethyl, 2-(3-hydroxyphenyl)ethyl, 2-(4-hydroxyphenyl)ethyl, 2-(2-benzyloxyphenyl)ethyl, 2-(3-benzyloxyphenyl)ethyl and 2-(4-benzyloxyphenyl)ethyl groups. Examples of the lower alkyl group substituted by a thiazolyl group are 2-thiazolylmethyl, 4-thiazolylmethyl, 5-thiazolylmethyl, 2-(2-thiazolyl)ethyl, 2-(4-thiazolyl)ethyl and 2-(5-thiazolyl)ethyl groups. Examples of the lower alkyl group substituted by a thienyl group are 2-thienylmethyl, 3-thienylmethyl, 2-(2-thienyl)ethyl and 2-(3-thienyl)ethyl groups. Examples of the (lower alkyl substituted-4-imidazolyl)methylthiomethyl group are (5-methyl-4-imidazolyl)methylthiomethyl, (5-ethyl-4-imidazolyl)methylthiomethyl, (5-propyl-4-imidazolyl)methylthiomethyl, (5-isopropyl-4-imidazolyl)methylthiomethyl, (2-methyl-4imidazolyl)-methylthiomethyl, (2-ethyl-4-imidazolyl)methylthiomethyl, (2-propyl-4-imidazolyl)methylthiomethyl and (2-isopropyl-4-imidazolyl)methylthiomethyl groups. Examples of the carbamoyl lower alkyl group are carbamoylmethyl, 1-carbamoylethyl, 2-carbamoylethyl, 1-carbamoylpropyl, 2-carbamoylpropyl, 3-carbamoylpropyl, 1-carbamoyl-1-methylethyl, 2-carbamoyl-1-methylethyl, lcarbamoylbutyl, 2-carbamoylbutyl, 3-carbamoylbutyl, 4carbamoylbutyl, 1-carbamoyl-1-methylpropyl and 1-methyl-2-carbamoylpropyl groups.

Examples of the N-benzyloxycarbonyl-ω-amino lower linear alkyl group are N-benzyloxycarbonylaminomethyl, N-benzyloxycarbonyl-2-aminoethyl, N-benzyloxycarbonyl-3-aminopropyl, N-benzyloxycarbonyl-4-aminobutyl, N-benzyloxycarbonyl-5-aminopentyl and N-benzyloxycarbonyl-6-aminohexyl groups.

$R^{62}$ means a hydrogen atom, a phenyl group, a benzyl group, a carboxy group, a carbamoyl group or an N-phenylcarbamoyl group, or together with $R^8$ forms a single bond.

$R^{72}$ means a hydrogen atom, a lower alkyl group, a phenyl group, a benzyl group, a 3-indolylmethyl group, a carbamoyl group or an N-phenylcarbamoyl group. Examples of the lower alkyl group are methyl, ethyl, propyl, isopropyl, butyl, isobutyl, sec-butyl, tert-butyl, pentyl, isopentyl, neopentyl, tert-pentyl and hexyl groups.

$R^8$ means a hydrogen atom, a lower alkyl group, a lower alkoxy group or a hydroxyl group, or together with $R^{62}$ forms a single bond. Examples of the lower alkyl group are methyl, ethyl group, and examples of the lower alkoxy group are methoxy and ethoxy groups.

$R^{91}$ means a hydrogen atom, a lower alkyl group or a benzyl group. Examples of the lower alkyl group are methyl, ethyl, propyl, isopropyl, butyl, isobutyl, sec-butyl, pentyl, isopentyl, neopentyl and hexyl groups.

$R^{92}$ means a hydrogen atom, a lower alkyl group, a carboxymethyl group, a lower alkylsulfonyl group, or a phenylsulfonyl group wherein one to five optional hydrogen atoms on the benzene ring may be replaced independently by a lower alkyl group or a halogen atom. Examples of the lower alkyl group are methyl, ethyl, propyl, isopropyl and butyl groups, examples of the is lower alkylsulfonyl group are methylsulfonyl, ethylsulfonyl and propylsulfonyl groups, and examples of the phenylsulfonyl group wherein one to five optional hydrogen atoms on the benzene ring may be replaced independently by a lower alkyl group or a halogen atom are phenylsulfonyl, p-tolylsulfonyl, 2,4,6-trimethylphenylsulfonyl, 2,4,6-triisopropylphenylsulfonyl and 2,3,4,5,6-pentafluorophenylsulfonyl groups.

$R^{93}$ means a hydrogen atom or a lower alkyl group. Examples of the lower alkyl group are methyl, ethyl, propyl, isopropyl and butyl groups.

$R^{63}$ means a hydrogen atom, a lower alkyl group, a carboxy lower alkyl group or the group of the formula $Ar^4$—$(CH_2)_w$— (wherein $Ar^4$ and W are as defined above). Examples of the lower alkyl group are methyl, ethyl and propyl groups, examples of the carboxy lower alkyl group are carboxymethyl and 2-carboxyethyl groups, and examples of the group of the formula $Ar^4$—$(CH_2)_w$— are benzyl, 2-furylmethyl, 3-furylmethyl, 2-thienylmethyl and 3-thienylmethyl groups.

Now, the meanings of various abbreviations used in this specification will be given. The abbreviations relating to amino acids and their protective groups are in accordance with the recommendation by IUPAC-IUB Commission on Biochemical Nomenclature (Biochemistry, 11, 1726 (1972)) and common usage.

DAla D-alanine
βAla βB-alanine
DβAba (R)-3-aminobutanoic acid
DβAba-ONBu4 tetrabutylammonium (R)-3-aminobutanoate
DAps-ONa sodium (R)-2-aminopropanesulfonate
Asp L-aspartic acid DAsp D-aspartic acid
DAsn D-asparagine
Aib 2-amino-2-methylpropionic acid
Ams aminomethanesulfonic acid
Ams-ONa sodium aminomethanesulfonate
DCyS D-cysteine
Dha dehydroalanine
DGln D-glutamine
Gly glycine
DHis D-histidine
Ile L-isoleucine
DLIse DL-isoserine
Leu L-leucine
DLys D-lysine
MeLeu N-methyl-L-leucine
DMeTrp N-methyl-D-tryptophan
IO
Nle L-norleucine
DNle D-norleucine
Nva L-norvaline
DPhe D-phenylalanine
DPhg D-phenylglycine
DLβPhe DL-3-amino-3-phenylpropionic acid
Ser L-serine
DSer D-serine
DLSer DL-serine
Tau 2-aminoethanesulfonic acid
Tau-ONa sodium 2-aminoethanesulfonate
DLTha OL-3-(2-thienyl)alanine
DThg 0-(2-thienyl)glycine
DTrp D-tryptophan
DTrp(CHO) N$^{in}$-formyl-D-tryptophan
DLTza DL-3-(2-thiazolyl)alanine
DTyr D-tyrosine
DVal D-valine
Adm 1-adamantyl
Boc tert-butoxycarbonyl
Me methyl
Et ethyl
$^i$Pr isopropyl
Bu butyl
$^t$Bu tert-butyl
Ph phenyl
Bzl benzyl
CDI 1,1'-carbonyldiimidazole
DCC N,N'-dicyclohexylcarbodiimide
DIPC N,N'-diisopropylcarbodiimide
DMAP 4-(dimethylamino)pyridine
DMF N,N-dimethylformamide
NMP N-methylpyrrotidone
DMSO dimethylsulfoxide
EDCI.HCl 1-ethyl-3-(3-dimethylaminopropyl)carbodiimide hydrochloride
Fmoc 9-fluorenylmethoxycarbonyl
HOBT.H₂O 1-hydroxy-1H-benzotriazole mono hydrate
Iva isovaleryl
TEA triethyiamine
TFA trifluoroacetic acid
THF tetrahydrofuran
TosOH p-toluenesulfonic acid
Tos p-toluenesulfonyl
Trt trytyl
Z benzyloxycarbonyl
MOPS 3-morphorinopropanesulfonic acid
HEPES 2-[4-(2-hydroxyethyl)-1-piperazinyl]ethanesulfonic acid
Tris tris(hydroxymethyl)aminomethane
PMSF phenylmethanesulfonyl fluoride Now, the process for producing the novel peptide derivatives of the present invention will be described.

The peptide derivatives of the present invention can be prepared by condensing amino acids in a solution or on a solid support according to conventional methods in the area of peptide chemistry. (a) Liquid-phase Synthesis A peptide derivative of the present invention can be prepared by a method wherein amino acids composing the target peptide derivative are condensed one by one, or by a method wherein condensation products of amino acids are further condensed with each other, and when, if necessary, removing a C-terminal and/or side-chain protective group(s) (Method 1). Peptide derivatives prepared by Method 1 can be converted into other peptide derivatives of the present invention, as the case requires, by a combination of the following reactions: (1) acylation, alkoxycarbonylation, aryloxycarbonylation, carbamoylation or thiocarbamoylation of the N-terminal a-amino group after removal of an N-terminal amino-protecting group (Method 2 and 3), (2) formylation at the 1-position (Method 4) or oxidation at the 2-position (Method 6) of the indole ring of tryptophan, (3) conversion of a seryl residue to a dehydroalanyl residue (Method 5), (4) condensation of the C-terminal carboxyl group with ammonia, a primary or secondary amine, or an alkane- or arene-sulfonamide. Furthermore, these peptide derivatives can, if necessary, be converted to pharmaceutically acceptable salts.

Each method will be detailed as follows.

Method 1

Method 1 is a conventional synthetic method for peptides, that is, a method wherein amino acids are condensed one by one, or a method wherein peptide fragments are condensed with each other, to prepare a desired peptide derivative. Furthermore, after condensation, a C-terminal and/or sidechain protective group(s) can be removed by alkaline hydrolysis or catalytic hydrogenation. Condensation can be conducted according to known methods such as a DCC method, an azide method, an active ester method and a mixed acid anhydride method (discribed, for example, by M. Bodansky and M. A. Ondetti in Peptide Synthesis, Interscience, New York, 1966; by F. M. Finn and K. Hofmann in The Proteins, Vol. 2, ed. by H. Henrath and R. L. Hill, Academic Press Inc., New York, 1976; by Noboru Izumiya et al. in Peptide Synthesis, Maruzen, 1975).

For example, in the case wherein condensation is carried out by a DCC method, an N$^α$-derivatized amino acid or an O$^α$-derivatized α-hydroxyalkanoic acid of the formula:

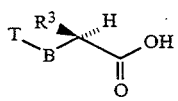
(XIII)

wherein T is A¹ or an α-amino-protecting group, and A¹, B and R³ are as defined before, is treated with a condensing reagent such as DCC(or EDCI.HCl)-HOBT.H₂O in a suitable solvent such as DMSO, NMP, DMF, THF, 1,4-dioxane, acetonitrile, dichloromethane or chloroform at around −40° C. to room temperature, then condensed with an amino acid of the formula:

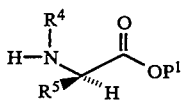

(XIV)

wherein P¹ is an α-carboxyl-protecting group, and R⁴ and R⁵ are as defined before, to afford a dipeptide derivative of the formula:

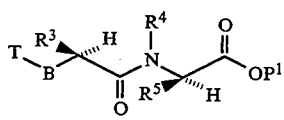

(XV)

wherein T, B, R³, R⁴ and p¹ are as defined before. An N-terminal α-amino-protecting group is usually selected from the groups well-known to those skilled in the art, for example, from urethane type protective groups such as a Z group, a Boc group, a p-methoxybenzyloxycarbonyl group and a p-nitrobenzyloxycarbonyl group, while the C-terminal a-carboxyl group is usually protected as, for example, a methyl ester, an ethyl ester, a benzyl ester or a tert-butyl ester. Each protective group should be selected so that it can be selectively deprotected after condensation. For example, in the case that a Boc group is selected as an N-terminal protective group, it is preferable to protect the C-terminus as a methyl group, an ethyl group or a benzyl group. A Boc group will be readily removed by use of a mild acid such as TFA, while the carboxyl-protecting groups described above will be usually intact under these conditions. On the other hand, a methyl, ethyl or benzyl ester will be easily deprotected by alkaline hydrolysis and a benzyl ester will be also deprotected by catalytic hydrogenation, while a Boc group will be intact under these conditions.

In the case that T is an α-amino-protecting group, the group T will be formally converted to A¹ by removal of T from the dipeptide derivative (XV) followed by N-acylation, N-alkoxycarbonylation, N-aryloxycarbonylation, N-carbamoylation or N-thiocarbamoylation which will be carried out under the reaction conditions described later in Method 2.

A C-terminal protective group of the dipeptide derivative (XV) prepared in the above-mentioned manner is now removed, and the resulting deprotected dipeptide is treated with a condensation reagent (for example, EDCI.HCl-HOBT.H₂O) in the same manner described above and then with an amino acid or a peptide derivative whose C-terminal carboxyl group is protected, to afford a desired peptide derivative.

In the case that B is —NR²—, the dipeptide derivative (XV) may be treated with an excess amount of hydrazinc in a solvent such as methanol or DMF at room temperature to afford the corresponding hydrazide, which can be converted to a desired peptide derivative by an azide method. Namely, the hydrazide is first converted to the corresponding azide on treatment with a reagent such as a lower alkyl ester of nitrous acid (for example, tert-butyl nitrite or isoamyl nitrite) or an alkaline metal salt of nitrous acid (for example, sodium nitrite or potassium nitrite) in the presence of a strong acid such as hydrochloric acid or sulfuric acid (this reaction can be performed in a solvent such as water, and/or DMF, THF or 1,4-dioxane at around −60° C. to −15° C.). Then, the azide is mixed with a tertiary amine such as TEA, and a C-terminal ester derivative of an amino acid or a dipeptide at −70° C. to −60° C., and then allowed to react at −20° C. to room temperature to afford a desired peptide derivative. A tert-butylammonium-, triethylammonium-, sodium- or potassium- salt of an amino acid or a dipeptide can also be used instead of the C-terminal ester derivative.

In the process so far described, a C-terminal amino acid or a C-terminal dipeptide is lastly condensed to give a target peptide derivative. The alternative process wherein an N-terminal amino acid is lastly condensed to give a target product is also available. Namely, a compound of the formula:

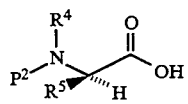

(XVI)

wherein P² is an α-amino-protecting group, and R⁴ and R⁵ are as defined before, is condensed with a compound of the formula (X) or its derivative whose sidechain functional group is, if necessary, protected by a DCC method or an azide method to afford an N-terminal protected peptide derivative. A suitable α-amino-protecting group can be selected from the urethane type protective groups described before, a sidechain functional group, for example, a hydroxyl group can be protected as a benzyl or a tert-butyl ether, and a C-terminal carboxyl group can be protected as an ester. In the case that a C-terminal carboxyl group is s protected as a methyl or an ethyl ester, a Z group is preferable for a N-terminal amino-protecting group. A Z group will be readily removed by catalytic hydrogenation, while under these conditions these C-terminal carboxyl-protecting groups will be intact. Next, an N-terminal amino-protecting group of the peptide derivative is removed and the deprotected derivative is condensed with a compound of the formula (XI) by, for example, a DCC method or an azide method to afford a target peptide derivative elongated toward the N-terminus. A peptide derivative of the formula (I) wherein X² is a sulfur atom, can be prepared by condensation of a compound of the formula (XVI) with a compound of the formula (X) whose C-terminal carboxyl group is protected, followed by conversion of the resulting amide bond to the thioamide bond on treatment with, for example, the Lawesson's reagent, then condensed with a compound of the formula (XI) in the same manner described above. A C-terminal and/or sidechain protective group(s) of a peptide derivatives prepared by the method so far described, can be deprotected by a suitable method, if necessary. For example, in the case that a carboxyl group is protected as a methyl or an ethyl ester, the protective group can be readily removed by alkaline hydrolysis, that is, by treatment with solution of an alkaline metal hydroxide such as NaOH, KOH or LiOH in a solvent such as methanol, ethanol, acetone, 1,4-dioxane or DMF at 0° C. to room temperature. In the case that a carboxylic acid is protected as a benzyl ester, the protective group can be readily removed by catalytic hydrogenation, that is, by hydrogenation under 1 to 4 atmospheric pressures of hydrogen in the presence of a catalyst such as Pd-C or palladium black in a solvent such as methanol, ethanol, DMF, THF, 1,4-dioxane or acetic acid. In the case that a hydroxyl group is protected as a benzyl ether, the protective group can be removed by catalytic hydrogenation in the same manner described above. While, in the case that a hydroxyl group is protected as a tert-butyl ether, the protective group can be removed by treatment with a mild acid such as TFA.

Method 2

Method 2 is a process for producing a peptide derivative which possesses an acyl, an alkoxycarbonyl, an aryloxycarbonyl, a carbamoyl or a thiocarbamoyl group at the N-terminus, by condensation of a precursor prepared by Method 1 with a carboxylic acid ($R^{11}COOH$) according to, for example, a DCC method, by treatment with an acid chloride such as an acyl chloride ($R^{11}COCl$), a chloroformate ($R^{12}OCOCl$) or a carbamoyl chloride ($R^{13}R^{14}NCOCl$) in the presence of a base, or by treatment with an isocyanate ($R^{13}NCO$) or an isothiocyanate ($R^{13}NCS$), after removal of an N-terminal protective group (wherein $R^{11}$, $R^{12}$, $R^{13}$ and $R^{14}$ are as defined before), furthermore optionally removing a C-terminal and/or sidechain protective group(s) by alkaline hydrolysis or catalytic hydrogenation. An N-terminal protective group of the precursor can be readily removed by a conventional method such as catalytic hydrogenation (a Z group) or by treatment with a mild acid such as TFA (a Boc group). The condensation of the resulting deprotected peptide derivative with a carboxylic acid can be performed in the same manner described in Method 1 (for example, a DCC method). The reaction with an acid chloride such as an acyl chloride ($R^{11}COCl$), a chloroformate ($R^{12}O$-$COCl$) or a carbamoyl chloride ($R^{13}R^{14}NCOCl$) can be performed in a suitable solvent such as chloroform, dichloromethane, THF, 1,4-dioxane, toluene or pyridine in the presence of a base such as TEA, DMAP, N-methylmorpholine or pyridine at 0° C. to the boiling point of the solvent. The reaction with an isocyanate ($R^{13}NCO$) or an isothiocyanate ($R^{13}NCS$) can be performed in a solvent such as chloroform, dichloromethane, THF, 1,4-dioxane or toluene at 0° C. to the boiling point of the solvent.

A C-terminal and/or sidechain protective group(s) of peptide derivatives prepared by the above-mentioned method can be removed by alkaline hydrolysis or catalytic hydrogenation in the same manner described in Method 1, if necessary.

Method 3

Method 3 is a process for producing a peptide derivative which possesses a carbamoyl group at the N-terminus, by treatment of a peptide derivative (prepared by Method 1 or 2) having an aryloxycarbonyl group at the N-terminus, with a primary or secondary amine $R^{13}NHR^{14}$ wherein $R^{11}$ and $R^{14}$ are as defined before, furthermore optionally removing a C-terminal and/or sidechain protective group(s) by alkaline hydrolysis or catalytic hydrogenation. That is, a peptide derivative possessing a carbamoyl group at the N-terminus can be prepared by dissolving a peptide derivative possessing an aryloxycarbonyl group at the N-terminus in a solvent such as chloroform, dichloromethane, THF, 1,4-dioxane, toluene or pyridine, followed by addition of the primary or secondary amine described above, optional addition of a tertiary amine such as TEA or DMAP, and allowing them to react at room temperature to the boiling point of the solvent. A C-terminal and/or sidechain protective group(s) of the product can be removed, if necessary, by alkaline hydrolysis or catalytic hydrogenation in the same manner described in Method 1.

Method 4

Method 4 is a process for formylation at the 1position of the indole ring of a tryptophanyl residue.

That is, the formylation can be performed on treatment of a peptide derivative possessing a tryptophanyl residue with formic acid saturated with hydrogen chloride at −20° C. to room temperature.

Method 5

Method 5 is a process for converting a seryl residue to a dehydroalanyl residue on treatment of a peptide derivative possessing a seryl residue with a suitable dehydrating agent, furthermore deprotecting a C-terminal carboxyl-protecting group by alkaline hydrolysis in the same manner described in Method 1, if necessary.

Method 6

Method 6 is a process for oxidation at the 2-position of the indole ring of a tryptophanyl residue.

That is, the oxidation of the indole ring at the 2-position can be performed on treatment of a peptide derivative possessing a tryptophanyl residue with a mixed solution of dimethyl sulfoxide, conc. hydrochloric acid and acetic acid at 0° C. to room temperature.

Method 7

Method 7 is a process for producing a target peptide derivative by condensation of a C-terminal free carboxylic acid with ammonia, a primary or secondary amine, or an alkane- or arene-sulfonamide in the same manner described in Method 1.

All reaction intermediates and products so far described can be purified by well-known methods such as recrystallization, reprecipitation, partition procedures, normal- or reverse-phase chromatography, and ion-exchange chromatography.

(b) Solid-phase Synthesis

A desired peptide derivative of the present invention can be obtained by successive condensations of amino acids on an insoluble support such as a chloromethyl resin (Biochemistry, 3, 1385 (1964)), an oxymethyl resin (Chem. Ind. (London), 1966, 1597), a palkoxybenzylalcohol resin (J. Am. Chem. Soc., 95., 1328 (1973) or a functionalized polyamide resin (Bioorganic Chemistry, 8, 351–370 (1979)). Firstly, an amino group of an amino acid selected for the C-terminus, is protected. If a reactive functional group is present in the sidechain, such a sidechain functional group is also protected. Then, it is attached as a form of a carboxylic acid ester to an insoluble support in accordance with a conventional method. An amino-protecting group is removed, and then a second amino acid derivative (an a-amino group and, if necessary, a sidechain functional group are protected) is condensed by simultaneous addition of a condensing reagent such as DCC or DIPC, and, if necessary, an additive such as $HOBT.H_2O$. The amino acid derivative can be used as a pre-activated form such as a pentafluorophenyl ester or an acid azide. Such deprotection and condensation are repeated to afford a desired resin-bound peptide derivative. A protective group of an amino group is selected usually from the groups well-known to those skilled in the art, for example, from urethane type protective groups such as a Z group, a Boc group, a Fmoc group, a p-methoxybenzyloxycarbonyl group and a p-nitrobenzyloxycarbonyl group. For the protection of an a-amino group, it is preferable to use a Fmoc group or a Boc group. A Fmoc group can be readily deprotected after condensation with a relatively mild base such as a 20% solution of piperidine in DMF. On the other hand, a Boc group can be readily deprotected with a relatively mild acid such as TFA. When a Fmoc group is used for is the protection of an α-amino group, the sidechain carboxyl group of e.g. aspartic acid may be protected as a tert-butyl ester or a trityl ester, the hydroxyl group of e.g. serine, isoserine or tyrosine may be protected as a tert-butyl ether, and the imidazolyl group of histidine may be protected by a tosyl group, so that these protective groups are stable under the conditions for the removal of a Fmoc group, and that after elongation of the peptide chain and cleavage of the peptide derivative from the insoluble support, all such protective groups can be simultaneously deprotected with a mild acid such as TFA. On the other hand, when a Boc group is used for the protection of an α-amino group, the sidechain carboxyl group of e.g. aspartic acid may be protected as a benzyl ester, the hydroxyl group of e.g. serine, isoserine or tyrosine may be protected as a benzyl ether, the imidazolyl group of histidine may be protected by a tosyl group, the indolyl group of tryptophan may be protected by a formyl group so that these protective groups are stable under the conditions for the removal of a Boc group, and that after elongation of the peptide chain and cleavage of the peptide derivative from the insoluble support, all such protective groups can be simultaneously removed by, for example, catalytic hydrogenation, treatment with hydrogen fluoride or treatment with trimethylsilyl trifluoromethanesulfonate/thioanisole/TFA (Chem. Pharm. Bull., 35, 3447–52 (1987)).

Cleavage of the peptide derivative from the insoluble support after elongation of the peptide chain, can be conducted by various methods well-known to those skilled in the art. For example, when solid-phase synthesis is conducted by use of a p-alkoxybenzyl alcohol resin as an insoluble support, it is possible to obtain a peptide derivative having a free carboxyl group as the C-terminus by treatment of a resin-bound peptide derivative with a mild acid such as TFA. On the other hand, when solid-phase synthesis is conducted by use of a p-nitrobenzoyloxime resin, it is possible to obtain a peptide derivative having an amide group as the C-terminus by treatment of a resin-bound peptide derivative with ammonia.

The liberated peptide derivative can be separated from the insoluble support, for example, by direct filtration of the suspension of reaction mixture in a solvent in which the peptide derivative is soluble, or by a series of treatment consisting of precipitation of the peptide derivative followed by filtration, redissolution of the precipitate in a suitable solvent such as acetic acid, and subsequent removal of the insoluble support by filtration. Removal of the support, concentration of the resulting solution, and purification of the residue by a conventional method such as recrystallization, reprecipitation, partition procedures, normal- or reverse-phase chromatography, or ion-exchange chromatography afford the peptide derivative of the present invention.

Process for producing a peptide derivative of the present invention by solid-phase synthesis will be detailed in Methods 8 and 9.

Method 8

An acylated peptide derivative at the N-terminus of the present invention can be prepared as follows.

An amino protected derivative of an amino acid selected for the C-terminus, is attached as a carboxylic acid ester to an insoluble support in accordance with a conventional method (a sidechain functional group is protected, if necessary, with a suitable protective group), and an amino-protecting group is removed, and then an a-amino protected derivative of a second amino acid (a sidechain functional group is protected, if necessary) is condensed by simultaneous addition of a condensing reagent such as DCC or DIPC, and, if necessary, an additive such as $HOBT \cdot H_2O$. The α-amino protected derivative can be used as a pre-activated form such as a pentafluorophenyl ester, an acid azide or a symmetric acid anhydride. Such deprotection and condensation are repeated to afford a desired resinbound peptide derivative. The resulting resin-bound peptide derivative is deprotected at the N-terminus, and condensed with a carboxylic acid (this carboxylic acid may also be used as a carboxyl-activated derivative) corresponding to an N-terminal acyl group in the same manner described above, to afford the N-terminal acylated resin-bound peptide derivative. When solid-phase synthesis is performed by use of a p-alkoxybenzyl alcohol resin as an insoluble support, it is possible to obtain a desired peptide derivative having a free carboxyl group as the C-terminus and an acylated N-terminus by cleavage of the peptide derivative from the support followed by deprotection of a sidechain protective group(s) on treatment with TFA, if necessary. A peptide derivative having a protected sidechain functional group(s) and a free carboxyl group as the C-terminus may also be obtained, if the cleavage is carried out under the milder conditions, and if the sidechain protective group(s) is selected so as to be stable under the conditions. Furthermore, the resulting peptide derivative having a free carboxyl group at the C-terminus can be converted to the corresponding ester or amide in a usual manner, and subsequent removal of a sidechain protective group(s) affords a peptide derivative of the present invention.

[Method 9]

A compound of the present invention having a carboxyl group at the C-terminus can be prepared by successive condensation of amino acids toward the N-terminus on a suitable resin according to a conventional solid-phase synthesis, followed by condensation with an N-terminal amino acid derivative in which the a-amino group has previously been acylated, alkoxycarbonylated, aryloxycarbonylated, carbamoylated, or thiocarbamoylated in a usual manner, and final cleavage of a desired peptide derivative from the resins with simultaneous deprotection of a sidechain functional group(s) on treatment with, for example, hydrogen fluoride. The method also provides a process for producing a peptide derivative having a C-terminal ester or amide. Namely, cleavage of a peptide derivative from the resins can be done without removal of a sidechain protective group(s). The resulting sidechain protected peptide derivative having a free carboxylic acid at the C-terminus can be converted into its corresponding ester or amide in a usual manner, and subsequent removal of a sidechain protective group(s) gives a desired peptide derivative.

The peptide derivative thus obtained may be subjected, if necessary, to formation or exchange of a salt of an alkaline metal or an alkaline earth metal such as sodium, potassium, calcium, etc.; a salt of a non-toxic organic amine such as dimethylamine, TEA, benzylamine, dicyclohexylamine, etc.; a salt of a basic amino acid such as lysine, arginine, etc.; a salt of an amide derivative of an amino acid such as phenylalanine amide, leucine amide, etc.; a salt of a mineral acid such as hydrochloric acid, sulfuric acid, etc.; a salt of an acidic amino acid such as aspartic acid, gulutamic acid, etc.; or a salt of an organic acid such as maleic acid, fumalic acid, tataric acid, malic acid, citric acid, etc.

Starting materials used in the methods so far described are commercially available except for the following materials, which are prepared by the known methods in the literature.

D- and L-3-amino-4-phenylbutylic acids and D-3-amino-4-(3-indolyl)butylic acid: J. Med. Chem., 13, 177 (1970); Tetrahedron, 43, 3509 (1987).

D-N-methyltryptophan methyl ester hydrochloride: Helv. Clin. Acta, 46, 577 (1963).

D- and L-N-aminoprolines: JP-82-18611.

cis- and trans-2-aminocyclopropanecarboxylic acids: J. Org. Chem., 40, 182 (1975).

D-N$^{in}$-dimethoxyphosphoryltryptophan: J. Org. Chem., 54, 1664 (1989).

DL-3-(3-ethoxycarbonylphenyl)alanine and DL-3-(4-methoxycarbonylphenyl)alanine: Synthesis, 53 (1984).

D-3-(3-benzo[b]thienyl)alanine and D-3-(1,1-dioxo-3-benzo[b]thienyl)alanine: Chem. Pharm. Bull., 24, 3149 (1976).

2,2,6,6-tetramethylpiperidinocarbonyl chloride: Helv. Chim. Acta, 61, 2237 (1978).

D-(S)-(5-methyl-4-imidazolylmethyl)cysteine dihydrochlorides, (R)-2-amino-3-phenylpropanesulfonic acid and (1,3-dithiol-2-ylidene)malonic acid mono methyl ester are prepared in the manner described in Referential Example 1-3.

The chemical structures, experimental Nos. and compound Nos. of the prepared peptide derivatives in the present invention show in Tables 1-4.

TABLE 1

| Exp. No. | Compd No. | A$^1$ | A$^2$ |
|---|---|---|---|
| 1 | 1 | Boc | DβAba—OH |
| 2 | 2 | Boc | DTrp—OH |
| 3 | 3 | Boc | DLeu—OH |
| 4 | 4 | Boc | DHis—OH |
| 5 | 5 | Boc | —NH(CH$_2$)$_3$CO$_2$H |
| 6 | 6 | Boc | —NH(CH$_2$)$_5$CO$_2$H |
| 7 | 7 | Boc | DSer—OH |
| 8 | 8 | Boc | DLys(Z)—OH |
| 9 | 9 | Boc | DAsn—OH |
| 10 | 10 | Boc | DGln—OH |
| 11 | 11 | Boc | DNle—OH |
| 12 | 12 | Boc | —NH-(3-COOH-C$_6$H$_4$) |
| 13 | 13 | Boc | Aib—OH |
| 14 | 14 | Boc | DLβPhe—OH |
| 15 | 15 | Boc | DLTha—OH |
| 16 | 16 | Boc | DLTza—OH |
| 17 | 17 | Boc | DLIse—OH |
| 18 | 18 | Boc | —NH—CH(Me)—CO$_2$H |
| 19 | 19 | Boc | —NH—CH(CH$_2$-indolyl)—CH$_2$—COOH |
| 20 | 20 | Boc | —NH—CH(CH$_2$Ph)—CH$_2$—COOH |
| 21 | 21 | Boc | —NH—CH(CH$_2$Ph)—CH$_2$—COOH |

TABLE 1-continued

[Structure: A¹-NH-CH((CH₃)₂CHCH₂)-CO-N(H)-CH(CH₂-indole)-CO-A²]

| Exp. No. | Compd No. | A¹ | A² |
|---|---|---|---|
| 22 | 22 | Boc | -NH-CH(COOH)-CH₂-S-CH₂-(5-methyl-imidazol-4-yl) .TFA |
| 23 | 23 | Boc | Gly—Gly—OH |
| 24 | 24 | Boc | Ams—OH.TEA |
| 25 | 25 | Boc | Tau—OH.TEA |
| 26 | 26 | Boc | -NH-CH(CH₂Ph)-CH₂-SO₃H.TEA |
| 27 | 27 | Boc | -NHCH₂P(=O)(OH)-O⁻.N⁺Bu₄ |
| 29 | 29 | Boc | βAla—OH |
| 31 | 31 | Boc | Gly—OH |
| 33 | 33 | Iva | βAla—OH |
| 34 | 34 | Iva | DHis—OH |
| 35 | 35 | Boc | DAsp(OBzl)—NH₂ |
| 35 | 36 | Boc | DAsp—NH₂ |
| 36 | 37 | Boc | Asp(OBzl)—NH₂ |
| 36 | 38 | Boc | Asp—NH₂ |
| 37 | 39 | Boc | DPhe—OH |
| 38 | 40 | Boc | DPhg—OH |
| 39 | 41 | Boc | DAla—OH |
| 40 | 42 | Boc | DThg—OH |
| 41 | 43 | Boc | DVal—OH |
| 42 | 44 | Boc | DAsp—NHPh |
| 43 | 45 | Boc | Asp—NHPh |
| 44 | 46 | Iva | DAsp—OH |
| 45 | 47 | (hexamethyleneimino)CO— | DHis—OMe |
| 45 | 48 | (hexamethyleneimino)CO— | DHis—OH |
| 46 | 49 | (hexamethyleneimino)CO— | DTrp—OMe |
| 46 | 50 | (hexamethyleneimino)CO— | DTrp—OH |

TABLE 1-continued

| Exp. No. | Compd No. | A¹ | A² |
|---|---|---|---|
| 47 | 51 | cycloheptyl-NCO— | DβAba—OMe |
| 47 | 52 | cycloheptyl-NCO— | DβAba—OH |
| 48 | 53 | cycloheptyl-NCO— | Tau—OH.TEA |
| 51 | 55 | 2-thienyl-CO— | βAla—OH |
| 52 | 56 | 3-thienyl-CO— | βAla—OH |
| 53 | 57 | 2-furyl-CO— | βAla—OH |
| 54 | 58 | 3-furyl-CO— | βAla—OH |
| 55 | 59 | 2-thienyl-CH₂-CO— | βAla—OH |
| 56 | 60 | 3-thienyl-CH₂-CO— | βAla—OH |
| 57 | 61 | cyclopentyl-CH₂-CO— | βAla—OH |
| 58 | 62 | cyclopentyl-CO— | βAla—OH |

TABLE 1-continued

Structure: (CH₃)₂CHCH₂ group on α-carbon; A¹-NH-CH(CH₂CH(CH₃)₂)-CO-NH-CH(CH₂-indol-3-yl)-CO-A²

| Exp. No. | Compd No. | A¹ | A² |
|---|---|---|---|
| 59 | 63 | cyclohexyl-CH₂-CO— | βAla—OH |
| 60 | 64 | cyclohexyl-CO— | βAla—OH |
| 61 | 65 | cyclopropyl-CO— | βAla—OH |
| 62 | 66 | (1,3-dithiol-2-ylidene)-C(CO₂Me)-CO— | βAla—OH |
| 62 | 67 | (1,3-dithiol-2-ylidene)-CH-CO— | βAla—OH |
| 63 | 68 | (CH₃)₃C-CH₂-CO— | βAla—OH |
| 64 | 69 | ᵗBuCO— | βAla—OH |
| 65 | 70 | PhCH₂CO— | βAla—OH |
| 66 | 71 | ⁱPrOCO— | βAla—OH |
| 67 | 72 | PhOCO— | βAla—OH |
| 68 | 73 | Me₂NCO— | βAla—OH |
| 69 | 74 | 2,2,6,6-tetramethylpiperidin-1-yl-CO— | βAla—OH |
| 70 | 75 | Iva | Gly—OH |
| 71 | 76 | Ph(Me)NCO— | βAla—OH |
| 72 | 77 | Et₂NCO— | βAla—OH |
| 73 | 78 | EtOCO— | Tau—ONa |
| 74 | 79 | Iva | Ams—ONa |
| 75 | 80 | ᵗBuNHCO— | DβAba—OH |
| 76 | 81 | ᵗBuNHCO— | DTrp—OH |
| 77 | 82 | ᵗBuNHCO— | DHis—OH |
| 78 | 83 | ᵗBuNHCO— | Ams—ONa |
| 79 | 84 | PhNHCO— | βAla—OH |
| 80 | 85 | ᵗBuNHCO— | βAla—OH |
| 81 | 86 | cyclohexyl-NHCO— | βAla—OH |

TABLE 1-continued

[Structure: (CH₃)₂CHCH₂ group on chiral carbon, A¹-NH-CH-CO-NH-CH(CH₂-indole)-CO-A²]

| Exp. No. | Compd No. | A¹ | A² |
|---|---|---|---|
| 82 | 87 | 2-Cl-C₆H₄-NHCO— | βAla—OH |
| 83 | 88 | 4-Cl-C₆H₄-NHCO— | βAla—OH |
| 84 | 89 | ⁱPrNHCO— | Gly—OH |
| 85 | 90 | PhNHCO— | Gly—OH |
| 86 | 91 | PhNHCS— | Gly—OH |
| 87 | 92 | cycloheptyl-NCO— | βAla—OEt |
| 87 | 93 | cycloheptyl-NCO— | βAla—OH |
| 88 | 94 | 2-(hydroxymethyl)cyclohexyl-NCO— | βAla—OEt |
| 88 | 95 | 2-(hydroxymethyl)cyclohexyl-NCO— | βAla—OH |
| 89 | 96 | 4-hydroxycyclohexyl-NCO— | βAla—OH |
| 90 | 97 | 2-methylcyclohexyl-NCO— | βAla—OH |
| 91 | 98 | 4-methylcyclohexyl-NCO— | βAla—OH |

TABLE 1-continued

Structure: (CH₃)₂CHCH₂ group on central carbon; A¹—NH—CH—C(=O)—NH—CH(CH₂-indole)—C(=O)—A²

| Exp. No. | Compd No. | A¹ | A² |
|---|---|---|---|
| 92 | 99 | 4-methylcyclohexyl-NCO— | βAla—OH |
| 93 | 100 | 2,6-dimethylcyclohexyl-NCO— | βAla—OH |
| 94 | 101 | cyclohexyl-NCO— | βAla—OH |
| 95 | 102 | morpholinyl-NCO— (O in ring) | βAla—OH |
| 96 | 103 | 4-methylpiperazinyl-NCO— (MeN in ring) | βAla—OH |
| 97 | 104 | tetrahydroisoquinolinyl-NCO— | βAla—OH |
| 98 | 105 | tetrahydroisoquinolinyl-NCO— (isomer) | βAla—OH |
| 99 | 106 | thiomorpholinyl-NCO— (S in ring) | βAla—OH |
| 100 | 107 | cyclooctyl-NCO— | βAla—OH |
| 101 | 108 | 3,3,5-trimethylcycloheptyl-NCO— | βAla—OH |

TABLE 1-continued

[Structure: (CH₃)₂CHCH₂ and H on chiral center bonded to A¹-N(H)-, C(=O)-N(H)-, chiral center with CH₂-indole side chain, C(=O)-A²]

| Exp. No. | Compd No. | A¹ | A² |
|---|---|---|---|
| 102 | 109A | 2-(hydroxymethyl)piperidine-NCO— | βAla—OH |
| 102 | 109B | 2-(hydroxymethyl)piperidine-NCO— | βAla—OH |
| 103 | 110 | pyrrolidine-NCO— | βAla—OH |
| 104 | 111 | 2,5-dimethylpyrrolidine-NCO— | βAla—OH |
| 105 | 112 | thiazolidine-NCO— | βAla—OH |
| 106 | 113 | AdmNHCO— | βAla—OH |
| 107 | 114 | ≡—C(CH₃)₂—NHCO— | βAla—OH |
| 108 | 115 | PhCH₂NHCO— | βAla—OH |
| 109 | 116 | (CH₃)₂C(CH₃)—CH₂—NHCO— | βAla—OH |
| 110 | 117 | cyclopropyl-NHCO— | βAla—OH |
| 111 | 118 | cyclopentyl-NHCO— | βAla—OH |
| 112 | 119 | ⁱPr₂NCO— | βAla—OH |
| 113 | 120 | (cyclohexyl)₂NCO— | βAla—OH |

TABLE 1-continued

[Structure: (CH₃)₂CHCH₂ group on a stereocenter bearing H, with A¹—NH— on one side and —C(O)—N(H)—CH(CH₂-indol-3-yl)—C(O)—A² on the other]

| Exp. No. | Compd No. | A¹ | A² |
|---|---|---|---|
| 114 | 121 | (CH₃)₂C(NCO—)CH₂CH₂OH | βAla—OH |
| 115 | 122 | (CH₃)₂C(NCO—)CH₂Ph | βAla—OH |
| 116 | 123 | 3-Me-C₆H₄-NHCO— | βAla—OH |
| 117 | 124 | 3-MeO-C₆H₄-NHCO— | βAla—OH |
| 118 | 125 | 3-Cl-C₆H₄-NHCO— | βAla—OH |
| 119 | 126 | 4-Me-C₆H₄-NHCO— | βAla—OH |
| 120 | 127 | 2-MeO-C₆H₄-NHCO— | βAla—OH |
| 121 | 128 | 2-Me-C₆H₄-NHCO— | βAla—OH |
| 122 | 129 | (CH₃)(CH₃CH₂)C(CH₃)—NHCO— | βAla—OMe |
| 122 | 130 | (CH₃)(CH₃CH₂)C(CH₃)—NHCO— | βAla—OH |

TABLE 1-continued
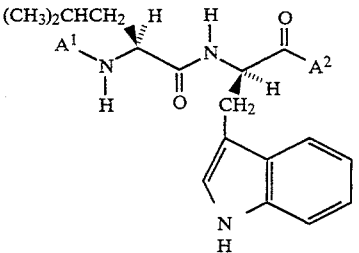
| Exp. No. | Compd No. | A¹ | A² |
|---|---|---|---|
| 125 | 133 | Boc | Dha—OH |
| 126 | 134 | 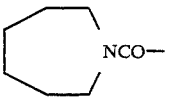 | βAla—NHMe |
| 127 | 135 | 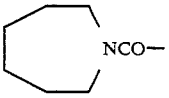 | βAla—NH$_2$ |
| 128 | 136 | 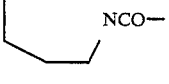 | βAla—NMe$_2$ |
| 129 | 137 | Boc | DTyr(Bzl)—OH |
| 129 | 138 | Boc | DTyr—OH |
| 131 | 140 | 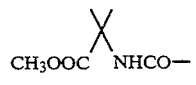 | βAla—OH |
| 132 | 141 |  | βAla—OH |
| 135 | 144 | Boc | DLIse—OMe |
| 135 | 145 | Boc | DLIse(Me)—OMe |
| 135 | 146 | Boc | DLIse(Me)—OH |
| 136 | 147 | Boc | NH—N(CH$_2$COOH)$_2$ |
| 137 | 148 | Boc | NH—NH—CH$_2$COOH |
| 138 | 149 | Boc | 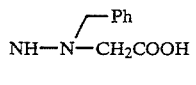 |
| 139 | 150 | 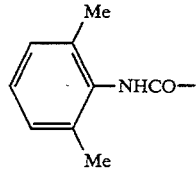 | βAla—OH |
| 140 | 151 | 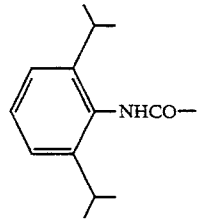 | βAla—OH |

TABLE 1-continued

| Exp. No. | Compd No. | A¹ | A² |
|---|---|---|---|
| 141 | 152 | (pyrrolidine)N—NHCO— | βAla—OH |
| 146 | 157 | (azepane)NCO— | βAla—NHSO₂Ph |
| 147 | 158 | (azepane)NCO— | βAla—NHSO₂Me |
| 148 | 159 | (dicyclopentylamino)NCO— | βAla—OH |
| 149 | 160 | (azepane)NCO— | DAps—ONa |
| 152 | 163 | (azepane)NCO— | NH—DPro—ONa |
| 153 | 164 | (azepane)NCO— | NH—Pro—ONa |
| 154 | 165 | (azepane)NCO— | cyclopropane with NH at 3 and COOH at 2 (2R,3S) or (2S,3R) |
| 154 | 166 | (azepane)NCO— | cyclopropane with NH at 3 and COOH at 2 (2S,3R) or (2R,3S) |
| 155 | 167 | (azepane)NCO— | NH—C(CH₃)=CH—COOEt |

TABLE 1-continued

| Exp. No. | Compd No. | A¹ | A² |
|---|---|---|---|
| 155 | 168 | azepane-N-CO- | NH-C(CH₃)=CH-COOEt |
| 156 | 169 | (CH₃)₂C(CH₂CH₂OH)-NCO- | DTrp—OMe |
| 156 | 170 | (CH₃)₂C(CH₂CH₂OH)-NCO- | DTrp—OH |
| 157 | 171 | (CH₃)₂C(Me)-NCO- | DTrp—OH |
| 158 | 172 | cyclopentyl-N(CH₂CH(CH₃)₂)-CO- | DTrp—OH |
| 159 | 173 | 2,2-dimethylpyrrolidine-N-CO- | DTrp—OH |
| 162 | 176 | cyclopentyl-N(CH₂CH₂OH)-CO- | DTrp—OH |
| 163 | 178 | cyclopentyl-N(iPr)-CO- | DTrp—OH |

TABLE 1-continued
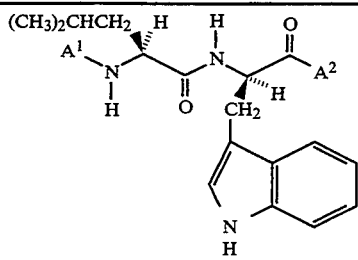
| Exp. No. | Compd No. | A¹ | A² |
|---|---|---|---|
| 164 | 180 | (iPr)₂N-CO— | DTrp—OH |
| 165 | 182 | cyclopentyl(n-Pr)N-CO— | DTrp—OH |
| 166 | 184 | cyclopentyl(n-Bu)N-CO— | DTrp—OH |
| 177 | 200 | cycloheptyl-CO— | DTrp—OH |
| 180 | 203 | azocanyl-CO— | NH—(3)cyclopropane(2)—COOH (2S,3S):(2R,3R) = 1:1 |
TABLE 2
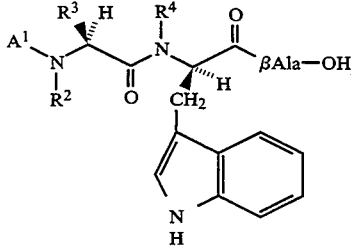
| Exp. No. | Compd No. | A¹ | R² | R³ | R⁴ |
|---|---|---|---|---|---|
| 28 | 28 | Boc | H | —(CH₂)₂CH₃ | H |
| 30 | 30 | Boc | Me | —CH₂CH(CH₃)₂ | H |
| 32 | 32 | Boc | H | —CH₂CH(CH₃)₂ | Me |
| 49 | 30 | Boc | Me | —CH₂CH(CH₃)₂ | H |
TABLE 2-continued
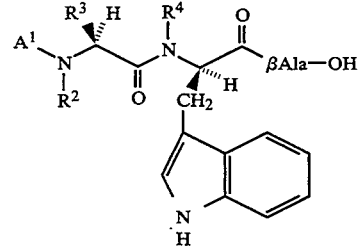
| Exp. No. | Compd No. | A¹ | R² | R³ | R⁴ |
|---|---|---|---|---|---|
| 50 | 54 | Boc | H | (S)—*CH(CH₃)—CH₂CH₃ | H |
| 133 | 142 | Iva | H | —(CH₂)₃CH₃ | H |
| 134 | 143 | Boc | H | —CH₂C(CH₃)₃ | H |

TABLE 3

[Structure: (CH₃)₂CHCH₂ group on chiral carbon with A¹-NH, connected via C(=O)-NH to chiral center (*) bearing R⁵, terminating in C(=O)-A²]

| Exp. No. | Compd No. | A¹ | * | R⁵ | A² |
|---|---|---|---|---|---|
| 123 | 131 | azocane-N-CO– (8-membered ring with NCO) | (R) | –CH₂–(2-NCHO-phenyl) | βAla—OH |
| 124 | 132 | azepane-N-CO– (7-membered ring with NCO) | (R) | –CH₂–(2-NCHO-phenyl) | DβAba—OH |
| 130 | 139 | azepane-N-CO– | (R) | –CH₂–(2-oxoindolin-3-yl) | DβAba—OH |
| 145 | 156 | azepane-N-CO– | (R) | –CH₂–(2-NCHO-phenyl) | DHis—OH |
| 150 | 161 | azepane-N-CO– | (R) | –CH₂–(2-NCHO-phenyl) | Tau—ONa |
| 151 | 162 | azepane-N-CO– | (R) | –CH₂–(2-NCHO-phenyl) | DAps—ONa |
| 160 | 174 | (CH₃)₃C–N(Me)–CO– | (R) | –CH₂–(2-NCHO-phenyl) | DTrp—OH |
| 161 | 175 | cyclopentyl–N(Me)–CO– | (R) | –CH₂–(2-NCHO-phenyl) | DTrp—OH |

TABLE 3-continued (CH₃)₂CHCH₂ — A¹ — NH — CH(H) — C(=O) — NH — *CH(R⁵) — C(=O) — A²

| Exp. No. | Compd No. | A¹ | * | R⁵ | A² |
|---|---|---|---|---|---|
| 163 | 177 | cyclopentyl-N(iPr)-CO— | (R) | —CH₂-(2-(NCHO)indenyl) | DTrp—OH |
| 164 | 179 | (iPr)₂N-CO— | (R) | —CH₂-(2-(NCHO)indenyl) | DTrp—OH |
| 165 | 181 | cyclopentyl-N(n-Pr)-CO— | (R) | —CH₂-(2-(NCHO)indenyl) | DTrp—OH |
| 166 | 183 | cyclopentyl-N(n-Bu)-CO— | (R) | —CH₂-(2-(NCHO)indenyl) | DTrp—OH |
| 167 | 185 | hexamethyleneimino-CO— | (R) | —CH₂-(2-(NCHO)indenyl) | DTrp—OBzl |
| 167 | 186 | hexamethyleneimino-CO— | (R) | —CH₂-(2-(NCHO)indenyl) | DTrp—OH |
| 168 | 187 | hexamethyleneimino-CO— | (R) | —CH₂-(2-(NCOCH₃)indenyl) | DTrp—OH |
| 169 | 188 | hexamethyleneimino-CO— | (R) | —CH₂-(2-(NCOOMe)indenyl) | DTrp—OH |
| 170 | 189 | hexamethyleneimino-CO— | (R) | —CH₂-(2-(NCH₂COOMe)indenyl) | DTrp—OH |

TABLE 3-continued

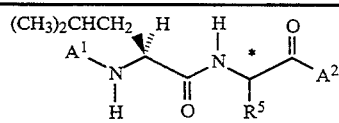

| Exp. No. | Compd No. | A$^1$ | * | R$^5$ | A$^2$ |
|---|---|---|---|---|---|
| 170 | 190 | (azepane)-NCO— | (R) | —CH$_2$-(2-(NCH$_2$COOH)-vinyl-phenyl) | DTrp—OH |
| 171 | 191 | (azepane)-NCO— | (R) | —CH$_2$-(2-(NPO$_3$Me$_2$)-vinyl-phenyl) | DTrp—OH |
| 171 | 192 | (azepane)-NCO— | (R) | —CH$_2$-(2-(NPO$_3$H$_2$)-vinyl-phenyl) | DTrp—OH |
| 172 | 193 | (azepane)-NCO— | (R) | —CH$_2$-(benzothiophen-3-yl) | DTrp—OH |
| 173 | 194 | (azepane)-NCO— | (R) | —CH$_2$-(benzothiophene S,S-dioxide-3-yl) | DTrp—OH |
| 174 | 195 | (azepane)-NCO— | (RS) | —CH$_3$, 3-COOEt phenyl | DTrp—OH |
| 174 | 196 | (azepane)-NCO— | (RS) | —CH$_2$-(3-COOH-phenyl) | DTrp—OH |
| 175 | 197 | (azepane)-NCO— | (RS) | —CH$_2$-(4-COOMe-phenyl) | DTrp—OH |
| 175 | 198 | (azepane)-NCO— | (RS) | —CH$_2$-(4-COOH-phenyl) | DTrp—OH |

* shows the absolute configuration of the remarked carbon atom

TABLE 4

| Exp. No. | Compd No. | A¹ | B | X² | A² |
|---|---|---|---|---|---|
| 142 | 153 | (hydantoin-like ring with HN-C(=O)-N, gem-dimethyl, C=O) | O | O | βAla—OH |
| 143 | 154 | (hydantoin-like ring with HN-C(=O)-N, C=O) | O | O | βAla—OH |
| 144 | 155 | (cyclopentyl-N, N-Me imidazolidinedione) | O | O | DTrp—OH |
| 176 | 199 | (cycloheptyl-NCO—) | NH | S | DTrp—OH |
| 178 | 201 | (cycloheptyl-CO—) | O | O | DTrp—OH |
| 179 | 202 | (cycloheptyl-NCO—) | O | O | DTrp—OH |

Now, the endothelin antagonistic properties of the peptide derivatives of the present invention will be described.

Endothelin binding inhibition test

The smooth muscle tissue of porcine aorta was homogenized in a buffer solution of 10 mM MOPS, pH 7.4, at 4° C. by a polytron. To the homogenate, sucrose was added to a concentration of 20%, and the mixture was centrifuged at 1,000×g for 15 minutes, and the supernatant was further centrifuged at 10,000×g for 15 minutes. The supernatant thereof was further centrifuged at 90,000×g for 40 minutes. The membrane precipitate thereby obtained was suspended in a buffer solution of 5 mM HEPES/Tris, pH 7.4, at a concentration of 25 mg/ml.

Then, 16 μl of this membrane suspension was added to 340 μl of 50 mM Tris/HCl buffer, pH 7.4, containing 10 μM calcium chloride, 10 μM magnesium chloride, 0.1 mM PMSF, 1 μM pepstatin A, 2 μM leupeptin, 1 mM 1,10-phenanthroline and 0.1% bovine serum albumin. To this suspension, 4 μl of (A) endothelin-1 (for nonspecific binding; 0.2 μM as the final concentration), (B) buffer solution A (for total control binding), or (C) a test compound (1.1 μM or 10 μM as the final concentration), was added. Further, to each suspension, 40 μl of $^{125}$I-endothelin-1 (12000–18000 cpm) was added. These mixtures were incubated at 25° C. for 4 hours, then subjected to filtration on a glass filter GF/C and then washed with 5 mM HEPES/Tris, pH 7.4, containing 0.3% bovine serum albumin. Then, the radioactivity trapped by the glass filter was measured, and the $^{125}$I-endothelin-1 binding inhibition D (%) at 1.1 μM or 10 μM of the test compound was determined by the following equation.

$$D(\%) = 100 - \frac{(C) - (A)}{(B) - (A)} \times 100$$

Each test was performed in triplicate.

As shown in Table 5, the compounds of the present invention were found to be very potent inhibitor of endothelin binding. The test compounds are indicated by Compound Nos.

TABLE 5

$^{125}$I-endothelin-1 binding inhibition by 1.1 μM or 10 μM of the test compounds

| Compd No. | Inhibition (%) |
|---|---|
| 1 | 74 |
| 2 | 83 |
| 3 | 31 |
| 4 | 80 |
| 5 | 33 |
| 6 | 37* |
| 7 | 35 |
| 8 | 56 |
| 9 | 55* |
| 10 | 32 |
| 11 | 41 |
| 12 | 31 |
| 13 | 39 |
| 14 | 64 |
| 15 | 71 |
| 16 | 74 |
| 17 | 38 |
| 18 | 35 |
| 19 | 53* |
| 20 | 44 |
| 21 | 39 |
| 22 | 36* |
| 23 | 33 |
| 24 | 45* |
| 25 | 65 |
| 26 | 36* |
| 27 | 57* |
| 28 | 38 |
| 29 | 69 |
| 30 | 44 |
| 31 | 45 |
| 32 | 32* |
| 33 | 26 |
| 34 | 45 |
| 35 | 35 |
| 36 | 65 |
| 37 | 29* |
| 38 | 22 |
| 39 | 75 |
| 40 | 36 |
| 41 | 65 |
| 42 | 56 |
| 43 | 36* |
| 44 | 30 |
| 45 | 39* |
| 46 | 41* |

TABLE 5-continued $^{125}$I-endothelin-1 binding inhibition by 1.1 μM or 10 μM of the test compounds

| Compd No. | Inhibition (%) |
|---|---|
| 47 | 75 |
| 48 | 82 |
| 49 | 85 |
| 50 | 87 |
| 51 | 68 |
| 52 | 84 |
| 53 | 86 |
| 54 | 39 |
| 55 | 54 |
| 56 | 32 |
| 57 | 41* |
| 58 | 33 |
| 59 | 65 |
| 60 | 32 |
| 61 | 52 |
| 62 | 28 |
| 63 | 57* |
| 64 | 45 |
| 65 | 45* |
| 66 | 77 |
| 67 | 63 |
| 68 | 58* |
| 69 | 71* |
| 70 | 32 |
| 71 | 29 |
| 72 | 34* |
| 73 | 61* |
| 74 | 70 |
| 75 | 32* |
| 76 | 52 |
| 77 | 47 |
| 78 | 24 |
| 79 | 27* |
| 80 | 73 |
| 81 | 84 |
| 82 | 76 |
| 83 | 26 |
| 84 | 70 |
| 85 | 77 |
| 86 | 70 |
| 87 | 69 |
| 88 | 20* |
| 89 | 55* |
| 90 | 46 |
| 91 | 51* |
| 92 | 40 |
| 93 | 78 |
| 94 | 49* |
| 95 | 76 |
| 96 | 49 |
| 97 | 82 |
| 98 | 67 |
| 99 | 80 |
| 100 | 82 |
| 101 | 79 |
| 102 | 65* |
| 103 | 53 |
| 104 | 64 |
| 105 | 62 |
| 106 | 79 |
| 107 | 78 |
| 108 | 83 |
| 109A | 79 |
| 109B | 80 |
| 110 | 65 |
| 111 | 83 |
| 112 | 55 |
| 113 | 69 |
| 114 | 68 |
| 115 | 33 |
| 116 | 43 |
| 117 | 28 |
| 118 | 79 |
| 119 | 81 |
| 120 | 68 |
| 121 | 82 |
| 122 | 83 |
| 123 | 33 |
| 124 | 24 |
| 125 | 41 |
| 126 | 27* |
| 127 | 33 |
| 128 | 38 |
| 129 | 33 |
| 130 | 81 |
| 131 | 88 |
| 132 | 85 |
| 133 | 41 |
| 134 | 32 |
| 135 | 39 |
| 136 | 32 |
| 137 | 46 |
| 138 | 72 |
| 139 | 66 |
| 140 | 70* |
| 141 | 85 |
| 142 | 43* |
| 143 | 48* |
| 146 | 70* |
| 147 | 57* |
| 148 | 82* |
| 149 | 58* |
| 150 | 51* |
| 151 | 78* |
| 152 | 58* |
| 155 | 70 |
| 156 | 86 |
| 157 | 69 |
| 158 | 57 |
| 159 | 79 |
| 160 | 86 |
| 161 | 84 |
| 162 | 86 |
| 163 | 76 |
| 164 | 71 |
| 165 | 86 |
| 166 | 81 |
| 167 | 73* |
| 168 | 59* |
| 169 | 75 |
| 170 | 88 |
| 171 | 87 |
| 172 | 87 |
| 173 | 84 |
| 174 | 81 |
| 175 | 87 |
| 176 | 89 |
| 177 | 90 |
| 178 | 88 |
| 179 | 90 |
| 180 | 87 |
| 181 | 89 |
| 182 | 88 |
| 183 | 88 |
| 184 | 88 |
| 185 | 80 |
| 186 | 90 |
| 187 | 77 |
| 188 | 91 |
| 189 | 85* |
| 190 | 87 |
| 191 | 74* |
| 192 | 64* |
| 193 | 89 |
| 195 | 74* |
| 196 | 45* |
| 199 | 75 |
| 200 | 87 |
| 201 | 69 |
| 202 | 85 |
| 203 | 84 |

Activities against endothelin-induced contraction of isolated procine coronary arteries The coronary artery of pig was extracted, and a spiral preparation having a width of 1 mm and a length of 10 mm was prepared therefrom. The preparation having the endothelial cells denuded, was hanged in a 5 ml organ bath filled with a Krebs.Henseleit solution saturated with a gas mixture of 95% $O_2$ and 5% $CO_2$, and a change in the tension was isometrically measured and recorded.

Endothelin-1 was added into the organ bath in a cumulatively increasing manner, whereby the influence of a compound of the present invention to the concentration-response curve for endothelin-1 was examined. The compound was added into the organ bath 20 minutes prior to the addition of endothelin-1.

Figure 2:
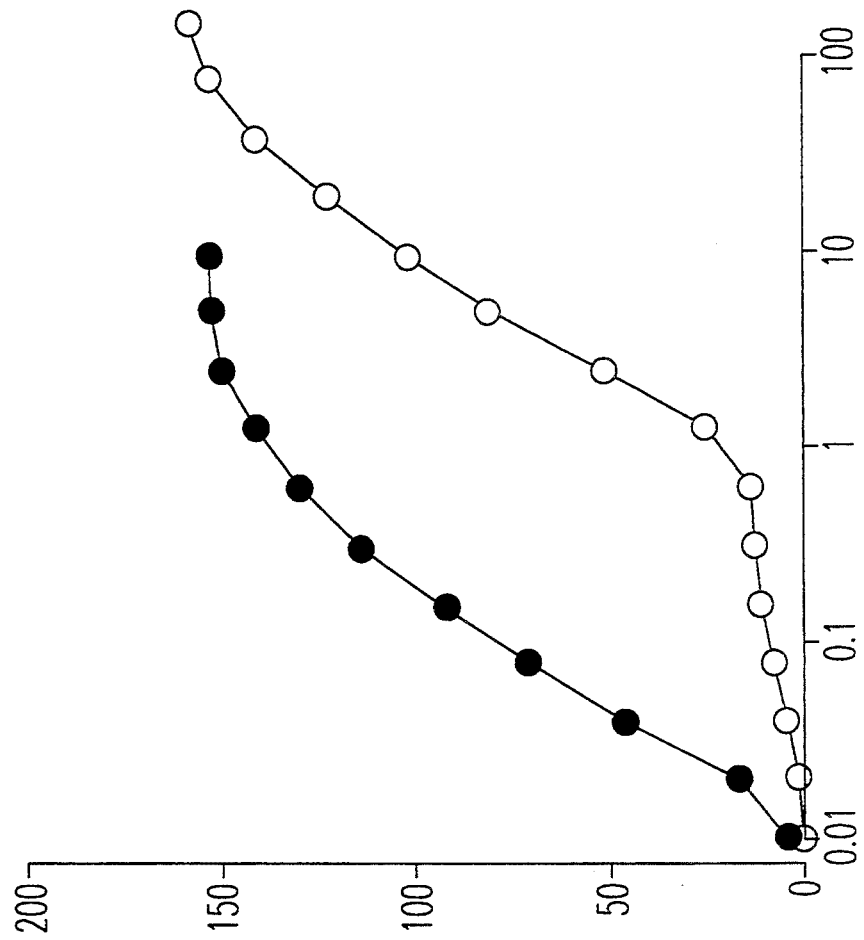
FIG. 2 shows the activities of Compound 93 (o) against endothelin-induced contraction of isolated porcine coronary artery as compared with the case in which no drug is present ( ).
Figure 3:
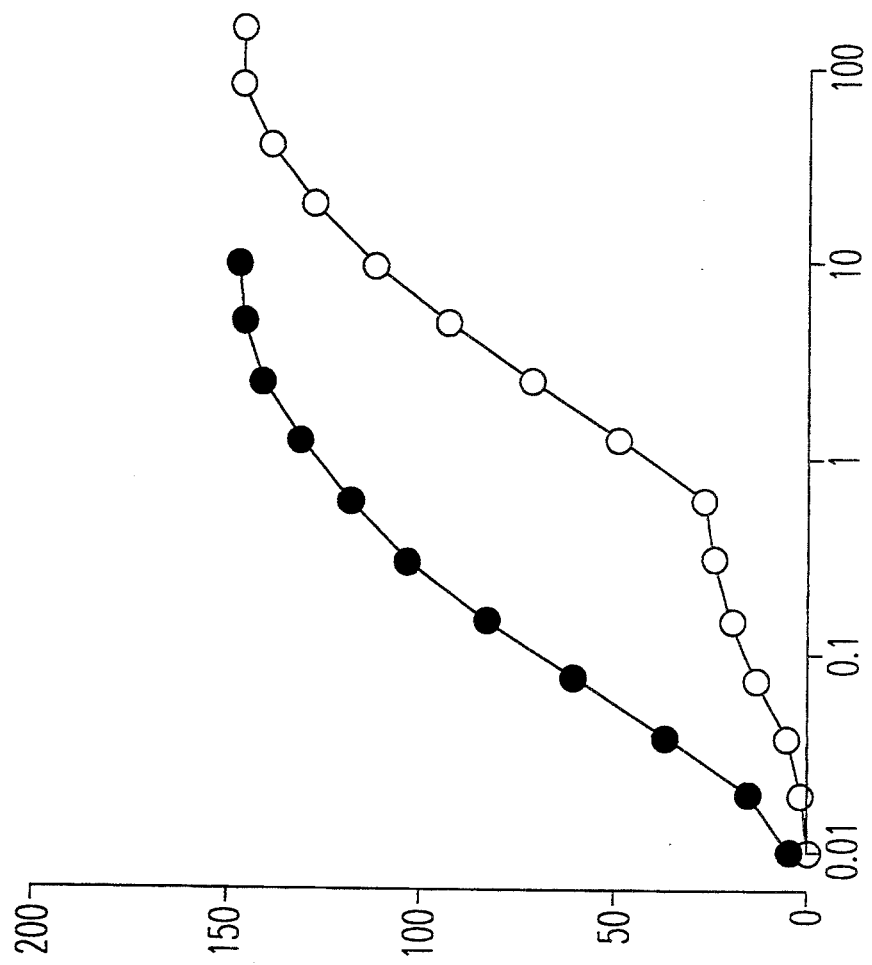
FIG. 3 shows the activities of Compound 121 (o) against endothelin-induced contraction of isolated porcine coronary artery as compared with the case in which no drug is present (574).

As shown in FIGS. 1 to 3, Compound 50 (2 μM) (FIG. 1), Compound 93 (6 μM) (FIG. 2) and Compound 121 (6 μM) (FIG. 3) remarkably shifted the concentration-response curves of endothelin-1 to the right and did not affect the maximum response. Further, the compounds showed no effects to the isolated coronary artery when applied alone. As is evident from the above, the compounds showed remarkable antagonistic activities against endothelin-induced contraction of isolated procine coronary artery.

Activities against endothelin-induced contraction of isolated guinea pig trachea The trachea of a guinea pig was extracted, and the trachea was cut into rings to afford a preparation. The preparation having the endothelial cells denuded, was hanged in a 5 ml organ bath filled with a Krebs.Henseleit solution saturated with a gas mixture of 95% $O_2$ and 5% $CO_2$, and a change in the tension was isometrically measured and recorded.

Endothelin-1 was added into the organ bath in a cumulatively increasing manner, and the influence of a compound of the present invention to the concentration-response curve for endothelin was examined. The compound was added into the organ bath 20 minutes prior to the addition of endothelin-1.

Figure 4:
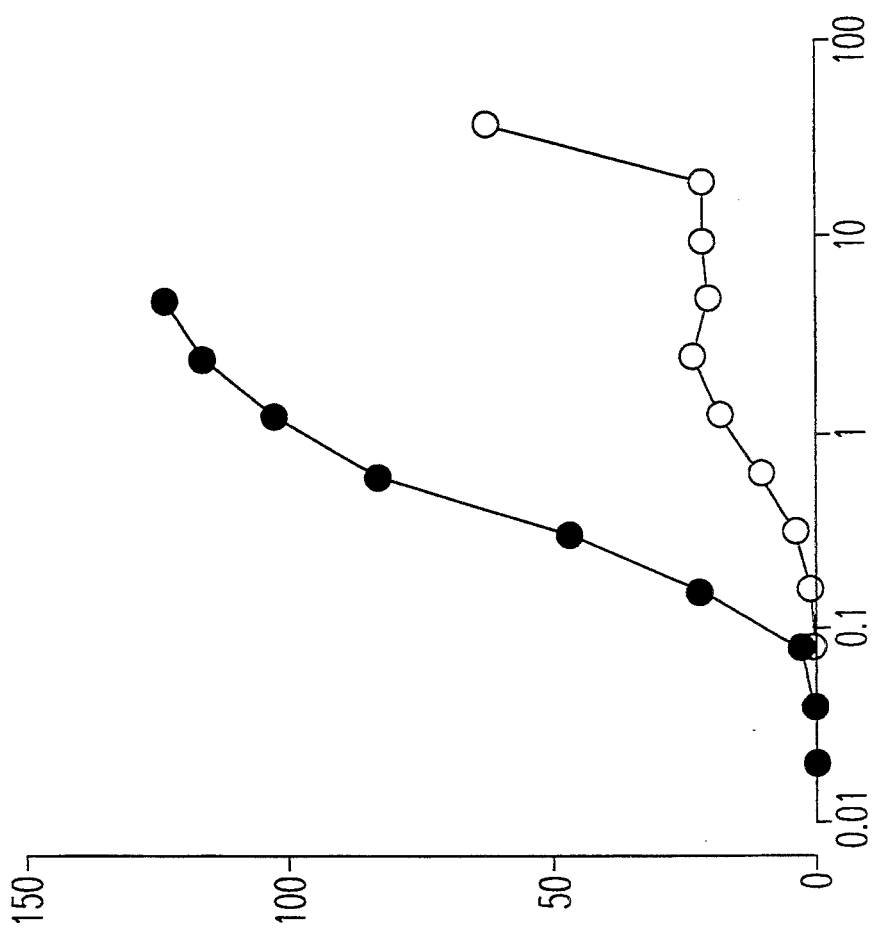
FIG. 4 shows the activities of Compound 50 (o) against endothelin-induced contraction of isolated guinea pig trachea as compared with the case in which no drug is present ( ).
Figure 5:
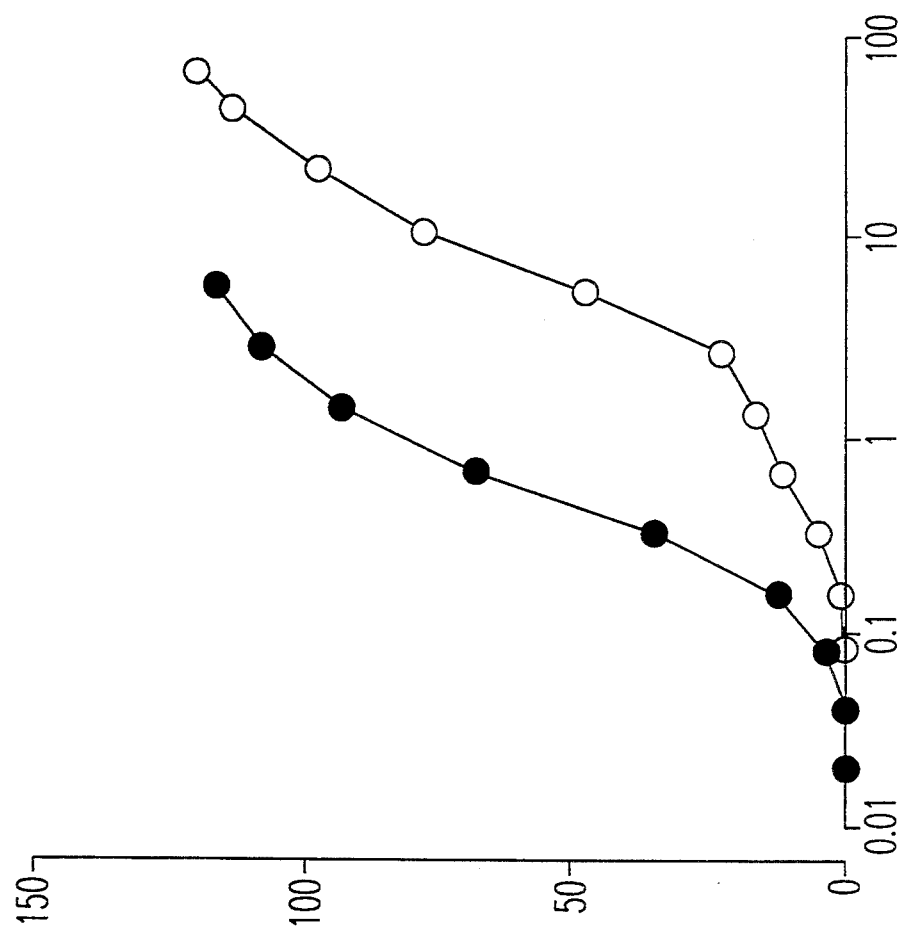
FIG. 5 shows the activities of Compound 93 (o) against endothelin-induced contraction of isolated guinea pig trachea as compared with the case in which no drug is present ( ).
Figure 6:
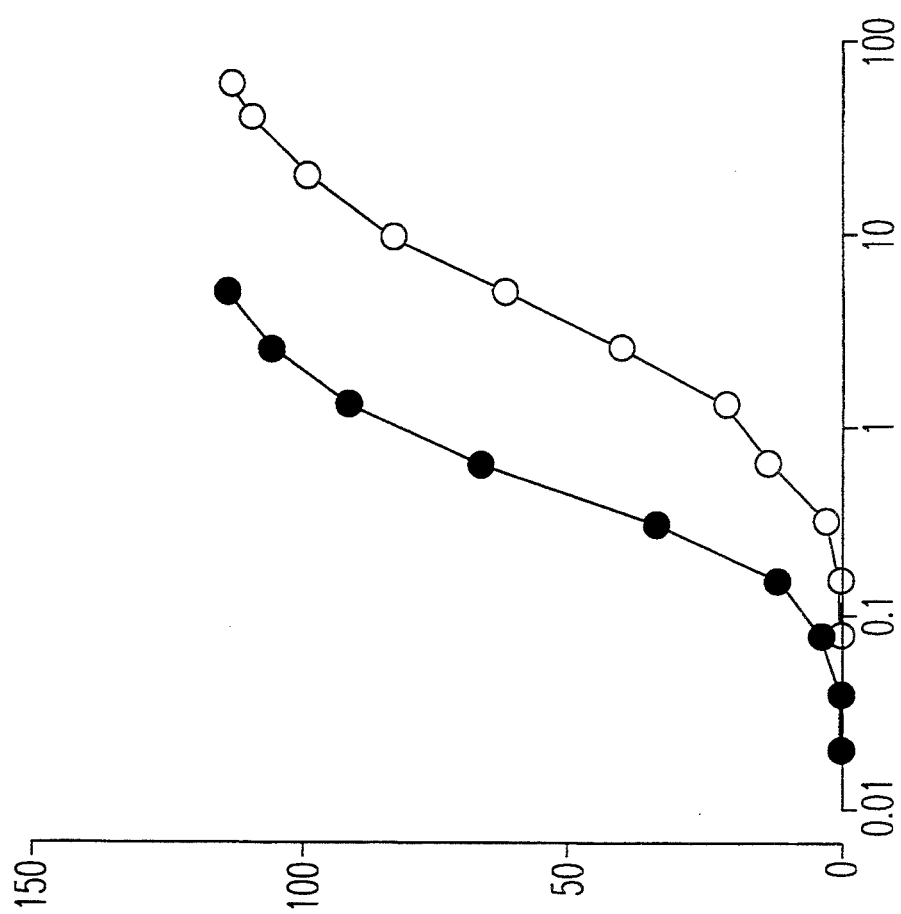
FIG. 6 shows the activities of Compound 121 (o) against endothelin-induced constraction of isolated guinea pig trachea as compared with the case in which no drug, is present ( ).

As shown in FIGS. 4 to 6, Compound 50 (6 μM) (FIG. 4), Compound 93 (6 μM) (FIG. 5) and Compound 121 (6 μM) (FIG. 6) remarkably shifted the concentration-response curves for endothelin-1 to the right in isolated trachea and did not affect the maximum response. Further, the compounds showed no effects to the isolated trachea when applied alone. As is evident from the foregoing, the compounds showed remarkable antagonistic activities against endothelin-induced contraction of isolated guinea big trachea.

Effects on the increased perfusion pressure induced by endothelin in isolated rat heart The heart of a male Sprague Dohrie (SD) rat was extracted, and the perfusion pressure was measured and recorded according to the Langendorff's method. The perfusion pressure was evaluated on the basis that the state where a Krebs.Henseleit solution saturated with a gas mixture of 95% $O_2$ and 5% $CO_2$ was infused at a rate of 10 ml/min, was taken as a standard.

Endothelin-1 was cumulatively added to the perfusate, whereby the influence of a compound of the present invention to the concentration-response curve for endothelin-1 was examined. The compound which was dissolved in the perfusate had been infused from 20 minutes prior to the addition of endothelin-1 till just after finishing measurement of the concentration-response curve for endothelin-1.

Figure 7:
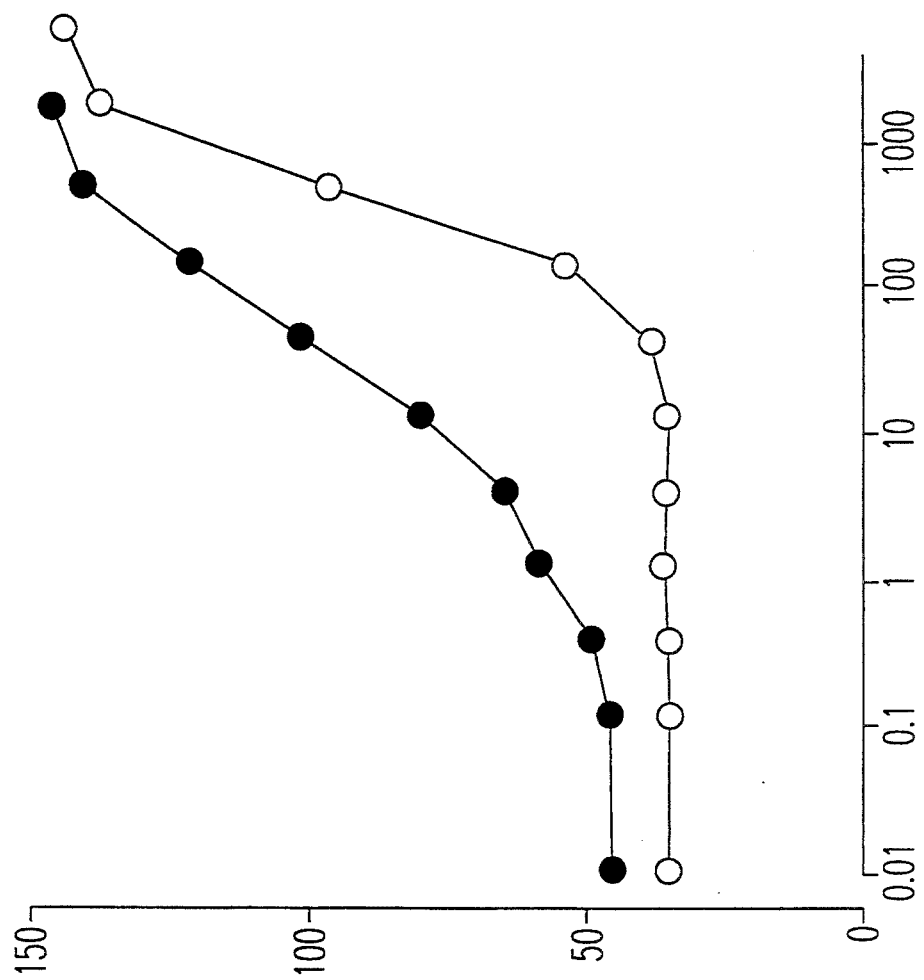
FIG. 7 shows the effects of Compound 48 (o) against the increased perfusion pressure induced by endothelin in isolated rat heart as compared with the case in which no drug is present ( ).
Figure 8:
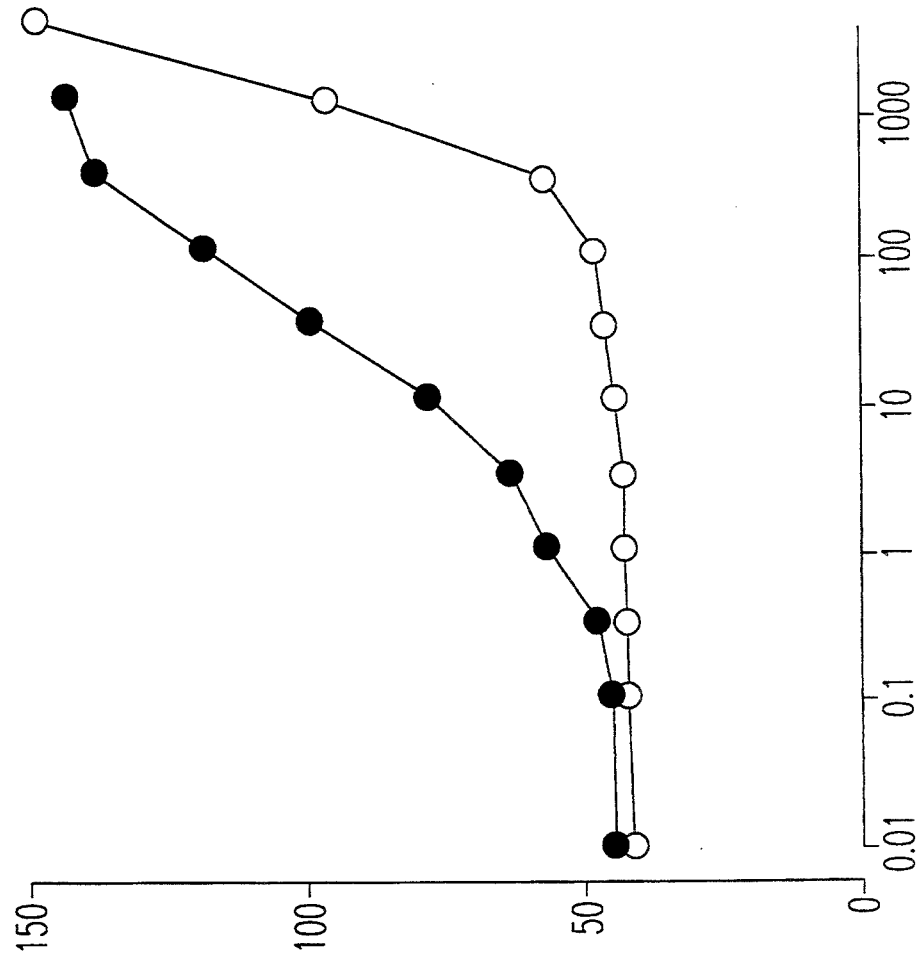
FIG. 8 shows the effects of Compound 50 (o) against the increased perfusion pressure induced by endothelin in isolated rat heart as compared with the case in which no drug is present ( ).

As shown in FIGS. 7 and 8, Compound 48 (1 μM) (FIG. 7) and Compound 50 (1 μM) (FIG. 8) moved the concentration-response curve for endothelin-1 to the right and did not affect the maximum response. Further, the compounds did not affect the perfusion pressure when applied alone. As is evident from the foregoing, the compounds showed remarkable antagonistic activities against the increased perfusion pressure induced by endothelin.

Thus, the compounds of the present invention have excellent endothelin antagonistic activities and are useful as vasodilators or bronchodilators in the field of medicines, and they can be drugs for treating hypertension, pulmonary hypertension, Raynaud's disease, acute renal failure, myocardial infarction, angina pectoris, cerebral infarction, cerebral vasospasm, arteriosclerosis, asthma, endotoxin shock, endo-toxin-induced multiple organ failure or disseminated intravascular coagulation, and/or cyclosporin-induced renal failure or hypertension. When used as drugs for treating such diseases, the compounds of the present invention can be used alone or in combination with other drugs for treatment.

The compounds of the present invention may be used in the form of drug formulations suitable for parenteral administration, oral administration or external administration by mixing them with solid or liquid excipient carriers known in this field. The drug formulations include a liquid formulation such as an injection formulation, an inhalant formulation, a syrup formulation or an emulsion, a solid formulation such as tablets, capsules or granules, and an external drug such as an ointment or a suppository. Further, these drug formulations may contain additives which are commonly employed, such as an adjuvant, a stabilizer, a wetting agent, an emulsifier, an absorption-promoting agent or a surfactant, as the case requires. As the additives, distilled water for injection, physiological saline, Ringer's solution, glucose, sugar syrup, gelatin, vegetable oil, cacao butter, ethylene glycol, hydroxypropyl cellulose, lactose, sucrose, corn starch, magnesium stearate and talc may be mentioned.

The dose of a compound of the present invention as an endothelin antagonist varies depending upon the manner of administration, the age and body weight of the patient and the condition of the patient to be treated. However, a typical administration method for an adult is oral administration or parenteral administration. The daily dose in the case of oral administration to an adult patient is from 0.1 to 100 mg/kg body weight, and the daily dose in the case of parenteral administration is from 0.01 to 10 mg/kg body weight.

The following Examples and Referential Examples illustrate the present invention more specifically. It should be understood that the present invention is not limited to these examples alone.

EXAMPLE 1

Synthesis of Compound 1

(1) Preparation of Boc-Leu-DTrp-OMe

To a suspension of Boc-Leu-OH.H$_2$O (0.997 g) and DTrp-OMe.HCl (1.021 g) in dichloromethane (10 ml) were added TEA (0.6 ml) and HOBT.H$_2$O (0.615 g) under argon. EDCI.HCl (0.769 g) was added to the mixture at 0°-5° C. The resulting reaction mixture was stirred at room temperature for 16 h, washed successively with water, 10% aq. citric acid, sat. NaHCO₃ and brine, dried over MgSO₄, filtered, and concentrated under reduced pressure. The residue was triturated with hexane to give the product (1.665 g). FAB-MS(m/e,($C_{23}H_{33}N_3O_5$+H)⁺):432

(2) Preparation of Boc-Leu-DTrp-NHNH₂

To a solution of the compound obtained in (1) (430 mg) in DMF (10 ml) was added hydrazine monohydrate (1.0 ml) at room temperature and the solution was stirred overnight. To the reaction mixture was added dry-ice and the resulting solution was concentrated to give a residue, which was triturated with water to afford the product (406 mg).

FAB-MS(m/e,($C_{22}H_{33}N_5O_4$+H)⁺):432

(3) Preparation of Compound 1

To a solution of the compound obtained in (2) (40.0 mg) in DMF (0.5 ml) was added 3.1M HCl/1,4-dioxane (103 μl) at −60° C. under nitrogen to adjust the pH of the solution to 3. Isoamyl nitrite (15 μl) was added and the temperature of the reaction mixture was slowly raised to −20° C. The mixture was stirred for 30 min at the same temperature and cooled again to −60° C. A solution of TEA (70 μl) and DβAba-ONBu₄ (prepared from 10% aq. tetrabutylammonium hydroxide (260 μl) and DβAba-OH (10.5 mg)) in DMF (0.5 ml) was added. The temperature of the solution was slowly raised to −20° C. and the reaction mixture was allowed to stand at the same temperature overnight. The solvent was evaporated and the residue was dissolved in ethyl acetate. The solution was washed successively with 10% aq. citric acid and brine, dried over MgSO₄, filtered, and concentrated to afford a residue. The residue was purified by reverse-phase MPLC (Nacalai Tesque, Cosmosil 75 C₁₈-OPN) with methanol/water=2/1 for elution to give the title compound (44.1 mg) as a colorless powder.

m.p.: 110.5°–112.5° C.
IR(KBr,cm⁻¹):3412,2968,1656,1524,1461,1395,1371,1251,1167,741
FAB-MS(m/e,($C_{26}H_{38}N_4O_6$+H)⁺):503
¹H-NMR(300 MHz,DMSO-d₆,βppm):0.69(3H,d,J=7.1 Hz),0.72(3H,d,J=6.7 Hz),1.00–1.40(3H,m),1.08(3H,d,J=6.6 Hz),1.36(9H,s),2.09(1H,dd,J=8.6 Hz,15.2 Hz),2.29(1H,dd,J=4.9 Hz,15.2 Hz),2.87(1H,dd,J=9.6 Hz,14.4 Hz),3.08–3.20(1H,m),3.80–3.92(1H,m),3.96–4.12(1H,m),4.32–4.44(1H,m),6.87(1H,d,J=7.0 Hz),6.93(1H,t,J=7.3 Hz),7.02(1H,t,J=7.3 Hz),7.06(1H,d,J=1.7 Hz),7.28(1H,d,J=7.3 Hz),7.55(1H,d,J=7.3 Hz),7.85(1H,d,J=7.3 Hz),7.99(1H,d,J=8.1 Hz),10.78(1H,d,J=1.7 Hz),12.15(1H,brs)

According to the procedure described in Example 1-(3), each Compound 2-27 was prepared using a tetrabutylammonium salt (Example 2-23 and 27) or a triethylammonium salt (Example 24-26) of the corresponding amino acid.

EXAMPLE 2

Compound 2 m.p.: 174°–176° C.
IR(KBr,cm⁻¹):3424,2962,1665,1515,1464,1440,1395,1371,1344,1248
FAB-MS(m/e,($C_{33}H_{41}N_5O_6$+H)⁺):604
¹H-NMR(300 MHz,DMSO-d₆,βppm):0.67–0.78(6H,m),1.04–1.40(2H,m),1.35(9H,s),1.51–1.65(1H,m),2.80–2.93(1H,m),3.14–3.40(3H,m),3.84–3.95(1H,m),4.46–4.62(2H,m),6.79(1H,d,J=7.5Hz),6.91–7.13(5H,m),7.17(1H,d,J=1.5Hz),7.29(1H,d,J=7.9 Hz),7.33(1H,d,J=7.9Hz),7.52(1H,d,J=7.9 Hz),7.57(1H,d,J=7.9 Hz),7.96(1H,d,J=8.0 Hz),8.15(1H,d,J=7.3 Hz),10.78(1H,brs),10.82(1H,brs),12.28(1H,brs)

EXAMPLE 3

Compound 3 m.p.: 99°–102° C.
IR(KBr,cm⁻¹):3412,3058,2962,2872,1662,1521,1464,1395,1371,1248
High Resolution FAB-MS(m/e,($C_{28}H_{42}N_4O_6$+H)⁺): Calcd: 531.3182 Found: 531.3183
¹H-NMR(300 MHz,DMSO-d₆,βppm):0.65–0.80(6H,m),0.84(3H,d,J=6.4 Hz),0.90(3H,d,J=6.4 Hz),1.02–1.25(3H,m),1.33(9H,s),1.49–1.78(3H,m),2.85(1H,dd,J=10.1 Hz,14.5 Hz),3.15–3.40(1H,m),3.80–3.90(1H,m),4.18–4.30(1H,m),4.48–4.60(1H,m),6.80(1H,d,J=6.8 Hz),6.94(1H,t,J=7.6 Hz),7.02(1H,t,J=7.6 Hz),7.08(1H,d,J=1.9 Hz),7.28(1H,d,j=7.6 Hz),7.57(1H,d,J=7.6Hz),7.99(1H,d,J=8.3Hz),8.02(1H,d,j=8.8 Hz),10.78(1H,d,J=1.9 Hz)

EXAMPLE 4

Compound 4 m.p.: 127°–138° C.
IR(KBr,cm⁻¹):3406,2926,1662,1515,1395,1371,1107
High Resolution FAB-MS(m/e,($C_{28}H_{38}N_6O_6$+H)⁺): Calcd: 555.2931 Found: 555.2953
¹H-NMR(300 MHz,DMSO-d₆,βppm):0.69–0.82(6H,m),1.03–1.21(3H,m),32(9H,s),2.82–3.02(3H,m),3.15(1H,dd,J=3.6 Hz,14.6 Hz),3.91(1H,ddd,J=5.8 Hz,7.5 Hz,7.8 Hz),4.20–4.26(1H,m),4.48(1H,ddd,J=3.6 Hz,8.1 Hz,10.3 Hz),6.75(1H,d,J=7.5 Hz),6.75(1H,s),6.93(1H,t,J=7.5 Hz),7.03(1H,t,J=7.5 Hz),7.07(1H,d,J=1.5 Hz),7.28(1H,d,J=7.5 Hz),7.50(1H,s),7.55(1H,d,J=8.1 Hz),7.98(1H,d,J=8.1 Hz),8.03(1H,d,J=7.5 Hz),10.78(1H,d,J=1.5 Hz)

EXAMPLE 5

Compound 5 m.p.: 100°–108° C.
IR(KBr,cm⁻¹):3328,2962,1698,1659,1530,1371,1251,1167,741
FAB-MS(m/e,($C_{26}H_{38}N_4O_6$+H)⁺):503
¹H-NMR(300 MHz,DMSO-d₆,βppm):0.67(3H,d,J=5.3 Hz),0.71(3H,d,J=5.3 Hz),1.08–1.29(3H,m),1.35(9H,s),1.56–1.71(2H,m),2.17(2H,t,J=7.5 Hz),2.86(1H,dd,J=8.8Hz,15.0 Hz),2.93–3.06(1H,m),3.06–3.25(2H,m),3.80–3.89(1H,m),4.34–4.44(1H,m),6.92–7.00(2H,m),7.02(1H,t,J=7.9 Hz),7.05(1H,d,j=2.2 Hz),7.28(1H,d,J=7.9 Hz),7.53(1H,d,J=7.9 Hz),7.80(1H,t,J=5.5 Hz),8.09(1H,d,J=8.0 Hz),10.77(1H,d,J=2.2 Hz),12.03 (1H,brs)

EXAMPLE 6

Compound 6 m.p.: 90°–94° C.

IR(KBr,cm$^{-1}$):3346,2938,1701,1653,1539,1371,1251,-1167,741

High Resolution FAB-MS(m/e,(C$_{28}$H$_{42}$N$_4$O$_6$+H)$^+$): Calcd: 531.3182 Found: 531.3180

$^1$H-NMR(300 MHz,DMSO-d$_6$, δppm):0.68(3H,d,J=4.6 Hz),0.72(3H,d,J=4.6 Hz),1.10–1.31(7H,m),1.36(9H,s),1.-42–1.55(2H,m),2.15(2H,t,J=7.2 Hz),2.87(1H,dd,J=11.0 Hz,15.0 Hz),2.93–3.24(3H,m),3.80–3.90(1H,m),4.-32–4.44(1H,m),6.94(1H,t,J=7.6 Hz),6.93–7.00(1H,m),7.02(1H,t,J=7.6 Hz),7.05(1H,brs),7.29(1H,d,J=7.6 Hz),7.53(1H,d,J=7.6 Hz),7.74(1H,t,J=3.6 Hz),8.11(1H,d,J=8.7 Hz),10.78(1H,brs)

EXAMPLE 7

Compound 7 m.p.: 175°–179° C.

IR(KBr,cm$^{-1}$):3406,2962,1659,1518,1371,1251,1164,-1047,741

High Resolution FAB-MS(m/e,(C$_{25}$H$_{36}$N$_4$O$_7$+H)$^+$): Calcd: 505.2662 Found: 505.2661

$^1$H-NMR(300 MHz,DMSO-d$_6$,δppm):0.73(6H,d,J=6.7Hz), 1.10–1.40(3H,m),1.35(9H,s),2.96(1H,dd,J=8.8 Hz,14.9 Hz),3.15–3.26(1H,m),3.30–3.66(2H,m),3.-88–4.00(2H,m),4.50–4.60(1H,m),6.74(1H,d,J=8.5 Hz),6.93(1H,t,J=7.8 Hz),7.02(1H,t,J=7.8 Hz),7.10(1H,brs),7.28(1H,d,J=7.8 Hz),7.56(1H,d,J=7.8 Hz),7.58–7.70(1H,m),7.93–7.99(1H,m),10.79(1H,brs)

EXAMPLE 8

Compound 8 m.p.: 94°–95° C.

IR(KBr,cm$^{-1}$):3334,2956,1704,1527,1461,1395,1371,-1251,1167

FAB-MS(m/e,(C$_{36}$H$_{49}$N$_5$O$_8$+H)$^+$):680

$^1$H-NMR(300 MHz,DMSO-d$_6$δppm):0.68(3H,d,J=6.1 Hz),0.69(3H,d,J=6.1 Hz),1.04–1.80(9H,m)1.33(9H,s),2,86(1H,dd,J=10.5 Hz,18.6 Hz),2,91–3.10(3H,m),3.82–3.93(1H,m),4.-09–4.17(1H,m),4.-50–4.60(1H,m),4.99(2H,s),6.75(1H,d,J=7.9 Hz),6.93(1H,t,J=7.8 Hz),7.02(1H,t,J=7.8 Hz),7.07(1H,d,J=2.0 Hz),7.22(1H,t,J=5.5 Hz),7.25–7.40(7H,m),7.57(1H,d,j=7.8 Hz),7.96–8.03(2H,m),10.77(1H,d,J=2.0 Hz)

EXAMPLE 9

Compound 9 m.p.: 107–120° C.

IR(KBr,cm$^{-1}$):3358,2962,1677,1524,1173,744 High Resolution FAB-MS(m/e,(C$_{26}$H$_{37}$N$_5$O$_7$+H)$^+$): Calcd: 532.2771 Found: 532.2763

$^1$H-NMR(300 MHz,DMSO-d$_6$,δppm):0.70(6H,d,J=6.4 Hz),1.05–1.40(3H,m)1.34(9H,s),2.43(1H,dd,J=6.4 Hz,15.6 Hz),2.62(1H,dd,J=6.3 Hz,15.6 Hz),2.87(1H,dd,J=10.1 Hz,14.6 Hz),3.15(1H,dd,J=3.6 Hz,14.6 Hz),4.48–4.62(3H,m),6.73(1H,d,j=7.8 Hz),6.89(1H,brs),6.93(1H,t,J=7.9Hz),7.02(1H,t,J=7.9 Hz),7.08(1H,d,J=2.0 Hz),7.28(1H,d,J=7.9 Hz),7.35(1H,brs),7.58(1H,d,J=7.9 Hz),7.95(1H,d,J=8.3 Hz),8.24(1H,d,J=7.8 Hz),10.77(1H,d,J=2.0 Hz)

EXAMPLE 10

Compound 10 m.p.: 146°–155° C.

IR(KBr,cm$^{-1}$):3412,2962,1668,1524,1167,745

FAB-MS(m/e,(C$_{27}$H$_{39}$N$_5$O$_7$+H)$^+$):546

$^1$H-NMR(300 MHz,DMSO-d$_6$, δppm):0.69(6H,d,J=6.4 Hz),1.00–1.40(3H,m),1.33(9H,s),1.78–1.90(1H,m),1.-90–2.08(1H,m),2.16(2H,t,J=7.9 Hz),2.87(1H,dd,J=10.8 Hz,14.4 Hz),3.19(1H,dd,J=3.7 Hz,14.4 Hz),3.70–3.90(1H,m),4.15–4.25(1H,m),4.-50–4.60(1H,m),6.76(1H,brs),6.77(1H,d,J=7.3 Hz),6.94(1H,t,J=7.8 Hz),7.03(1H,t,J=7.8 Hz),7.08(1H,d,j=1.8 Hz),7.23(1H,brs),7.29(1H,d,J=7.8 Hz),7.59(1H,d,j=7.8 Hz),7.97(1H,d,J=8.3 Hz),8.17(1H,d,J=7.6 Hz),10.77(1H,d,J=1.8 Hz)

EXAMPLE 11

Compound 11 m.p.: 113.5°–115.5° C.

IR(KBr,cm$^{-1}$):3352,2962,1662,1518,1461,1395,1371,-1248,1167,741

High Resolution FAB-MS(m/e,(C$_{28}$H$_{42}$N$_4$O$_6$+H)$^+$): Calcd: 531.3182 Found: 531.3203

$^1$H-NMR(300 MHz,DMSO-d$_6$,δppm):0.65–0.95(9H,m),1.-05–1.45(7H,m)1.33(9H,s)1.-50–1.80(2H,m),2.87(1H,dd,j=9.9 Hz,14.3 Hz),3.18(1H,dd,J=3.1 Hz,14.3 Hz),3.80–3.93(1H,m),4.-06–4.17(1H,m),4.48–4.58(1H,m),6.77(1H,d,j=7.6 Hz),6.93(1H,t,J=7.4 Hz),7.02(1H,t,J=7.4 Hz),7.07(1H,brs),7.28(1H,d,J=7.4 Hz),7.57(1H,d,J=7.4 Hz),7.98(1H,d,J=6.8 Hz),7.99(1H,d,J=8.0 Hz),10.78(1H,brs)

Optical Rotation: [α]$_D$°=+9.7° (c 0.40, MeOH)

EXAMPLE 12

Compound 12 m.p.: 129°131° C.

IR(KBr,cm$^{-1}$):3424,2926,1698,1554,1392,1371,1254,-1167

High Resolution FAB-MS(m/e,(C$_{29}$H$_{36}$N$_4$O$_6$+H)$^+$): Calcd: 537.2713 Found: 537.2712

$^1$H-NMR(300 MHz,DMSO-d$_6$, δppm):0.65–0.90(6H,m)1.-08–1.42(3H,m),1.31(9H,s),3.00(1H,dd,J=9.8 Hz,14.7 Hz),3.11–3.42(1H,m),3.87–3.98(1H,m),4.-60–4.74(1H,m),6.88–7.06(1H,m),6.93(1H,t,J=7.4 Hz),7.02(1H,t,J=7.4 Hz),7.12(1H,brs),7.29(1H,d,J=7.4 Hz),7.36(1H,t,J=8.1 Hz),7.53–7.67(1H,m),7.60(1H,d,J=7.4 Hz),7.75+7.84(1H,d×2,J=8.1 Hz,J=8.1 Hz),8.13+8.20(1H,s×2),8.26(1H,d,J=7.6 Hz),9.98+10.18(1H,s×2),10.82(1H,brs)

EXAMPLE 13

Compound 13 m.p.: 97°–103° C.

IR(KBr,cm$^{-1}$):3358,3058,2962,2878,1668,1521,1464,-1395,1371,1344

FAB-MS(m/e,(C$_{26}$H$_{38}$N$_4$O$_6$+H)$^+$):503

$^1$H-NMR(300 MHz,DMSO-d$_6$,δppm):0.69–0.81(6H,m)1.01–1.52(3H,m),1.35 (3H,S),1.38(9H,s),1.41(3H,s),2.88(1H,dd,J=10.4 Hz,14.6 Hz),3.25–3.40(1H,m),3.80–3.91(1H,m),4.-

42–4.55(1H,m),6.89(1H,d,J=6.8 Hz),6.97(1H,t,J=7.4 Hz),7.06(1H,t,J=7.4 Hz),7.11(1H,d,J=1.9 Hz),7.32(1H,d,J=7.4 Hz),7.59(1H,d,J=7.4 Hz),7.87(1H,s),8.11(1H,d,j=8.3 Hz),10.81(1H,d,J=1.9 Hz),12.11(1H,brs)

EXAMPLE 14

Compound 14 m.p.: 121.5°–132.5° C.
IR(KBr,cm$^{-1}$):3328,3064,2962,1656,1524,1461,1395,1371,1248,1164,741
High Resolution FAB-MS(m/e,($C_{31}H_{40}N_4O_6$+H)$^+$): Calcd: 565.3026 Found: 565.3047
$^1$H-NMR(300 MHz,DMSO-d$_6$,δppm):0.63–0.80(6H,m),0.98–1.30(3H,m),1.29+1.33(9H,s×2),2.54–2.64(1H,m),2.64–2.76(1H,m),2.76–2.93(1H,m),3.08–3.20(1H,m),3.81–3.93(1H,m),4.37–4.54(1H,m),5.12–5.27(1H,m).6.77+6.87–7.11(4H,d,m,J=7.6 Hz),7.15–7.40(6H,m),7.50+7.56(1H,d×2,J=7.8 Hz,J=7.6 Hz),7.96+8.13(1H,d×2,J=7.6 Hz,J=7.3 Hz),8.25+8.31(1H,d×2,J=7.8 Hz,J=8.1 Hz),10.77(1H,brs),12.20(1H,brs)
Optical Rotation: [α]$_D^{20}$=+13.8° (c 0.36,MeOH)

EXAMPLE 15

Compound 15 m.p.: 108°–122° C.
IR)KBr,cm$^{-1}$):3340,2962,1668,1521,1395,1371;1251;1164;741,700
High Resolution FAB-MS(m/e,($C_{29}H_{38}N_4O_6S$+H)$^+$): Calcd: 571.2590 Found: 571.2599
$^1$H-NMR(300 MHz,DMSO-d$_6$,δppm):0.71(6H,d,J=6.4 Hz),0.97–1.35(3H,m),1.34(9H,s),2.70–3.33(4H,m),3.84–3.97(1H,m),4.36–4.49(1H,m),4.49–4.61(1H,m),6.69+6.75(1H,d×2,J=7.8 Hz,J=7.09 Hz),6.83–7.09(5H,m),7.26–7.34(2H,m),7.52–7.59(1H,m),7.94+7.96(1H,d×2,J=8.1 Hz,J=7.8 Hz),8.22+8.32(1H,d×2,J=8.0 Hz,J=7.5 Hz),10.75+10.77(1H,d×2,J=1.2 Hz,J=1.7 Hz)
Optical Rotation: [α]$_D^{20}$=+7.2° (c 0 33,MeOH)

EXAMPLE 16

Compound 16 m.p.: 111°–116.5° C.
IR(KBr,cm$^{-1}$):3418,2962,1665,1515,1461,1395,1371,1248,1167,741
High Resolution FAB-MS(m/e,($C_{28}H_{37}N_5O_6S$+H)$^+$): Calcd: 572.2543 Found: 572.2574
$^1$H-NMR(300 MHz,DMSO-d$_6$,δppm):0.71(3H,d,J=6.3 Hz),0.76(3H,d,J=6.6 Hz),0.99–1.24(3H,m),1.34(9H,s),2.70–2.83(1H,m),2.84–3.07(1H,m),3.10–3.54(2H,m),3.82–3.98(1H,m),4.47–4.58(1H,m),4.60–4.71(1H,m),6.68+6.74(1H,d×2,J=8.6 Hz,J=7.6 Hz),6.89–7.10(3H,m),7.24–7.31(1H,m),7.48–7.59(2H,m),7.66–7.73(1H,m),7.93+7.96(1H,d×2,J=8.8 Hz,J=8.2 Hz),8.35+8.45(1H,d×2,J=8.0 Hz,J=8.6 Hz),10.74+10.76(1H,d×2,J=1.3 Hz,J=1.3 Hz),12.87(1H,brs)
Optical Rotation: [α]$_D^{20}$=+7.8° (c 0.41,MeOH)

EXAMPLE 17

Compound 17 m.p.: 118.5°–122° C.
IR(KBr,cm$^{-1}$):3328,2962,1665,1521,1371,1248,1164
High Resolution FAB-MS(m/e,($C_{25}H_{36}N_4O_7$+H)$^+$): Calcd: 505.2662 Found: 505.2691
$^1$H-NMR(300 MHz,DMSO-d$_6$,δppm):0.62–0.87(6H,m),1.03–1.51(3H,m),1.35(9H,s),2.79–2.99(1H,m),3.02–3.54(4H,m),3.76–4.11(2H,m),4.35–4.60(1H,m),6.73–6.86(1H,m),6.93(1H,t,J=7.4 Hz),7.02(1H,t,J=7.4 Hz),7.08(1H,brs),7.28(1H,d,J=7.4 Hz),7.47–7.62(1H,m),7.89–8.16(2H,m),10.66–10.85(1H,m)
Optical Rotation: [α]$_D^°$=+8.5° (c 0.39,MeOH)

EXAMPLE 18

Compound 18 m.p.: 97°–110° C.
IR(KBr,cm$^{-1}$):3280,2962,2878,1662,1578,1464,1389,1371,1254,1167,1104,1050,741
FAB-MS(m/e,($C_{26}H_{38}N_4O_6$+H)$^+$):503
$^1$H-NMR(300 MHz,DMSO-d$_6$,δppm):0.68–0.76(6H,m),1.15–1.24(6H,m),1.35(9H,s),2.01–2.28(1H,m),2.86(1H,dd,j=10.4 Hz,14.5 Hz)2.96–3.20(3H,m),3.82–3.96(1H,m),4.32–4.44(1H,m),6.90(1H,d,J=7.5 Hz),6.93(1H,t,J=7.5 Hz),7.02(1H,t,j=7.5 Hz),7.06(1.5H,d,J=1.5 Hz),7.27(1H,d,J=7.5 Hz),7.53(1H,d,J=7.5 Hz),7.99–8.13(2H,m),10.79(1H,d,J=1.5 Hz)

EXAMPLE 19

Compound 19 m.p.: 53°–56° C.
IR(KBr,cm$^{-1}$):3256,2962,2854,1695,1581,1389,1251,1167,1125,1071
High Resolution FAB-MS(m/e,($C_{34}H_{43}N_5O_6$+H)$^+$): Calcd: 618.3292 Found: 618.3276
$^1$H-NMR(300 MHz,DMSO-d$_6$,δppm):0.71(3H,d,J=5.7 Hz),0.73(3H,d,J=5.9 Hz),1.04–1.24(3H,m),1.35(9H,s),2.20–2.34(2H,m),2.74–2.96(2H,m),3.01–3.20(2H,m),3.80–3.92(1H,m),4.20–4.36(1H,m),4.36–4.53(1H,m),6.85(1H,d,J=7.8 Hz),6.93(1H,t,J=7.5 Hz),6.96(1H,t,J=7.5 Hz),7.01(1H,t,J=7.5 Hz),7.05(1H,t,J=7.5 Hz),7.06(1H,d,J=1.8 Hz),7.12(1H,d,J=1.8 Hz),7.28(1H,d,J=7.5 Hz),7.32(1H,d,J=7.5 Hz),7.55(1H,d,J=7.5 Hz),7.62(1H,d,J=7.5 Hz),7.90(1H,d,J=8.4 Hz),7.80–8.08(1H,m),10.77(1H,d,J=1.8 Hz),10.80(1H,d,J=1.8 Hz)

EXAMPLE 20

Compound 20 m.p.: 112°–120° C.
IR(KBr,cm$^{-1}$):3346,3064,2962,1656,1527,1461,1443,1395,1371,1344,1251,1164,1104,1047
FAB-MS(m/e,($C_{32}H_{42}N_4O_6$+H)$^+$):579
$^1$H-NMR(300 MHz,DMSO-d$_6$,δppm):0.72(3H,d,J=6.1 Hz),0.73(3H,d,J=6.4 Hz),1.04–1.24(3H,m),1.37(9H,s),2.22–2.36(2H,m),2.67–2.82(2H,m),2.83(1H,dd,J=9.5 Hz,14.5 Hz),3.05(1H,dd,J=4.1 Hz,14.5 Hz),3.82–3.96(1H,m),4.18–4.32(1H,m),4.42 (1H,ddd,J=4.1 Hz,8.4 Hz,9.5

EXAMPLE 21

Compound 21 m.p.: 109°–114° C.
IR(KBr,cm$^{-1}$):3346,2926,1700,1665,1524,1164,740
High Resolution FAB-MS(m/e,($C_{32}H_{42}N_4O_6$+H)$^-$): Calcd: 579.3182 Found: 579.3206
$^1$H-NMR(300 MHz,DMSO-d$_6$,δppm):0.68(3H,d,J=6.5 Hz),0.71(3H,d,J=5.6 Hz),1.04–1.24(3H,m),1.36(9H,s),2.32–2.43(2H,m),2.61–2.81(3H,m),2.97(1H,dd,J=4.2 Hz,14.5 Hz),3.77–3.96(1H,m),4.12–4.33(1H,m),4.29–4.48(1H,m),6.81(1H,d,J=7.2 Hz),6.97(1H,t,J=7.5 Hz),7.02(1H,t,J=7.5 Hz),7.09–7.25(5H,m),7.14(1H,d,J=1.2 Hz),7.28(1H,d,J=7.5 Hz),7.51(1H,d,J=7.5 Hz),7.84(1H,d,J=8.1 Hz),7.96(1H,d,J=8.7 Hz),10.75(1H,d,J=1.2 Hz),12.20(1H,brs)

EXAMPLE 22

Compound 22 m.p.: 117°–123° C.
IR(KBr,cm$^{-1}$):3406,2962,2926,1677,1515,1170,744
High Resolution FAB-MS(m/e,($C_{30}H_{42}N_6O_6S$+H)$^+$): Calcd: 615.2964 Found: 615.2960
$^1$H-NMR(300 MHz,DMSO-d$_6$,δppm):0.70(3H,d,J=6.4 Hz),0.71(3H,d,J=6.4 Hz),1.05–1.40(3H,m),1.33(9H,s),2.18(3H,s),2.75–3.25(4H,m),3.77(2H,s),3.87–3.95(1H,m),4.37–4.45(1H,m),4.55–4.63(1H,m),6.77(1H,d,J=8.1 Hz),6.94(1H,t,j=7.6 Hz),7.03(1H,t,J=7.6 Hz),7.10(1H,d,J=2.0 Hz),7.29(1H,d,J=7.6 Hz),7.59(1H,d,J=7.6 Hz),8.04(1H,d,J=8.4 Hz),8.12(1H,s),8.45(1H,d,J=7.8 Hz),10.80(1H,d,J=2.0 Hz)

EXAMPLE 23

Compound 23 m.p.: 130°–132° C.
IR(KBr,cm$^{-1}$):3316,2962,1662,1539,1461,1395,1371,1251,1164,744
High Resolution FAB-MS(m/e,($C_{26}H_{37}N_5O_7$+H)$^+$): Calcd: 532.2772 Found: 532.2781
$^1$H-NMR(300 MHz,DMSO-d$_6$,δppm):0.69(3H,d,J=6.7 Hz),0.72(3H,d,J=6.7 Hz),1.06–1.40(3H,m),1.33(9H,s),2.92(1H,dd,J=9.0 Hz,14.6 Hz),3.17(1H,dd,J=3.6 Hz,14.6 Hz),3.66(1H,dd,J=5.9 Hz,14.6 Hz),3.73(2H,d,J=5.9 Hz),3.78(1H,dd,J=5.9 Hz,16.4 Hz),3.89(1H,q,J=7.5 Hz),4.47(1H,dt,J=3.6 Hz,9.0 Hz),6.86(1H,d,J=7.5 Hz),6.93(1H,t,J=7.02 Hz),7.02(1H,t,J=7.5 Hz),7.09(1H,d,J=1.9 Hz),7.28(1H,d,J=7.5 Hz),7.55(1H,d,J=7.5 Hz),8.00(1H,t,J=5.9 Hz),8.08(1H,d,J=9.0 Hz),8.25(1H,t,J=5.9 Hz),10.78(1H,d,J=1.9 Hz),12.50(1H,brs) Optical Rotation: [α]$_D^{20}$= +3.6°(c 0.52,MeOH)

EXAMPLE 24

Compound 24 m.p.: 166° C.(dec.)
IR(KBr,cm$^{-1}$):3430,2962,1662,1530,1461,1395,1371,1197,1047
FAB-MS(m/e,($C_{23}H_{34}N_4O_7S \cdot C_6H_{15}N$+H)$^+$):612
$^1$H-NMR(300 MHz,DMSO-d$_6$,δppm):0.70(3H,d,J=6.3 Hz),0.72(3H,d,J=6.3 Hz),1.06–1.42(3H,m),1.16(9H,t,J=7.2 Hz),1.34(9H,s),2.91(1H,dd,J=9.0 Hz,14.4 Hz),3.05–3.20(1H,m),3.07(6H,q,J=7.2 Hz),3.80–4.00(3H,m),4.50–4.60(1H,m),6.75(1H,d,J=8.1 Hz),6.92(1H,t,J=7.7 Hz),7.01(1H,t,J=7.7 Hz),7.14(1H,d,J=1.6 Hz),7.27(1H,d,J=7.7 Hz),7.56(1H,d,J=7.7 Hz),7.85(1H,d,J=8.7 Hz),8.18–8.26(1H,m),10.76(1H,d,J=1.6 Hz)

EXAMPLE 25

Compound 25 m.p.: 112°–120° C.
IR(KBr,cm$^{-1}$):3406,2962,1659,1530,1464,1371,1248,1215,1167,1041
High Resolution FAB-MS(m/e,($C_{24}H_{36}N_4O_7S \cdot C_6H_{15}N$+Na)$^+$): Calcd: 648.3406 Found: 648.3361
$^1$H-NMR(300 MHz,DMSO-d$_6$,δppm):0.70(3H,d,J=5.8 Hz),0.73(3H,d,J=5.8 Hz),1.15(9H,t,J=7.4 Hz),1.15–1.30(3H,m),1.34(9H,s),2.50–2.60(2H,m),2.88(1H,dd,J=8.7 Hz,14.2 Hz),3.06(6H,q,J=7.4 Hz),3.12–3.24(1H,m),3.48–3.60(2H,m),3.80–3.93(1H,m),4.32–4.43(1H,m),6.85(1H,d,J=6.7 Hz),6.94(1H,t,J=7.7 Hz),7.02(1H,t,J=7.7 Hz),7.04(1H,d,J=1.8 Hz),7.28(1H,d,J=7.7 Hz),7.53(1H,d,J=7.7 Hz),7.82(1H,d,J=5.1 Hz),8.02(1H,d,J=7.7 Hz),10.78(1H,d,J=1.8 Hz)

EXAMPLE 26

Compound 26 m.p.: 95°–100° C.
IR(KBr,cm$^{-1}$):3424,2968,1656,1521,1170,1038,744
High Resolution FAB-MS(m/e,($C_{31}H_{42}N_4O_7S$+H)$^+$): Calcd: 615.2852 Found: 615.2827
$^1$H-NMR(300 MHz,DMSO-d$_6$,δppm):0.74(3H,d,J=6.1 Hz),0.75(3H,d,J=6.1 Hz),1.10–1.40(3H,m),1.17(9H,t,J=7.3 Hz),1.37(9H,s),2.45–2.55(2H,m),2.78–2.90(2H,m),3.05–3.20(8H,m),3.90–3.98(1H,m),4.12–4.22(1H,m),4.34–4.40(1H,m),6.72(1H,d,J=8.3 Hz),6.93(1H,t,J=7.5 Hz),7.02(1H,t,J=7.5 Hz),7.08(1H,d,J=1.5 Hz),7.14–7.24(5H,m),7.28(1H,d,J=7.5 Hz),7.55(1H,d,J=7.5 Hz),7.87(1H,d,J=7.3 Hz),7.89(1H,d,J=6.7 Hz),10.76(1H,d,J=1.5 Hz)

EXAMPLE 27

Compound 27

IR(KBr,cm$^{-1}$):3412,2962,1713,1656,1395,1248,1167,1110
High Resolution FAB-MS(m/e,($C_{24}H_{37}N_4O_7P$+H)$^+$): Calcd: 525.2479 Found: 525.2502
$^1$H-NMR(300 MHz,DMSO-d$_6$,δppm):0.68–0.80(6H,m),0.90–1.00(12H,t,J=7.3 Hz),1.15–1.65(21H,m),1.36(9H,s),2.85–3.00(1H,m),3.10–3.50(11H,m),3.82–3.95(1H,m),4.35–4.48(1H,m),6.90–7.00(2H,m),7.02(1H,t,J=7.7 Hz),7.06(1H,brs),7.29(1H,d,J=7.7 Hz),7.54(1H,d,J=7.7 Hz),7.89–8.02(1H,m),8.03–8.13(1H,m),10.80(1H,brs)

EXAMPLE 28

Synthesis of Compound 28

Compound 28 was prepared using Boc-Nva-OH and βAla-OH as starting materials in the same manner described in Example 1.

m.p.: 91°–93.5° C.

IR(KBr,cm$^{-1}$):3406,2968,1656,1530,1461,1395,1371,1251,1167

High Resolution FAB-MS(m/e,($C_{24}H_{34}N_4O_6$+H)$^+$): Calcd: 475.2556 Found: 475.2543

$^1$H-NMR(300 MHz,DMSO-d$_6$,δppm):0.68(3H,t,J=7.2 Hz),0.80–1.05(2H,m),1.20–1.48(2H,m),1.36(9H,s),2.35(2H,dt,J=3.2 Hz,7.1 Hz),2.86(1H,dd,J=9.8 Hz,14.4 Hz),3.08–3.42(3H,m),3.77–3.88(1H,m),4.34–4.47(1H,m),6.86(1H,d,J=7.1 Hz),6.94(1H,t,J=7.6 Hz),7.03(1H,t,J=7.6 Hz),7.06(1H,d,J=2.1 Hz),7.29(1H,d,J=7.6 Hz),7.54(1H,d,J=7.6 Hz),7.92(1H,t,J=5.5 Hz),8.07(1H,d,J=8.1 Hz),10.77(1H,d,J=2.1 Hz),12.20(1H,brs)

Optical Rotation: $[α]_D^{20}$=+6.9° (c 0.63,MeOH)

EXAMPLE 29

Synthesis of Compound 29

(1) Preparation of Boc-Leu-DTrp-βAla-OEt

To a solution of Boc-Leu-DTrp-NHNH$_2$ (39 mg) obtained in Example 1-(2) in DMF (0.5 ml) was added 3.1 M HCl/14,-dioxane (81 μl) at −60° C. The temperature of the solution was raised to −20° C. and isoamyl nitrite (15 μl) was added. The reaction mixture was stirred at −20° C. to −15° C. for 1.5 h and cooled at −60° C. A solution of βAla-OEt.HCl (17 mg) in DMF (0.5 ml) and TEA (50 μl) were added. The reaction mixture was stirred at 5° C. overnight and concentrated under reduced pressure. The residue was partitioned between water and dichloromethane. The organic layer was washed with water, dried over MgSO$_4$, filtered, and concentrated under reduced pressure. The residue was purified by preparative TLC (Merck, Kieselgel 60 F$_{254}$) with chloroform/methanol=30/1 for development to give the product (41 mg).

(2) Preparation of Compound 29

To a solution of the compound obtained in (1) (20 mg) in ethanol (0.2 ml) was added 1N NaOH (45 μl) at 0°–5° C. The reaction mixture was stirred at the same temperature for 30 min and room temperature for 2 h, and partitioned between water and dichloromethane. The pH of the aqueous solution was adjusted to 3 by treatment with 10% aq. citric acid. The solution was extracted with dichloromethane and the combined organic layers were washed with water, dried over MgSO$_4$, filtered, and concentrated to give the title compound (18 mg) as a colorless powder.

m.p.: 103°–107° C.

IR(KBr,cm$^{-1}$):3406,2962,1656,1527,1461,1395,1371,1251,1167,741

High Resolution FAB-MS(m/e,($C_{25}H_{36}N_4O_6$+H)$^+$): Calcd: 489.2713 Found: 489.2701

$^1$H-NMR(300 MHz,DMSO-d$_6$,δppm):0.68(3H,d,J=5.9 Hz),0.72(3H,d,J=5.9 Hz),1.08–1.28(3H,m),1.35(9H,s),2.24–2.44(2H,m),2.86(1H,dd,J=9.7 Hz,14.4 Hz),3.10–3.25(3H,m),3.83–3.90(1H,m),4.34–4.45(1H,m),6.93(1H,d,J=6.8 Hz),6.94(1H,t J=8.0 Hz) 7.02(1H,t,J=8.0 Hz),7.05(1H,d,J=1.9 Hz),7.29(1H,d,J=8.0 Hz),7.53(1H,d,J=8.0 Hz),7.90(1H,t,J=5.7 Hz),8.09(1H,d,J=8.4 Hz),10.78(1H,d,J=1.9 Hz)

EXAMPLE 30

Synthesis of Compound 30

Compound 30 was prepared using Boc-MeLeu-OH as a starting material in the same manner described in Examples 1-(1), -(2) and 29.

m.p.: 87.5°–89.0° C.

IR(KBr,cm$^{-1}$):3316,2962,1671,1521,1458,1395,1371,1341,1326,1155

FAB-MS(m/e,($C_{26}H_{38}N_4O_6$+H)$^+$):503

$^1$H-NMR(300 MHz,DMSO-d$_6$,δppm):0.79(6H,brs),1.10–1.42(3H,m),1.34+1.36(9H,brs×2),2.33(2H,t,J=7.0 Hz),2.58+2.60(3H,brs×2),2.86–3.03(1H,m),3.06(1H,dd,J=5.0 Hz,14.3 Hz),3.17–3.34(2H,m),4.26–4.60(2H,m),6.94(1H,t,J=7.7 Hz),7.03(1H,t,J=7.7 Hz),7.07(1H,d,J=1.9 Hz),7.29(1H,d,J=7.7 Hz),7.56(1H,d,J=7.7 Hz),7.62–7.74+7.76–7.90(1H,m×2),7.94–8.14(1H,m),10.79(1H,brs),12.19(1H,brs)

Optical Rotation: $[α]_D^{20}$=−10.5°(c 0.86,MeOH)

EXAMPLE 31

Synthesis of Compound 31

Compound 31 was prepared using Gly-OEt.HCl as a starting material in the same manner described in Example 29.

m.p.: 1.08°–124° C.

IR(KBr,cm$^{-1}$):3346,2962,1665,1530,1395,1371,1251,1167

High Resolution FAB-MS(m/e,($C_{24}H_{34}N_4O_6$+H)$^+$): Calcd: 475.2556 Found: 475.2561

$^1$H-NMR(300 MHz,DMSO-d$_6$,δppm):0.68(3H,d,J=6.1 Hz),0.72(3H,d,J=6.1 Hz),1.07–1.32(3H,m),1.34(9H,s),2.89(1H,dd,J=10.0 Hz,14.4 Hz),3.34–3.49(1H,m),3.70(1H,dd,J=5.7 Hz,17.6 Hz),3.80(1H,dd,J=5.7 Hz,17.6 Hz),3.80–3.93(1H,m),4.44–4.55(1H,m),6.87(1H,d,J=7.6 Hz),6.94(1H,t,J=7.6 Hz),7.03(1H,t,J=7.6 Hz),7.08(1H,d,J=2.0 Hz),7.29(1H,d,J=7.6 Hz),7.55(1H,d,J=7.6 Hz),8.13(1H,d,J=7.9 Hz),8.24(1H,t,J=5.7 Hz),10.78(1H,d,J=2.0 Hz)

EXAMPLE 32

Synthesis of Compound 32

Compound 32 was prepared using DMeTrp-OMe.HCl in the same manner described in Examples 1-(1), -(2) and 29.

m.p.: 110°–113° C.

IR(KBr,cm$^{-1}$):3352,2962,2932,1653,1536,1461,1398,1371,1251,1167,1104,741

FAB-MS(m/e,($C_{26}H_{38}N_4O_6$+H)$^+$):503

$^1$H-NMR(300 MHz,DMSO-d$_6$,δppm):0.54(3H,d,J=6.6 Hz),0.57(3H,d,J=6.6 Hz),0.77–0.93(2H,m),0.93–1.08(1H,m),1.33(9H,s),2.28–2.40(2H,m),2.90(3H,s),3.05–3.40(4H,m),4.10–4.20(1H,m),5.33(1H,dd,J=4.1 Hz,11.3 Hz),6.79(1H,d,J=6.5 Hz),6.92(1H,t,J=7.3 Hz),7.02(1H,t,J=7.3 Hz),7.04(1H,brs),7.27(1H,d,J=7.3 Hz),7.54(1H,d,J=7.3 Hz),7.73–7.78(1H,m),10.79(1H,brs)

EXAMPLE 33

Synthesis of Compound 33

(1) Preparation of Iva-Leu-DTrp-OH

To Boc-Leu-DTrp-OMe (1.5 g) prepared in the same manner described in Example 1-(1) was added 20% ethanedithiol/TFA (10 ml) at 0°~5° C. The solution was stirred at 0° C. for 15 min and then at room temperature for 15 min, and concentrated under reduced pressure. To the residue was added toluene and the solution was again concentrated under reduced pressure. The procedures were repeated 3 times. The resulting residue was partitioned between sat. NaHCO$_3$ and ethyl acetate. The organic layer was dried over MgSO$_4$, filtered, and concentrated under reduced pressure to afford a solid, which was dissolved in dichloromethane (20 ml). To the solution were added isovaleric acid (0.56 g), N-methylmorpholine (0.60 ml), HOBT.H$_2$O (0.85 g) and EDCI.HCl (1.06 g) at 0°~5° C. and the mixture was stirred at room temperature overnight, washed successively with water, 1N HCl, sat. NaHCO$_3$ and brine, dried over MgSO$_4$, filtered, and concentrated under reduced pressure. The resulting residue was dissolved in methanol (35 ml) and 1N NaOH (3.9 ml) was added. The reaction mixture was stirred at room temperature for 12 h and concentrated under reduced pressure. The residue was dissolved in water and the solution was washed with ether. The pH of the aqueous solution was adjusted to 3 with 1N HCl and the solution was extracted with ethyl acetate. The combined organic layers were dried over MgSO$_4$, filtered, and concentrated under reduced pressure to afford a residue, which was purified by preparative TLC (Merck, Kieselgel 60 F$_{254}$) with chloroform/methanol/acetic acid=20/1/1 for development followed by reverse-phase chromatography (Nacalai Tesque, Cosmosil 75 C$_{18}$-OPN) with methanol for elution to give the product (0.55 g).

FAB-MS(m/e,(C$_{22}$H$_{31}$N$_3$O$_4$+H)$^+$): 402

(2) Preparation of Compound 33

To a solution of the compound obtained in (1) (33.0 mg) in dichloromethane (3 ml) were added HOBT.H$_2$O (15.3 mg), EDCI.HCl (19.1 mg), βAla-OEt.HCl (15.0 mg) and N-methylmorpholine (11 μl) at room temperature. The reaction mixture was stirred overnight, washed successively with water, 1N HCl, sat. NaHCO$_3$ and brine, dried over Na$_2$SO$_4$, filtered, and concentrated under reduced pressure to give a residue, which was dissolved in methanol (1 ml). 1N NaOH (76 μl) was added to the solution and the mixture was stirred vigorously at room temperature for 12 h, concentrated under reduced pressure. The residue was dissolved in water, and the solution was washed with ether. The pH of the aqueous layer was adjusted to 2 with 1N HCl and the solution was extracted with ethyl acetate. The combined organic layers were dried over Na$_2$SO$_4$, filtered, and concentrated under reduced pressure to give a residue, which was purified by preparative TLC (Analytichem International, Empore sheet) with chloroform/methanol/acetic acid=10:1:1 for development to give the title compound (24 mg) as a yellow powder.

m.p.: 136°-140° C.
IR(KBr,cm$^{-1}$):3304,3070,2962,1722,1656,1545,1464,1443,1392,1212,1101 High Resolution
FAB-MS(m/e,(C$_{25}$H$_{36}$N$_4$O$_5$+H)$^+$): Calcd: 473.2764 Found: 473.2792
$^1$H-NMR(300 MHz,DMSO-d$_6$,δppm):0.68(3H,d,J=5.6 Hz),0.74(3H,d,J=5.6 Hz),0.78-0.92(6H,m),1.08-1.32(4H,m),1.88-2.02(2H,m),2.28-2.44(2H,m),2.85(1H,dd,J=10.3 Hz,14.0 Hz),3.08-3.20(1H,m),3.20-3.40(2H,m),4.08-4.18(1H,m),4.30-4.43(1H,m),6.95(1H,t,J=7.5 Hz),7.03(1H,t,J=7.5 Hz),7.06(1H,d,J=1.2 Hz),7.29(1H,d,J=7.5 Hz),7.54(1H,d,J=7.5 Hz),7.87-8.04(2H,m),8.20(1H,d,J=7.5 Hz),10.78(1H,d,J=1.2 Hz)
Optical Rotation: [α]$_D^{20}$=+6.4°(c 0.30,DMSO)

EXAMPLE 34

Synthesis of Compound 34

Compound 34 was prepared using DHis-OMe.2HCl as a starting material in the same manner described in Example 33-(2).

m.p.: 155°-165° C.
IR(KBr,cm$^{-1}$):3436,2962,1647,1530,1395
High Resolution
FAB-MS(m/e,(C$_{28}$H$_{38}$N$_6$O$_5$+H)$^+$): Calcd: 539.2982 Found: 539.3010
$^1$H-NMR(300 MHz,DMSO-d$_6$,δppm):0.65-0.88(12H,m),1.05-1.42(3H,m),1.88-2.00(3H,m),2.78-3.70(4H,m),4.08-4.32(2H,m),4.39-4.51(1H,m),6.74(1H,s),6.94(1H,t,J=7.5 Hz),7.03(1H,t,J=7.5 Hz),7.09(1H,d,J=1.5 Hz),7.29(1H,d,J=7.5 Hz),7.49(1H,s),7.56(1H,d,J=7.5 Hz),7.85(1H,d,J=8.1 Hz),7.90-8.06(1H,m),8.05(1H,d,J=8.4 Hz),10.79(1H,brs)

EXAMPLE 35

(1) Synthesis of Compound 35

Compound 35 was prepared using DAsp(OBzl)-NH$_2$ as a starting material in the same manner described in Example 29-(1).

m.p.: 159°-167° C.
IR(KBr,cm$^{-1}$):3424,1680,1515,1371,1170,745
High Resolution
FAB-MS(m/e,(C$_{33}$H$_{43}$N$_5$O$_7$+H)$^+$): Calcd: 622.3241 Found: 622.3243
$^1$H-NMR(300 MHz,DMSO-d$_6$,δppm):0.64(3H,d,J=5.2 Hz),0.68(3H,d,J=5.2 Hz),1.05-1.40(3H,m),1.32(9H,s),2.64(1H,dd,J=8.6 Hz,16.1 Hz),2.85-2.95(2H,m),3.20-3.40(1H,m),3.80-3.90(1H,m),4.35-4.44(1H,m),4.58-4.68(1H,m),5.07(1H,d,J=12.5 Hz),5.13(1H,d,J=12.5 Hz),6.92(1H,brs),6.93(1H,d,J=8.1 Hz),6.94(1H,t,J=7.7 Hz),7.03(1H,t,J=7.7 Hz),7.12(1H,d,J=2.0 Hz),7.21(1H,brs),7.30(1H,d,J=7.7 Hz),7.35(5H,s),7.55(1H,d,J=7.7 Hz),8.04(1H,d,J=8.3 Hz),8.23(1H,d,J=7.6 Hz),10.80(1H,d,J=2.0 Hz)

(2) Synthesis of Compound 36

To a solution of Compound 35 (51 mg) obtained in (1) in methanol (5.0 ml) was added 10% Pd-C (50 mg). The mixture was vigorously stirred at room temperature under atmospheric pressure of hydrogen for 4 h. The catalyst was filtered off and the filtrate was concentrated under reduced pressure. The residue was triturated with ether to give the title compound as a colorless powder.

m.p.: 145°-156° C.
IR(KBr,cm$^{-1}$):3418,2962,1677,1518,1167,741
High Resolution
FAB-MS(m/e,(C$_{26}$H$_{37}$N$_5$O$_7$+H)$^+$): Calcd: 532.2771 Found: 532.2776
$^1$H-NMR(300 MHz,DMSO-d$_6$,δppm):0.64(3H,d,J=5.3 Hz),0.69(3H,d,J=5.3 Hz),1.05-1.23(3H,m),1.34(9H,s),2.40-2.50(1H,m),2.60(1H,dd,J=5.8 Hz,14.8 Hz),2.89(1H,dd,J=10.3 Hz,14.8 Hz),3.22(1H,dd,J=3.4 Hz,14.8 Hz),3.80-3.90(1H,m),4.33-4.42(1H,m),4.-

45–4.55(1H,m),6.92(1H,d,J=6.6 Hz),6.94(1H,t,J=7.4 Hz),7.03(1H,t,J=7.4 Hz),7.07(2H,brs),7.12(1H,d,J=2.0 Hz),7.29(1H,d,J=7.4 Hz),7.55(1H,d,J=7.4 Hz),8.06(1H,d,J=8.2 Hz),8.23(1H,d,J=7.7 Hz),10.80(1H,d,J=2.0 Hz)

Each Compound 37–45 in the following Examples 36–43 was prepared using a benzyl ester of each corresponding amino acid in the same manner described in Example 35.

EXAMPLE 36

(1) Compound 37
m.p.: 97°–99° C.
IR(KBr,cm$^{-1}$):3418,1518,1461,1392,1371,1251,1170,741
High Resolution
FAB-MS(m/e,($C_{33}H_{43}N_5O_7$+H)+): Calcd: 622.3241 Found: 622.3226
$^1$H-NMR(300 MHz,DMSO-d$_6$,δppm):0.71(3H,d,J=5.1 Hz),0.72(3H,d,J=5.1 Hz),1.12–1.30(3H,m),1.33(9H,s),2.43–2.49(1H,m),2.76(1H,dd,J=6.2 Hz,16.0 Hz),2.90(1H,dd,J=9.5 Hz,14.4 Hz),3.08(1H,dd,J=4.5 Hz,14.4 Hz),3.86–3.95(1H,m),4.37–4.46(1H,m),4.57–4.65(1H,m),5.05(2H,s),6.79(1H,d,J=7.6 Hz),6.93(1H,t,J=7.7 Hz),7.02(1H,t, J=7.7 Hz),7.10(1H,d,J=1.4 Hz),7.20(2H,d,J=9.4 Hz),7.29(1H,d,J=7.7 Hz),7.32–7.38(5H,m),7.55(1H,d,J=7.7 Hz), 8.02(1H,d,J=7.2 Hz),8.30(1H,d,J=8.6 Hz),10.80(1H,d,J=1.34 Hz)

(2) Compound 38
m.p.: 128°–147° C.
IR(KBr,cm$^{-1}$):3418,2962,1677,1521,1398,1371,1167
High Resolution
FAB-MS(m/e,($C_{26}H_{37}N_5O_7$+H)+): Calcd: 532.2772 Found: 532.2794
$^1$H-NMR(300 MHz,DMSO-d$_6$,δppm):0.703H,d,J=5.5 Hz),0.72(3H,d,J=5.5 Hz)1.10–1.28(3H,m),1.34(9H,s),2.37(1H,dd,J=7.4 Hz,16.5 Hz),2.63(1H,dd,J=6.0 Hz,16.5 Hz),2.91(1H,dd,J=9.5 Hz,14.6 Hz),3.10(1H,dd,J=4.3 Hz,14.6 Hz),3.84–3.93(1H,m),4.38–4.55(2H,m),6.79(1H,d,J=7.9 Hz),6.94(1H,t,J=8.0 Hz),7.03(1H,t,J=8.0 Hz),7.10(1H,d,J=2.3 Hz),7.11(1H,brs),7.15(1H,brs),7.29(1H,d,J=8.0 Hz),7.56(1H,d,J=8.0 Hz),7.98(1H,d,J=7.1 Hz),8.23(1H,d,J=7.7 Hz),10.79(1H,d,J=2.3 Hz)

EXAMPLE 37

Compound 39
m.p.: 119°–122° C.
IR(KBr,cm$^{-1}$):3418,2962,1662,1518,1461,1395,1371,1251,1164,741
High Resolution
FAB-MS(m/e,($C_{31}H_{40}N_4O_6$+H)+): Calcd: 565.3026 Found: 565.3036
$^1$H-NMR(300 MHz,DMSO-d$_6$,δppm):0.70(6H,d,J=6.6 Hz),1.02–1.45(3H,m),1.34(9H,s),2.84(1H,dd,J=10.3 Hz,15.0 Hz),2.94(1H,dd,J=7.6 Hz,13.5 Hz),3.03–3.18(2H,m),3.84–3.97(1H,m),4.25–4.38(1H,m),4.43–4.58(1H,m),6.72(1H,d,J=8.3 Hz),6.93(1H,t,J=7.5 Hz),7.02(1H,t,J=7.5 Hz),7.05(1H,d,J=1.8 Hz),7.13–7.26(5H,m),7.28(1H,d,J=7.5 Hz),7.54(1H,d,J=7.5 Hz),7.93–8.03(1H,m),7.94(1H,d,J=8.9 Hz),10.77(1H,brs)

EXAMPLE 38

Compound 40
m.p.: 128°–132° C.
IR(KBr,cm$^{-1}$):3424,2926,1671,1518,1461,1371,1251,1167
High Resolution
FAB-MS(m/e,($C_{30}H_{38}N_4O_6$+H)+): Calcd: 551.2869 Found: 551.2894
$^1$H-NMR(300 MHz,DMSO-d$_6$,δppm):0.74+0.80(6H,d×2,J=6.2 Hz,J=6.2 Hz),1.03–1.26(3H,m),1.26+1.30(9H,s×2),2.81(1H,dd,J=9.5 Hz,14.6 Hz),3.01–3.55(1H,m),3.89–4.19(1H,m),4.40–4.73(1H,m),5.04–5.18(1H,m),6.73+6.79(1H,d×2,J=8.3 Hz,J=8.3 Hz),6.96+6.98(1H,t×2,J=7.4 Hz,J=7.4 Hz),7.05(1H,t, J=7.4 Hz),7.11(1H,d,J=1.5 Hz),7.22–7.37(5H,m),7.39(1H,d,J=7.4 Hz),7.54+7.61(1H,d×2,J=7.4 Hz,J=7.4 Hz),7.96+8.05(1H,d×2,J=8.1 Hz,J=8.1 Hz),7.90–7.96+8.35–8.46(1H,m×2),10.83+10.86(1H,brs×2)

EXAMPLE 39

Compound 41
m.p.: 107°–115° C.
IR(KBr,cm$^{-1}$):3346,3064,2962,1662,1524,1461,1395,1371,1251,1164,1104
High Resolution
FAB-MS(m/e,($C_{25}H_{36}N_4O_6$+H)+): Calcd: 489.2713 Found: 489.2711
$^1$H-NMR(300 MHz,DMSO-d$_6$,δppm):0.68(3H,d,J=6.3 Hz),0.69(3H,d,J=5–8 Hz),0.95–1.25(3H,m),1.28(3H,d,J=7.5 Hz),1.33(9H,s),2.86(1H,dd,J=10.2 Hz,14.4 Hz),3.18(1H,dd,J=4.4 Hz,14.4 Hz),3.85(1H,dt,J=7.3 Hz,7.3 Hz),4.22(1H,dq,J=7.3 Hz,7.5 Hz),4.53(1H,ddd,J=4.4 Hz,7.3 Hz,10.2 Hz),6.80(1H,d,J=7.3 Hz),6.93(1H,t,J=7.5 Hz),7.02(1H,t,J=7.5 Hz),7.08(1H,d,J=1.4 Hz),7.29(1H,d,J=7.5 Hz),7.58(1H,d,J=7.5 Hz),8.06(1H,d,J=7.3 Hz),8.12(1H,d,J=7.3 Hz),10.78(1H,d,J=1.4 Hz), 12.42(1H,brs)

EXAMPLE 40

Compound 42
m.p.: 102°–113° C.
IR(KBr,cm$^{-1}$):3412,2926,1665,1515,1464,1389,1371,1242,1167,1104,741
High Resolution
FAB-MS(m/e,($C_{28}H_{36}N_4O_6S$+H)+): Calcd: 557.2433 Found: 557.2440
$^1$H-NMR(300 MHz,DMSO-d$_6$,δppm):0.63–0.91(6H,m),0.98–1.26(3H,m),1.31+1.33(9H,s×2),2.86–3.02(1H,m),3.06–3.20(1H,m),3.85–4.02(1H,m),4.54–4.72(1H,m),5.34–5.67(1H,m),6.70+6.75(1H,d×2,J=8.4 Hz,J=8.7 Hz),6.92–6.96(2H,m),7.03(1H,t,J=7.5 Hz),7.08–7.28(3H,m),7.29(1H,d,J=7.5 Hz),7.37–7.47(1H,m),7.53–7.66(1H,m),7.93–8.14(1H,m),10.80(1H,d,J=1.2 Hz)

EXAMPLE 41

Compound 43
m.p.: 119°–128° C.

IR(KBr,cm$^{-1}$):3418,2968,1662,1518,1464,1395,1371,1254,1167

High Resolution

FAB-MS(m/e,(C$_{27}$H$_{40}$N$_4$O$_6$+H)$^+$): Calcd: 517.3026 Found: 517.3038

$^1$H-NMR(300 MHz,DMSO-d$_6$,δppm):0.69(6H,d,J=6.1 Hz),0.88(3H,d,J=6.6 Hz),0.90(3H,d,J=4.6 Hz),0.98-1.30(3H,m),1.33(9H,s),2.00-2.14(1H,m),2.86(1H,dd,J=10.1 Hz,15.0 Hz),3.14(1H,dd,J=3.4 Hz,15.0 Hz),3.90(1H,ddd,J=4.6 Hz,5.4 Hz,6.6 Hz),4.14(1H,dd,J=5.9 Hz,8.4 Hz),4.60(1H,ddd,J=3.4 Hz,7.8 Hz,10.1 Hz),6.75(1H,d,J=7.7 Hz),6.93(1H,t,J=7.5 Hz),7.03(1H,t,J=7.5 Hz),7.07(1H,d,J=2.0 Hz),7.28(1H,d,J=7.5 Hz),7.57(1H,d,J=7.5 Hz),7.90(1H,d,J=8.4 Hz),7.99(1H,d,J=7.8 Hz),10.78(1H,d,J=2.0 Hz)

EXAMPLE 42

Compound 44 m.p.: 119°-124° C.

IR(KBr,cm$^{-1}$):3406,1674,1605,1530,1449,1395,1371,1248,1167

High Resolution

FAB-MS(m/e,(C$_{32}$H$_{41}$N$_5$O$_7$+H)$^+$): Calcd: 608.3084 Found: 608.3053

$^1$H-NMR(300 MHz,DMSO-d$_6$, δppm):0.63(3H,d,J=5.7 Hz),0.68(3H,d,J=5.7 Hz),1.05-1.37(3H,m),1.26(9H,s),2.65(1H,dd,J=8.7 Hz,16.6 Hz),2.85(1H,dd,J=5.4 Hz,16.6 Hz),2.91(1H,dd,J=10.8 Hz,14.7 Hz),3.17-3.30(1H,m),3.83-3.93(1H,m),4.37-4.47(1H,m),4.70-4.81(1H,m),6.93(1H,t,J=7.3 Hz),7.00-7.10(3H,m),7.14(1H,d,J=2.0 Hz),7.28(2H,t,J=7.8 Hz),7.29(1H,d,J=7.3 Hz),7.55(1H,d,J=7.3 Hz),7.63(2H,d,J=7.8 Hz),8.14(1H,d,J=8.1 Hz),8.34(1H,d,J=7.1 Hz),9.44(1H,s),10.81(1H,d,J=2.0 Hz)

EXAMPLE 43

Compound 45 m.p.: 121°-126° C.

IR(KBr,cm$^{-1}$):3334,1665,1602,1539,1449,1371,1251,1164

FAB-MS(m/e,(C$_{32}$H$_{41}$N$_5$O$_7$+H)$^+$):608

$^1$H-NMR(300 MHz,DMSO-d$_6$,δppm):0.72(6H,d,J=6.4 Hz),1.10-1.40(3H,m),1.31(9H,s),2.44-2.52(1H,m),2.69(1H,dd,J=6-1 Hz,16.6 Hz),2.94(1H,dd,J=9.7 Hz,14.6 Hz),3.11(1H,dd,J=4.9 Hz,14.6 Hz),3.90-4.01(1H,m),4.40-4.52(1H,m),4.69-4.76(1H,m),6.81(1H,d,J=8.2 Hz),6.95(1H,t,J=7.9 Hz),7.04(2H,t,J=7.9 Hz),7.14(1H,d,J=2.0 Hz),7.28(2H,t,J=7.9 Hz),7.30(1H,d,J=7.9 Hz),7.58(1H,d,J=7.9 Hz),7.67(2H,d,J=7.9 Hz),8.07(1H,d,J=6.8 Hz),8.51(1H,d,J=7.1 Hz),9.77(1H,s),10.81(1H,d,J=2.0 Hz)

EXAMPLE 44

Synthesis of Compound 46

Compound 46 was prepared using DAsp(OBzl)-OBzl.TsOH as a starting material in the same manner described in Examples 33-(2) and 35-(2).

m.p.: 132°-134° C.

IR(KBr,cm$^{-1}$):3418,3064,2962,1738,1650,1530,1464,1392,1371,1344,1221

FAB-MS(m/e,(C$_{26}$H$_{36}$N$_4$O$_7$+H)$^+$):517

$^1$H-NMR(300 MHz,DMSO-d$_6$, δppm):0.67(3H,d,J=6.3 Hz),0.70-0.79(3H,m),0.79-1.00(6H,m),1.00-1.32(4H,m),1.85-2.04(2H,m),2.48-2.58(1H,m),2.72(1H,dd,J=6.4 Hz,15.0 Hz),2.85(1H,dd,J=10.4 Hz,14.8Hz),3.10-3.25(1H,m),4.12-4.23(1H,m),4.44-4.62(2H,m),6.95(1H,t,J=7.5 Hz),7.04(1H,t,J=7.5 Hz),7.09(1H,d,J=1.2 Hz),7.28(1H,d,J=7.5 Hz),7.57+7.58(1H,d×2,J=7.5 Hz,J=7.5 Hz),7.85+7.86(1H,d×2,J=9.8 Hz,J=9.8 Hz),8.12+8.15(1H,d×2,J=8.5 Hz,J=8.5 Hz),8.24-8.31(1H,m),10.77(1H,d,J=1.2 Hz)

Optical Rotation: [α]$_D^{20}$=+8.3°(c 0.64,DMSO)

EXAMPLE 45

Synthesis of Compound 47 and 48

(1) Preparation of N-[(1-perhydroazepinyl)carbonyl]-L-leucine benzyl ester

TEA (0.73 ml) was added dropwise to a suspension of Leu-OBzl.TsOH (1.97 g) and CDI (0.85 g) in THF (10 ml) at 0°~5° C. over a period of 5 min and the mixture was stirred at the same temperature for 1 h. Perhydroazepine (0.67 ml) was added and the reaction mixture was stirred at room temperature for 14 h, and poured into water (100 ml). The resulting precipitate was collected by filtration to afford the product (1.75 g).

FAB-MS(m/e,(C$_{20}$H$_{30}$N$_2$O$_3$+H)$^+$):365

(2) Preparation of N-[(1-perhydroazepinyl)carbonyl]-L-leucine

The compound obtained in (1) (1.75 g) was dissolved in methanol (30 ml). 10% Pd-C (0.30 g) was added and the mixture was stirred vigorously at room temperature under atmospheric pressure of hydrogen for 1.5 h. The catalyst was filtered off and the filtrate was concentrated to give the product (1.2 g) as a colorless foam.

FAB-MS(m/e,(C$_{13}$H$_{24}$N$_2$O$_3$H)$^+$):257

(3) Preparation of N-[N-[(1-perhydroazepinyl)carbonyl]-L-leucyl]-D-tryptophan methyl ester The compound obtained in (2) (1.08 g) and DTrp-Ome.Hcl (1.02 g) were dissolved in DMF (10 ml), and TEA (0.57 ml), HOBT.H$_2$O (613 mg) and EDCI.HCl (805 mg) were added at 0°~5° C. The reaction mixture was stirred at 0°~5° C. for 1.5 h and at room temperature for 4 h. Water was added to the reaction mixture and the resulting mixture was extracted with ethyl acetate. The combined organic layers were washed with 1N HCl and sat. NaHCO$_3$, dried over MgSO$_4$, filtered, and concentrated under reduced pressure. The residue was purified by MPLC (Merck, LiChroprep Si 60) with dichloromethane/methanol=30/1 for elution to give the product (1.55 g) as a colorless powder.

FAB-MS(m/e,(C$_{25}$H$_{36}$N$_4$O$_4$+H)$^+$):457

(4) Preparation of N-[N-[(1-perhydroazepinyl)carbonyl]-L-leucyl]-D-tryptophan

The compound obtained in (3) (1.29 g) was dissolved in methanol (5.0 ml) and 1N NaOH (3.1 ml) was added at 0°~5° C. Then the reaction mixture was stirred at room temperature for 2 h. 1N HCl (3.1 ml) was added to the mixture and the resulting mixture was concentrated under reduced pressure. The residue was dissolved in ethyl acetate. The solution was washed with 1N HCl and brine, dried over MgSO$_4$, filtered, and concentrated under reduced pressure. The residue was crystallized from methanol (5 ml)/ethyl acetate (30 ml)/hexane (60 ml) to give the product (0.97 g) as colorless crystals.

FAB-MS(m/e,(C$_{24}$H$_{34}$N$_4$O$_4$+H)$^+$):443

(5) Preparation of Compound 47

The compound obtained in (4) (44 mg) and DHis-OMe.2HCl (29 mg) was dissolved in DMF (1.0 ml). TEA (33 μl), HOBT.H$_2$O (18 mg) and EDCI.HCl (23 mg) were added at 0°~5° C., and the resulting mixture was stirred at 0°~5°C. for 2 h and at room temperature for 5 h. Sat. NaHCO$_3$ was added to the reaction mixture and the resulting mixture was extracted with dichloromethane. The combined organic layers were dried over MgSO$_4$, filtered, and concentrated under reduced pressure. The residue was purified by preparative TLC (Merck, Kieselgel 60 F$_{254}$) with chloroform/methanol=10/1 for elution to give Compound 47 (49 mg) as a pale yellow powder.

m.p.: 115°–123° C.
IR(KBr,cm$^{-1}$):3412,2932,1743,1671,1536
High Resolution
FAB-MS(m/e,(C$_{31}$H$_{43}$N$_7$O$_5$+H)$^+$): Calcd: 594.3404 Found: 594.3375
$^1$H-NMR(300 MHz,CDCl$_3$, δppm):0.86(3H,d,J=5.9 Hz),0.87(3H,d,J=5.9 Hz),1.40–1.70(11H,m),2.97(1H,dd,J=10.3 Hz,14.9 Hz),3.10–3.35(6H,m),3.44–3.52(1H,m),3.65–3.80(1H,m),3.71(3H,s),4.50–4.57(1H,m),4.64(1H,d,J=6.5 Hz),4.73–4.80(1H,m),6.29(1H,d,J=8.3 Hz),6.72(1H,s),6.79(1H,s),7.10(1H,dt,J=1.2 Hz,7.7 Hz),7.19(1H,dt,J=1.2 Hz,7.7 Hz),7.27(1H,s),7.40(1H,dd,J=1.2 Hz,7.7 Hz),7.46(1H,d,J=7.3 Hz),7.55(1H,dd,J=1.2 Hz,7.7 Hz),8.35(1H,brs)

(6) Preparation of Compound 48

Compound 47 obtained in (5) (32 mg) was dissolved in methanol (0.30 ml) and 1N NaOH (80 μl) was added. The mixture was stirred at room temperature for 3 h. 1N HCl (80 μl) was added to the mixture and the resulting mixture was concentrated under reduced pressure. The residue was dissolved in water (10 ml) and the aqueous solution was charged on a SEP-PAK C$_{18}$ cartridge (Waters). The cartridge was washed with water and eluted with methanol. The eluate was concentrated under reduced pressure and the residue was triturated with ether to give the title compound (31 mg) as a colorless powder.

m.p.: 157°–162° C.
IR(KBr,cm$^{-1}$):3406,2926,2860,1629,1533,1464,1446,1395,743
FAB-MS(m/e,(C$_{30}$H$_{41}$N$_7$O$_5$+H)$^+$):580
$^1$H-NMR(300 MHz,DMSO-d$_6$, δppm):0.72(3H,d,J=6.1 Hz),0.76(3H,d,J=6.1 Hz),1.15–1.65(11H,m),2.84(1H,dd,J=10.0 Hz,14.9 Hz),2.93–3.05(2H,m),3.20–3.50(5H,m),4.00–4.08(1H,m),4.35–4.52(2H,m),6.02(1H,d,J=7.1 Hz),6.82(1H,s),6.94(1H,t,J=7.6 Hz),7.03(1H,t,J=7.6 Hz),7.07(1H,d,J=2.3 Hz),7.29(1H,d,J=7.6 Hz),7.54(1H,s),7.55(1H,d,J=7.6 Hz),8.02(1H,d,J=8.3 Hz),8.30(1H,d,J=7.7 Hz),10.76(1H,d,J=2.3 Hz)

Each Compound 49–53 described in the following Examples 46–48 was prepared using each corresponding amino acid in the same manner described in Example 45-(5) and -(6).

EXAMPLE 46

(1) Compound 49
m.p.: 114°–116° C.
IR(KBr,cm$^{-1}$):3418,1750,1668,1635,1521,1469,1444,741
FAB-MS(m/e,(C$_{36}$H$_{46}$N$_6$O$_5$+H)$^+$):643
$^1$H-NMR(300 MHz,DMSO-d$_6$, δppm):0.71(3H,d,J=5.8 Hz),0.76(3H,d,J=5.8 Hz),1.14–1.65(11H,m),2.82(1H,dd,J=10.2 Hz,14.5 Hz),3.08–3.30(7H,m),3.50(3H,s),3.96–4.06(1H,m),4.46–4.54(2H,m),6.07(1H,d,J=7.1 Hz),6.93(1H,t,J=7.9 Hz),7.00(2H,t,J=7.9 Hz),7.06(1H,t,J=7.9 Hz),7.06(1H,d,J=2.0 Hz),7.17(1H,d,J=2.0 Hz),7.29(1H,d,J=7.9 Hz),7.33(1H,d,J=7.9 Hz),7.46(1H,d,J=7.9 Hz),7.53(1H,d,J=7.9 Hz),8.05(1H,d,J=7.5 Hz),8.44(1H,d,J=7.5 Hz),10.77(1H,d,J=2.0 Hz),10.83(1H,d,J=2.0 Hz)

(2) Compound 50
m.p.: 148°–153° C.
IR(KBr,cm$^1$):3418,2932,1638,1521,1464,1443,741
High Resolution
FAB-MS(m/e,(C$_{35}$H$_{44}$N$_6$O$_5$+H)$^+$): Calcd: 629.3452 Found: 629.3424
$^1$H-NMR(300 MHz,DMSO-d$_6$,δppm):0.73(3H,d,J=7.2 Hz),0.75(3H,d,J=7.2 Hz),1.14–1.65(11H,m),2.75–2.90(1H,m),3.00–3.35(7H,m),4.05–4.16(1H,m),4.20–4.33(1H,m),4.39–4.50(1H,m),6.02(1H,d,J=6.9 Hz),6.92(2H,t,J=7.6 Hz),7.01(2H,t,J=7.6 Hz),7.04(1H,brs),7.12(1H,brs),7.28(2H,d,J=7.6 Hz),7.51(2H,d,J=7.6 Hz),7.85–8.03(2H,m),10.72(1H,brs),10.75(1H,brs)
Optical Rotation: [α]$_D^{20}$=+25.2 (c 0.38,MeOH)

EXAMPLE 47

(1) Compound 51
m.p.: 169°–173° C.
IR(XBr,cm$^{-1}$):3292,2932,1737,1635,1527,1461,1443,1305,1197,741
High Resolution
FAB-MS(m/e,(C$_{29}$H$_{43}$N$_5$O$_5$+H)$^+$): Calcd: 542.3342 Found: 542.3382
$^1$H-NMR(300 MHz,CDCl$_3$,δppm):0.83(6H,d,J=6.1 Hz),1.09(3H,d,J=6.9 Hz),1.42–1.72(1H,m),2.22(1H,dd,J=8.0 Hz,15.4 Hz),2.52(1H,dd,J=4.9 Hz,15.4 Hz),3.14–3.55(6H,m),3.62(3H,s),3.76–3.87(1H,m),4.25–4.38(1H,m),4.58(1H,d,J=6.7 Hz),4.73–4.80(1H,m),6.21(1H,d,J=8.8 Hz),7.05(1H,d,J=7.9 Hz),7.08(1H,d,J=1.3 Hz),7.10(1H,dt,J=1.3 Hz,7.5 Hz),7.19(1H,dt,J=1.3 Hz,7.5 Hz),7.35(1H,dd,J=1.3 Hz,7.5 Hz),7.61(1H,dd,J=1.3 Hz,7.5 Hz),8.08(1H,d,J=1.3 Hz)

(2) Compound 52
m.p.: 117°–120° C.
IR(KBr,cm$^{-1}$):3322,2932,1716,1638,1536,1461,1299,1194,741
High Resolution
FAB-MS(m/e,(C$_{28}$H$_{41}$N$_5$O$_5$+H)$^+$): Calcd: 528.3186 Found: 528.3203
$^1$H-NMR(300 MHz,DMSO-d$_6$,δppm):0.69(3H,d,J=6.2 Hz),0.76(3H,d,J=6.2 Hz),1.12(3H,d,J=6.5 Hz),1.10–1.65(11H,m),2.12(1H,dd,J=9.2 Hz,15.5 Hz),2.36(1H,dd,J=4.9 Hz,15.5 Hz),2.84(1H,dd,J=10.5 Hz,14.7 Hz),3.17–3.41(5H,m),3.89–3.98(1H,m),4.00–4.17(1H,m),4.28–4.36(1H,m),6.08(1H,d,J=6.6 Hz), 6.94(1H,dt,J=1.3 Hz,7.6 Hz),7.03(1H,dt,J=1.3 Hz,7.6 Hz),7.07(1H,d,J=1.8 Hz),7.29(1H,dd,J=1.3 Hz,7.6 Hz),7.53(1H, dd,J=1.3 Hz,7.6 Hz),7.87(1H,d,J=8.1 Hz),8.11(1H,d,J=8.5 Hz),10.76(1H,d,J=1.8 Hz),12.11(1H,brs)

EXAMPLE 48

Compound 53
m.p.: 151°–159° C.
IR(KBr,cm$^{-1}$):3322,2932,1641,1533,1461,1212,1047
High Resolution
FAB-MS(m/e,(C$_{26}$H$_{39}$N$_5$O$_6$S+H)$^+$): Calcd: 550.2699 Found: 550.2724
$^1$H-NMR(300 MHz,DMSO-d$_6$, δppm):0.71+0.80(3H,d×2,J=6.0 Hz,J=6.0 Hz),0.78+0.85(3H,d×2,J=6.0 Hz,J=6.0 Hz),1.23–1.66(11H,m),2.-50–2.60(2H,m),2.88(1H,dd,J=9.7 Hz,15.2 Hz),3.04(1H,dd,J=6.0 Hz,15.2 Hz),3.18–3.48(6H,m),3.-98–4.15(1H,m),4.29–4.40(1H,m),6.08(1H,d,J=7.3 Hz),6.93(1H,t,J=7.9 Hz),7.03(1H,t,J=7.9 Hz),7.05(1H,d,J=2.2 Hz),7.29(1H,d,J=7.9 Hz),7.50+7.52(1H,d×2,J=7.9 Hz,J=7.9 Hz),7.62+8.01(1H,d×2,J=7.8 Hz,J=8.5 Hz),7.80+7.97(1H,t×2,J=5.5 Hz,J=5.5 Hz),10.78(1H,d,J=2.2 Hz)

EXAMPLE 49

Synthesis of Compound 30

(1) Preparation of Z-DTrp-βAla-OEt

Z-DTrp-OH (3.21 g) and βAla-OEt.HCl (1.49 g) were suspended in dichloromethane (30 ml), and N-methylmorpholine (1.05 g) and HOBT.H$_2$O (1.59 g) were added at room temperature, and then EDCI.HCl (11.99 g) was added at 0°~5° C. The reaction mixture was stirred at room temperature overnight, diluted with dichloromethane, washed successively with sat. NaHCO$_3$, 1N HCl and brine, dried over MgSO$_4$, filtered, and concentrated under reduced pressure. The residue was purified by dry column flash chromatography (Merck, Kieselgel 60) with dichloromethane/methanol=30/1 for elution to give the product (3.02 g).

FAB-MS(m/e,(C$_{24}$H$_{27}$N$_3$O$_5$+H)$^+$):438

(2) Preparation of DTrp-βAla-OEt

The compound obtained in (1) (650 mg) was dissolved in methanol (10 ml) and 10% Pd-C (118 mg) was added. The resulting mixture was vigorously stirred at room temperature under atmospheric pressure of hydrogen overnight. The catalyst was filtered off through Celite and the filtrate was concentrated under reduced pressure to give the product (450 mg).

FAB-MS(m/e,(C$_{16}$H$_{21}$N$_3$O$_3$+H)$^+$):304

(3) Preparation of Boc-MeLeu-DTrp-βAla-OEt

The compound obtained in (2) (605 mg), Boc-MeLeu-OH (490 mg) and HOBT.H$_2$O (306 mg) were dissolved in dichloromethane (10 ml), and EDCI.HCl (383 mg) was added at 0°~5° C. The reaction mixture was stirred at room temperature overnight, washed successively with sat. NaHCO$_3$ and brine, dried over Na$_2$SO$_4$, filtered, and concentrated under reduced pressure. The residue was purified by MPLC (Merck, LiChroprep Si 60) with dichloromethane/methanol=40/1 for elution to give the product (726 mg).

FAB-MS(m/e,(C$_{28}$H$_{42}$N$_4$O$_6$+H)$^+$):531

(4) Preparation of Compound 30

Compound 30 (53.1 mg) was prepared by alkaline hydrolysis of the compound obtained in (3) (56.1 mg) in the same manner described in Example 29-(2). The product was identified as the expected compound by comparing its
m.p., and its data in
IR,
FAB-MS, $^1$H-NMR and optical rotation with those of the authentic sample of Compound 30 obtained in Example 30.

EXAMPLE 50

Synthesis of Compound 54

Compound 54 was prepared using Boc-Ile-OH as a starting material in the same manner described Example 49-(3) and -(4).

m.p.: 113°–114.5° C.
IR(KBr,cm$^{-1}$):3328,2974,2932,1653,1536,1461,1395,-1371,1248,1167,741
High Resolution
FAB-MS(m/e,(C$_{25}$H$_{36}$N$_4$O$_6$+H)$^+$): Calcd: 489.2713 Found: 489.2701
$^1$H-NMR(300 MHz,DMSO-d$_6$,δppm):0.47(3H,d,J=6.6 Hz),0.65(3H,t,J=7.1 Hz),0.77–0.97(1H,m),1.10–1.26(1H,m),1.36(9H,s),1.36–1.56(1H,m),2.28–2.39(2H,m),2.89(1H,dd,J=9.3 Hz,14.9 Hz),3.14(1H,dd,J=3.9 Hz,14.9 Hz),3.16–3.32(2H,m), 3.73(1H,t,J=7.5 Hz),4.38–4.49(1H,m),6.74(1H,d,J=7.5 Hz),6.94(1H,t,J=7.6 Hz),7.02(1H,t,J=7.6 Hz),7.08(1H,d,J=1.1 Hz),7.28(1H,d,J=7.6 Hz),7.54(1H,d,J=7.6 Hz),7.92(1H,t,J=5.3 Hz),8.10(1H,d,J=8.1 Hz),10.74(1H,d,J=1.1 Hz),12.19(1H,brs)

Optical Rotation: $[\alpha]_D^{20}$=+10.3°(c 0.64,MeOH),

EXAMPLE 51

Synthesis of Compound 55

(1) Preparation of Leu-DTrp-βAla-OEt

To Boc-Leu-DTrp-βAla-OEt (760 mg) obtained in Example 29-(1) was added 20% ethanedithiol/TFA (25 ml) at 0°~5° C. The reaction mixture was stirred at 0°~5° C. for 30 min, and concentrated under reduced pressure. Toluene was added to the residue and the solution was again concentrated under reduced pressure. These procedures were repeated 3 times. The resulting residue was dissolved in ether (5 ml). Addition of hexane (ca. 10 ml) caused precipitation. Filtration of a precipitate, followed by drying in vacuo gave Leu-DTrp-βAla-OEt.TFA (781 mg) as a pale yellow solid. To the solid (781 mg) was added sat. NaHCO$_3$. Extraction with chloroform, followed by drying the organic layer over MgSO$_4$, and concentration of the resulting solution under reduced pressure, gave the product (479 mg).

(2) Preparation of N-[N-(N-thenoyl-L-leucyl)-D-tryptophanyl-β-alanine ethyl ester To a solution of 2-thiophenecarboxylic acid (16.6 mg), HOBT.H$_2$O (21.6 mg) and EDCI.HCl (27.0 mg) in dichloromethane (1 ml) was added a solution of the compound obtained in (1) (49.0 mg) in dichloromethane (1 ml). The reaction mixture was stirred at room temperature overnight, washed successively with water, sat. NaHCO$_3$, 1N HCl and brine, dried over Na$_2$SO$_4$, filtered, and concentrated under reduced pressure. The residue was purified by preparative TLC (Merck, Kieselgel 60 F$_{254}$) with chloroform/methanol=10/1 for development to give the product (48.3 mg).

(3) Preparation of Compound 55

The compound obtained (2) (42.9 mg) was dissolved in ethanol (1 ml) and 1N NaOH (90 μl) was added. The mixture was stirred at room temperature for 5 h and concentrated under reduced pressure. The residue was diluted with water and washed with ether to remove soluble materials in ether. The aqueous solution was acidified to pH 3 with 1N HCl and extracted with ethyl acetate. The combined organic layers were dried over $Na_2SO_4$, filtered, and concentrated to give the title compound (39.3 mg) as a colorless powder.

m.p.: 105°–107° C.
IR(KBr,cm$^{-1}$):3414,2962,1719,1638,1548,1464,1425,1362,1341,1290
High Resolution
FAB-MS(m/e,($C_{25}H_{30}N_4O_5S$+H)$^+$): Calcd: 499.2015 Found: 499.2011
$^1$H-NMR(300MHz,DMSO-d$_6$,δppm):0.73(3H,d,J=6.0 Hz),0.78(3H,d,J=6.0 Hz),1.19–1.43(3H,m),2.38(2H,t,J=7.2 Hz),2.88(1H,dd,J=10.0 Hz,14.4 Hz),3.11–3.35(3H,m),4.31–4.48(2H,m),6.92(1H,t,J=7.7 Hz),7.02(1H,t,J=7.7 Hz),7.08(1H,d,J=2.2 Hz),7.11(1H,dd,J=3.8 Hz,5.1 Hz),7.29(1H,d,J=7.7 Hz),7.56(1H,d,J=7.7 Hz),7.75(1H,dd,J=1.4 Hz,5.1 Hz),7.87(1H,dd,J=1.4 Hz,3.8 Hz),7.98(1H,t,J=8.0 Hz),8.30(1H,d,J=8.3 Hz),8.46(1H,d,J=7.3 Hz),10.77(1H,d,J=2.2 Hz),12.18(1H,brs)

Each Compound 56–65 in the following Examples 52–61 was prepared using each corresponding amino acid in the same manner described in Example 51-(2) and -(3).

EXAMPLE 52

Compound 56
m.p.: 110°–112° C.
IR(KBr,cm$^{-1}$):3412,3100,2956,1719,1644,1548,1461,1443,1341,1284
High Resolution
FAB-MS(m/e,($C_{25}H_{30}N_4O_5S$+H)$^+$): Calcd: 499.2015 Found: 499.2031
$^1$H-NMR(300 MHz,DMSO-d$_6$,δppm):0.73(3H,d,J=6.0 Hz),0.78(3H,d,J=6.0 Hz),1.19–1.42(3H,m),2.38(2H,t,J=7.2 Hz),2.88(1H,dd,J=10.0 Hz,14.7 Hz),3.12–3.35(3H,m),4.30–4.45(2H,m),6.92(1H,t,J=8.0 Hz),7.02(1H,t,J=8.0 Hz),7.08(1H,d,J=1.8 Hz),7.29(1H,d,J=8.0 Hz),7.51–7.60(3H,m),7.99(1H,t,J=5.6 Hz),8.20(1H,dd,J=1.4 Hz,2.8 Hz),8.26(1H,d,J=6.8 Hz),8.27(1H,d,J=8.5 Hz),10.77(1H,d,J=1.8 Hz),12.18(1H,brs)

EXAMPLE 53

Compound 57
m.p.: 131°–132° C.
IR(KBr,cm$^{-1}$):3418,2962,1719,1653,1596,1533,1464,1443,1341,1290
High Resolution
FAB-MS(m/e,($C_{25}H_{30}N_4O_6$+H)$^+$): Calcd: 483.2244 Found: 483.2230
$^1$H-NMR(300 MHz,DMSO-d$_6$,δppm):0.71–0.81(6H,m),1.20–1.43(3H,m),2.17–2.28(2H,m),2.89(1H,dd,J=9.5 Hz,14.4 Hz),3.10–3.40(3H,m),4.34–4.48(2H,m),6.60(1H,dd,J=1.4 Hz,3.2 Hz),6.91(1H,t,J=7.1 Hz),7.01(1H,t,J=7.1 Hz),7.06(1H,d,J=1.5 Hz),7.22(1H,d,J=3.2 Hz),7.28(1H,d,J=7.1 Hz),7.55(1H,d,J=7.1 Hz),7.81(1H,d,J=1.4 Hz),8.06–8.15(1H,m),8.49(1H,d,J=8.7 Hz),8.31(1H,d,J=8.1 Hz),10.77(1H,brs),12.15(1H,brs)

EXAMPLE 54

Compound 58
m.p.: 103°–110° C.
IR(KBr,cm$^{-1}$):3322,2962,1722,1647,1539,1461,1443,1392,1344,1236,1197,1164,1071
High Resolution
FAB-MS(m/e,($C_{25}H_{30}N_4O_6$+H)$^+$): Calcd: 483.2244 Found: 483.2216
$^1$H-NMR(300 MHz,DMSO-d$_6$,δppm):0.72(3H,d,J=5.9 Hz),0.77(3H,d,J=5.8 Hz),1.20–1.40(3H,m),2.37(2H,t,J=7.1 Hz),2.88(1H,dd,J=10.3 Hz,14.7 Hz),3.08–3.35(3H,m),4.30–4.45(2H,m),6.90(1H,dd,J=0.9 Hz,1.8 Hz),6.93(1H,dt,J=0.8 Hz,7.5 Hz),7.03(1H,dt,J=0.8 Hz,7.5 Hz),7.08(1H,d,J=1.6 Hz),7.28(1H,d,J=7.5 Hz),7.56(1H,d,J=7.5 Hz),7.70(1H,dd,J=1.5 Hz,1.8 Hz),7.99(1H,t,J=5.4 Hz),8.16(1H,d,J=7.2 Hz),8.22(1H,dd,J=0.9 Hz,1.5 Hz),8.29(1H,d,J=9.0 Hz),10.77(1H,d,J=1.6 Hz),12.08(1H,brs)

EXAMPLE 55

Compound 59
m.p.: 98°–105° C.
IR(KBr,cm$^{-1}$):3304,3076,2962,1725,1647,1548,1443,1344,1236,1194
High Resolution
FAB-MS(m/e,($C_{26}H_{32}N_4O_5S$+H)$^+$): Calcd: 513.2172 Found: 513.2142
$^1$H-NMR(300 MHz,DMSO-d$_6$,δppm):0.66(3H,d,J=5.8 Hz),0.71(3H,d,J=5.9 Hz),1.08–1.26(3H,m),2.34(2H,t,J=6.4 Hz),2.85(1H,dd,J=10.3 Hz,14.4 Hz),3.14(1H,dd,J=3.4 Hz,14.4 Hz),3.20(2H,dt,J=5.4 Hz,5.1 Hz),3.62(1H,d,J=1.52 Hz),3.67(1H,d,J=15.2 Hz),4.12–4.22(1H,m),4.38(1H,ddd,J=3.4 Hz,7.8 Hz,10.3 Hz),6.86(1H,dd,J=0.9 Hz,3.3 Hz),6.89(1H,dd,J=3.3 Hz,4.2 Hz),6.96(1H,dt,J=1.2 Hz,7.5 Hz),7.03(1H,dt,J=1.2 Hz,7.5 Hz),7.07(1H,d,J=8 Hz),7.29(1H,d,J=7.5 Hz),7.31(1H,dd,J=0.9 Hz,4.2 Hz),7.56(1H,d,J=7.5Hz),7.95(1H,t,J=5.4 Hz),8.23(1H,d,J=7.5 Hz),8.28(1H,d,J=8.7 Hz),10.78(1H,d,J=1.8 Hz),12.17(1H,brs)

EXAMPLE 56

Compound 60
m.p.: 94°–102° C.
IR(KBr,cm$^{-1}$): 3418,2962,1719,1647,1542,1461,1443,1344,1233,1194
High Resolution FAB-MS(m/e, ($C_{26}H_{32}N_4O_5S$+H)$^+$): Calcd: 513.2172 Found: 513.2133
$^1$H-NMR(300 MHz,DMSO-d$_6$,δppm): 0.66(3H,d,J=5.8 Hz),0.72(3H,d,J=5.9 Hz),1.08–1.25(3H,m),2.31(2H,t,J=7.1 Hz),2.85(1H,dd,J=10.3 Hz,14.4 Hz),3.14(1H,dd,J=4.3 Hz,14.4 Hz),3.22(2H,dt,J=5.1 Hz,7.1 Hz),3.40(1H,d,J=15.3 Hz),3.45(1H,d,J=15.3 Hz),4.12–4.22(1H,m),4.40(1H,ddd,J=4.3 Hz,7.2 Hz,10.3 Hz),6.93(1H,dt,J=1.8 Hz,7.5 Hz),6.96(1H,dd,j=1.5 Hz,4.8 Hz),7.03(1H,dt,J=1.8 Hz,7.5 Hz),7.06(1H,d,J=2.0 Hz),7.19(1H,dd,J=1.5 Hz,3.0 Hz),7.29(1H,d,J=7.5 Hz),7.40(1H,dd,J=3.0 Hz,4.8 Hz),7.56(1H,d,J=7.5 Hz),7.94(1H,t,J=5.1 Hz),7.17(1H,d,J=7.2 Hz),8.25(1H,d,J=7.5 Hz),10.78(1H,d,J=2.0 Hz),12.15(1H,brs)

EXAMPLE 57

Compound 61 m.p.: 85°–90° C.
IR(KBr,cm$^{-1}$):
3424,2956,2866,1716,1647,1545,1461,1392,1233,744
High Resolution FAB-MS(m/e,(C$_{27}$H$_{38}$N$_4$O$_5$+H)$^+$): Calcd: 499.2921 Found: 499.2915
$^1$H-NMR(300 MHz,DMSO-d$_6$,δppm):
0.68(3H,d,J=5.7 Hz),0.74(3H,d,J=5.7 Hz),1.01–1.35(6H,m),1.38–1.71(6H,m),2.02–2.15(2H,m),2.37 (2H,t,J=7.2 Hz),2.85(1H,dd,J=10.3 Hz,14.1 Hz),3.13–3.37(3H,m),4.05–4.18(1H,m),4.31–4.42(1H,m),6.94(1H,t,J=7.6 Hz),7.02(1H,t,J=7.6 Hz),7.07(1H,d,J=1.9 Hz),7.29(1H,d,J=7.6 Hz),7.54(1H,d,J=7.6 Hz),7.92(1H,d,J=6.8 Hz),7.96(1H,t,J=5.4 Hz),8.19(1H,d,J=8.2 Hz),10.77(1H,brs),12.17(1H,brs)

EXAMPLE 58

Compound 62 m.p.: 215° C.(dec.)
IR(KBr,cm$^{-1}$):
3442,3286,2962,1647,1584,1566,1425,651
High Resolution FAB-MS(m/e,(C$_{26}$H$_{36}$N$_4$O$_5$+H)$^+$): Calcd: 485.2764 Found: 485.2741
$^1$H-NMR(300 MHz,DMSO-d$_6$,δppm):
0.70(3H,d,J=5.7 Hz),0.76(3H,d,J=5.7 Hz),1.20–1.29(3H,m),1.41–1.76(8H,m),1.95–2.08(2H,m),2.55–2.67(1H,m),2.89(1H,dd,J=10.7 Hz,15.0 Hz),3.09–3.42(3H,m),4.15–4.27(1H,m),4.30–4.41(1H,m),6.94(1H,t,J=7.5 Hz),7.02(1H,t,J=7.5 Hz),7.07(1H,brs),7.29(1H,d,J=7.5 Hz),7.54(1H,d,J=7.5 Hz),8.04–8.17(2H,m),8.18–8.31(1H,m),10.85(1H,brs)

EXAMPLE 59

Compound 63 m.p.: 115°–122° C.
IR(KBr,cm$^{-1}$): 3298,2926,2854,1719,1650,1548,1194
High Resolution FAB-MS(m/e,(C$_{28}$H$_{40}$N$_4$O$_5$+H)$^+$): Calcd: 513.3077 Found: 513.3101
$^1$H-NMR(300 MHz,DMSO-d$_6$,δppm):
0.67(3H,d,J=5.9 Hz),0.74(3H,d,J=5.6 Hz),0.88–98(3H,m),0.99–1.36(6H,m),1.87–2.03(2H,m),2.37(2H,t,J=7.3 Hz),2.84(1H,dd,J=10.8 Hz,14.6 Hz), 3.08–3.30(3H,m),4.08–4.14(1H,m),4.32–4.36(1H,m),6.94(1H,t,J=7.5 Hz),7.03(1H,t,J=7.5 Hz),7.06(1H,d,J=1.2 Hz),7.29(1H,d,J=7.5 Hz),7.54(1H,d,J=7.5 Hz),7.88–8.03(2H,m),8.22(1H,d,J=8.6 Hz),10.78(1H,d,J=1.2 Hz),12.21(1H,brs)

EXAMPLE 60

Compound 64 m.p.: 158°–164° C.
IR(KBr,cm$^{-1}$):
3316,3064,2932,2860,1719,1650,1539,1455,1392,1344,1212,1098
High Resolution FAB-MS(m/e,(C$_{27}$H$_{38}$N$_4$O$_5$+H)$^+$): Calcd: 499.2921 Found: 499.2908
$^1$H-NMR(300 MHz,DMSO-d$_6$,δppm):
0.67(3H,d,J=5.6 Hz),0.73(3H,d,J=5.9 Hz),0.80–0.92(3H,m),1.02–1.41(6H,m),1.48–1.75(5H,m),2.13(2H,t,J=7.0 Hz),2.85(1H,dd,J=10.1 Hz,14.4 Hz),3.14(1H,dd,J=3.6 Hz,14.4 Hz),3.20–3.40(2H,m),4.04–4.15(1H,m),4.30–4.47(1H,m),6.93(1H,t,J=7.5 Hz),7.03(1H,t,J=7.5 Hz),7.05(1H,d,J=1.2 Hz),7.29(1H,d,J=7.5 Hz),7.53(1H,d,J=7.5 Hz),7.80(1H,d,J=7.2 Hz),7.92–8.05(1H,m),8.10(1H,d,J=8.4 Hz),10.77(1H,d,J=1.2 Hz),12.17(1H,brs)

EXAMPLE 61

Compound 65 m.p.: 173°–178° C.
IR(KBr,cm$^{-1}$):
3418,3298,1635,1566,1416,1252,1229,740
High Resolution FAB-MS(m/e,(C$_{24}$H$_{32}$N$_4$O$_5$+H)$^+$): Calcd: 457.2451 Found: 457.2445
$^1$H-NMR(300 MHz,DMSO-d$_6$,δppm):
0.66–0.82(6H,m),1.11–1.42(5H,m),1.48–1.95(3H,m),1.95–2.20(2H,m),2.86(1H,dd,J=10.5 Hz,14.0 Hz),3.03–3.30(3H,m),4.14–4.27(1H,m),4.28–4.43(1H,m),6.93(1H,t,J=7.5 Hz),7.03(1H,t,J=7.5 Hz),7.06(1H,d,J=1.2 Hz),7.29(1H,d,J=7.5 Hz),7.54(1H,d,J=7.5 Hz),7.84–8.14(1H,m),8.39(1H,d,J=7.1 Hz),8.39(1H,d,J=7.1 Hz),10.85(1H,d,J=1.2 Hz)

EXAMPLE 62

(1) Synthesis of Compound 66

Leu-DTrp-βAla-OEt.TFA (39.8 mg) obtained in Example 51-(1), (1,3-dithiol-2-ylidene)malonic acid monomethyl ester (16.4 mg), N-methylmorpholine (8.3 μl) and HOBT.H$_2$O (18.4 mg) were suspended in DMF (0.38 ml) and EDCI.HCl (23.0 mg) was added at 0°–5° C. The reaction mixture was stirred at room temperature for 5 h and concentrated under reduced pressure. A chloroform solution of the residue was washed with 10% aq. citric acid and sat. NaHCO$_3$, dried over MgSO$_4$, filtered, and concentrated under reduced pressure. The residue was purified by preparative TLC (Merck, Kieselgel 60 F$_{254}$) with chloroform/methanol=10/1 for development to give a colorless powder (35.2 mg). The powder (6.2 mg) was suspended in methanol (0.45 ml) and 1N NaOH (50 μl) was added. The mixture was stirred at room temperature for 20 h and purified by TLC (Analytichem International, Empore sheet) with chloroform/acetic acid/water=10/1/1 for development followed by reverse-phase chromatography (Waters, SEP-PAK C$_{18}$ cartridge) with methanol for elution. The methanolic eluate was concentrated under reduced pressure to give the title compound (5.2 mg) as a pale yellow powder.

m.p.: 153°–161° C.
IR(KBr,cm$^{-1}$): 3322,2926,1671,1605,1524,1392
High Resolution FAB-MS(m/e,(C$_{22}$H$_{32}$N$_4$O$_7$S$_2$+H)$^+$): Calcd: 589.1791 Found: 589.1789
$^1$H-NMR(300 MHz,DMSO-d$_6$,δppm):
0.70–0.80(6H,m),1.15–1.35(3H,m),2.20–2.35(2H,m),2.89(1H,dd,J=9.8 Hz,14.4 Hz),3.15–3.50(3H,m),3.79(3H,s),4.30–4.50(2H,m),6.94(1H,t,J=7.3 Hz),7.03(1H,t,J=7.3 Hz),7.09(1H,brs),7.30(1H,d,J=7.3 Hz),7.52(2H,s),7.57(1H,d,J=7.3 Hz),8.00–8.10(1H,m),8.36(1H,d,J=8.4 Hz),8.51(1H,d,J=6.8 Hz),10.80(1H,brs)

(2) Synthesis of Compound 67

Compound 66 obtained (1) (20.0 mg) was suspended in methanol (1.5 ml) and 1N NaOH was added. The mixture was refluxed for 3.5 h and cooled to room temperature. 1N HCl (160 μl) was added, and the resulting mixture was stirred at 50° C. for 2 h and concentrated under reduced pressure. The residue was purified by TLC (Analytichem International, Empore sheet) with chloroform/methanol=1/1 for development followed by reverse-phase chromatography (Waters, SEPPAK C$_{18}$ cartridge) with methanol for elution. The methanolic eluate was concentrated to give the title compound (16.5 mg) as a pale orange powder.

m.p.: 163°–169° C.
IR(KBr,cm$^{-1}$): 3406,3320,1656,1620,1551,1518,1209
High Resolution FAB-MS(m/e,(C$_{25}$H$_{30}$N$_4$O$_5$S$_2$+H)$^+$): Calcd: 531.1736 Found: 531.1763
$^1$H-NMR(300 MHz,DMSO-d$_6$,δppm): 0.68(3H,d,J=6.2 Hz),0.74(3H,d,J=6.2 Hz),1.05–1.25(3H,m),2.-30–2.50(2H,m),2.88(1H,dd,J=10.6 Hz,14.5 Hz),3.15–3.40(3H,m),4.15(1H,q,J=6.9 Hz),4.35–4.45(1H,m),6.24(1H,s),6.-80–6.90(2H,m),6.95(1H,t,J=7.2 Hz),7.03(1H,t,J=7.2 Hz),7.09(1H,d,J=2.1 Hz),7.30(1H,d,J=7.2 Hz),7.56(1H,d,J=7.2 Hz),7.83(1H,d,J=6.9 Hz),8.00–8.10(1H,m),8.36(1H,d,J=8.4 Hz),10.77(1H,d,J=2.1 Hz)

EXAMPLE 63

Synthesis of Compound 68

(1) Preparation of N-[N-[N-(3,3-dimethylbutyryl)-L-leucyl]-D-tryptophanyl]-β-alanine ethyl ester To a solution of Leu-DTrp-βAla-OEt.TFA (33.0 mg) obtained in Example 51-(1) in pyridine (0.5 ml) was added 3,3-dimethylbutyryl chloride (12.8 ml) at 0° C. under nitrogen. The reaction mixture was stirred for 10 min, quenched with water (0.1 ml), and concentrated under reduced pressure. The residue was purified by preparative TLC (Merck, Kieselgel 60 F$_{254}$) with chloroform/methanol=15/1 for development to give the product (21.8 mg).

(2) Preparation of Compound 68

The compound obtained in (1) (14.7 mg) was suspended in ethanol (0.2 ml) and 1N NaOH (43 μl) was added. The mixture was stirred at room temperature for 5 h and concentrated under reduced pressure. The residue was purified by preparative TLC (Analytichem International, Empore sheet) with chloroform/methanol/acetic acid=15/1/1 for development followed by reverse-phase flash chromatography (Nacalai Tesque, Cosmosil 75 C$_{18}$-OPN) with methanol for elution to give the title compound (8.5 mg) as a colorless powder.

m.p.: 65°–70° C.
IR(KBr,cm$^{-1}$): 3310,3064,2956,2920,2854,1719,1650,1539,1464,1443
High Resolution FAB-MS(m/e,(C$_{26}$H$_{38}$N$_4$O$_5$+H)$^+$): Calcd: 487.2921 Found: 487.2910
$^1$H-NMR(300 MHz,DMSO-d$_6$,δppm): 0.68(3H,d,J=5.7 Hz),0.75(3H,d,J=5.7 Hz),0.93(9H,s),1.07–1.26(3H,m),1.94(1H,d,J=12.0 Hz),2.04(1H,d,J=12.0 Hz),2.33–2.60(2H,m),2.85(1H,dd,J=10.1 Hz,14.5 Hz),3.13–3.50(3H,m),4.03–4.15(1H,m),4.-32–4.43(1H,m),6.95(1H,t,J=7.7 Hz),7.04(1H,t,J=7.7 Hz),7.08(1H,d,J=1.9 Hz),7.30(1H,d,J=7.7 Hz),7.55(1H,d,J=7.7 Hz),7.88(1H,d,J=6.7 Hz),7.98(1H,t,J=5.2 Hz),8.23(1H,d,J= 8.2 Hz),10.78(1H,brs)

Each Compound 69-75 in the following Examples 64-70 was prepared using each corresponding acid chloride in the same manner described in Example 63.

EXAMPLE 64

Compound 69 m.p.: 156°–159° C.
IR(KBr,cm$^{-1}$): 3424,3088,2962,2926,1716,1659,1551,1464,1443,1392
High Resolution FAB-MS(m/e,(C$_{25}$H$_{36}$N$_4$O$_5$+H)$^+$): Calcd: 473.2764 Found: 473.2699
$^1$H-NMR(300 MHz,DMSO-d$_6$,δppm): 0.71(3H,d,J=5.8 Hz),0.77(3H,d,J=5.8 Hz),1.07(9H,s),1.21–1.42(3H,m),2.34 2H,d,J=6.8 Hz),2.88(1H,dd,J=9.8 Hz,14.6 Hz),3.08–3.43(3H,m),4.-11–4.22(1H,m),4.34–4.46(1H,m),6.94(1H,t,J=7.6 Hz),7.03(1H,t,J=7.6 Hz),7.06(1H,brs),7.29(1H,d,J=7.6 Hz),7.39(1H,d,J=7.6 Hz),7.55(1H,d,J=7.6 Hz),7.99(1H,d,J=7.6 Hz),7.99(1H,d,J=7.6 Hz),10.79(1H,brs)

EXAMPLE 65

Compound 70 m.p.: 95°–97° C.
IR(KBr,cm$^{-1}$): 3316,2962,1719,1650,1545
High Resolution FAB-MS(m/e,(C$_{28}$H$_{34}$N$_4$O$_5$+H)$^+$): Calcd: 507.2607 Found: 507.2599
$^1$H-NMR(300 MHz,DMSO-d$_4$,δppm): 0.66(3H,d,J=5.6 Hz),0.72(3H,d,J=5.6 Hz),1.10–1.40(3H,m),2.33(2H,t,J=7.4 Hz),5.69(1H,dd,J=10.2 Hz,14.6 Hz),3.10–3.39(3H,m),3.40(1H,d,J=14.2 Hz),3.47(1H,d,J=14.2 Hz),4.10–4.21(1H,m),4.-33–4.47(1H,m),6.95(1H,t,J=7.8 Hz),7.04(1H,t,J=7.8 Hz),7.07(1H,d,J=1.8 Hz),7.14–7.28(5H,m),7.30(1H,d,J=7.8 Hz),7.57(1H,d,J=7.8 Hz),7.95(1H,t,J=5.5 Hz),8.22(1H,d,J=7.0 Hz),8.26(1H,d,J=8.6 Hz),10.79(1H,d,J=1.8 Hz)

EXAMPLE 66

Compound 71 m.p.: 180°–183° C.
IR(KBr,cm$^{-1}$): 3412,2962,1701,1659,1536,1257,1182,1110,741
High Resolution FAB-MS(m/e,(C$_{24}$H$_{34}$N$_4$O$_6$+H)$^-$): Calcd: 475.2556 Found: 475.2529
$^1$H-NMR(300 MHz,DMSO-d$_6$,δppm): 0.69(3H,d,J=6.2 Hz),0.72(3H,d,J=6.2 Hz),1.13(3H,d,J=6.1 Hz),1.14(3H,d,J=6.1 Hz),1.15–1.28(3H,m),2.35(2H,t,J=7.1 Hz),2.87(1H,dd,J=9.8 Hz,14.6 Hz),3.12–3.25(1H,m),3.-20–3.30(2H,m),3.86–3.95(1H,m),4.35–4.44(1H,m),4.-68–4.79(1H,m),6.94(1H,t,J=7.9 Hz),7.02(1H,t,J=7.9 Hz),7.05(1H,d,J=2.5 Hz),7.12(1H,d,J=7.3 Hz),7.29(1H,d,J=7.9 Hz),7.54(1H,d,J=7.9 Hz),7.91(1H,t,J=5.2 Hz),8.10(1H,d,J=8.0 Hz),10.78(1H,d,J=2.5 Hz)

EXAMPLE 67

Compound 72 m.p.: 159°–160° C.
IR(KBr,cm$^{-1}$): 3328,2956,2926,1728,1656,1536,1497,1386,1209,1026,7-41 FAB-MS(m/e,(C$_{29}$,H$_{36}$N$_4$O$_6$+H)$^+$): 537

¹H-NMR(300 MHz,DMSO-d₆,δppm): 0.75(3H,d,J=6.1 Hz),1.16(3H,t,J=7.5 Hz),1.20–1.40(3H,m),2.33(2H,t,J=7.1 Hz),2.88(1H,dd,J=9.7 Hz,14.4 Hz),3.12(1H,dd,J=4.4 Hz,14.4 Hz),3.20–3.32(2H,m),4.03(2H,q,J=7.5 Hz),3.98–4.08(1H,m),4.45(1H,ddd,J=4.4 Hz,8.4 Hz,9.7 Hz),6.94(1H,t,J=7.5 Hz),7.00–7.07(3H,m),7.08(1H,d,J=1.2 Hz),7.18(1H,t,J=7.8 Hz),7.29(1H,d,J=7.5 Hz),7.35(2H,t,J=7.8 Hz),7.56(1H,d,J=7.5 Hz),7.86(1H,d,J=7.8 Hz),7.92(1H,t,J=5.7 Hz),8.23(1H,d,J=8.4 Hz),10.80(1H,d,J=1.2 Hz)

EXAMPLE 68

Compound 73 m.p.: 105°–107.5° C.
IR(KBr,cm⁻¹): 3328,2956,1719,1650,1542,1464,1443,1389,1233,744
High Resolution FAB-MS(m/e,($C_{23}H_{33}N_5O_5$+H)⁺): Calcd: 460.2560 Found: 460.2578
¹H-NMR(300 MHz,DMSO-d₆,δppm): 0.69(3H,d,J=5.6 Hz),0.76(3H,d,J=5.9 Hz),1.03–1.37(3H,m),2.28–2.57(2H,m),2.77(6H,s),2.86(1H,dd,J=10.2 Hz,14.7 Hz),3.09–3.58(3H,m),3.86–3.98(1H,m),4.26–4.37(1H,m),6.19(1H,d,J=6.6 Hz),6.94(1H,t,J=7.5 Hz),7.03(1H,t,J=7.5 Hz),7.07(1H,d,J=2.0 Hz),7.29(1H,d,J=7.5 Hz),7.53(1H,d,J=7.5 Hz),8.00–8.10(1H,m),8.17(1H,d,J=8.3 Hz),10.78(1H,d,J=2.0 Hz)
Optical Rotation: $[\alpha]_D^{20}$=26.7°(c 0.42,MeOH)

EXAMPLE 69

Compound 74 m.p.: 100°–115° C.
IR(KBr,cm⁻¹): 3382,2968,2926,1716,1644,1560
High Resolution FAB-MS(m/e,($C_{30}H_{45}N_5O_5$+H)⁺): Calcd: 556.3499 Found: 556.3488
¹H-NMR(300 MHz,DMSO-d₆,δppm): 0.66(3H,d,J=6.0 Hz),0.71(3H,d,J=6.0 Hz),0.96–1.74(7H,m),1.14(3H,s),1.16(3H,s),1.52(3H,s),1.61(3H,s),1.78–1.99(2H,m),2.33–2.45(2H,m),2.83(1H,dd,J=10.3 Hz,14.6 Hz),3.11–3.40(3H,m),3.86–3.97(1H,m),4.27–4.43(1H,m),5.85(1H,d,J=6.6 Hz),6.94(1H,t,J=7.7 Hz),7.02(1H,t,J=7.7 Hz),7.07(1H,d,J=2.5 Hz),7.28(1H,d,J=7.7 Hz),7.55(1H,d,J=7.7 Hz),8.02–8.15(1H,m),8.25(1H,d,J=8.3 Hz),10.76(1H,d,J=2.5 Hz),12.14(1H,brs)

EXAMPLE 70

Compound 75 m.p.: 148°–151° C.
IR(KBr,cm⁻¹): 3418,3304,2962,1647,1539,1464,1395,741
FAB-MS(m/e,($C_{24}H_{34}N_4O_5$+H)⁺): 459
−¹H-NMR(300 MHz,DMSO-d₆,δppm): 0.71(3H,d,J=6.4 Hz),0.74(3H,d,J=6.4 Hz),0.81(3H,d,J=5.2 Hz),0.83(3H,d,J=5.2 Hz),1.08–1.40(3H,m),1.86–1.99(3H,m),2.93(1H,dd,J=9.2 Hz,14.3 Hz),3.13(1H,dd,J=4.5 Hz,14.3 Hz),3.40–3.60(2H,m),4.20–4.30(1H,m),4.36–4.47(1H,m),6.91(1H,t,J=7.7 Hz),7.01(1H,t,J=7.7 Hz),7.08(1H,d,J=1.7 Hz),7.27(1H,d,J=7.7 Hz),7.52(1H,d,J=7.7 Hz),7.55–7.67(1H,m),8.14–8.28(1H,m),8.28–8.41(1H,m),10.77(1H,d,J=1.7 Hz)

EXAMPLE 71

Compound 76

Synthesis of Compound 76

(1) Preparation of Ph(Me)NCO-Leu-DTrp-βAla-OBzl
Leu-DTrp-βAla-OBzl.TFA (50 mg) prepared in the same manner described in Examples 29-(1) and 51-(1) was dissolved in chloroform (1 ml), and TEA (26 μl) and N-methyl-N-phenylcarbamoyl chloride (16 mg) were successively added to the solution at 0° C. under nitrogen. The mixture was stirred at room temperature for 18 h and at 50° C. for 6.5 h, diluted with chloroform, washed with 1N HCl and water, dried over MgSO₄, filtered, and concentrated under reduced pressure. The residue was purified by MPLC (Merck, LiChroprep Si60) with chloroform/methanol=50/1 for elution to give the product (43 mg).
FAB-MS(m/e,($C_{35}H_{41}N_5O_5$+H)⁺): 612

(2) Preparation of Compound 76
Compound 76 (25 mg) was prepared by catalytic hydrogenation of the compound obtained in (1) (40 mg) in the same manner described in Example 35-(2).
m.p.: 108°–114° C.
IR(KBr,cm⁻¹): 3322,2956,1719,1647,1596,1518,1461,1362,1194,1104
High Resolution FAB-MS(m/e,($C_{28}H_{35}N_5O_5$+H)⁺): Calcd: 522.2717 Found: 522.2704
¹H-NMR(300 MHz,DMSO-d₆,δppm): 0.70(6H,d,J=6.1 Hz),1.04–1.27(3H,m),2.23(2H,t,J=6.9 Hz),2.87(1H,dd,J=9.9 Hz,14.5 Hz),3.05–3.70(3H,m),3.13(3H,s),4.03–4.15(1H,m),4.29–4.40(1H,m),5.73(1H,d,J=7.6 Hz),6.92(1H,t,J=7.5 Hz),7.01(1H,t,J=7.5 Hz),7.05(1H,d,J=1.7 Hz),7.11–7.24(3H,m),7.28(1H,d,J=7.5 Hz),7.31–7.42(2H,m),7.53(1H,d,J=7.5 Hz),7.95–8.05(1H,m),8.15(1H,d,J=8.4 Hz),10.79(1H,d,J=1.7 Hz)
Optical Rotation: $[\alpha]_D^{20}$= +83.8° (c 0.77,DMSO)

EXAMPLE 72

Synthesis of Compound 77

Compound 77 was prepared using N,N-diethylcarbamoyl chloride as a starting material in the same manner described in Example 71.
m.p.: 82°–91° C. High Resolution FAB-MS(m/e,($C_{25}H_{37}N_5O_5$+H)⁻): Calcd: 488.2873 Found: 488.2868 ¹H-NMR(300 MHz,DMSO-d₆,δppm): 0.62–0.74(3H,m),0.74–0.80(3H,m),0.77–0.89(3H,m),0.92–1.09(6H,m),2.15–2.33(2H,m),2.78–2.95(1H,m),3.06–3.45(7H,m),3.88–4.11(1H,m),4.25–4.44(1H,m),6.03–6.18(1H,m),6.93(1H,t,J=7.5 Hz),7.02(1H,t,J=7.5 Hz),7.03–7.11(1H,m),7.29(1H,d,J=7.5 Hz),7.48(1H,d,J=7.5 Hz),7.89–8.23(2H,m),10.72–10.82(1H,m)

EXAMPLE 73

Synthesis of Compound 78

Compound 25 (34 mg) obtained in Example 25 was dissolved in 20% ethanedithiol/TFA (3.4 ml). The mixture was stirred at 0°∼5° C. for 15 min and at room temperature for 10 min, and concentrated under reduced pressure. The residue was triturated with ether to give a colorless powder (28 mg). The obtained powder (26 mg) was dissolved in pyridine (0.20 ml) and ethyl chloroformate (6 μl) was added at 0°~5° C. The mixture was stirred at 0°~5° C. for 1 h and then for another 1 hour after further addition of ethyl chloroformate (6 μl), and concentrated under reduced pressure. Water (2 ml) was added to the residue and insoluble materials were filtered off. The filtrate was passed through columns of cation exchange resins (Amberlite IR-120B:H+-form and then Amberlite IRC-50:Na+-form) and the resins were washed with water. The eluate and washing water is were combined and concentrated under reduced pressure. The residue was dissolved in water (4 ml) and purified by reverse-phase short column chromatography (Waters, SEP-PAK $C_{18}$ cartridge) with water for washing and methanol for elution. The eluate was concentrated under reduced pressure to give the title compound (20 mg) as a colorless powder.

m.p.: 152°–158° C.

IR(KBr,cm⁻¹): 3424,2962,1662,1536,1215,1047,741

High Resolution FAB-MS(m/e,($C_{22}H_{31}N_4NaO_7S$+H)+): Calcd: 519.1890 Found: 519.1882

¹H-NMR(300 MHz,DMSO-d₆,δppm): 0.72(3H,d,J=7.1 Hz),0.74(3H,d,J=7.1 Hz),1.14(3H,t,J=7.1 Hz),1.14–1.32(3H,m),2.50–2.58(2H,m),2.90(1H,dd,J=9.2 Hz,14.4 Hz),3.13(1H,dd,J=4.6 Hz,14.4 Hz),3.24–3.35(2H,m),3.90–3.98(1H,m),3.97(2H,q,J=7.1 Hz),4.32–4.42(1H,m),6.93(1H,t,J=7.8 Hz),7.02(1H,t,J=7.8 Hz),7.05(1H,d,J=1.5 Hz),7.15(1H,d,J=8.1 Hz),7.28(1H,d,J=7.8 Hz),7.53(1H,d,J=7.8 Hz),7.82(1H,t,J=5.7 Hz),8.06(1H,d,J=7.9 Hz),10.79(1H,d,J=1.5 Hz)

EXAMPLE 74

Synthesis of Compound 79

Compound 79 was prepared using isovaleryl chloride and sodium aminomethanesulfonate as starting materials in the same manner described in Example 73.

m.p.: 169°–193° C.

IR(KBr,cm⁻¹): 3310,2962,1656,1536,1194,1047,741

High Resolution FAB-MS(m/e,($C_{23}H_{33}N_4NaO_6S$+H)+): Calcd: 517.2097 Found: 517.2097

¹H-NMR(300 MHz,DMSO-d₆,δppm): 0.68(3H,d,J=6.6 Hz),0.71(3H,d,J=6.6 Hz),0.80(3H,d,J=6.0 Hz),0.82(3H,d,J=6.0 Hz),1.01–1.33(3H,m),1.84–1.98(3H,m),2.90(1H,dd,J=9.3 Hz,14.7 Hz),3.10(1H,dd,J=4.3 Hz,14.7 Hz),3.85(1H,dd,J=6.0 Hz,13.2 Hz),3.92(1H,dd,J=6.0 Hz,13.2 Hz),4.18–4.30(1H,m),4.57–4.62(1H,m),6.92(1H,t,J=7.8 Hz),7.01(1H,t,J=7.8 Hz),7.15(1H,d,J=2.2 Hz),7.27(1H,d,J=7.8 Hz),7.58(1H,d,J=7.8 Hz),7.79(1H,d,J=8.0 Hz),7.87(1H,d,J=8.1 Hz),8.23(1H,t,J=6.0 Hz),10.77(1H,d,J=2.2 Hz)

EXAMPLE 75

Synthesis of Compound 80

To Compound 1 (15.8 mg) obtained in Example 1-(3) was added 20% ethanedithiol/TFA (3 ml) at 0°–5° C. The mixture was stirred at room temperature overnight and concentrated under reduced pressure. The residue was dissolved in chloroform (2 ml) and the pH of the solution was adjusted to 9 with TEA. After tert-butyl isocyanate (100 μl) was added, the reaction mixture was stirred at room temperature overnight and concentrated under reduced pressure. The residue was purified by dry column flash chromatography (Merck, Kieselgel 60) with chloroform/methanol/acetic acid=10/1/1 for elution followed by reverse-phase short column chromatography (Waters, SEP-PAK $C_{18}$ cartridge) with methanol/water=1/10 to methanol for elution. The methanolic eluate was concentrated under reduced pressure to give the title compound (6.36 mg) as a colorless powder.

m.p.: 114.5°–118.5° C.

IR(KBr,cm⁻¹): 3376,2962,2926,1716,1650,1557,1461,1368,1209,741

FAB-MS(m/e,($C_{26}H_{39}N_5O_5$+H)+): 502

¹H-NMR(300 MHz,DMSO-d₆,δppm): 0.68(3H,d,J=6.2 Hz),0.71(3H,d,J=5.8 Hz),0.79–0.92(2H,m),1.08(3H,d,J=6.3 Hz),1.09–1.38(1H,m),1.19(9H,s),1.96(1H,dd,J=7.6 Hz,14.4 Hz),2.11(1H,dd,J=3.2 Hz,14.4 Hz),2.87(1H,dd,J=9.6 Hz,14.5 Hz),3.17(1H,dd,J=4.4 Hz,14.5 Hz),3.85–4.10(2H,m),4.29–4.41(1H,m),6.02(1H,s),6.04(1H,d,J=S.3 Hz),6.93(1H,t,J=7.1 Hz),7.02 (1H,t,J=7.1 Hz),7.08(1H,d,J=1.9 Hz),7.28(1H,d,J=7.1 Hz),7.55(1H,d,J=7.1 Hz),8.08–8.20(2H,m),10.79(1H,d,J=1.9 Hz)

Each Compound 81–83 in the following Examples 76–78 was prepared using Compound 2, 4 or 24 in the same manner described in Example 75.

EXAMPLE 76

Compound 81 m.p.: 126°–128° C.

IR(KBr,cm⁻¹): 3424,2962,2926,1653,1557,1461,1395,1368,1209,744

High Resolution FAB-MS(m/e,($C_{33}H_{42}N_6O_5$+H)+): Calcd: 603.3295 Found: 603.3274

¹H-NMR(300 MHz,DMSO-d₆,δppm): 0.64–0.73(6H,m),0.90–1.14(2H,m),1.18(9H,s),1.50–1.65(1H,m),2.82(1H,dd,J=10.1 Hz,14.8 Hz),3.03–3.45(3H,m),3.98–4.07(1H,m),4.34–4.47(1H,m),4.47–4.58(1H,m),5.77(1H,d,J=7.8 Hz),5.82(1H,s),6.90–7.08(4H,m),7.08(1H,d,J=2.1 Hz),7.16(1H,d,J=2.1 Hz),7.29(1H,d,J=8.0 Hz),7.31(1H,d,J=8.0 Hz),7.53(1H,d,J=8.0 Hz),7.58(1H,d,J=8.0 Hz),8.10(1H,d,J=8.4 Hz),8.10(1H,d,J=8.4 Hz),10.76(2H,brs)

EXAMPLE 77

Compound 82 m.p.: 68°–78° C.

IR(KBr,cm⁻¹): 3454,2926,1680,1206,1185,1137

High Resolution FAB-MS(m/e,($C_{28}H_{39}N_7O_5$+H)+): Calcd: 554.3091 Found: 554.3098

¹H-NMR(300 MHz,DMSO-d₆,δppm): 0.67(6H,d,J=6.4 Hz),0.97–1.15(3H,m),1.17(9H,s),2.78–2.96(2H,m),3.06(1H,dd,J=4.4 Hz,13.9 Hz),3.18(1H,dd,J=2.7 Hz,14.4 Hz),3.97–4.14(2H,m),4.42–4.53(1H,m),5.77(1H,d,J=7.8 Hz),5.84(1H,s),6.81(1H,s),6.94(1H,t,J=7.5 Hz),7.02(1H,t,J=7.5 Hz),7.09(1H,d,J=1.2 Hz),7.29(1H,d,J=7.5 Hz),7.55(1H,s),7.58(1H,d,J=7.5 Hz),8.13–8.24(2H,m),10.77(1H,d,J=1.2 Hz)

EXAMPLE 78

Compound 83

IR(KBr,cm⁻¹): 3412,2962,1659,1551,1461,1209,1137,1047

High Resolution FAB-MS(m/e,($C_{23}H_{34}N_5NaO_6S$+H)+): Calcd: 532.2206 Found: 532.2236

¹H-NMR(300 MHz,DMSO-d₆,δppm): 0.65(3H,d,J=6.2 Hz),0.66(3H,d,J=6.2 Hz),0.95-1.18(3H,m),1.18(9H,s),2.89(1H,dd,J=9.8 Hz,14.4 Hz),3.06-3.15(1H,m),3.82-3.90(1H,m),3.90-3.98(1H,m),3.99-4.10(1H,m),4.53-4.62(1H,m),5.72(1H,d,J=8.0 Hz),5.80(1H,s),6.92(1H,t,J=7.5 Hz),7.01(1H,t,J=7.5 Hz),7.15(1H,d,J=1.9 Hz),7.27(1H,d,J=7.5 Hz),7.61(1H,d,J=7.5 Hz),8.05(1H,d,J=8.6 Hz),8.25-8.32(1H,m),10.75(1H,d,J=1.9 Hz)

EXAMPLE 79

Synthesis of Compound 84

(1) Preparation of PhNHCO-Leu-DTrp-βAla-OEt

To a solution of Leu-DTrp-βAla-OEt.TFA (40.6 mg) obtained in Example 51-(1) in chloroform (2 ml) were added TEA (20 μl) and phenyl isocyanate (15 μl) at room temperature under nitrogen. The reaction mixture was stirred for 1 h, and concentrated under reduced pressure. The residue was purified by dry column flash chromatography (Merck, Kieselgel 60) with chloroform/methanol=10/1 for elution to give the product (39.6 mg).

FAB-MS(m/e,(C₂₉H₃₇N₅O₅+H)⁺): 536

(2) Preparation of Compound 84

Alkaline hydrolysis of the compound obtained in (1) (18.7 mg) in the same manner described in Example 51-(3), gave the title compound (17.4 mg) as a colorless powder.

m.p.: 208°-214° C.(dec.)
IR(KBr,cm⁻¹):
3406,2945,1653,1599,1557,1446,1410,1317,1239,744,695
High Resolution FAB-MS(m/e,(C₂₇H₃₃N₅O₅+H)⁺): Calcd: 508.2560 Found: 508.2561
¹H-NMR(300 MHz,DMSO-d₆,δppm): 0.71(3H,d,J=5.5 Hz),0.73(3H,d,J=5.5 Hz),1.15-1.30(3H,m),2.20-2.35(2H,m),2.87(1H,dd,J=10.5 Hz,14.3 Hz),3.18-3.40(3H,m),4.10-4.20(1H,m),4.37-4.47(1H,m),6.73-6.83(1H,m),6.85(1H,t,J=7.3 Hz),6.94(1H,t,J=7.3 Hz),7.02(1H,t,J=7.5 Hz),7.05(1H,d,J=2.0 Hz),7.18(2H,d,J=7.5 Hz),7.29(1H,d,J=7.3 Hz),7.38(2H,d,J=7.5 Hz),7.56(1H,d,J=7.3 Hz),8.02(1H,t,J=5.5 Hz),8.40(1H,d,J=8.6 Hz),9.03(1H,s),10.78(1H,d,J=2.0 Hz)

Each Compound 85-91 in the following Examples 80-86 was prepared using each corresponding isocyanate or isothiocyanate in the same manner described in Example 79.

EXAMPLE 80

Compound 85 m.p.: 133°-140° C.
IR(KBr,cm⁻¹):
3400,2962,1650,1557,1458,1395,1368,1278,1215,741
High Resolution FAB-MS(m/e,(C₂₅H₃₇N₅O₅+H)⁺): Calcd: 488.2873 Found: 488.2863
¹H-NMR(300 MHz,DMSO-d₆,δppm): 0.66(3H,d,J=5.4 Hz),0.71(3H,d,J=5.4 Hz),1.03-1.23(3H,m),1.19(9H,s),2.26-2.35(2H,m),2.84(1H,dd,J=11.0 Hz,12.8 Hz),3.15-3.30(3H,m),3.91-4.00(1H,m),4.32-4.42(1H,m),5.85-5.93(1H,m),5.89(1H,s),6.94(1H,t,J=7.4 Hz),7.02(1H,t,J=7.4 Hz),7.08(1H,d,J=2.0 Hz),7.29(1H,d,J=7.4 Hz),7.54(1H,d,J=7.4 Hz),8.08(1H,t,J=5.6 Hz),8.24(1H,d,J=8.3 Hz),10.76(1H,d,J=2.0 Hz)

EXAMPLE 81

Compound 86 m.p.: 136°-155° C.
IR(KBr,cm⁻¹):
3406,2932,2860,1647,1560,1458,1344,1236,741
High Resolution FAB-MS(m/e,(C₂₇H₃₉N₅O₅+H)⁺): Calcd: 514.3029 Found: 514.3002
¹H-NMR(300 MHz,DMSO-d₆,δppm): 0.67(3H,d,J=5.3 Hz),0.72(3H,d,J=5.3 Hz),0.95-1.35(9H,m),1.44-1.80(5H,m),2.27-2.43(2H,m),2.85(1H,dd,J=11.5 Hz,13.7 Hz),3.10-3.30(3H,m),3.92-4.07(1H,m),4.29-4.43(1H,m),5.88-6.02(2H,m),6.94(1H,t,J=7.3 Hz),7.02(1H,t,J=7.3 Hz),7.08(1H,brs),7.28(1H,d,J=7.3 Hz),7.54(1H,d,J=7.3 Hz),8.02-8.12(1H,m),8.28(1H,d,J=8.3 Hz),10.80(1H,brs)

EXAMPLE 82

Compound 87 m.p.: 109°-112° C.
IR(KBr,cm⁻¹):
3352,2956,1650,1590,1551,1473,1443,1305,1233,744
High Resolution FAB-MS(m/e,(C₂₇H₃₂N₅O₅Cl+H)⁺): Calcd: 542.2170 Found: 542.2181
¹H-NMR(300 MHz,DMSO-d₆,δppm): 0.70-0.78(6H,m),1.09-1.28(3H,m),2.34(2H,t,J=7.2 Hz),2.88(1H,dd,J=10.4 Hz,14.2 Hz),3.11-3.35(3H,m),4.10-4.21(1H,m),4.37-4.49(1H,m),6.93(1H,t,J=8.0 Hz),6.94(1H,t,J=7.5 Hz),7.03(1H,t,J=7.5 Hz),7.10(1H,d,J=2.1 Hz),7.20(1H,t,J=8.0 Hz),7.25(1H,d,J=7.4 Hz),7.29(1H,d,J=7.5 Hz),7.37(1H,dd,J=1.6 Hz,8.0 Hz),7.59(1H,d,J=7.5 Hz),8.01(1H,t,J=5.3 Hz),8.12(1H,dd,J=1.6 Hz,8.0 Hz),8.16(1H,s),8.24(1H,d,J=8.2 Hz),10.78(1H,d,J=2.1 Hz),12.20(1H,brs)

EXAMPLE 83

Compound 88 m.p.: 116°-127° C.
IR(KBr,cm⁻¹):
3418,2962,1728,1650,1554,1497,1443,1404,1341,1308,1236,1095,744
High Resolution FAB-MS(m/e,(C₂₇H₃₂N₅O₅Cl+H)⁺): Calcd: 542.2170 Found: 542.2191
¹H-NMR(300 MHz,DMSO-d₆,δppm): 0.71(6H,d,J=5.4 Hz),1.07-1.31(3H,m),2.35(2H,t,J=7.2 Hz),2.87(1H,dd,J=10.5 Hz,14.5 Hz),3.15(1H,dd,J=4.2 Hz,14.5 Hz),3.22-3.42(2H,m),4.12-4.22(1H,m),4.41(1H,ddd,J=4.2 Hz,8.6 Hz,10.5 Hz),6.31(1H,d,J=7.8 Hz),6.94(1H,t,J=7.5 Hz),7.03(1H,t,J=7.5 Hz),7.10(1H,d,J=1.5 Hz),7.22(2H,d,J=9.1 Hz),7.27(1H,d,J=7.5 Hz),7.37(2H,d,J=9.1 Hz),7.59(1H,d,J=7.5 Hz),8.03(1H,t,J=5.2 Hz),8.37(1H,d,J=8.6 Hz),8.70(1H,s),10.78(1H,d,J=1.5 Hz),12.19(1H,brs)

EXAMPLE 84

Compound 89 m.p.: 132°-142° C.
IR(KBr,cm⁻¹):
3430,2957,2923,1644,1557,1460,1387,1158,745

FAB-MS(m/e,($C_{23}H_{33}N_5O_5$+H)+):460
$^1$H-NMR(300 MHz,DMSO-$d_6$,δppm): 0.68(3H,d,J=6.4 Hz),0.71(3H,d,J=6.4 Hz),0.98(3H,d,J=6.4 Hz),0.99(3H,d,J=6.4 Hz),1.00–1.20(3H,m),2.88(1H,dd,J=10.5 Hz,14.7 Hz),3.20(1H,dd,J=3.6 Hz,14.7 Hz),3.56–3.66(1H,m),3.69–3.76(2H,m),4.04(1H,q,J=6.8 Hz),4.46(1H,ddd,J=3.6 Hz,8.7 Hz,10.8 Hz),5.81(1H,d,J=7.6 Hz),5.82(1H,d,J=7.2 Hz),6.95(1H,t,J=7.5 Hz),7.03(1H,t,J=7.5 Hz),7.12(1H,d,J=2.2 Hz),7.29(1H,d,J=7.5 Hz),7.58(1H,d,J=7.5 Hz),8.29(1H,d,J=8.7 Hz),8.29–8.40(1H,m),10.78(1H,d,J=2.2 Hz)

EXAMPLE 85

Compound 90 m.p.: 165°–170° C.

IR(KBr,cm$^{-1}$): 3430,2920,1653,1602,1554,1506,1445,1317,1233,745,697

High Resolution FAB-MS(m/e,($C_{26}H_{31}N_5O_5$+H)+): Calcd: 494.2404 Found: 494.2384

$^1$H-NMR(300 MHz,DMSO-$d_6$,δppm): 0.70(6H,d,J=6.4 Hz),1.08–1.26(3H,m),2.90(1H,dd,J=10.5 Hz,14.4 Hz),3.19–3.30(1H,m),3.73(1H,dd,J=6.1 Hz,17.0 Hz),3.81(1H,dd,J=5.9 Hz,17.0 Hz),4.19(1H,q,J=7.3 Hz),4.48–4.56(1H,m),6.24(1H,d,J=7.3 Hz),6.87(1H,t,J=7.3 Hz),6.95(1H,t,J=7.3 Hz),7.03(1H,t,J=7.3 Hz),7.13(1H,d,J=2.3 Hz),7.16–7.37(4H,m),7.43(1H,d,J=7.3 Hz),7.61(1H,d,J=7.3 Hz),8.37–8.45(2H,m),8.53(1H,s),10.79(1H,d,J=2.3 Hz)

EXAMPLE 86

Compound 91 m.p.: 163°–165° C.

IR(KBr,cm$^{-1}$): 3442,2930,1653,1539,1389,1240,1160,1089,746

High Resolution FAB-MS(m/e,($C_{26}H_{31}N_5O_4S$+H)−): Calcd: 510.2175 Found: 510.2143

$^1$H-NMR(300 MHz,DMSO-$d_6$,δppm): 0.67–0.73(6H,m),1.15–1.38(3H,m),2.86–2.96(1H,m),3.15–3.25(1H,m),3.50–3.75(2H,m),4.45–4.56(1H,m),4.80–4.92(1H,m),6.93(1H,t,J=7.7 Hz),6.98–7.08(2H,m),7.14(1H,brs),7.23–7.33(3H,m),7.48(2H,d,J=7.6 Hz),7.60(1H,d,J=7.7 Hz),7.88–8.10(2H,m),8.43(1H,d,J=8.5 Hz),9.92(1H,brs),10.78(1H,brs)

EXAMPLE 87

(1) Synthesis of Compound 92

Compound 72 (34.9 mg) obtained in Example 67 was suspended in chloroform (1.2 ml) and perhydroazepine (147 82 l) and TEA (100 μl) were added. The reaction mixture was stirred at 55° C. under nitrogen for 3 h and concentrated under reduced pressure. A solution of the residue in ethyl acetate was washed with 1N HCl, sat. NaHCO$_3$ and brine, dried over MgSO$_4$, filtered, and concentrated under reduced pressure. The residue was purified by dry column flash chromatography (Merck, Kieselgel 60) with ethyl acetate for elution to give the title compound (33.0 mg) as a colorless powder.

m.p.: 115°–125° C.

IR(KBr,cm$^{-1}$): 3418,2932,1728,1656,1632,1539,1191

High Resolution FAB-MS(m/e,($C_{29}H_{43}N_5O_5$+H)+): Calcd: 542.3342 Found: 542.3369

$^1$H-NMR(300 MHz,CDCl$_3$,δppm): 0.83(3H,d,J=6.2 Hz),0.84(3H,d,J=6.2 Hz),1.21(3H,t,J=7.2 Hz),1.40–1.75(11H,m),2.35–2.55(2H,m),3.15–3.55(9H,m),3.81(1H,q,J=6.8 Hz),4.07(2H,q,J=7.2 Hz),4.58(1H,d,J=6.8 Hz),4.75–4.85(1H,m),6.22(1H,d,J=8.8 Hz),7.07(1H,d,J=2.6 Hz),7.10(1H,t,J=7.4 Hz),7.19(1H,dt,J=1.1 Hz,7.4 Hz),7.36(1H,d,J=7.4 Hz),7.30–7.40(1H,m),7.61(1H,dd,J=1.1 Hz,7.4 Hz),8.11(1H,brs)

(2) Synthesis of Compound 93

Alkaline hydrolysis of Compound 92 (27.1 mg) obtained in (1) in the same manner described in Example 51-(3), gave the title compound (22.6 mg) as a colorless powder.

m.p.: 110°–115° C.

IR(KBr,cm$^{-1}$): 3406,2932,1719,1647,1629,1536,1419

High Resolution FAB-MS(m/e,($C_{27}H_{39}N_5O_5$+H)+): Calcd: 514.3030 Found: 514.2983

$^1$H-NMR(300 MHz,DMSO-$d_6$,δppm): 0.71(3H,d,J=5.6 Hz),0.78(3H,d,J=5.6 Hz),1.15–1.35(3H,m),1.35–1.50(4H,m),1.50–1.65(4H,m),2.30–2.40(2H,m),2.86(1H,dd,J=10.1 Hz,14.1 Hz),3.15–3.40(7H,m),3.90–4.05(1H,m),4.25–4.40(1H,m),6.11(1H,d,J=6.3 Hz),6.95(1H,t,J=7.4 Hz),7.04(1H,t,J=7.4 Hz),7.07(1H,brs),7.30(1H,d,J=7.4 Hz),7.54(1H,d,J=7.4 Hz),8.05–8.15(1H,m),8.14(1H,d,J=8.7 Hz),10.78(1H,brs)

Each Compound 94–130 in the following Examples 88–122 was prepared using each corresponding primary or secondary amine in the same manner described in Example 87.

EXAMPLE 88

(1)

Compound 94 m.p.: 83°–87° C.

IR(KBr,cm$^{-1}$): 3310,1731,1656,1533,1269,1185

High Resolution FAB-MS(m/e,($C_{29}H_{43}N_5O_6$+H)+): Calcd: 558.3292 Found: 558.3316

$^1$H-NMR(300 MHz,DMSO-$d_6$,δppm): 0.69(3H,d,J=6.0 Hz),0.74(3H,d,J=6.0 Hz),1.12–1.59(8H,m),1.68–1.78(1H,m),1.17(3H,t,J=7.2 Hz),2.43(2H,t,J=7.2 Hz),2.60–2.75(1H,m),2.86(1H,dd,J=10.0 Hz,14.6 Hz),3.13–3.53(5H,m),3.77–3.87(1H,m),3.90–4.00(1H,m),4.00–4.10(1H,m),4.04(2H,q,J=7.2 Hz),4.26–4.37(1H,m),4.66(1H,t,J=5.1 Hz),6.23(1H,d,J=6.2 Hz),6.94(1H,t,J=7.6 Hz),7.03(1H,t,J=7.6 Hz),7.07(1H,d,J=2.2 Hz),7.29(1H,d,J=7.2 Hz),7.53(1H,d,J=7.6 Hz),8.06(1H,t,J=5.2 Hz),8.14(1H,d,J=8.9 Hz),10.77(1H,brs)

(2) Compound 95 m.p.: 110°–113° C.

IR(KBr,cm$^{-1}$): 3406,2944,1725,1650,1539,1389,1270,1050

High Resolution FAB-MS(m/e,($C_{27}H_{39}N_5O_6$+H)+): Calcd: 530.2979 Found: 530.3004

$^1$H-NMR(300 MHz,DMSO-$d_6$,δppm): 0.69(3H,d,J=5.7 Hz),0.76(3H,d,J=5.7 Hz),1.11–1.59(8H,m),1.68–1.79(1H,m),2.36(2H,t,J=7.2 Hz),2.61–2.77(1H,m),2.86(1H,dd,J=10.3 Hz,14.7 Hz),3.15–3.52(6H,m),3.75–3.89(1H,m),3.90–4.00(1H,m),4.00–4.10(1H,m),4.27–4.38(1H,m),6.23(1H,d,J=6.9 Hz),6.94(1H,t,J=7.3

Hz),7.03(1H,t,J=7.3 Hz),7.29(1H,d,J=7.3 Hz),8.05(1H,t,J=5.4 Hz),10.76(1H,d,J=2.2 Hz) Hz),7.07(1H,d,J=2.2 Hz),7.53(1H,d,J=7.3 Hz),8.13(1H,d,J=8.6

EXAMPLE 89

Compound 96 m.p.: 113°–121° C.
IR(KBr,cm$^{-1}$):3406,2956,1719,1644,1542,1443,1371,-
1341,1269,1236,1194,1059,744
High Resolution FAB-MS(m/e,(C$_{26}$H$_{37}$-N$_5$O$_6$+H)$^+$): Calcd: 516.2822 Found: 516.2815
$^1$H-NMR(300 MHz,DMSO-d$_6$,δppm):0.69(3H,d,J=5.9 Hz),0.76(3H,d,J=5.5 Hz),1.09–1.33(5H,m),1.58–1.72(2H,m),2.37(2H,t,J=7.0 Hz),2.76–2.94(2H,m),2.82(1H,dd,J=10.0 Hz,14.0 Hz), 3.14–3.40(3H,m),3.53–3.66(1H,m),3.-66–3.76(2H,m),3.92(1H,ddd,J=6.8 Hz,6.8 Hz,7.8 Hz),4.32(1H,ddd,J=3.9 Hz,8.6 Hz,10.5 Hz),4.65(1H,brs),6.42(1H,d,J=6.8 Hz),6.94(1H,t,J=7.7 Hz),7.03(1H,t,J=7.7 Hz),7.07(1H,d,J=1.8 Hz),7.29(1H,d,J=7.7 Hz),7.52(1H,d,J=7.7 Hz), 8.03(1H,t,J=5.3 Hz), 8.18(1H,d,J=8.5 Hz),10.77(1H,d,J=1.8Hz),12.16(1H,brs)

EXAMPLE 90

Compound 97 m.p.: 103°–118° C.
IR(KBr,cm$^{-1}$):3322,2938,1719,1635,1536,1272,1188
FAB-MS(m/e,(C$_{27}$H$_{39}$N$_5$O$_5$+H)$^+$):514
$^1$H-NMR(300 MHz,DMSO-d$_6$, δppm):0.69(3H,d,J=4.9 Hz),0.76(3H,d,J=4.9 Hz),1.07+1.09(3H,d×2,J=7.1Hz,J=7.1 Hz),1.12–1.62(9H,m),2.-35–2.50(2H,m),2.72(1H,t,J=13.0 Hz),2.84(1H,dd,J=10.7 Hz,14.5 Hz),3.15–3.35(3H,m),3.68–3.86(1H,m),3.-89–3.99(1H,m),4.-20–4.37(2H,m),6.30+6.32(1H,d×2,J=5.4 Hz, J=5.4 Hz),6.94(1H,t,J=7.5 Hz),7.03(1H,t,J=7.5 Hz),7.07(1H,brs),7.29(1H,d,J=7.5 Hz),7.53(1H,d,J=7.5 Hz),8.04–8.11(1H,m),8.17+8.20(1H,d×2,J=7.5 Hz,J=7.5 Hz),10.77 (1H,brs)

EXAMPLE 91

Compound 98 m.p.: 113°–120° C.
IR(KBr,cm$^{-1}$):3322,2956,2872,1719,1644,1539,1461,-1446,1266,1239
High Resolution FAB-MS(m/e,(C$_{27}$H$_{39}$-N$_5$O$_5$+H)$^+$): Calcd: 514.3029 Found: 514.2982
$^1$H-NMR(300 MHz,DMSO-d$_6$,δppm):0.68(3H,d,J=4.6 Hz),0.76(3H,d,J=4.6 Hz),0.80 (3H,d,J=6.6 Hz),0.95–1.47(6H,m),1.-47–1.60(1H,m),1.66–1.76(1H,m),2.-22–2.48(4H,m),2.85(1H,dd,J=10.5 Hz,14.4 Hz),3.18–3.40(3H,m),3.72–3.95(3H,m),4.-27–4.36(1H,m),6.38+6.40(1H,d×2,J=6.2 Hz,J=6.2 Hz),6.94(1H,dt,J=1.2 Hz,7.7 Hz),7.03(1H,dt,J=1.2 Hz,7.7 Hz),7.07(1H,d,J=2.1 Hz),7.29(1H,dd,J=1.2Hz, 7.7 Hz),7.53(1H,dd,J=1.2 Hz,7.7 Hz),8.05(1H,t,J=5.7 Hz),8.17+8.19(1H,d×2,J=8.2 Hz,J=8.2 Hz),10.77(1H,d,J=2.1 Hz),12.15(1H,brs)

EXAMPLE 92

Compound 99 m.p.: 217°–218° C.
IR(KBr,cm$^{-1}$):3418,2926,1716,1647,1542,1458,1248,-1210,1082,741
High Resolution FAB-MS(m/e,(C$_{27}$H$_{39}$-N$_5$O$_5$+H)$^+$): Calcd: 514.3029 Found: 514.3008
$^1$H-NMR(300 MHz,DMSO-d$_6$, δppm):0.69(3H,d,J=5.9 Hz),0.77(3H,d,J=5.9 Hz), 0.87(3H,d,J=6.0 Hz),0.91–1.04(2H,m),1.-11–1.35(3H,m),1.40–1.60(3H,m),2.31–2.42(2H,m),2.-55–2.69(2H,m),2.85(1H,dd,J=10.4 Hz,14.5 Hz),3.15–3.32(3H,m),3.86–4.01(3H,m),4.-25–4.36(1H,m),6.40(1H,d,J=6.6 Hz),6.95(1H,t,J=7.7 Hz),7.03(1H,t,J=7.7 Hz),7.08(1H,d,J=1.8 Hz),7.30(1H,d,J=7.7 Hz),7.53(1H,d,J=7.7 Hz),8.05(1H,t,J=5.5 Hz), 8.18(1H,d,J=8.6 Hz),10.78(1H,d,J=1.8 Hz),12.20(1H,brs)

EXAMPLE 93

Compound 100 m.p.: 120°–126° C.
IR(KBr,cm$^{-1}$):3412,2944,1719,1656,1533,1461,1443,-1392,1344,1236,1194,741
High Resolution FAB-MS(m/e,(C$_{28}$H$_{41}$-N$_5$O$_5$+H)$^+$): Calcd: 528.3186 Found: 528.3173
$^1$H-NMR(300 MHz,DMSO-d$_6$δppm):0.70(3H,d,J=6.1 Hz),0.77(3H,d,J=5.9 Hz),1.04(3H,d,J=6.7 Hz),1.08(3H,d,J=6.8 Hz),1.13–1.78(9H,m),2.-31–2.46(2H,m),2.84(1H,dd,J=10.4 Hz,14.6 Hz),3.10–3.35(3H,m),3.91–4.01(1H,m),4.-07–4.23(2H,m),4.24–4.38(1H,m),6.15(1H,d,J=6.6 Hz),6.94(1H,t,J=7.6 Hz),7.03(1H,t,J=7.6 Hz),7.07(1H,d,J=1.9 Hz),7.29(1H,d,J=7.6 Hz),7.53(1H,d,J=7.6 Hz),8.08(1H,t,J=5.5 Hz),8.19(1H,d,J=8.2 Hz),10.77(1H,d,J=1.9 Hz),12.13(1H,brs)

EXAMPLE 94

Compound 101 m.p.: 203°–204° C. (dec.)
IR(KBr,cm$^{-1}$):3412,2938,1719,1638,1539,1446,1260,-1236,1180,740
High Resolution FAB-MS(m/e,(C$_{26}$H$_{37}$-N$_5$O$_5$+H)$^+$): Calcd: 500.2873 Found: 500.2870
$^1$H-NMR(300 MHz,DMSO-d$_6$,δppm):0.69(3H,d,J=5.9 Hz),0.76(3H,d,J=5.9 Hz),1.13–1.43(7H,m),1.44–1.57(2H,m),2.37(2H,t,J=7.5 Hz),2.86(1H,dd,J=10.2 Hz,14.4 Hz),3.17–3.40(7H,m),3.88–3.98(1H,m),4.-26–4.37(1H,m),6.38(1H,d,J=6.8 Hz), 6.94(1H,t,J=7.3 Hz),7.03(1H,t,J=7.3 Hz),7.07(1H,d,J=1.9 Hz),7.29(1H,d,J=7.3 Hz),7.53(1H,d,J=7.3 Hz),8.04(1H, t,J=5.4 Hz),8.17(1H,d,J=8.6 Hz),10.77(1H,d,J=1.9 Hz),12.20(1H,brs)

EXAMPLE 95

Compound 102 m.p.: 119°–122° C.
IR(KBr,cm$^{-1}$):3418,2962,1716,1638,1536,1263
High Resolution FAB-MS(m/e,(C$_{25}$H$_{35}$-N$_5$O$_6$+H)$^+$): Calcd: 502.2665 Found: 502.2674
$^1$H-NMR(300 MHz,DMSO-d$_6$δppm):0.70(3H,d,J=5.7 Hz),0.77(3H,d,J=5.4 Hz),1.15–1.35(3H,m),2.-

25-2.45(2H,m),2.87(1H,dd,J=10.3 Hz,14.0 Hz),3.20-3.45(7H,m),3.45-3.60(4H,m),3.95-4.05(1H,m),4.30-4.40(1H,m),6.53(1H,d,J=6.1 Hz),6.95(1H,t,J=7.3 Hz),7.04(1H,t,J=7.3 Hz),7.08(1H,brs),7.30(1H,d,J=7.3 Hz),7.54(1H,d,J=7.3 Hz),7.95-8.10(1H,m),8.19(1H,d,J=8.6 Hz),10.79(1H,brs)

EXAMPLE 96

Compound 103 m.p.: 135°–140° C.

IR(KBr,cm$^{-1}$):3412,3330,2956,1650,1545,1464,1404,1269

High Resolution FAB-MS(m/e,($C_{26}H_{38}N_6O_5$+H)$^+$): Calcd: 515.2982 Found: 515.2950

$^1$H-NMR(300 MHz,DMSO-d$_6$, δppm):0.70(3H,d,J=5.9 Hz),0.77(3H,d,J=5.9 Hz),1.15-1.35(3H,m),2.15(3H,s),2.15-2.30(4H,m),2.33(2H,t,J=7.4 Hz),2.87(1H,dd,J=10.3 Hz,14.7 Hz),3.20-3.40(7H,m),3.90-4.00(1H,m),4.30-4.40(1H,m),6.50(1H,d,J=6.8 Hz),6.95(1H,t,J=7.5 Hz),7.04(1H,t,J=7.5 Hz),7.08(1H,d,J=2.2 Hz),7.30(1H,d,J=7.5 Hz),7.54(1H,d,J=7.5 Hz),8.04(1H,t,J=5.5 Hz),8.19(1H,d,J=8.3 Hz),10.79(1H,d,J=2.2 Hz)

EXAMPLE 97

Compound 104 m.p.: 121.0°–122.5° C.

IR(KBr,cm$^{-1}$):3418,2956,1719,1641,1539,1461,1344,1290,1236,744

High Resolution FAB-MS(m/e,($C_{30}H_{37}N_5O_5$+H)$^+$): Calcd: 548.2873 Found: 548.2898

$^1$H-NMR(300 MHz,DMSO-d$_6$, δppm):0.70(3H,d,J=5.9 Hz),0.77(3H,d,J=5.5 Hz),1.15-1.37(3H,m),2.36-2.47(2H,m),2.70-2.80(2H,m),2.86(1H,dd,J=10.6 Hz,14.5 Hz),3.16-3.31(3H,m),3.56(2H,t,J=5.7 Hz),3.95-4.05(1H,m),4.28-4.39(1H,m),4.47(1H,d,J=18.8 Hz),4.55(1H,d,J=18.8 Hz),6.53(1H,d,J=6.8 Hz),6.93(1H,t,J=8.0 Hz),7.03(1H,t,J=8.0 Hz),7.07(1H,d,J=2.0 Hz),7.09-7.21(4H,m),7.29(1H,d,J=8.0 Hz),7.54(1H,d,J=8.0 Hz),8.04(1H,t,J=5.5 Hz),8.24(1H,d,J=8.3 Hz),10.77(1H,d,J=2.0 Hz),2.21(1H,brs)

EXAMPLE 98

Compound 105 m.p.: 146–160° C.

IR(KBr,cm$^{-1}$):3436,2956,1644,1578,1533,1461,1407,1251,744

High Resolution FAB-MS(m/e,($C_{30}H_{37}N_5O_5$+H)$^+$): Calcd: 548.2873 Found: 548.2911

$^1$H-NMR(300 MHz,DMSO-d$_6$, δppm):0.70+0.76(3H,d×2,J=5.5 Hz,J=5.5 Hz),0.74+0.78(3H,d×2,J=5.5 Hz,J=5.5 Hz),1.18-1.39(4H,m)1.71-1.88(1H,m),2.12-2.30(2H,m),2.60-2.79(2H,m),2.80-2.97(1H,m),3.12-3.36(3H,m),3.51-3.66(1H,m),3.97-4.19(1H,m),4.28-4.43(1H,m),4.44-4.60(1H,m),6.57-6.69(1H,m),6.92(1H,t,J=7.5 Hz),7.01(1H,t,J=7.5 Hz),7.02-7.20(4H,m),7.28(1H,d,J=8.1 Hz),7.29+7.35(1H,d×2,J=7.5 Hz,J=7.5 Hz),7.52+7.55(1H,d×2,J=7.5 Hz,J=7.5 Hz),8.01-8.15(1H,m),8.16-8.20(1H,m),10.77+10.79(1H,brs×2)

EXAMPLE 99

Compound 106 m.p.: 121°–128° C.

IR(KBr,cm$^{-1}$):3418,2956,1719,1641,1539,1464,1443,1254,1233,952,744

High Resolution FAB-MS(m/e,($C_{25}H_{35}N_5O_5S$+H)$^+$): Calcd: 518.2437 Found: 518.2410

$^1$H-NMR(300 MHz,DMSO-d$_6$, δppm):0.70(3H,d,J=5.9 Hz),0.77(3H,d,J=5.9 Hz),1.16-1.45(3H,m),2.36(2H,t,J=7.0 Hz),2.40-2.55(4H,m),2.86(1H,dd,J=10.2 Hz,14.4 Hz),3.17-3.32(3H,m),3.55-3.67(4H,m),3.92-4.02(1H,m),4.30-4.39(1H,m),6.51(1H,d,J=6.9 Hz),6.94(1H,t,J=7.8 Hz),7.03(1H,t,J=7.8 Hz),7.07(1H,d,J=1.8 Hz),7.29(1H,d,J=7.8 Hz),7-53(1H,d,J=7.8 Hz),7.99(1H,t,J=5.5 Hz),8.16(1H,d,J=8.5 Hz),10.77(1H,d,J=1.8 Hz),12.19(1H,brs)

EXAMPLE 100

Compound 107 m.p.: 117°–124° C.

IR(KBr,cm$^{-1}$):3406,2926,1719,1635,1536,1446,1359,1233,1101,741

High Resolution FAB-MS(m/e,($C_{28}H_{41}N_5O_5$+H)$^+$): Calcd: 528.3186 Found: 528.3161

$^1$H-NMR(300 MHz,DMSO-d$_6$, δppm):0.70(3H,d,J=5.8 Hz),0.77(3H,d,J=5.8 Hz),1.12-1.34(3H,m),1.35-1.65(10H,m),2.31-2.45(2H,m),2.84(1H,dd,J=10.1 Hz,14.5 Hz),3.09-3.29(6H,m),3.92-4.03(1H,m),4.27-4.39(1H,m),6.00(1H,d,J=6.8 Hz),6.94(1H,t,J=7.5 Hz),7.03(1H,t,J=7.5 Hz),7.06(1H,d,J=2.0 Hz),7.29(1H,d,J=7.5 Hz),7.53(1H,d,J=7.5 Hz),8.09(1H,t,J=5.6 Hz),8.13(1H,d,J=8.6 Hz),10.77(1H,d,J=2.0 Hz),12.15(1H,brs)

EXAMPLE 101

Compound 108 m.p: 114.5°–123.5° C.

IR(KBr,cm$^{-1}$):3418,2956,1719,1632,1536,1464,1197,741

High Resolution FAB-MS(m/e,($C_{30}H_{45}N_5O_5$+H)$^+$): Calcd: 556.3499 Found: 556.3505

$^1$H-NMR(300 MHz,DMSO-d$_6$, δppm):0.69(3H,d,J=5.6 Hz),0.76(3H,d,J=5.6 Hz),0.81-0.91(9H,m),1.03-1.87(8H,m),2.31-2.45(2H,m),2.65-2.90(2H,m),3.20-3.47(6H,m),3.88-3.98(1H,m),4.28-4.36(1H,m),6.10+6.11(1H,d×2,J=6.5 Hz,J=6.5 Hz),6.94(1H,t,J=7.4 Hz),7.03(1H,t,J=7.4 Hz),7.06(1H,d,J=1.8 Hz),7.29(1H,d,J=7.4 Hz),7.53(1H,d,J=7.4 Hz),8.07-8.20(2H,m),10.77(1H,d,J=1.8 Hz),12.13(1H,brs)

EXAMPLE 102

Compound 109A m.p.: 104°–113.5° C.

IR(KBr,cm$^{-1}$):3352,2932, 1716,1650,1539,1272,1071,741

High Resolution FAB-MS(m/e,($C_{28}H_{41}N_5O_6$+H): Calcd: 544.3135 Found: 544.3184

¹H-NMR(300 MHz,DMSO-d₆, δppm):0.69(3H,d,J=5.7 Hz),0.76(3H,d,J=5.7 Hz),1.13-1.82(11H,m),2.37(2H,t,J=7.4 Hz),2.60-2.74(1H,m)2.85(1H,dd,J=10.1 Hz,14.5 Hz),3.15-3.40(5H,m),3.80-3.97(2H,m),4.-12-4.19(1H,m),4.29-4.36(1H,m),4.-45-4.60(1H,m),6.26(1H,d,J=6.1 Hz),6.94(1H,t,J=7.6 Hz),7.03(1H,t,J=7.6 Hz),7.07(1H,d,J=1.9 Hz),7.29(1H,d,J=7.6 Hz),7.54(1H,d,J=7.6 Hz),8.03(1H,t,J=5.2 Hz),8.15(1H,d,J= 8.6 Hz),10.77(1H,d,J=1.9 Hz)

Compound 109B

High Resolution FAB-MS(m/e,(C₂₈H₄₁N₅O₆+H)⁺): Calcd: 544.3135 Found: 544.3163
¹H-NMR(300 MHz,DMSO-d₆, δppm):0.67(3H,d,J=5.6 Hz),0.75(3H,d,J=5.6 Hz),1.10-1.85(11H,m),2.35-2.45(2H,m),2.-55-2.65(1H,m),2.84(1H,dd,J=11.0 Hz,14.7 Hz),3.17-3.40(5H,m),3.85-3.95(2H,m),4.-05-4.17(1H,m),4.28-4.38(1H,m),4.-65-4.80(1H,m),6.34(1H,d,J=6.8 Hz),6.94(1H,t,J=7.6 Hz),7.03(1H,t,J=7.6 Hz),7.07(1H,d,J=2.2 Hz),7.29(1H,d,J=7.6 Hz),7.52(1H,d,J=7.6 Hz),8.04(1H,t,J=5.6 Hz),8.26(1H,d,J=8.9 Hz),10.77(1H,d,J=2.2 Hz),12.13(1H,brs)

EXAMPLE 103

Compound 110 m.p.: 200.5°-202° C.
IR(KBr,cm⁻¹):3316,2956,2872,1719,1644,1536,1443,-1416,1233,1197,744
High Resolution FAB-MS(m/e,(C₂₅H₃₅N₅O₅+H)⁺): Calcd: 486.2717 Found: 486.2727
¹H-NMR(300 MHz,DMSO-d₆, δppm):0.69(3H,d,J=5.4 Hz),0.76(3H,d,J=5.7 Hz),1.10-1.36(3H,m),1.50-1.82(4H,m),2.39(2H,t,J=7.6 Hz),2.86(1H,dd,J=10.5 Hz,14.3 Hz),3.07-3.36(7H,m),3.88-4.01(1H,m),4.-26-4.38(1H,m),5.99(1H,d,J=6.6 Hz),6.94(1H,t,J=7.5 Hz),7.03(1H,t,J=7.5 Hz),7.07(1H,d,J=1.5 Hz),7.29(1H,d,J=7.5 Hz),7.53(1H,d,J=7.5 Hz),8.09(1H,t,J= 5.3 Hz),8.18(1H,d,J=8.1 Hz),10.77(1H,d,J=1.5 Hz), 12.09(1H,brs)
Optical Rotation: [α]_D²⁰=+38.5° (c 0.30,MeOH),

EXAMPLE 104

Compound 111 m.p.: 120°-122° C.
IR(KBr,cm⁻¹):3316,2962,1719,1635,1536,1446,1386,-1344,1200
High Resolution FAB-MS(m/e,(C₂₂H₃₉N₅O₅+H)⁺): Calcd: 514.3029 Found: 514.3004
¹H-NMR(300 MHz,DMSO-d₆, δppm):0.70(3H,d,J=5.7 Hz),0.76(3H,d,J=5.7 Hz),1.10(3H,d,J=6.2 Hz),1.14(3H,d,J=6.2 Hz),1.16-1.32(3H,m),1.46-1.59(2H,m),1.-83-1.96(2H,m),2.36-2.46(2H,m),2.85(1H,dd,J=10.2 Hz,14.6 Hz),3.15-3.34(3H,m),3.-74-3.90(2H,m),3.98(1H,q,J=6.9 Hz),4.33(1H,ddd,J=3.8 Hz,8.6 Hz, 10.2 Hz),5.79(1H,d,J=6.9 Hz),6.94(1H,t,J=7.5 Hz),7.03(1H,t,J=7.5 Hz),7.06(1H,d,J=2.0 Hz),7.29(1H,d,J=7.5 Hz),7.53(1H,d,J=7.5 Hz),8.12(1H,t,J=5.6 Hz),8.19(1H,d,J=8.6 Hz),10.77(1H,d,J=2.0 Hz),12.18(1H,brs)

EXAMPLE 105

Compound 112 m.p.: 106°-114° C.
IR(KBr,cm⁻¹):3412,2956,1722,1641,1542,1464,1392,-1344,1230,1194,744
High Resolution FAB-MS(m/e,(C₂₄H₃₃N₅O₅S+H)⁺): Calcd: 504.2281 Found: 504.2295
¹H-NMR(300 MHz,DMSO-d₆, δppm):0.70(3H,d,J=6.1 Hz),0.76(3H,d,J=5.9 Hz),1.16-1.35(3H,m),2.37(2H,t,J=7.3 Hz),2.86(1H,dd,J=10.1 Hz,14.5 Hz),2.94(2H,t,J=6.2 Hz),3.18-3.35(3H,m),3.49 (1H,td,J=6.2 Hz,11.3 Hz),3.61(1H,td,J=6.2 Hz,11.3 Hz),3.92-4.03(1H,m),4.-30-4.41(1H,m),4.34(1H,d,J=9.0 Hz),4.44(1H,d,J=9.0 Hz),6.58(1H,d,J=7.1 Hz),6.94(1H,t,J=7.7 Hz) 7.03(1H,t,J=7.7 Hz),7.07(1H,d,J=1.9 Hz),7.29(1H,d,J=7.7 Hz),7.54(1H,d,J=7.7 Hz),7.97(1H,t,J=5.6 Hz),8.18(1H,d,J=8.1 Hz),10.77(1H,d,J=1.9 Hz),12.14(1H,brs)

EXAMPLE 106

Compound 113 m.p.: 139°-144° C.
IR(KBr,cm⁻¹):3418,2908,1716,1650,1577,1462,1365,-1298,1242,1080,744
High Resolution FAB-MS(m/e,(C₃₁H₄₃N₅O₅+H)⁺): Calcd: 566.3342 Found: 566.3356
¹H-NMR(300 MHz,DMSO-d₆, δppm):0.65(3H,d,J=5.5 Hz),0.71(3H,d,J=5.5 Hz),1.01-1.18(3H,m),1.57(6H,s),1.82(6H,s),1.96(3H,s),-2.38-2.60(2H,m),2.82(1H,dd,J=10.8 Hz,14.5 Hz),3.18-3.40(3H,m),3.83-3.89(1H,m),4.-30-4.38(1H,m),5.69(1H,s),5.85(1H,d,J=6.1 Hz),6.94(1H,t,J=7.1 Hz),7.02(1H,t,J=7.1 Hz),7.07(1H,d,J=1.9 Hz),7.29(1H,d,J=7.1 Hz),7.54(1H,d,J=7.1 Hz),8.12(1H,t,J=5.6 Hz),8.28(1H,d,J=8.6 Hz),10.76(1H,d,J=1.9 Hz),12.20(1H,brs)

EXAMPLE 107

Compound 114 m.p.: 122°-127° C.
IR(KBr,cm⁻¹):3310,2956,1719,1653,1551,1461,1443,-1365,1260,741
High Resolution FAB-MS(m/e,(C₂₆H₃₅N₅O₅+H)⁺): Calcd: 498.2717 Found: 498.2739
¹H-NMR(300 MHz,DMSO-d₆, δppm):0.66(3H,d,J=5.7 Hz),0.70(3H,d,J=5.1 Hz),0.95-1.16(3H,m),1.44(6H,s),2.-34-2.45(2H,m),2.84(1H,dd,J=10.7 Hz,13.7 Hz),3.00(1H,s),3.14-3.28(3H,m),3.91-4.02(1H,m),4.-31-4.43(1H,m),5.93(1H,d,J=6.5 Hz),6.22(1H,s),6.94(1H,t,J=7.4 Hz),7.02(1H,t,J=7.4 Hz),7.08(1H,d,J=2.0 Hz),7.29(1H,d,J=7.4 Hz),7.56(1H,d,J=7.4 Hz),8.09(1H,t,J=5.7 Hz),8.31(1H,d,J=8.6 Hz),10.77(1H,d,J=2.0 Hz),12.19(1H,brs)

EXAMPLE 108

Compound 115 m.p.: 108°-111° C.
IR(KRr,cm⁻¹):3412,2956,1722,1644,1566,1461,1344,-1242,1095,741,699
High Resolution FAB-MS(m/e,(C₂₈H₃₅N₅O₅+H)⁺): Calcd: 522.2717 Found: 522.2687

¹H-NMR(300 MHz,DMSO-d₆,δppm):0.67(3H,d,J=5.9 Hz),0.72(3H,d,J=5.8 Hz),1.03-1.21(3H,m),2.35(2H,t,J=7.3 Hz),2.84(1H,dd,J=10.3 Hz,14.6 Hz),3.09-3.35(3H,m),3.97-4.08(1H,m),4.19 (2H,d,J=5.9 Hz),4.31-4.43(1H,m),6.14(1H,d,J=7.1 Hz),6.43(1H,t,J=5.9 Hz),6.94(1H,t,J=7.5 Hz),7.03(1H,t,J=7.5 Hz),7.08(1H,d,J=1.7 Hz),7.16-7.35(6H,m),7.55(1H,d,J=7.5 Hz),8.05(1H,t,J=5.2 Hz),8.29(1H,d,J=8.5 Hz),10.77(1H,d,J=1.7 Hz),12.08(1H,brs)

EXAMPLE 109

Compound 116 m.p.: 118°–121° C.
IR(KBr,cm⁻¹):3394,2956,1716,1647,1560,1464,1443,1368,1248,1212,741
High Resolution FAB-MS(m/e,(C₂₆H₃₉N₅O₅+H)⁺): Calcd: 502.3029 Found: 502.3031
¹H-NMR(300 MHz,DMSO-d₆,δppm):0.67(3H,d,J=6.2 Hz),0.72(3H,d,J=5.9 Hz),0.79(9H,s),1.02-1.21(3H,m),2.33-2.46(2H,m),2.70-2.90(3H,m),3.11-3.29(3H,m),3.91-4.02(1H,m),4.29-4.40(1H,m),5.98(1H,t,J=6.1 Hz),5.99(1H,d,J=7.1 Hz),6.94(1H,t,J=7.8 Hz),7.02(1H,t,J=7.8 Hz),7.08(1H,d,J=2.1 Hz),7.29(1H,d,J=7.8 Hz),7.55(1H,d,J=7.8 Hz),8.06(1H,t,J=5.5 Hz),8.28(1H,d,J=8.6 Hz),10.77(1H,d,J=2.1 Hz),12.19(1H,brs)

EXAMPLE 110

Compound 117 m.p.: 109°–113° C.
IR(KBr,cm⁻¹):3322,2990,1723,1647,1554,1440,1340
High Resolution FAB-MS(m/e,(C₂₄H₃₃N₅O₅+H)⁺): Calcd: 472.2560 Found: 472.2576
¹H-NMR(300 MHz,DMSO-d₆,δppm):0.24-0.35(2H,m),0.50-0.59(2H,m),0.68(3H,d,J=5.9 Hz),0.72(3H,d,J=5.9 Hz),1.1.05-1.35(3H,m),2.35-2.45(1H,m),2.41(2H,t,J=7.2 Hz),2.86(1H,dd,J=10.2 Hz,14.5 Hz),3.11-3.35(3H,m),3.95-4.05(1H,m),4.31-4.41(1H,m),5.88(1H,d,J=7.4 Hz),6.20(1H,d,J=2.4 Hz),6.94(1H,t,J=7.5 Hz),7.02(1H,t,J=7.5 Hz),7.08(1H,d,J=1.7 Hz),7.29(1H,d,J=7.5 Hz),7.55(1H,d,J=7.5 Hz),8.07(1H,t,J=5.5 Hz),8.25(1H,d,J=8.3 Hz),10.77(1H,brs),12.15(1H,brs)

EXAMPLE 111

Compound 118 m.p.: 120°–130° C.
IR(KBr,cm⁻¹):3322,2956,1719,1644,1557
High Resolution FAB-MS(m/e,(C₂₆H₃₇N₅O₅+H)⁺): Calcd: 500.2873 Found: 500.2867
¹H-NMR(300 MHz,DMSO-d₆,δppm):0.67(3H,d,J=5.9 Hz),0.71(3H,d,J=5.9 Hz),0.96-1.34(5H,m),1.39-1.66(4H,m),1.67-1.85(2H,m),2.36-2.42(2H,m),2.84(1H,dd,J=10.7 Hz,14.6 Hz),3.12-3.40(3H,m),3.81(1H,sext,J=6.6 Hz),3.91-4.04(1H,m),4.30-4.39(1H,m),5.82(1H,d,J=7.3 Hz),5.97(1H,d,J=7.4 Hz),6.93(1H,t,J=7.8 Hz),7.02(1H,t,J=7.8 Hz),7.08(1H,d,J=1.9 Hz),7.29(1H,d,J=7.8 Hz),7.55(1H,d,J=7.8 Hz),8.07(1H,t,J=5.3Hz),8.27(1H,d,J=8.3 Hz),10.76(1H,d,J=1.9 Hz)

EXAMPLE 112

Compound 119 m.p.: 89.5°–94° C.
IR(KBr,cm⁻¹):3328,2962,1719,1635,1527,1461,1344
High Resolution FAB-MS(m/e,(C₂₇H₄₁N₅O₅+H)⁺): Calcd: 516.3186 Found: 516.3153
¹H-NMR(300 MHz,DMSO-d₆,δppm):0.68(3H,d,J=5.9 Hz),0.74(3H,d,J=5.9 Hz),0.98-1.38(3H,m),1.13(6H,d,J=6.5 Hz),1.14(6H,d,J=6.5 Hz),2.22-2.54(2H,m),2.84(1H,dd,J=10.2 Hz,14.7 Hz),3.11-3.45(3H,m),3.71(2H,sept,J=6.5 Hz),3.87-3.98(1H,m),4.28-4.38(1H,m),5.82(1H,d,J=6.7 Hz),6.94(1H,t,J=7.7 Hz),7.03(1H,t,J=7.7 Hz),7.07(1H,d,J=1.8 Hz),7.29(1H,d,J=7.7 Hz),7.53(1H,d,J=7.7 Hz),8.07(1H,t,J=5.8Hz),8.15(1H,d,J=8.7 Hz),10.77(1H,d,J=1.8 Hz),12.17(1H,brs)
Optical Rotation: [α]_D^{20}=+21.7° (c 0.44,MeOH)

EXAMPLE 113

Compound 120 m.p.: 116.5°–120.5° C.
IR(KBr,cm⁻¹):3400,2932,2860,1716,1626,1518,1458,1242
High Resolution FAB-MS(m/e,(C₃₃H₄₉N₅O₅+H)⁺): Calcd: 596.3812 Found: 596.3789
¹H-NMR(300 MHz,DMSO-d₆,δppm):0.66(3H,d,J=6.3 Hz),0.74(3H,d,J=6.4 Hz),0.93-1.91(23H,m),2.21-2.61(2H,m),2.84(1H,dd,J=10.7 Hz,14.7 Hz),3.13-3.45(5H,m),3.81-3.91(1H,m),4.27-4.38(1H,m),5.93(1H,d,J=6.2 Hz),6.94(1H,t,J=7.5 Hz),7.03(1H,t,J=7.5 Hz),7.06(1H,d,J=2.0 Hz),7.29(1H,d,J=7.5 Hz),7.53(1H,d,J=7.5 Hz),8.12(1H,t,J=5.6 Hz),8.18(1H,d,J=8.8 Hz),10.77(1H,d,J=2.0 Hz),12.20(1H,brs)

Example 114

Compound 121 m.p.: 100°–109.5° C.
IR(KBr,cm⁻¹):3316,2962,1719,1644,1551,1395,1365,1245,1197
High Resolution FAB-MS(m/e,(C₂₇H₄₁N₅O₆+H)⁺): Calcd: 532.3135 Found: 532.3135
¹H-NMR(300 MHz,DMSO-d₆,δppm):0.67(3H,d,J=5.8 Hz),0.74(3H,d,J=5.9 Hz),1.9-1.41(3H,m),1.28(9H,s),2.21-2.60(2H,m),2.85(1H,dd,J=10.5 Hz,14.7 Hz),3.10-3.42(5H,m),3.44-3.53(2H,m),3.82-3.92(1H,m),4.33(1H,ddd,J=3.6 Hz,8.6 Hz,10.5Hz),6.84(1H,d,J=5.9 Hz),6.94(1H,t,J=7.6 Hz),7.03(1H,t,J=7.6 Hz),7.06(1H,d,J=1.9 Hz),7.29(1H,d,J=7.6 Hz),7.53(1H,d,J=7.6 Hz),8.05(1H,t,J=5.3 Hz),8.16(1H,d,J=8.6 Hz),10.76(1H,d,J=1.9 Hz)

EXAMPLE 115

Compound 122 m.p.: 122°–129° C.
IR(KBr,cm⁻¹):3412,2962,1716,1644,1515,1458,1350,1239,1200,741,699
High Resolution FAB-MS(m/e,(C₃₂H₄₃N₅O₅+H)⁺): Calcd: 578.3342 Found: 578.3369

$^1$H-NMR(300 MHz,DMSO-d$_6$,δppm):0.61(3H,d,J=5.6 Hz),0.65(3H,d,J=5.6 Hz),0.99-1.13(3H,m),1.28(9H,s),2.28-2.45(2H,m),2.84(1H,d,J=10.4 Hz,14.5 Hz),3.10-3.45(3H,m),3.91-4.01(1H,m),4.30-4.49(1H,m),4.48(1H,d,J=17.5 Hz),4.53(1H,d,J=17.5 Hz),5.79(1H,d,J=6.7 Hz),6.93(1H,t,J=7.8 Hz),7.02(1H,t,J=7.8 Hz),7.06(1H,d,J=1.8 Hz),7.16-7.39(6H,m),7.53(1H,d,J=7.8 Hz),8.01(1H,t,J=5.6 Hz),8.13(1H,d,J=8.5 Hz),10.77(1H,d,J=1.8 Hz)

EXAMPLE 116

Compound 123 m.p.: 160°-165° C.
IR(KBr,cm$^{-1}$):3364,2962,1653,1557,1461,1443,1296,1236
High Resolution FAB-MS(m/e,(C$_{28}$H$_{35}$N$_5$O$_5$+H)$^+$): Calcd: 522.2717 Found: 522.2703
$^1$H-NMR(300 MHz,DMSO-d$_6$,δppm):0.70(3H,d,J=5.2 Hz),0.72(3H,d,J=5.2 Hz),1.07-1.24(3H,m),2.22(3H,s),2.36(2H,t,J=7.3 Hz),2.87(1H,dd,J=10.3 Hz,14.3 Hz),3.16(1H,dd,J=4.0 Hz,14.3 Hz),3.20-3.30(2H,m),4.10-4.18(1H,m),4.38-4.48(1H,m),6.26(1H,d,J=7.3 Hz),6.69(1H,d,J=6.4 Hz),6.94(1H,t,J=7.8 Hz),7.03(1H,t,J=7.8 Hz),7.04-7.14(3H,m),7.19(1H,s),7.29(1H,d,J=7.8 Hz),7.58(1H,d,J=7.8 Hz),8.05(1H,t,J=5.4 Hz),8.38(1H,d,J=8.6 Hz),8.45(1H,s),10.78(1H,d,J=1.8 Hz),12.17(1H,brs)

EXAMPLE 117

Compound 124 m.p.: 99°-114° C.
IR(KBr,cm$^{-1}$):3412,1653,1557,1500,1461,1437,1287,1236
High Resolution FAB-MS(m/e,(C$_{28}$H$_{35}$N$_5$O$_6$+H)$^+$): Calcd: 538.2665 Found: 538.2711
$^1$H-NMR(300 MHz,DMSO-d$_6$,δppm):0.71(3H,d,J=6.1 Hz),0.72(3H,d,J=6.1 Hz),1.09-1.29(3H,m),2.35(2H,t,J=7.1 Hz),2.88(1H,dd,J=10.2 Hz,14.5 Hz),3.15(1H,dd,J=4.4 Hz,14.5 Hz),3.18-3.33(2H,m),3.69(3H,s),4.12-4.21(1H,m),4.39-4.48(1H,m),6.26(1H,d,J=7.6 Hz),6.47(1H,dd,J=1.6 Hz,7.9 Hz),6.83(1H,dd,J=1.6 Hz,7.9 Hz),6.95(1H,t,J=7.5 Hz),7.03(1H,t,J=7.5 Hz),7.06-7.14(3H,m),7.30(1H,t,J=7.5 Hz),7.59(1H,d,J=7.5 Hz),8.05(1H,t,J=5.7 Hz),8.38(1H,d,J=8.3 Hz),8.55(1H,s),10.78(1H,d,J=1.5 Hz),12.19(1H,brs)

Example 118

Compound 125

High Resolution FAB-MS(m/e,(C$_{27}$H$_{32}$ClN$_5$O$_5$+H)$^+$): Calcd: 542.2170 Found: 542.2161
$^1$H-NMR(300 MHz,DMSO-d$_6$,δppm):0.71(6H,d,J=6.1 Hz),1.10-1.35(3H,m),2.34(2H,t,J=7.2 Hz),2.87(1H,dd,J=10.6 Hz,13.6 Hz),3.12-3.20(1H,m),3.20-3.30(2H,m),4.13-4.22(1H,m),4.39-4.48(1H,m),6.34(1H,d,J=7.8 Hz),6.91(1H,d,J=9.1 Hz),6.94(1H,t,J=7.5 Hz),7.03(1H,t,J=7.5 Hz),7.10(1H,d,J=2.1 Hz),7.12(1H,d,J=9.1 Hz),7.21(1H,t,J=9.1 Hz),7.39(1H,d,J=7.5 Hz),7.59(1H,d,J=7.5 Hz),7.60(1H,s),8.05(1H,t,J=5.3 Hz),8.38(1H,d,J=8.3 Hz),8.76(1H,s),10.78(1H,d,J=2.1 Hz),12.19(1H,brs)

EXAMPLE 119

Compound 126 m.p.: 90°-100° C.
IR(KBr,cm$^{-1}$):3328,2962,2926,1719,1650,1554,1461,1236,741
High Resolution FAB-MS(m/e,(C$_{28}$H$_{35}$N$_5$O$_5$+H)$^+$): Calcd: 522.2717 Found: 522.2720
$^1$H-NMR(300 MHz,DMSO-d$_6$,δppm):0.71(3H,d,J=6.1 Hz),0.72(3H,d,J=6.4 Hz),1.06-1.41(3H,m),2.19(3H,s),2.31-2.39(2H,m),2.87(1H,dd,J=10.5 Hz,14.4 Hz),3.12-3.35(2H,m),3.16(1H,dd,J=3.8 Hz,14.4 Hz),4.06-4.19(1H,m),4.34-4.45(1H,m),6.21(1H,d,J=7.3 Hz),6.94(1H,t,J=7.4 Hz),7.00(2H,d,J=8.3Hz),7.03(1H,t,J=7.4 Hz),7.10(1H,d,J=2.1 Hz),7.22(2H,d,J=8.3Hz),7.29(1H,d,J=7.4 Hz),7.58(1H,d,J=7.4 Hz),8.04(1H,t,J=5.5 Hz),8.37 (1H,d,J=8.3 Hz),8.41(1H,s),10.77(1H,d,J=2.1 Hz),12.11(1H,brs)

EXAMPLE 120

Compound 127 m.p.: 80°-86° C.
IR(KBr,cm$^{-1}$):3346,2962,2932,1728,1647,1554,1464,1290,1254
High Resolution FAB-MS(m/e,(C$_{28}$H$_{35}$N$_5$O$_6$+H)$^+$): Calcd: 538.2665 Found: 538.2667
$^1$H-NMR(300 MHz,DMSO-d$_6$,δppm):0.70(3H,d,J=6.3 Hz),0.74(3H,d,J=6.3 Hz),1.06-1.40(3H,m),2.31-2.40(2H,m),2.86(1H,dd,J=10.5 Hz,14.5 Hz),3.13-3.38(3H,m),3.80(3H,s),4.03-4.15(1H,m),4.33-4.43(1H,m),6.79(1H,dt,J=1.7 Hz,7.7 Hz),6.85(1H,dt,J=1.9 Hz,7.7 Hz),6.93(1H,t,J=7.7 Hz),6.93(1H,dd,J=1.7 Hz,7.7 Hz),7.02(1H,t,J=7.7 Hz),7.05-7.11(1H,m),7.091(1H,d,J=2.5 Hz),7.28(1H,d,J=7.7 Hz),7.56(1H,d,J=7.7 Hz),7.98-8.06(1H,m),8.03(1H,dd,J=1.9 Hz,7.7 Hz),8.07(1H,s),8.35(1H,d,J=8.5 Hz),10.76(1H,d,J=2.5 Hz)

Example 121

Compound 128 m.p.: 93°-101° C.
IR(KBr,cm$^{-1}$):3316,2920,2854,1719,1638,1551,1461,1341,1251,1071
High Resolution FAB-MS (m/e,(C$_{28}$H$_{35}$N$_5$O$_5$+H)$^+$): Calcd: 522.2717 Found: 522.2722
$^1$H-NMR(300 MHz,DMSO-d$_6$,δppm):0.68-0.90(6H,m),1.08-1.38(3H,m),2.14(3H,s),2.35(2H,t,J=7.6 Hz),2.87(1H,dd,J=10.4 Hz, 14.5 Hz),3.10-3.45(3H,m),4.10-4.20(1H,m),4.38-4.47(1H,m),6.76(1H,d,J=8.0 Hz),6.84(1H,t,J=7.7 Hz),6.94(1H,t,J=7.7 Hz),6.99-7.12(2H,m),7.09(1H,d,J=7.7 Hz),7.10(1H,d,J=2.7 Hz),7.29(1H,d,J=7.7 Hz),7.59(1H,d,J=7.7 Hz),7.75(1H,s),7.81(1H,d,J=7.7 Hz),8.05(1H,t,J=5.6 Hz),8.37(1H,d,J=8.2 Hz),10.77(1H,d,J=2.7 Hz)

EXAMPLE 122

(1) Compound 129

IR(KBr,cm$^{-1}$):3412,2962,1739,1653,1557,1460,1443,1263,744

FAB-MS(m/e,(C$_{27}$H$_{41}$N$_5$O$_5$+H)$^+$):516

$^1$H-NMR(300 MHz,DMSO-d$_6$, δppm):0.66(3H,d,J=5.7 Hz),0.72(3H,d,J=5.7 Hz),0.73(3H,t,J=7.6 Hz),10.3–1.15(3H,m),1.13(6H,s),1.50–1.63(2H,m),2.38–2.45(2H,m),2.83(1H,dd,J=10.2 Hz,14.4 Hz),3.18–3.40(3H,m),3.59(3H,s),3.87–3.95(1H,m),4.31–4.40(1H,m),5.68(1H,s),5.86(1H,d,J=6.7 Hz),6.94(1H, t,J=7.3 Hz),7.03(1H,t,J=7.3 Hz),7.07(1H,d,J=1.8 Hz),7.29(1H,d,J=7.3 Hz),7.54(1H,d,J=7.3 Hz),8.11(1H,t,J=5.5Hz),8.26(1H,d,J=7.9 Hz),10.77(1H,d,J=1.8 Hz)

(2) Compound 130 m.p.: 129°–143° C.

IR(KBr,cm$^{-1}$):3412,2962,1650,1560,1459,1258,1180,744

High Resolution FAB-MS(m/e,(C$_{26}$H$_{39}$N$_5$O$_5$+H)$^+$): Calcd: 502.3029 Found: 502.3048

$^1$H-NMR(300 MHz,DMSO-d$_6$, δppm):0.66(3H,d,J=5.5 Hz),0.72(3H,d,J=5.5 Hz),0.73(3H,t,J=6.3 Hz),1.03–1.13(3H,m),1.13(6H,s),1.49–1.62(2H,m),2.25–2.38(2H,m),2.83(1H,dd,J=10.5 Hz,14.5 Hz),3.20(1H,dd,J=4.0 Hz,14.5 Hz),3.20–3.40(2H,m),3.92(1H,q,J=6.6 Hz),4.34(1H,ddd,J=4.0 Hz,9.0 Hz,10.5 Hz),5.75(1H,s),5.93(1H,d,J=6.6 Hz),6.94(1H,t,J=7.6 Hz),7.02(1H,t,J=7.6 Hz),7.07(1H,d,J=2.0 Hz),7.29(1H,d,J=7.6 Hz),7.54(1H,d,J=7.6 Hz),8.06(1H,t,J=5.5 Hz),8.24(1H,d,J=9.0 Hz),10.77(1H,d,J=2.0 Hz)

EXAMPLE 123

Synthesis of Compound 131

Compound 107 (7.9 mg) obtained in Example 100 was dissolved in formic acid (0.60 ml). To the solution was introduced dry hydrogen chloride at 0°~5° C. for 20 min. The reaction mixture was stirred at room temperature for 2 h and concentrated under reduced pressure. The residue was purified by TLC (Analytichem International, Empore sheet) with chloroform/methanol=2/1 for development followed by reverse-phase chromatography (Waters, SEP-PAK C$_{18}$ cartridge) with methanol for elution. The eluate was concentrated to give the title compound (6.4 mg) as a colorless powder.

m.p.: 97°–104° C.

IR(KBr,cm$^{-1}$):3316,2932,1713,1647,1635,1536,1464,1389

High Resolution FAB-MS(m/e,(C$_{29}$H$_{41}$N$_5$O$_6$+H)$^+$): Calcd: 556.3135 Found: 556.3165

$^1$H-NMR(300 MHz,DMSO-d$_6$,δppm):0.66(3H,d,J=5.9 Hz),0.72(3H,d,J=5.9 Hz),1.10–1.35(3H,m),1.35–1.50(6H,m),1.50–1.65(4H,m),2.35–2.45(2H,m),2.89(1H,dd,J=11.8 Hz,13.7 Hz),3.05–3.50(7H,m),3.90–4.00(1H,m),4.45–4.55(1H,m),6.00(1H,d,J=5.6 Hz),7.25–7.40(2H,m),7.45–7.65(1H,m),7.67(1H,d,J=8.4 Hz),7.95–8.45(3H,m),9.24+9.63(1H,brs×2)

EXAMPLE 124

Synthesis of Compound 132

Compound 132 was prepared from Compound 52 obtained in Example 47-(2) in the same manner described in Example 123.

m.p.: 185°–215° C.(dec.)

IR(KBr,cm$^{-1}$):3316,2926,1713,1656,1539,1464,1386

High Resolution FAB-MS(m/e,(C$_{29}$H$_{41}$N$_5$O$_6$+H)$^+$): Calcd: 556.3135 Found: 556.3165

$^1$H-NMR(300 MHz,DMSO-d$_6$, δppm):0.64(3H,d,J=6.0 Hz),0.70(3H,d,J=6.0 Hz),1.15(3H,d,J=6.6 Hz),1.10–1.65 (11H,m),2.01(1H,dd,J=9.2 Hz,15.2 Hz),2.23(1H,dd,J=2.2 Hz,15.2 Hz),2.88(1H,dd,J=10.8 Hz,14.8 Hz),3.16–3.40(5H,m),3.88–4.00(1H,m),4.05–4.22(1H,m),4.41–4.52(1H,m),6.09(1H,d,J=6–4 Hz),7.27–7.38(2H,m),7.50–7.61(1H,m),7.64–7.70(1H,m),7.99(1H,d,J=8.0 Hz),8.17–8.44(2H,m),9.24+9.63(1H,brs×2)

EXAMPLE 125

Synthesis of Compound 133

(1) Preparation of Boc-Leu-DTrp-Dha-OMe

Boc-Leu-DTrp-DLSer-OMe (49 mg) prepared in the same manner described in Example 29 was dissolved dichloromethane/TEA=1/1 (0.5 ml) and N-phenyltrifluoromethanesulfonimide (50 mg) was added. The mixture was stirred at room temperature for 9 h. Another 50 mg of N-Phenyltrifluoromethanesulfonimide was added and the mixture was additionally stirred at room temperature for 15 h, then diluted with dichloromethane, washed with 10% aq. citric acid and sat. NaHCO$_3$, dried over MgSO$_4$, filtered, and concentrated under reduced pressure. The residue was purified by MPLC (Merck, LiChroprep Si60) with hexane/ethyl acetate=1/1 for elution to give the product (28 mg).

(2) Preparation of Compound 133

The compound obtained in (1) (28 mg) was dissolved in methanol (0.5 ml) and 2N NaOH (40 μl) was added at 0°~5° C. The reaction mixture was stirred at 0°~5°0 C. for 2 h and at room temperature for 5 h, and concentrated under reduced pressure. The residue was diluted with water and washed with ether. The pH of the aqueous solution was adjusted to pH 3 with 10% aq. citric acid and the solution was extracted with ether. The organic layer was washed with brine, dried over MgSO$_4$, filtered, and concentrated under reduced pressure to give the title compound (24 mg) as a colorless powder.

m.p.: 104°–110° C.

IR(KBr,cm$^{-1}$):3412,2962,1695,1524,1167,741

FAB-MS(m/e,(C$_{25}$H$_{34}$N$_4$O$_6$+H)$^+$):487

$^1$H-NMR(300 MHz,DMSO-d$_6$δppm):0.72(6H,d,J=6.4 Hz),1.05–1.40(3H,m),1.33(9H,s),2.98(1H,dd,J=9.7 Hz,14.6 Hz),3.16(1H,dd,J=3.8 Hz,14.6 Hz),3.85–3.95(1H,m),4.54–4.70(1H,m),5.70(1H,s),6.24(1H,s),6.78(1H,d,J=7.8 Hz),6.94(1H,t,J=7.8 Hz),7.03(1H,t,J=7.8 Hz),7.10(1H,d,J=1.9 Hz),7.29(1H,d,J=7.8 Hz),7.56(1H,d,J=7.8 Hz),8.19(1H,d,J=7.8 Hz),9.12(1H,s),10.81(1H,d,J=1.9 Hz)

Example 126

Synthesis of Compound 134

Compound 93 (6.2 mg) obtained in Example 87-(2), methylamine hydrochloride (0.8 mg), N-methylmorpholine (1.3 μl) and HOBT.H$_2$O (2.8 mg) were dissolved in DMF (0.12 ml), and EDCI.HCl (3.5 mg) was added at 0°~5° C. The reaction mixture was stirred at room temperature for 3 h, and concentrated in vacuo. The residue was purified by preparative TLC (Analytichem International, Empore sheet) with chloroform/methanol=5/1 for development to give the title compound (4.5 mg) as a colorless powder.

m.p.: 89°–97° C.
IR(KBr,cm$^{-1}$):3310,2932,1656,1539,741
High Resolution FAB-MS(m/e,(C$_{28}$H$_{42}$N$_6$O$_4$+H)$^+$): Calcd: 527.3345 Found: 527.3328
$^1$H-NMR(300 MHz,DMSO-d$_6$, δppm):0.71(3H,d,J=5.8 Hz),0.78(3H,d,J=5.9 Hz),1.15–1.40 (3H,m),1.40–1.50 (4H,m),1.50–1.65(4H,m),2.-15–2.35(2H,m),2.56(3H,d,J=4.7 Hz),2.87(1H,dd,J=10.1 Hz,14.4 Hz),3.15–3.40(7H,m),3.99(1H,q,J=7.1 Hz),4.30–4.40(1H,m),6.09(1H,d,J=7.1 Hz),6.95(1H,t,J=7.5 Hz),7.04(1H,t,J=7.5 Hz),7.07(1H,d,J=2.1 Hz),7.30(1H,d,J=7.5 Hz),7.54(1H,d,J=7.5 Hz),7.72(1H,q,J=4.7 Hz),8.06(1H,t,J=5.5 Hz),8.10(1H,d,J=9.0 Hz),10.78(1H,d,J=2.1 Hz)

EXAMPLE 127

Synthesis of Compound 135

Compound 135 was prepared chloride as a starting material in the same manner described in Example 126.

m.p.: 101°~106° C.
IR(KBr,cm$^{-1}$):3310,2932,1665,1626,1539
FAB-MS(m/e,(C$_{27}$H$_{40}$N$_6$O+H)$^+$):513
$^1$H-NMR(300 MHz,DMSO-d$_6$, δppm):0.71(3H,d,J=5.7 Hz),0.78(3H,d,J=5.9 Hz),1.40–1.50 (3H,m),1.50–1.65(4H,m),1.-50–1.65(4H,m),2.15–2.35(2H,m),2.86(1H,dd,J=10.3 Hz,14.9 Hz),3.15–3.40(7H,m),3.99(1H,q,J=6.8 Hz),4.30–4.40(1H,m),6.09(1H,d,J=6.8 Hz),6.79(1H,brs),6.95(1H,t,J=7.3 Hz),7.04(1H,t,J=7.3 Hz),7.07(1H,d,J=2.2 Hz),7.29(1H,brs),7.30(1H,d,J=7.3 Hz),7.54(1H,d,J=7.3 Hz),8.06(1H,t,J=5.5 Hz),8.12(1H,d,J=8.2 Hz),10.78(1H,d,J=2.2 Hz)

Example 128

Synthesis of Compound 136

Compound 136 was prepared using dimethylamine hydrochloride as a starting material in the same manner described in Example 126.

m.p.: 86°–93° C.
IR(KBr,cm$^{-1}$):3298,2932,1635,1536,741
FAB-MS(m/e,(C$_{29}$H$_{44}$N$_6$O$_4$+H)$^+$):541
$^1$H-NMR(300 MHz,DMSO-d$_6$,δppm):0.72(3H,d,J=5.8 Hz),0.78(3H,d,J=1.15–1.40(3H,m),1.40–1.50(4H,m)1.5-0–1.65(4H,m),2.30–2.50(2H,m),2.80(3H,s),2.-80–2.90(1H,m),2.90(3H,s),3.-15–3.40(7H,m),3.99(1H,q,J=6.8 Hz),4.30–4.40(1H,m),6.11 (1H,d,J=6.8 Hz),6.95(1H,t,J=7.5 Hz),7.03(1H,t,J=7.5 Hz),7.07(1H,d,J=2.3 Hz),7.30(1H,d,J=7.5 Hz),7.53(1H,d,J=7.5 Hz),8.00(1H,t,J=5.6 Hz),8.10(1H,d,J=8.8 Hz),10.78(1H,d,J=2.3 Hz)

EXAMPLE 129

(1) Synthesis of Compound 137

Compound 137 was prepared using DTyr(Bzl)-OH as a starting material in the same manner described in Example 1-(3).

m.p.: 99°–105° C.
IR(KBr,cm$^{-1}$):3412,2962,2932,1660,1619,1513,1458,-1442,1395,1368

High Resolution FAB-MS(m/e,(C$_{38}$H$_{46}$N$_4$O$_7$+H)$^+$): Calcd: 671.3444 Found: 671.3404
$^1$H-NMR(300 MHz,DMSO-d$_6$, δppm):0.70(6H,d,J=6.3 Hz),1.03–1.40(3H,m),1.33(9H,s),2.80–3.40(4H,m),3.-85–3.97(1H,m),4.20–4.32 (1H,m),4.44–4.56(1H,m),5.03(2H,s),6.74(1H,d,J=7.8 Hz),6.88(2H,d,J=8.4 Hz),6.93(1H,t,J=7.5 Hz),7.02(1H,t,J=7.5 Hz),7.06(1H,d,J=1.9Hz),7.10(2H,d,J=8.4 Hz),7.25–7.46(6H,m),7.55(1H,d,J=7.5 Hz),7.94(1H,d,J=8.1 Hz),7.94(1H,d,J=8.1 Hz),10.77(1H,d,J=1.9Hz)

(2) Synthesis of Compound 138

Compound 138 was prepared by the removal of a benzyl group from Compound 137 obtained in (1) in the same manner described in Example 35-(2).

m.p.: 110°–115° C.
IR(KBr,cm$^{-1}$):3352,2962,1662,1518,1461,1395,1371,-1341,1248,1164
FAB-MS(m/e,(C$_{31}$H$_{40}$O$_7$+H)$^+$):581
$^1$H-NMR(300 MHz,DMSO-d$_6$, δppm):0.71(6H,d,J=6.7 Hz),0.99–1.42(3H,m),1.34(9H,s),2.97–3.44(4H,m),3.-83–3.94(1H,m),4.18–4.30(1H,m),4.-40–4.56(1H,m),6.63(2H,d,J=8.9 Hz),6.74(1H,d,J=8.0 Hz),6.93(1H,t,J=7.3 Hz),6.98(2H,d,J=8.9 Hz),7.02(1H,t,J=7.3 Hz),7.06(1H,d,J=1.7Hz),7.28(1H,d,J=7.3 Hz),7.55(1H,d,J=7.3 Hz),7.92(1H,d,J=7.7 Hz),7.92(1H,d,J=7.7 Hz),9.13(1H,s),10.77(1H,d,J=1.7Hz)

Example 130

Synthesis of Compound 139

Compound 52 (68 mg) obtained in Example 47-(2) was dissolved in DMSO/conc. HCl/acetic acid=1/10/20 (0.12 ml). The solution was stirred at room temperature for 30 min and concentrated under reduced pressure. The resulting residue was triturated with ether to give the title compound (7.0 mg) as an off-white powder.

m.p.: 115°–130° C.
IR(KBr,cm$^{-1}$):3286,2932,1713,1626,1536,1476,1299,-1209
High Resolution FAB-MS(m/e,(C$_{28}$H$_{41}$N$_5$O$_6$+H)$^+$): Calcd: 544.3135 Found: 544.3136
$^1$H-NMR(300 MHz,DMSO-d$_6$, δppm):0.80+0.82(3H,d×2, J=6.1 Hz,J=6.1 Hz),0.86+0.88(3H,d×2, J=6.1Hz,J=6.1 Hz),1.11+1.12 (3H,d×2,J=6.6 Hz,J=6.6 Hz),1.30–1.70(11H,m),1.83–2.05 (1H,m),2.05–2.50(3H,m),3.18–3.30(4H,m),3.-96–4.16(2H,m),4.-50–4.61(1H,m),6.20+6.21(1H,d×2,J=6.9 Hz,J=6.9

Hz),6.80+6.82(1H,d×2,J=7.6 Hz,J=7.6
Hz),6.88+6.94(1H,t×2,J=7.6 Hz,J=7.6
Hz),6.88-7.10(1H,m),7.15+7.17(1H,t×2,J=7.6
Hz,J=7.6 Hz),7.26(1H,d,J=7.6
Hz),7.89+7.92(1H,d×2,J=9.0 Hz,J=8.4
Hz),8.42+8.43(1H,d×2,J=8.7 Hz,J=8.3
Hz),10.33+10.40(1H,s×2),12.15(1H,brs)

Each Compound 140 or 141 in the following Example 131 or 132 was prepared using each corresponding primary or secondary amine in the same manner described in Example 87.

Example 131

Compound 140 m.p.: 112°116° C.
IR(KBr,cm$^{-1}$):3376,2956,1728,1653,1557,1290,1233,-1155
High Resolution FAB-MS(m/e,($C_{26}H_{37}$-$N_5O_7$+H)$^+$): Calcd: 532.2772 Found: 532.2764
$^1$H-NMR(300 MHz,DMSO-$d_6$, δppm):0.66(3H,d,J=6.2 Hz),0.70(3H,d,J=6.1 Hz),0.78-1.15(3H,m),1.29(3H,s),1.31(3H,s),2.-32-2.41(2H,m),2.83(1H,dd,J=10.3 Hz,14.8 Hz),3.08-3.48(2H,m),3.16(1H,dd,J=4.7 Hz,14.8 Hz),3.52(3H,s),3.92-4.02(1H,m),4.37(1H,ddd,J=4.7 Hz,8.5 Hz,10.3 Hz),5.99(1H,d,J=7.1 Hz),6.38(1H,s),6.94(1H,t,J=7.5 Hz),7.02(1H,t,J=7.5 Hz),7.07(1H,d,J=2.7 Hz),7.29(1H,d,J=7.5 Hz),7.56(1H,d,J=7.5 Hz),8.04(1H,t,J=5.6 Hz),8.26(1H,d,J=8.5 Hz),10.76(1H,d,J=2.7 Hz)

Example 132

Compound 141 m.p.: 80°95° C.
IR(KBr,cm$^{-1}$):3328,3065,2962,1716,1641,1530,1464,-1365,1248,1179,741
High Resolution FAB-MS(m/e,($C_{26}H_{39}$-$N_5O_5$+H)$^+$): Calcd: 502.3029 Found: 502.3029
$^1$H-NMR(300 MHz,DMSO-$d_6$, δppm):0.67(3H,d,J=5.9 Hz),0.74(3H,d,J=5.9 Hz),1.11-1.27 (3H,m),1.27(9H,s),2.25-2.60(2H,m),2.73(3H,s),2.84(1H,dd,J=10.4 Hz,14.8 Hz),3.11-3.45(3H,m),3.-81-3.90(1H,m),4.27-4.38(1H,m),6.10(1H,d,J=6.4 Hz),6.94(1H,t,J=7.4Hz),7.03(1H,t,J=7.4 Hz,7.06(1H,d,J=1.8 Hz),7.29(1H,d,J=7.4 Hz,7.53(1H,d,J=7.4Hz),8.02(1H,t,J=5.4 Hz),8.13(1H,d,J=8.8 Hz),10.77(1H,d,J=1.8 Hz)

Example 133

Synthesis of Compound 142

The title compound was prepared according to a conventional solid-phase method using an alkoxybenzyl alcohol resin (Kokusan Chemical Works: AA resin).

(1) Introduction of Fmoc-βAla-OH to an AA resin

Fmoc-βAla-OH (467 mg) was dissolved in DMF (3 ml), and DCC (154 mg) and DMAP (10 mg) were added. The reaction mixture was stirred at room temperature for 30 min, and added to a suspension of an AA resin (0.5 g) in DMF (3 ml). The mixture was vigorously stirred at room temperature for 4 h. The resin was collected by filtration, washed with DMF, methanol and dichloromethane, and dried in vacuo overnight to give an Fmoc-βAla-AA resin (528 mg). An Fmoc-βAla-AA resin (0.53 g) was suspended in dichloromethane (6 ml), and benzoyl chloride (0.15 ml) and pyridine (0.15 ml) were added. The mixture was vigorously stirred at room temperature for 1 h. The resin was collected by filtration, washed with dichloromethane, DMF and methanol, and dried in vacuo overnight to give a capped Fmoc-βAla-AA resin (462 mg).

(2) Preparation of Compound 142

The resin obtained in (1) (0.46 g) was packed in a polypropylene column (10 mm φ×60 mm) and solid-phase synthesis was performed as follows; 20% piperidine/DMF (3 ml) was added in the column and the column was vibrated for 30 min, then the solvent was removed out of the column. The resin in the column was washed with DMF by vibrating the column. DMF (3 ml) and a solution of Fmoc-DTrp-OH (136 mg), HOBT.$H_2O$ (149 mg) and DIPC (41 mg) in DMF (1.0 ml) were added successively into the column and the acylation reaction was completed by vibrating the column at room temperature overnight. A progress of reaction was checked by the Kaiser test. Excess reagents were removed, and the resin was washed with DMF and then suspended in DMF (3 ml). A solution of isovaleric acid (33 mg), HOBT.$H_2O$ (49 mg) and DIPC (40 mg) in DMF (1.0 ml) was added into the column and the column was vibrated at room temperature for 15 h. The resin-bound peptide derivative was cleaved by treatment with 5% phenol/TFA (10 ml). The resin was filtered off and the filtrate was concentrated under reduced pressure. The residue was triturated with hexane/ether to give the title compound (38.7 mg) as a colorless powder.

m.p.: 180°-185° C.
IR(KBr,cm$^{-1}$):3298,2962,1722,1647,1542,1464,1443,-1203
High Resolution FAB-MS(m/e,($C_{25}H_{36}$-$N_4O_5$+H)$^+$): Calcd: 473.2764 Found: 473.2785
$^1$H-NMR(300 MHz,DMSO-$d_6$,δppm):0.71(3H,t,J=7.1 Hz),0.83(6H,d,J=6.0 Hz),0.80-0.90(2H,m),0.90-1.18(3H,m),1.26-1.37 (2H,m),1.90-1.96(2H,m),2.37(2H,t,J=7.9 Hz),2.85(1H,dd,J=9.9 Hz,14.7 Hz),3.18(1H,dd,J=5.2 Hz,14.7 Hz),3.23(2H,dt,J=5.4 Hz,7.9 Hz),4.08(1H,dt,J=6.9 Hz,7.2 Hz),4.38(1H,ddd,J=5.2 Hz,8.4 Hz,9.9 Hz),6.94(1H,t,J=7.5 Hz),7.04(1H,t,J=7.5 Hz),7.08(1H,d,J=2.4 Hz),7.29(1H,d,J=7.5 Hz),7.55(1H,d,J=7.5 Hz),7.91(1H,d,J=6.9 Hz),7.98(1H,t,J=5.4 Hz),8.18(1H,d,J=8.4 Hz),10.78(1H,d,J=2.4 Hz),11.95(1H,brs)

EXAMPLE 134

Synthesis of Compound 143

The title compound was prepared using D-N-tert-butoxycarbonyl-2-amino-4,4-dimethylpentanoic acid as a starting material in the same manner described in Example 49.

m.p.: 106°-109.5° C.
IR(KBr,cm$^{31}$ $^1$):3328,2962,1699,1659,1524,1371,1248,1167,740
FAB-MS(m/e,($C_{26}H_{38}N_4O_6$+H)$^+$):503
$^1$H-NMR(300 MHz,DMSO-$d_6$,δppm):0.75(9H,s),1.25(1H,dd,J=4.5 Hz,9.3 Hz),1.31(1H,dd,J=4.5 Hz,9.3 Hz),1.36(9H,s),2.33(2H,t,J=7.4 Hz),2.90(1H,dd,J=8.5 Hz,14.5 Hz),3.10(1H,dd,J=4.6 Hz,14.5 Hz),3.16-3.30(2H,m),3.92(1H,dt,J=7.5 Hz, 4.5 Hz),4.36(1H,dt,J=4.6 Hz,8.5 Hz),6.90(1H,d,J=7.5 Hz),6.94(1H,t,J=7.3 Hz),7.02(1H,t,J=7.3 Hz),7.06(1H,d,J=2.2 Hz),7.29(1H,d,J=7.3

Hz),7.53(1H,d,J=7.3 Hz),7.90(1H,d,J=8.5Hz),7.93(1H,t,J=5.4 Hz),10.78(1H,d,J=2.2 Hz),12.18 (1H,brs)

Optical Rotation: $[\alpha]_D^{20} = 27.9°$ (c 0.35, MeOH)

EXAMPLE 135

Synthesis of Compounds 144, 145, 146

(1) Preparation of Compound 144, 145

Compound 17 obtained in Example 17 was treated with an excess amount of diazomethane/ether methanol/ether at 0° C. in the presence of silica gel to give Compounds 144 and 145.

Compound 144 m.p.: 71.5°–78.5° C.

IR(KBr,cm$^{-1}$):3334,2962,1746,1659,1533,1443,1371,1251,1167,1125,744

High Resolution FAB-MS(m/e,($C_{26}H_{38}N_4O_7$+H)$^+$): Calcd: 519.2819 Found: 519.2797

$^1$H-NMR(300 MHz,DMSO-d$_6$,δppm):0.73–0.95(6H,m),1.16–1.66(3H,m),1.39+1.40(9H,s×2),3.12–3.26(1H,m),3.32–3.50(2H,m)3.56–3.82(3H,m),3.72+3.73(3H,s×2),4.11–4.26(1H,m),4.71–4.91(2H,m),6.26–6.40(1H,m),6.82–6.98(1H,m),7.08–7.17(1H,m),7.13(1H,t,J=7.4 Hz),7.21(1H,t,J=7.4 Hz),7.37(1H,d,J=7.4 Hz),7.63(1H,d,J=7.4 Hz),8.11–8.20(1H,m)

Compound 145

High Resolution FAB-MS(m/e, ($C_{27}H_{40}N_4O_7$+H)$^+$): Calcd: 533.2975 Found: 533.2989

$^1$H-NMR(300 MHz,CDCl$_3$,δppm):0.78–0.90(6H,m),1.12–1.65(3H,m),1.41(9H,s),3.07–3.43(3H,m),3.26+3.28(3H,s×2),3.43–3.51(1H,m),3.55–3.78(1H,m),3.69+3.71(3H,s×2),3.83–4.00(1H,m),4.67–4.78(1H,m),4.78–4.90(1H,m),6.34–6.60(2H,m),7.08–7.16(2H,m),7.19(1H,t,J=7.7 Hz),7.32–7.38(1H,m),7.66+7.70(1H,d×2,J=7.7 Hz),8.05–8.12(1H,brs)

(2) Preparation of Compound 146

Compound 146 was prepared by alkaline hydrolysis of Compound 145 obtained in (1) with 1N NaOH in methanol.

m.p.: 70°–72° C.

IR(KBr,cm$^{-1}$):3340,2926,1662,1533,1461,1371,1257,1167,1122,741

High Resolution FAB-MS(m/e,($C_{26}H_{38}N_4O_7$+H)$^+$): Calcd: 519.2819 Found: 519.2805

$^1$H-NMR(300 MHz,DMSO-d$_6$,δppm):0.67–0.94(6H,m),1.05–1.42(3H,m),1.35+1.36(9H,s×2),2.88(1H,dd,J=10.1 Hz,14.0 Hz),3.07–3.53(3H,m),3.27(3H,s),3.67–3.79(1H,m),3.83–3.95(1H,m),4.39–4.51(1H,m),6.84(1H,t,J=8.2 Hz),6.94(1H,t,J=7.5 Hz),7.02(1H,t,J=7.5 Hz),7.08(1H,brs),7.29(1H,d,J=7.5 Hz),7.55+7.56(1H,d×2,J=7.5 Hz),7.94–8.10(2H,m),10.78(1H,brs)

EXAMPLE 136

Synthesis of Compounds 147

Boc-Leu-DTrp-N$_2$H$_3$ obtained in Example 1-(2) was allowed to react with methyl bromoacetate in DMF in the presence of potassium carbonate. The resulting ester was hydrolyzed in methanol with 1N NaOH to afford Compound 147.

m.p.: 167°–180° C.(dec.)

IR(KBr,cm$^{-1}$):3412,2926,1665,1560,1533,1395,1371,1164,1050

High Resolution FAB-MS(m/e($C_{26}H_{37}N_5O_8$+H)$^+$): Calcd: 548.2720 Found: 548.2733

$^1$H-NMR(300 MHz,DMSO-d$_6$,δppm):0.62–0.85(6H,m),1.02–1.30(3H,m),1.35(9H,s),2.85(1H,dd,J=9.5 Hz,14.0 Hz),2.98(1H,dd,J=4.5 Hz,14.0 Hz),3.58–3.70(4H,m),3.80–4.05(1H,m),4.38–4.52(1H,m),6.72(1H,d,J=8.1 Hz),6.93(1H,dt,J=0.8 Hz,7.5 Hz),7.03(1H,dt,J=0.8 Hz,7.5 Hz),7.06(1H,d,J=2.2 Hz),7.28(1H,d,J=7.5 Hz),7.58(1H,d,J=7.5 Hz),7.94(1H,d,J=8.6 Hz),9.52(1H,s),10.79(1H,d,J=2.2 Hz)

EXAMPLE 137

Synthesis of Compounds 148

Boc-Leu-DTrp-OH was treated with ethyl hydradinoacetate hydrochloride in the same manner described in Example 33-(2) to give Compound 148.

m.p.: 108°–111° C.

IR(KBr,cm$^{-1}$):3298,2962,1698,1665,1521,1461,1395,1371,1344,1248,1164

High Resolution FAB-MS(m/e, ($C_{24}H_{35}N_5O_6$+H)$^+$): Calcd: 490.2666 Found: 490.2628

$^1$H-NMR(300 MHz,DMSO-d$_6$,δppm):0.67–0.88(6H,m),1.04–1.30(3H,m),1.36(9H,s),2.90(1H,dd,J=9.8 Hz,14.3 Hz),3.08(1H,dd,J=4.9 Hz,14.3 Hz),3.30–3.45(3H,m),3.80–4.02(1H,m),4.38–4.57 (1H,m),6.84(1H,d,J=7.2 Hz),6.94(1H,dt,J=0.8 Hz,7.5 Hz),7.03(1H,dt,J=0.8Hz,7.8 Hz),7.06(1H,d,J=2.4 Hz),7.28(1H,d,J=7.5 Hz),7.55(1H,d,J=7.5 Hz),8.02(1H,d,J=6.3 Hz),9.34–9.51(1H,m),10.80(1H,d,J=2.4 Hz)

EXAMPLE 138

Synthesis of Compounds 149

The ethyl ester of Compound 148 was treated with benzyl bromide in DMF in the presence of potassium carbonate and then hydrolyzed in methanol with 1N NaOH to give Compound 149.

m.p.: 88°–96° C.

IR(KBr,cm$^{-1}$):3328,2962,1665,1512,1461,1395,1371,1248,1164,741

FAB-MS(m/e, ($C_{31}H_{41}N_5O_6$+H)$^+$):580

$^1$H-NMR(300 MHz,DMSO-d$_6$,δppm):0.67–0.88(6H,m),1.04–1.30(3H,m),1.36(9H,s),2.90(1H,dd,J=9.8 Hz,14.8 Hz),3.08(1H,dd,J=4.9 Hz,14.3 Hz),3.40–3.65(2H,m),3.76–4.01(1H,m),4.03(2H,s),4.28–4.43(1H,m),6.70(1H,d,J=8.3 Hz),6.92(1H,t,J=7.5 Hz),7.02(1H,d,J=2.0 Hz),7.03(1H,t,J=7.5 Hz),7.55–7.70(6H,m),7.49(1H,d,J=7.8 Hz),7.89(1H,d,J=8.0 Hz),9.27(1H,s),10.86(1H,d,J=2.0 Hz),12.47(1H,brs)

Each Compound 150 or 151 in the following Example 139 or 140 was prepared by treatment of Leu-DTrp-βAla-OBzl.TFA with each corresponding isocyanate in the same manner described in Example 79 followed by catalytic hydrogenation in methanol.

EXAMPLE 139

Compound 150 m.p.: 175°–183° C.

IR(KBr,cm$^{-1}$):3328,2926,1719,1644,1551,1464,1341,1236

High Resolution FAB-MS(m/e,($C_{29}H_{37}$-$N_5O_5$+H)+): Calcd: 536.2873 Found: 536.2913

$^1$H-NMR(300 MHz,DMSO-$d_6$,δppm):0.71(3H,d,J=6.4 Hz),0.73(3H,d,J=6.4 Hz),1.08–1.20(3H,m),2,10(6H,s),2.22(2H,t,J=7.3 Hz),2.85(1H,dd,J=10.5 Hz,14.5 Hz),3.05–3.30(3H,m),4.10–4.20(1H,m),4.-36–4.44(1H,m),6.22(1H,brs),7.09(1H,d,J=2.0 Hz),6.92–7.08(5H,m),7.29(1H,d,J=7.9 Hz),7.55(1H,s),7.57(1H,d,J=7.9 Hz),8.01(1H,t,J=5.1 Hz),8.27(1H,d,J=8.4 Hz),10.77(1H,d,J=2.0 Hz),12.08(1H,brs)

EXAMPLE 140

Compound 151 m.p.: 150° C.(dec.)

IR(KBr,cm$^{-1}$):3316,2962,2872,1650,1542,1467,1365,-1341,1254,1101,1056,741

High Resolution FAB-MS(m/e,($C_{33}H_{45}$-$N_5O_5$+H)+): Calcd: 592.3499 Found: 592.3530

$^1$H-NMR(300 MHz,DMSO-$d_6$,δppm):0.73(3H,d,J=5.8 Hz),0.75(3H,d,J=5.8 Hz),0.89–1.38(14H,m),1.-48–1.61(1H,m),2.09(2H,t,J=6.9 Hz),2.85(1H,dd,J=9.6 Hz,14.6 Hz),3.05–3.43(5H,m),4.13–4.25(1H,m),4.-35–4.57(1H,m),6.65–6.85(1H,m),6.96(1H,t,J=7.7 Hz),6.98–7.21(4H,m),7.02(1H,t,J=7.7 Hz),7.28(1H,d,J=7.7 Hz),7.56(1H,d,J=7.7 Hz),7.85–8.01(1H,m),8.03–8.14 (1H,m),8.19–8.31(1H,m),10.77(1H,s)

EXAMPLE 141

Synthesis of Compound 152

Compound 152 was prepared using N-aminopyrrolidine and CDI instead of the isocyanate in the same manner described in Example 139.

m.p.: 81°–91° C.

IR(KBr,cm$^{-1}$):3304,2962,1653,1539,1446,1341,1194,-1122,741

High Resolution FAB-MS(m/e,($C_{25}H_{36}$-$N_6O_5$+H)+): Calcd: 501.2825 Found: 501.2815

$^1$H-NMR(300 MHz,DMSO-$d_6$,δppm):0.71(3H,d,J=5.7 Hz),0.73(3H,d,J=5.7 Hz),1.02–1.48(3H,m),1.60–1.80(4H,m),2.34(2H,t,J=7.4 Hz),2,40–2.80(4H,m),2.87(1H,dd,J=9.7 Hz,J=14.4 Hz),3.06–3.41(3H,m),4.04–4.16(1H,m),4.-36–4.48(1H,m),6.33(1H,d,J=8.1 Hz),6.94(1H,t,J=7.6 Hz),7.03(1H,t,J=7.6 Hz),7.08(1H,d,J=2.0 Hz),7.13(1H,s),7.29(1H,d,J=7.6 Hz),7.56(1H,d,J=7.6 Hz),8.04(1H,t,J=5.9 Hz),8.19(1H,d,J=8.6 Hz),10.77(1H,d,J=2.0 Hz),12.16(1H,brs)

EXAMPLE 142

Synthesis of Compound 153

Compound 153 was prepared by treatment of Compound 140 obtained in Example 131 with 1N NaOH in methanol at room temperature.

m.p.: 97°–103° C.

IR(KBr,cm$^{-1}$):3376,2926,2854,1713,1551,1470,1434,-1341

High Resolution FAB-MS(m/e,($C_{25}H_{33}$-$N_5O_6$+H)+): Calcd: 500.2509 Found: 500.2482

$^1$H-NMR(300 MHz,DMSO-$d_6$,δppm):0.80(3H,d,J=6.6 Hz),0.81(3H,d,J=6.3 Hz),1.12–1.49(1H,m),1.23(6H,s),1.51–1.63(1H,m),1.-98–2.12(1H,m),2.31(2H,t,J=7.2 Hz),2.94(1H,dd,J=8.7 Hz,14.8 Hz),3.09(1H,dd,J=5.0 Hz,14.8 Hz),3.13–3.39(2H,m),4.36–4.49(2H,m),6.94(1H,t,J=7.4 Hz),7.03(1H,t,J=7.4 Hz),7.06(1H,d,J=1.9 Hz),7.29(1H,d,J=7.4 Hz),7.54(1H,d,J=7.4 Hz),7.88(1H,d,J=7.8 Hz),7.95(1H,t,J=5.6 Hz),8.29(1H,s),10.81(1H,d,J=1.9 Hz)

EXAMPLE 143

Synthesis of Compounds 154

PhOCO-Leu-DTrp-βAla-OBzl which was prepared in the same manner described in Example 131, was treated with TEA in chloroform and then catalytically hydrogenated to give Compound 154.

m.p.: 107°–108° C.

IR(KBr,cm$^{-1}$):3412,2956,2370,1770,1716,1665,1539,-1445

High Resolution FAB-MS(m/e,($C_{23}H_{29}$-$N_5O_6$+H)+): Calcd: 472.2196 Found: 472.2219

$^1$H-NMR(300 MHz,DMSO-$d_6$,δppm):0.80(6H,d,J=6.6 Hz),1.22–1.35(1H,m),1.60(1H,ddd,J=4.2 Hz,9.9 Hz,13.8 Hz),1.97(1H,ddd,J=4.2 Hz,11.1Hz,13.8 Hz),2.34(2H,t,J=7.2 Hz),2.91(1H,dd,J=9.3 Hz,14.4 Hz),3.12–3.40(3H,m),3.91(2H,s),4.-38–4.54(2H,m),6.95(1H,t,J=7.7 Hz),7.01–7.06(2H,m),7.30(1H,d,J=7.7 Hz),7.53(1H,d,J=7.7 Hz),7.77(1H,t,J=5.4 Hz),8.04 (1H,d,J=7.8 Hz),8.14(1H,s),10.80(1H,brs)

EXAMPLE 144

Synthesis of Compounds 155

N-[N-{N-cyclopentyl-N-(tert-butoxycarbonylmethyl)carbamoyl}-L-leucyl]-D-tryptophan methyl ester which was prepared from N-cyclopentylglycine tert-butyl ester, CDI, Leu-OBzl.TsOH and DTrp-OMe·HCl in the same manner described in Example 45, was cyclized in the same manner described in Example 142. The product was condensed with DTrp-OBzl, and then catalytically hydrogenated to give Compound 155.

m.p.: 136.5°–145.5° C.

IR(KBr,cm$^{-1}$):3418,2962,1767,1710,1521,1458,1431,-1395,1362,1233,744

High Resolution FAB-MS(m/e,($C_{36}H_{42}$-$N_6O_6$+H)+): Calcd: 655.3244 Found: 655.3286

$^1$H-NMR(300 MHz,DMSO-$d_6$,δppm):0.76(3H,d,J=6.2 Hz),0.77(3H,d,J=6.7 Hz),1.20–1.38(1H,m),1.-40–1.82(9H,m),1.97(1H,ddd,J=3.2 Hz,9.4 Hz,11.7 Hz),2.91(1H,dd,J=8.6 Hz,14.7 Hz),3.05(1H,dd,J=7.4 Hz,14.4 Hz),3.12–3.25(2H,m),3.89(1H,ABq,J=17.6 Hz),3.93(1H,ABq,J=17.6 Hz),4.22(1H,quint,J=7.4 Hz),4.34–4.45(1H,m),4.43(1H,dd,J=4.5 Hz,1.17 Hz),4.52(1H,dd,J=3.9 Hz,8.6 Hz),6.93(1H,t,J=7.0 Hz),6.95(1H,t,J=7.0 Hz),7.03(1H,t,J=7.0 Hz),7.04(1H,t,J=7.0 Hz),7.06(1H,d,J=1.6 Hz),7.12(1H,d,J=1.6 Hz),7.29(1H,d,J=7.0 Hz),7.31(1H,d,J=7.0 Hz),7.52(1H,d,J=7.0 Hz),7.54(1H,d,J=7.0 Hz),7.96–8.60(1H,m),7.98(1H,d,J=8.6 Hz),10.791(1H,d,J=1.6 Hz),10.795(1H,d,J=1.6 Hz)

EXAMPLE 145

Synthesis of Compound 156

Compound 156 was prepared from Compound 48 obtained in Example 45 in the same manner described in Example 123.

m.p.: 178°–182° C.

IR(KBr,cm$^{-1}$):3382,2932,2866,1632,1530,1464,1389
High Resolution FAB-MS(m/e,(C$_{31}$H$_{41}$N$_7$O$_6$+H)$^+$): Calcd: 608.3196 Found: 608.3192
$^1$H-NMR(300 MHz,DMSO-d$_6$,δppm):0.68(3H,d,J=5.7 Hz),0.71(3H,d,J=5.7 Hz),1.10–1.70(11H,m),2.30–2.60(2H,m),2.80–3.60-(6H,m),3.94–4.10(1H,m),4.35–4.55(1H,m),4.55–4.70(1H,m),5.95–6.10(1H,m),6.90–7.12(2H,m),7.-25–7.40(2H,m),7.45–8.55(5H,m),9.20+9.64(1H,brs×2)

EXAMPLE 146

Synthesis of Compound 157

Compound 93 obtained in Example 87-(2) was condensed with benzenesulfonamide in DMF in the presence of DMAP and EDCI.HCl to give Compound 157.
m.p.: 104°–112.5° C.
IR(KBr,cm$^{-1}$):3400,2926,1650,1536,1461,1344,1089,747
High Resolution FAB-MS(m/e,(C$_{33}$H$_{44}$N$_6$O$_6$+H)$^+$): Calcd: 653.3121 Found: 653.3129
$^1$H-NMR(300 MHz,CDCl$_3$,δppm):0.75(3H,d,J=6.5 Hz),0.77(3H,d,J=6.1 Hz),1.17–1.78(11H,m),2.28–2.58(2H,m),3.14–3.89(8H,m),4.60–4.71(1H,m),4.81–4.93(1H,m),6.-24–6.42(1H,m),6.99–7.71(10H,m),8.02–8.16(2H,m),8.-23–8.34(1H,m),10.90(1H,brs)

EXAMPLE 147

Synthesis of Compound 158

Compound 158 was prepared using methanesulfonamide instead of benzenesulfonamide in the same manner described in Example 146.
FAB-MS(m/e,(C$_{28}$H$_{42}$N$_6$O$_6$S+H)$^+$):591

EXAMPLE 148

Synthesis of Compound 159

Compound 159 was prepared in a similar manner described in Example 87.
m.p.: 80°–100° C.
IR(KBr,cm$^{31}$ 1):3316,2956,2872,1716,1626,1524,1458,1359,1194,741
High Resolution FAB-MS(m/e,(C$_{31}$H$_{45}$N$_5$O$_5$+H)$^+$): Calcd: 568.3499 Found: 568.3521
$^1$H-NMR(300 MHz,DMSO-d$_6$,δppm):0.66(3H,d,J=6.4 Hz),0.74(3H,d,J=6.4 Hz),1.00–1.32(3H,m),1.33–1.54(4H,m),1.-56–1.76(12H,m),2.20–2.38(2H,m),2,84(1H,dd,J=10.1 Hz,14.2 Hz),3.10–3.35(3H,m),3.70–3.86(2H,m),3.-85–3.96(1H,m),4.28–4.37(1H,m),5.95(1H,d,J=5.9 Hz),6.94(1H,t,J=7.6 Hz),7.03(1H,t,J=7.6 Hz),7.07(1H,d,J=1.8 Hz),7.30(1H,d,J=7.6 Hz),7.53(1H,d,J=7.6 Hz),7.97–8.04(1H,m),8.20(1H,d,J=8.1 Hz),10.77(1H,d,J=1.8Hz)

EXAMPLE 149

Synthesis of Compound 160

N-{N-(perhydroazepin-1-ylcarbonyl)-L-leucyl}-D-tryptophan obtained in Example 45-(4) was treated with N-hydroxysuccinimide in DMF in the presence of DCC to prepare the activated ester, which was allowed to react with DAps-ONa to give Compound 160.
m.p.: 167°–172° C.
IR(KBr,cm$^{31}$ 1):3412,2932,1638,1530,1464,1206,1044,741
FAB-MS(m/e,(C$_{27}$H$_{41}$N$_5$O$_6$S+Na)$^+$):586
$^1$H-NMR(300 MHz,DMSO-d$_6$,δppm):0.70(3H,d,J=5.8 Hz),0.77(3H,d,J=5.6 Hz),1.21(3H,d,J=6.6 Hz),1.15–1.70(11H,m),2.-25–2.70(2H,m),2.86(1H,dd,J=10.0 Hz,14.1 Hz),2.95–3.55(5H,m),3.92–4.15(2H,m),4.-25–4.40(1H,m),6.08(1H,d,J=7.1 Hz),6.92(1H,t,J=8.1 Hz),7.00(1H,t,J=8.1 Hz),7.06(1H,d,J=2.1 Hz),7.28(1H,d,J=8.1 Hz),7.54(1H,d,J=8.1 Hz),7.85(1H,d,J=7.5 Hz),7.98(1H,d,J=8.6 Hz),10.77(1H,brs)

EXAMPLE 150

Synthesis of Compounds 161

Formylation of N-{N-(perhydroazepin-1-ylcarbonyl)-L-leucyl}-D-tryptophan obtained in Example 45-(4), was carried out in the same manner described in Example 123. The product was condensed with Tau-ONa in the same manner described in Example 149 to give Compound 161.
158°–164° C.
IR(KBr,cm$^{-1}$):3376,2932,2866,1632,1536,1464,1416,1386,1341,1212,1050,747
FAB-MS(m/e,(C$_{27}$H$_{39}$N$_5$O$_7$S+Na)$^+$):600
$^1$H-NMR(300 MHz,DMSO-d$_6$,δppm):0.66(3H,d,J=6.0 Hz),0.71(3H,d,J=6.0 Hz),1.10–1.80(11H,m),2.-35–2.70(2H,m),2.90(1H,dd,J=10.0 Hz,14.3 Hz),3.10–3.70(7H,m),3.90–4.05(1H,m),4.-40–4.55(1H,m),6.10(1H,d,J=6.7 Hz),7.26–7.44(2H,m),7.47–7.63(1H,m),7.65(1H,d,J=6.8 Hz),7.90–8.50(3H,m),9.23+9.64(1H,brs×2)

EXAMPLE 151

Synthesis of Compound 162

Compound 162 was prepared in a similar manner described in Example 150.
m.p.: 172°–178° C.
IR(KBr,cm$^{-1}$):3418,2932,2866,1659,1533,1464,1389,1338,1194,1101,1044,792,747,618
FAB-MS(m/e,(C$_{28}$H$_{41}$N$_5$O$_7$S+Na)$^+$):614
$^1$H-NMR(300 MHz,DMSO-d$_6$,δppm):0.66(3H,d,J=5.5 Hz),0.71(3H,d,J=5.9 Hz),1.22(3H,d,J=6.4 Hz),1.08–1.68(11H,m),2.30–2.70(2H,m),2.8–2.96(1H,m),3.05–3.50(5H,m),3.87–4.18(2H,m),4.36–4.56(1H,m),6.-00–6.18(1H,m),7.25–7.45(2H,m),7.55(1H,s),7.-63–7.74(1H,m),7.80–8.35(3H,m),9.21+9.62(1H,brs×2)

Each Compound 163–171 in the following Examples 152–157 was prepared from a methyl or ethyl ester of each corresponding C-terminal amino acid in the same manner described in Example 45.

EXAMPLE 152

Compound 163 m.p.: 211°–220° C.
IR(KBr,cm$^{-1}$):3418,2932,1629,1524,1461,1410,741
FAB-MS(m/e,(C$_{29}$H$_{42}$N$_6$O$_5$+H)$^+$):555
$^1$H-NMR(300 MHz,DMSO-d$_6$,δppm):0.69(3H,d,J=6.2 Hz),0.77(3H,d,J=5.9 Hz),1.15–1.85(14H,m),1.-85–2.05(1H,m),2.88(1H,dd,J=10.1 Hz,14.5 Hz),3.10–3.40(8H,m),3.90–4.00(1H,m),4.-30–4.40(1H,m),6.28(1H,d,J=6.6 Hz),6.94(1H,t,J=7.5 Hz),7.03(1H,t,J=7.8 Hz),7.10(1H,d,J=1.9 Hz),7.31(1H,d,J=7.5 Hz),7.51(1H,d,J=7.5 Hz),8.31(1H,d,J=8.3 Hz),9.57(1H,brs),10.83(1H,d,J=1.9 Hz)

EXAMPLE 153

Compound 164 m.p.: 222°–229° C.
IR(KBr,cm$^{-1}$):3412,2932,1629,1563,1524,1464,1407,741
FAB-MS(m/e,($C_{29}H_{42}N_6O_5$+H)$^+$):555
$^1$H-NMR(300 MHz,DMSO-d$_6$,δppm):0.60–0.80(6H,m),1.00–2.20(15H,m),2.85–3.50(9H,m),3.75–3.95(1H,m),4.40–4.60(1H,m),6.15–6.35(1H,m),6.94(1H,t,J=7.5 Hz),7.04(1H,t,J=7.5 Hz),7.10(1H,d,J=1.4 Hz),7.30(1H,d,J=7.5 Hz),7.54(1H,d,J=7.5 Hz),8.40–8.60(1H,m),9.45–9.65(1H,m),10.75–10.95(1H,m)

EXAMPLE 154

Compound 165 m.p.: 94°–99° C.
IR(KBr,cm$^{-1}$):3316,2932,1716,1665,1635,1533,741
High Resolution FAB-MS(m/e,($C_{28}H_{39}N_5O_5$+H)$^+$): Calcd: 526.3030 Found: 526.3035
$^1$H-NMR(300 MHz,DMSO-d$_6$,δppm):0.70(3H,d,J=5.9 Hz),0.77(3H,d,J=5.9 Hz),1.15–1.65(10H,m),1.65–1.85(1H,m),1.85–2.00(1H,m),2.20–2.30(2H,m),2.90(1H,dd,J=10.2 Hz,15.1 Hz),3.10–3.50(5H,m),3.90–4.00(1H,m),4.35–4.45(1H,m),4.90–5.00(1H,m),6.16(1H,d,J=6.8 Hz),6.96(1H,t,J=7.3 Hz),7.04(1H,t,J=7.3 Hz),7.12(1H,d,J=1.6 Hz),7.31(1H,d,J=7.3 Hz),7.56(1H,d,J=7.3 Hz),8.19(1H,d,J=8.3 Hz),8.28(1H,d,J=9.0 Hz),10.80(1H,d,J=1.6 Hz)

Compound 166 m.p.: 96°–103° C.
IR(KBr,cm$^{-1}$):3412,2932,1716,1665,1635,1530,744
High Resolution FAB-MS(m/e,($C_{28}H_{39}N_5O_5$+H)$^+$): Calcd: 526.3030 Found: 526.3049
$^1$H-NMR(300 MHz,DMSO-d$_6$,δppm):0.70(3H,d,J=5.3 Hz),0.76(8H,d,J=5.6 Hz),1.10–1.80(11H,m),1.80–1.95(1H,m),2.10–2.20(2H,m),2.92(1H,dd,J=10.9 Hz,14.1 Hz),3.15–3.60(3H,m),3.90–4.00(1H,m),4.35–4.45(1H,m),4.95–5.05(1H,m),6.10(1H,d,J=6.5 Hz),6.95(1H,t,J=7.2 Hz),7.04(1H,t,J=7.2 Hz),7.11(1H,d,J=1.5 Hz),7.31(1H,d,J=7.2 Hz),7.56(1H,d,J=7.2 Hz),8.11(1H,d,J=9.0 Hz),8.19(1H,d,J=8.8 Hz),10.80(1H,d,J=1.5 Hz)

EXAMPLE 155

Compound 167

FAB-MS(m/e,($C_{30}H_{43}N_5O_5$+H)$^+$):554
$^1$H-NMR(300 MHz,CDCl$_3$,δppm):0.90(3H,d,J=6.1 Hz),0.92(3H,d,J=6.4 Hz),1.23(3H,t,J=7.1 Hz),1.30–1.90(11H,m),2.29(3H,s),3.15–3.46(6H,m),4.07(2H,q,J=7.1 Hz),4.43–4.57(1H,m),4.55(1H,d,J=8.3 Hz),4.78(1H,dt,J=7.4 Hz,6.3 Hz),4.84(1H,s),7.07(1H,t,J=7.5 Hz),7.12–7.20(1H,m),7.15(1H,t,J=7.5 Hz),7.18(1H,d,J=2.2 Hz),7.31(1H,d,J=7.5 Hz),7.58(1H,d,J=7.5 Hz),8.13(1H,brs),11.47(1H,s)

Compound 168

FAB-MS(m/e,($C_{30}H_{43}N_5O_5$+H)$^+$):554
$^1$H-NMR(300 MHz,CDCl$_3$,δppm):0.806(3H,d,J=6.1 Hz),0.811(3H,d,J=6.2 Hz),1.25(3H,t,J=7.1 Hz),1.35–1.85(11H,m),2.35(3H,s),3.15–3.45(5H,m),3.51(1H,dd,J=5.7 Hz,14.8 Hz),3.65–3.81(1H,m),4.12(2H,q,J=7.1 Hz),4.56(1H,d,J=6.6 Hz),4.88(1H,dt,J=8.8 Hz,5.7 Hz),6.26(1H,d,J=8.5 Hz),6.71(1H,s),7.07(1H,d,J=2.3 Hz),7.11(1H,t,J=7.6 Hz),7.20(1H,t,J=7.6 Hz),7.37(1H,d,J=5.6 Hz),7.57(1H,d,J=7.6 Hz),8.17(1H,brs),8.33(1H,s)

EXAMPLE 156

Compound 169 m.p.: 98°–102° C.
High Resolution FAB-MS(m/e,($C_{36}H_{48}N_6O_6$+H)$^+$): Calcd: 661.3713 Found: 661.3682
$^1$H-NMR(300 MHz,CDCl$_3$,δppm):0.83(3H,d,J=6.5 Hz),0.84(3H,d,J=6.5 Hz),1.35(9H,s),1.35–1.65(3H,m),3.05(1H,dd,J=6.3 Hz,14.6 Hz),3.15,(1H,dd,J=7.6 Hz,14.9 Hz),3.22–3.33(2H,m),3.33–3.40(2H,m),3.62(3H,s),3.68–3.76(2H,m),3.94–4.03(1H,m),4.71–4.80(2H,m),6.52(1H,d,J=7.6 Hz),6.64(1H,d,J=8.3 Hz),6.73(1H,d,J=2.2 Hz),6.79(1H,d,J=2.2 Hz),6.88(1H,d,J=8.3 Hz),7.05(1H,t,J=7.2 Hz),7.08(1H,t,J=7.2 Hz),7.17(1H,t,J=7.2 Hz),7.19(1H,t,J=7.2 Hz),7.30(1H,d,J=7.2 Hz),7.35(1H,d,J=7.2 Hz),7.50(1H,d,J=7.2 Hz),7.58(1H,d,J=7.2 Hz),7.75(1H,d,J=2.2 Hz),8.21(1H,d,J=2.2 Hz)

Compound 170 m.p.: 145°–148° C.
IR(KBr,cm$^{-1}$):3316,2962,1644,1530,1464,1362,1197,744
High Resolution FAB-MS(m/e,($C_{35}H_{46}N_6O_6$+H)$^+$): Calcd: 647.3557 Found: 647.3605
$^1$H-NMR(300 MHz,DMSO-d$_6$,δppm):0.69(3H,d,J=6.7 Hz),0.71(3H,d,J=6.7 Hz),1.06–1.17(2H,m),1.27(9H,s),1.50–1.62(1H,m),2.84(1H,dd,J=11.1Hz,16.6 Hz),2.93–3.28(5H,m),3.42–3.52(2H,m),3.90–4.00(1H,m),4.43–4.56(2H,m),5.41(1H,t,J=4.6 Hz),6.73(1H,d,J=6.6 Hz),6.93(1H,t,J=7.8 Hz),6.97(1H,t,J=7.8 Hz),7.00–7.10(2H,m),7.07(1H,d,J=2.2 Hz),7.18(1H,d,J=2.2 Hz),7.29(1H,d,J=7.8 Hz),7.32(1H,d,J=7.8 Hz),7.50(1H,d,J=7.8 Hz),7.55(1H,d,J=7.8 Hz),7.94(1H,d,J=8.5 Hz),8.12(1H,d,J=7.6 Hz),10.76(1H,d,J=2.2 Hz),10.81(1H,d,J=2.2 Hz)

EXAMPLE 157

Compound 171 m.p.: 130°–150° C.
IR(KBr,cm$^{-1}$):3412,2962,2926,1647,1518,1464,1398,1365,1344,1230,1173,1101,741
High Resolution FAB-MS(m/e,($C_{34}H_{44}N_6O_5$+H)$^+$): Calcd: 617.3452 Found: 617.3460
$^1$H-NMR(300 MHz,DMSO-d$_6$,δppm):0.70(3H,d,J=6.4 Hz),0.73(3H,d,J=6.4 Hz),1.08–1.39(3H,m),1.25(9H,s),2.70(3H,s),2.82(1H,dd,J=10.1 Hz,14.5 Hz),3.02–3.50(3H,m),3.92–4.04(1H,m),4.40–4.58(2H,m),5.96(1H,d,J=7.5 Hz),6.95(2H,t,J=7.6 Hz),6.99(1H,d,J=1.6 Hz),7.04(2H,t,J=7.6 Hz),7.16(1H,d,J=1.6 Hz),7.28(1H,d,J=7.6 Hz),7.31(1H,d,J=7.6 Hz),7.51(1H,d,J=7.6 Hz),7.55(1H,d,J=7.6 Hz),7.84–7.92(1H,m),8.-

02-8.16(1H,m),10.76(1H,d,J=1.6 Hz),10.79(1H,d,J=1.6 Hz)

EXAMPLE 158

Synthesis of Compound 172

Compound 172 was prepared using N-cyclopentyl-N-isobutylamine and CDI instead of the isocyanate in the same manner described in Example 139.

m.p.: 133° C.(dec.)
IR(KBr,cm$^{-1}$):3418,2962,2872,1638,1518,1464,1443,1392,1344,1233,741
High Resolution FAB-MS(m/e,(C$_{38}$H$_{50}$N$_6$O$_5$+H)$^+$): Calcd: 671.3921 Found: 671.3917
$^1$H-NMR(300 MHz,DMSO-d$_6$,δppm):0.71(3H,d,J=6.6 Hz),0.73(3H,d,J=6.6 Hz),0.77(6H,d,J=6.5 Hz),1.10-1.90(12H,m),2.79(1H,dd,J=9.9 Hz,13.7 Hz),2.90(2H,d,J=7.1 Hz),3.00-3.50(3H,m),3.92-4.16(2H,m),4.18-4.36(1H,m),4.38-4.54(1H,m),5.94(1H,d,J=7.3 Hz),6.93(2H,t,J=7.5 Hz),7.02(2H,t,J=7.5 Hz),7.04(1H,brs),7.12(1H,brs),7.28(1H,d,J=7.5 Hz),7.29(1H,d,J=7.5 Hz),7.51(1H,d,J=7.5 Hz),7.52(1H,d,J=7.5 Hz),7.88-8.08(1H,br),7.93(1H,d,J=8.1 Hz),10.74(1H,brs),10.75(1H,brs)

EXAMPLE 159

Synthesis of Compound 173

Compound 173 was prepared using 2,2-dimethylpyrrolidine and phosgene instead of the isocyanate in the same manner described in Example 139.

m.p.: 150°-156° C.
IR(KBr,cm$^{-1}$):3418,2932,1638,1521,1464,1443,741
FAB-MS(m/e,(C$_{35}$H$_{44}$N$_6$O$_5$+H)$^+$):629
$^1$H-NMR(300 MHz,DMSO-d$_6$,δppm):0.65-0.80(6H,m),1.24(6H,s),1.10-1.40(3H,m),1.60-1.80(4H,m),3.00-3.50(6H,m),4.00-4.60(3H,m),5.00-5.15(1H,m),6.90-7.40(8H,m),7.50-7.60(2H,m),7.90-8.10(2H,m),10.70-10.80(2H,m)

EXAMPLE 160

Synthesis of Compound 174

A solution of Boc-DTrp(CHO)-DTrp-OBzl prepared from Boc-DTrp(CHO)-OH and DTrp-OBzl, in formic acid was stirred at room temperature for 1 h and concentrated. 3.5N HCl/1,4-dioxane was added to the residue. The resulting colorless solid was collected by filtration to give HCl.DTrp(CHO)-DTrp-OBzl.HCl. The salt was condensed with N-(N-tert-butyl-N-methylcarbamoyl)-L-leucine which was prepared in the same manner described in Example 45, in the presence of N-methylmorpholine, EDCI.HCl and HOBT.H$_2$O, and the product was catalytically hydrogenated to give Compound 174.

m.p.: 125°-140° C.
IR(KBr,cm$^{31}$1):3412,2962,2926,1644,1521,1464,1389,1368,1341,1230,1179,744
FAB-MS(m/e,(C$_{35}$H$_{44}$N$_6$O$_6$+H)$^+$): 645
$^1$H-NMR(300 MHz,DMSO-d$_6$,δppm):0.67(3H,d,J=6.4 Hz),0.69(3H,d,J=6.4 Hz),1.04-1.30(3H,m),1.24(9H,s),2.70(3H,s),2.85(1H,dd,J=10.2 Hz,14.5 Hz),3.02-3.35(3H,m),3.90-4.02(1H,m),4.42-4.51(1H,m),4.61-4.71(1H,m),5.97(1H,d,J=7.8 Hz),6.97(1H,t,J=7.0 Hz),7.05(1H,t,J=7.0 Hz),7.18(1H,d,J=1.1 Hz),7.22-7.40(3H,m),7.52(2H,d,J=7.0 Hz),7.69(1H,d,J=7.0 Hz),7.91-8.32(3H,m),9.10-9.20+9.56-9.64(1H,brs×2),10.82(1H,d,J=1.1Hz)

EXAMPLE 161

Synthesis of Compound 175

Compound 175 was prepared in a similar manner described in Example 160.

m.p.: 117°-124° C.
IR(KBr,cm$^{31}$1):3376,2962,1635,1527,1464,1389,1341,1230,1200,744
FAB-MS(m/e,(C$_{36}$H$_{44}$N$_6$O$_6$+H)$^+$):657
$^1$H-NMR(300 MHz,DMSO-d$_6$,δppm):0.65(3H,d,J=5.4 Hz),0.69(3H,d,J=5.4 Hz),0.73-0.92(1H,m),1.10-1.72(10H,m),2.49(3H,s),2.84(2H,dd,J=10.7 Hz,14.1 Hz),3.02-3.30(2H,m),3.91-4.03(1H,m),4.37-4.52(2H,m),4.55-4.66(1H,m),6.07(1H,d,J=7.1 Hz),6.96(1H,t,J=7.5 Hz),7.05(1H,t,J=7.5 Hz),7.18(1H,d,J=1.7 Hz),7.21-7.36(3H,m),7.51(2H,d,J=7.5 Hz),7.66(1H,d,J=7.5 Hz),7.50-7.60+7.90-8.02(1H,brs×2),8.05-8.28(1H,m),8.20-8.37(1H,m),9.08-9.23+9.55-9.66(1H,m×2),10.79(1H,d,J=1.7 Hz)

EXAMPLE 162

Synthesis of Compound 176

Compound 176 was prepared using DTrp-DTrp-OBzl.HCl prepared from Boc-DTrp-OH and DTrp-OBzl, in the same manner described in Example 160.

m.p.: 129°-133° C.
IR(KBr,cm$^{31}$1):3418,2956,2370,1730,1632,1581,1534,1464
High Resolution FAB-MS(m/e,(C$_{36}$H$_{46}$N$_6$O$_6$+H)$^+$): Calcd: 659.3557 Found: 659.3539
$^1$H-NMR(300 MHz,DMSO-d$_6$,δppm):0.68(3H,d,J=6.3 Hz),0.72(3H,d,J=6.3 Hz),1.12-1.70(11H,m),2.81(1H,dd,J=10.7 Hz,14.6 Hz),3.08-3.61(5H,m),3.41-3.49(2H,m),3.97(1H,dt,J=6.6 Hz,7.8 Hz),4.22-4.36(1H,m),4.42-4.53(2H,m),5.15(1H,brs),6.50(1H,d,J=6.6 Hz),6.93(1H,t,J=7.9 Hz),6.97(1H,t,J=7.9 Hz),6.99(1H,t,J=7.9 Hz),7.05(1H,t,J=7.9 Hz),7.05(1H,d,J=1.8Hz),7.18(1H,d,J=1.8Hz),7.29(1H,d,J=7.9 Hz),7.32(1H,d,J=7.9 Hz),7.50(1H,d,J=7.9 Hz),7.54(1H,d,J=7.9 Hz),8.05(1H,d,J=8.7 Hz),8.27(1H,d,J=7.5 Hz),10.27(1H,brs),10.80(1H,brs),

EXAMPLE 163

(1) Synthesis of Compound 177

Compound 177 was prepared in a similar manner described in Example 160.

m.p.: 125°-130° C.
IR(KBr,cm$^{31}$1):3352,2962,1713,1521,1464,1389,1341,744
High Resolution FAB-MS(m/e,(C$_{38}$H$_{48}$N$_6$O$_6$+H)$^+$): Calcd: 685.3713 Found: 685.3742
$^1$H-NMR(300 MHz,DMSO-d$_6$,δppm):0.59(6H,d,J=5.8 Hz),0.99(3H,d,J=6.5 Hz),1.00(3H,d,J=6.5 Hz),1.03-1.25(3H,m),1.25-1.40(2H,m),1.40-1.77(6H,m),2.77(1H,dd,J=10.2 Hz,14.8 Hz),3.02-3.13(3H,m),3.52-3.67(1H,m),3.67-3.80(1H,m),3.89-4.09(1H,m),4.33-4.46(1H,m),4.54-4.69(1H,m),5.50-5.69(1H,m),6.89(1H,t,J=6.6 Hz),6.97(1H,t,J=6.6 Hz),7.15(1H,d,J=1.5

Hz),7.16–7.35(3H,m),7.35–7.60(1H,m),7.42(1H,d,J=6.6 Hz),7.61(1H,d,J=6.6 Hz),7.84–8.32(3H,m),9.11+9.55(1H,brs×2),10.74(1H,d,J=1.5 Hz)

(2) Synthesis of Compound 178

The precursor of Compound 177, the C-terminal benzyl ester, was hydrolyzed with 1N NaOH to give Compound 178.

m.p.: 118°–123° C.
IR(KBr,cm$^{31}$ 1):3328,2962,2872,1731,1635,1518,1464,1443,1344,1230,741
High Resolution FAB-MS(m/e,($C_{37}H_{48}N_6O_5$+H)$^+$): Calcd: 657.3765 Found: 657.3751
$^1$H-NMR(300 MHz,DMSO-d$_6$,δppm):0.70(3H,d,J=5.5 Hz),0.72(3H,d,J=5.5 Hz),1.07(3H,d,J=6.4 Hz),1.09(3H,d,J=6.4 Hz),1.14–1.33(3H,m),1.33–1.51(2H,m),1.54–1.83(6H,m),2.82(1H,dd,J=10.0 Hz,14.7 Hz),3.06–3.25(3H,m),3.63–3.77(1H,m),3.77–3–87(1H,m),4.00–4.15(1H,m),4.20–4.30(2H,m),5.67(1H,d,J=7.3 Hz),6.91–7.14(5H,m),7.17(1H,d,J=2.0 Hz),7.28(1H,d,J=7.9 Hz),7.32(1H,d,J=7.9 Hz),7.51(1H,d,J=7.9 Hz),7.56(1H,d,J=7.9 Hz),7.97(1H,d,J=8.6 Hz),8.18(1H,d,J=7.9 Hz),10.76(1H,d,J=2.0 Hz),10.82(1H,d,J=2.0 Hz)

Compounds 179–184 in the following Examples 164–166 were prepared in a similar manner described in Example 163.

EXAMPLE 164

Compound 179 m.p.: 125°–135° C.
IR(KBr,cm$^{-1}$):3328,2968,1701,1581,1521,1464,1389,1341,1230,744
High Resolution FAB-MS(m/e,($C_{36}H_{46}N_6O_6$+H)$^+$): Calcd: 659.3557 Found: 659.3529
$^1$H-NMR(300 MHz,DMSO-d$_6$,δppm):0.68(6H,d,J=6.1 Hz),1.09(6H,d,J=6.5 Hz),1.11(6H,d,J=6.6 Hz),1.02–1.31(3H,m),2.84(1H,dd,J=10.1 Hz,14.4 Hz),2.99–3.20(3H,m),3.70(2H,sept,J=6.6 Hz),3.99–4.10(1H,m),4.33–4.46(1H,m),4.60–4.69(1H,m),5.57–5.65(1H,m),6.96(1H,t,J=7.5 Hz),7.05(1H,t,J=7.5 Hz),7.52(1H,d,J=2.2 Hz),7.20–7.32(3H,m),7.47–7.60+7.89–8.00(1H,m×2),7.52(2H,d,J=7.5 Hz),7.70(1H,d,J=7.5 Hz),8.01–8.12(1H,m),8.14–8.30(1H,m),9.12–9.20+9.56–9.66(1H,m×2),10.80(1H,d,J=2.2 Hz)

Compound 180 m.p.: 140°–150° C.
IR(KBr,cm$^{-1}$):3412,2968,1728,1632,1515,1464,1446,1344,1212,1152,1104,741
FAB-MS(m/e,($C_{35}H_{46}N_6O_5$+H)$^+$):631
$^1$H-NMR(300 MHz,DMSO-d$_6$,δppm):0.70(3H,d,J=6.3 Hz),0.72(3H,d,J=6.3 Hz),1.12(12H,d,J=6.6 Hz),1.03–1.37(3H,m),2.81(1H,dd,J=9.7 Hz,14.6 Hz),3.04–3.30(3H,m),3.72(2H,sept,J=6.6 Hz),4.04–4.15(1H,m),4.33–4.45(1H,m),4.45–4.56(1H,m),5.64(1H,d,J=7.4 Hz),6.91–7.04(4H,m),7.06(1H,d,J=1.5 Hz),7.15(1H,d,J=1.5 Hz),7.28(1H,d,J=7.3 Hz),7.30(1H,d,J=7.3 Hz),7.51(1H,d,J=7.7 Hz),7.54(1H,d,J=7.7 Hz),7.95(1H,d,J=8.0 Hz),8.01–8.14(1H,m),10.75(1H,d,J=1.5 Hz),10.77(1H,d,J=1.5 Hz)

EXAMPLE 165

Compound 181 m.p.: 119°–124° C.
IR(KBr,cm$^{-1}$):3328,3064,2962,2872,1698,1524,1464,1389,1341,1230,1197,1101,792,744
High Resolution FAB-MS(m/e,($C_{38}H_{48}N_6O_6$+H)$^+$): Calcd: 685.3713 Found: 685.3737
$^1$H-NMR(300 MHz,DMSO-d$_6$,δppm):0.66(3H,d,J=5.7 Hz),0.69(3H,d,J=5.7 Hz),0.75(3H,t,J=7.2 Hz),1.08–1.27(3H,m),1.28–1.50(6H,m),1.50–1.72(4H,m),2.80(1H,dd,J=10.8 Hz,14.4 Hz),2.91–3.00(2H,m),3.07–3.39(3H,m),3.96–4.10(1H,m),4.10–4.25(1H,m),4.38–4.50(1H,m),4.59–4.60(1H,m),5.92–6.00(1H,m),6.97(1H,t,J=7.8 Hz),7.05(1H,t,J=7.5 Hz),7.17(1H,d,J=1.4 Hz),7.22–7.37(3H,m),7.43–7.60+7.92–8.20(1H,brs×2),7.51(2H,d,J=7.5 Hz),7.67(1H,d,J=7.5 Hz),8.13–8.26(1H,m),8.28–8.40(1H,m),9.16–9.23+9.58–9.68(1H,m×2),10.79(1H,d,J=1.4 Hz)

Compound 182 m.p.: 108°–115° C.
IR(KBr,cm$^{-1}$):3418,2962,2878,1731,1638,1584,1521,1464,1341,1233,1104,741
FAB-MS(m/e,($C_{37}H_{48}N_6O_5$+H)$^+$):657
$^1$H-NMR(300 MHz,DMSO-d$_6$,δppm):0.70(3H,d,J=5.8 Hz),0.74(3H,d,J=5.8 Hz),0.77(3H,t,J=7.4 Hz),1.13–1.34(5H,m),1.29–1.52(4H,m),1.50–1.75(4H,m),2.80(1H,dd,J=10.2 Hz,15.0 Hz),2.88–3.02(2H,m),8.04–3.20(3H,m),3.98–4.10(1H,m),4.12–4.28(1H,m),4.39–4.55(2H,m),5.96(1H,d,J=7.1 Hz),6.93(1H,t,J=8.0 Hz),6.97(1H,t,J=8.0 Hz),7.00–7.10(3H,m),7.17(1H,d,J=1.7 Hz),7.29(1H,d,J=8.0 Hz),7.82(1H,d,J=8.0 Hz),7.50(1H,d,J=8.0 Hz),7.53(1H,d,J=8.0 Hz),7.99(1H,d,J=8.4 Hz),8.21–8.30(1H,m),10.75(1H,d,J=1.7 Hz),10.79(1H,d,J=1.7 Hz)

EXAMPLE 166

Compound 183 m.p.: 141°–148° C.
IR(KBr,cm$^{-1}$):3412,2962,1632,1521,1464,1392,1341,744
High Resolution FAB-MS(m/e,($C_{39}H_{50}N_6O_6$+H)$^+$): Calcd: 699.3870 Found: 699.3799
$^1$H-NMR(300 MHz,DMSO-d$_6$,δppm):0.60–0.75(6H,m),0.80(3H,t,J=7.2 Hz),1.09–1.73(15H,m),2.82(1H,dd,J=9.9 Hz,14.8 Hz),2.91–3.42(5H,m),3.98–4.48(3H,m),4.54–4.64(1H,m),5.82–5.99(1H,m),6.94(1H,t,J=7.3 Hz),7.03(1H,t,J=7.3 Hz),7.13(1H,d,J=1.5 Hz),7.23–7.36(3H,m),7.44–7.60(1H,m),7.52(1H,d,J=7.3 Hz),7.65(1H,d,J=7.3 Hz),7,92–8.27(3H,m),9.10–9.22+9.56–9.67(1H,brs×2),10.72(1H,d,J=1.5 Hz)

Compound 184 m.p.: 93°–103° C.
IR(KBr,cm$^{-1}$):3412,2962,2932,2872,1728,1635,1584,1530,1464,741

FAB-MS (m/e, (C$_{38}$H$_{50}$N$_6$O$_5$+H)$^+$):671
$^1$H-NMR(300 MHz,DMSO-d$_6$,δppm):0.70(3H,d,J=5.9 Hz),0.74(3H,d,J=5.9 Hz),0.82(3H,t,J=7.3 Hz),1.05-1.75(15H,m),2.80(1H,dd,J=10.3 Hz,14.6 Hz),2.91-3.51(5H,m),3.95-4.07(1H,m),4.12-4.27(1H,m),4.40-4.56(2H,m),5.95(1H,d,J=7.0 Hz),6.90-7.09(4H,m),7.05(1H,d,J=1.9 Hz),7.18(1H,d,J=1.9 Hz),7.28(1H,d,J=8.0 Hz),7.32(1H,d,J=8.0 Hz),7.51(1H,d,J=8.0 Hz),7.54(1H,d,J=8.0 Hz),8.02(1H,d,J=8.9 Hz),8.22-8.31(1H,m),10.76(1H,d,J=1.9 Hz),10.81(1H,d,J=1.9 Hz)

EXAMPLE 167

Synthesis of Compound 185, 186

Compounds 185 and 186 were prepared in a similar manner described in Example 160.

Compound 185 m.p.: 149°-157° C.
IR(KBr,cm$^{-1}$):3310,2932,1746,1662,1632,1527,1464,1389,1341,1197,744
High Resolution FAB-MS(m/e,(C$_{43}$H$_{50}$N$_6$O$_6$+H)$^+$): Calcd: 747.3870 Found: 747.3834
$^1$H-NMR(300 MHz,DMSO-d$_6$,δppm):0.64(3H,d,J=5.9 Hz),0.68(3H,d,J=5.9 Hz),1.14-1.24(3H,m),1.36-1.45(4H,m),1.47-1.52(4H,m),2.83(1H,dd,J=10.7 Hz,14.6 Hz),3.00-3.36(7H,m),3.92-4.00(1H,m),4.57(1H,dd,J=7.6 Hz,14.6 Hz),4.61-4.72(1H,m),4.94(1H,d,J=12.7 Hz),5.01(1H,d,J=12.7 Hz),6.04(1H,d,J=6.8 Hz),6.98(1H,t,J=7.1 Hz),7.04-7.40(11H,m),7.47(1H,d,J=7.4 Hz),7.65(1H,d,J=7.4 Hz),8.18-8.21(1H,m),7.98+8.26(1H,brs×2),8.65(1H,d,J=7.4 Hz),9.20+9.65(1H,brs×2),10.85(1H,d,J=1.5 Hz)

Compound 186 m.p.: 144°-152° C.
IR(KBr,cm$^{-1}$):3412,2932,1662,1533,1464,1389,744
FAB-MS(m/e,(C$_{36}$H$_{44}$N$_6$O$_6$+H)$^+$):657
$^1$H-NMR(300 MHz,DMSO-d$_6$,δppm):0.68(3H,d,J=6.2 Hz),0.71(3H,d,J=5.5 Hz),1.15-1.26(3H,m),1.30-1.37(4H,m),1.48-1.60(4H,m),2.65-3.21(8H,m),3.97-4.09(1H,m),4.32-4.46(1H,m),4.57-4.68(1H,m),5.99-6.07(1H,m),6.96(1H,t,J=7.4 Hz),7.04(1H,t,J=7.4 Hz),7.16(1H,d,J=1.3 Hz),7.23-7.38(3H,m),7.43-7.60(1H,m),7.51(1H,d,J=7.4 Hz),7.66(1H,d,J=7.4 Hz),7.98-8.39(3H,m),9.18+9.63(1H,brs),10.78(1H,d,J=1.3 Hz)

EXAMPLE 168

Synthesis of Compound 187

Compound 187 was prepared using Boc-DTrp(COCH$_3$)-OH instead of Boc-DTrp(CHO)-OH in the same manner described in Example 160.
m.p.: 158°-169° C.
IR(KBr,cm$^{-1}$):3412,2932,1629,1533,1458,1395,1359,1338,1251,1224,744
High Resolution FAB-MS(m/e,(C$_{37}$H$_{46}$N$_6$O$_6$+H)$^+$): Calcd: 671.3557 Found: 671.3542
$^1$H-NMR(300MHz,DMSO-d$_6$,δppm):0.71(3H,d,J=6.3Hz),0.72(3H,d,J=6.4Hz),1.16-1.27(3H,m),1.28-1.31(4H,m),1.45-1.57 (4H,m),2.58(3H,s),2.82(1H,dd,J=9.2Hz,15.0Hz),3.003.30(7H,m),4.08-4.18(1H,m),4.19-4.29(1H,m),4.554.65 (1H,m),6.06(1H,d,J=7.5Hz),6.90(1H,t,J=6.9Hz),6.92(1H,t,J=6.9Hz),7.10(1H,d,J=1.7Hz),7,18-7.33(3H,m),7.52(1H,d,J=6.9Hz),7.53(1H,s),7.58(1H,d,J=6.9Hz),7.92(1H,d,J=8.2Hz),7.98-8.08(1H,m),8.25(1H,d,J=7.4Hz),10.72(1H, d,J=1.7Hz)

EXAMPLE 169

Synthesis of Compound 188

Compound 188 was prepared using Boc-DTrp(COOMe)-OH instead of Boc-DTrp(CHO)-OH in the same manner described in Example 160.
m.p.: 104°-134° C.
IR(KBr,cm$^{-1}$):3412,2932,2866,1737,1635,1533,1461,1386, 1344,1308,1260,1224,1095,744
High Resolution FAB-MS(m/e,(C$_{37}$H$_{46}$N$_6$O$_7$+H)$^+$): Calcd: 687.3506 Found: 687.3503
$^1$H-NMR(300MHz,DMSO-d$_6$,δppm):0.67(3H,d,J=6.9Hz),0.70(3H, d,J=6.9Hz),1.08-1.64(11H,m),2.87(1H,dd,J=11.2Hz,14.8 Hz),3.00-3.50(7H,m),3.95(3H,s),3.95-4.10(1H,m),4.304.48(1H,m),4.52-4.67(1H,m),5.99(1H,d,J=7.3Hz),6.96(1H, t,J=7.4Hz),7.04(1H,t,J=7.4Hz),7.17(1H,d,J=1.7Hz),7.20-7.41(3H,m),7.45(1H,s),7,52(1H,d,J=7.4Hz),7.64(1H,d, J=7.4Hz),8.04(1H,d,J=7.4Hz),8.15(1H,d,J=8.8Hz),8.158.30(1H,m),10,78(1H,d,J=1.7Hz)

EXAMPLE 170

(1) Synthesis of Compound 189

Compound 189 was prepared using Boc-DTrp(CH$_2$COOMe)-OH instead of Boc-DTrp(CHO)-OH in the same manner described in Example 160.
m.p.: 98°-108° C.
IR(KBr,cm$^{-1}$):3412,2932,1746,1635,1584,1536,1473,1446, 1371,1341,1272,1224,1104,741
High Resolution FAB-MS(m/e,(C$_{38}$H$_{48}$N$_6$O$_7$+H)$^+$): Calcd: 701.3663 Found: 701.3624
$^1$H-NMR(300MHz,DMSO-d$_6$,δppm):0.74(3H,d,J=6.2Hz),0.76(3H, d,J=6.2Hz),1.12-1.65(11H,m),2.81(1H,dd,J=9.7Hz,14.8Hz),3.04-3.40(7H,m),3.65(3H,s),4.07-4.29(1H,m),4.41-4.57(2H,m),4.95(1H,d,J=14.8Hz),5.03(1H,d,J=14.8Hz), 6.06(1H,d,J=7.1Hz),6.95-7.13(5H,m),7.18(1H,d,J=2.2Hz), 7.29(1H,d,J=7.4Hz),7.32(1H,d,J=7.4Hz),7.51(1H,d,J=7.4Hz),7.56(1H,d,J=7.4Hz),8.04(1H,d,J=8.4Hz),8.31(1H, d,J=8.1Hz),10.82(1H,d,J=2.2Hz)

(2) Synthesis of Compound 190

Compound 189 obtained in (1) was hydrolyzed in methanol with 1N NaOH to give Compound 190.
m.p.: 145°-155° C.
IR(KBr,cm$^{-1}$):3400,3058,2932,2866,1728,1635,1533,1473, 1446,1413,1341,1218,741
High Resolution FAB-MS(m/e,(C$_{37}$H$_{46}$N$_6$O$_7$+H)$^+$): Calcd: 687.3506 Found: 687.3517
$^1$H-NMR(300MHz,DMSO-d$_6$,δppm):0.65-1.05(6H,m),1.10-1.80 (11H,m),2.78-2.92(1H,m),3.00-3.90(7H,m),4.00-4.20(1H, m),4.38-4.58(2H,m),4.65-4.90(2H,m),6.-

02–6.15(1H,m), 6.90–7.65(10H,m),7.90–8.05(1H,m),8.-
10–8.30(1H,m),10.79 (1H,d,J=1.3Hz)

EXAMPLE 171

(1) Synthesis of Compound 191

Compound 191 was prepared using DTrp{P(=O)-(OMe)$_2$}-OBzl·HCl and DTrp-OBzl according to the condensation-hydrogenation process described in Example 45.

m.p.: 118°–150° C.

IR(KBr,cm$^{-1}$):3412,2932,1635,1581,1536,1458,1269,-1212, 1032,747

FAB-MS(m/e,(C$_{37}$H$_{49}$N$_6$O$_8$P+H)$^+$):737

$^1$H-NMR(300MHz,DMSO-d$_6$,δppm):0.70–0.83(6H,m),1.05–1.70 (11H,m),2.77–3.08(2H,m),3.07–3.55(6H,m),3.66(3H,d,J=5.3Hz),3.70(3H,d,J=5.3Hz),3.98–4.10(1H,m),4.-35–4.68 (2H,m),6.05(1H,d,J=7.3Hz),6.97(1H,t,J=7.5Hz),7.06(-1H, t,J=7.5Hz),7.16–7.40(3H,m),7.20(1H,s),7.24(1H,d,J=1-.2Hz),7.52(1H,d,J=7.5Hz),7,62(1H,d,J=7.5Hz),7.65(1-H, d,J=7.5Hz),8.19(1H,d,J=8.0Hz),8.37(1H,d,J=7.8Hz),-10.82 (1H,d,J=1.2Hz)

(2) Synthesis of Compound 192

Compound 191 obtained in (1) was allowed to react with a mixed solution of trifluoromethanesulfonic acid/trifluoroacetic acid/dimethyl sulfide/m-cresol=1/5/3/1 at room temperature for 1.5 h to give Compound 192.

m.p.: 115°–135° C.

IR(KBr,cm$^{-1}$):3412,3034,2938,1635,1533,1443,1263,-1227, 1161,1029,639

FAB-MS(m/e,(C$_{35}$H$_{45}$N$_6$O$_8$+H)$^+$):709

$^1$H-NMR(300MHz,DMSO-d$_6$,δppm):0.70–0.85(6H,m),1.14–1.60 (11H,m),2.70–4.10(9H,m),4.30–4.75(2H,m),6.07(1H,d,J=6.8Hz),6.85–7.30(6H,m),7.32(1H,d,J=7.9Hz),7.50(1-H,d, J=7.9Hz),7.57(1H,d,J=7.5Hz),7.77(1H,d,J=7.5Hz),8.-05–8.15(1H,m),8.28–8.35(1H,m),10.84–10.88(1H,m)

EXAMPLE 172

Synthesis of Compound 193

Compound 193 was prepared using D-3-(3-benzo[b]-thienyl)alanine methyl ester hydrochloride instead of DTrp-OMe·HCl in the same manner described in Example 45.

m.p.: 96°–101° C.

IR(KBr,cm$^{-1}$):3316,3064,2932,2860,1725,1638,1533,-1464, 1446,1362,1344,1263,1212,1101

High Resolution FAB-MS(m/e,(C$_{35}$H$_{43}$-N$_5$O$_5$+H)$^+$): Calcd: 646.3063 Found: 646.3045

$^1$H-NMR(300MHz,DMSO-d$_6$,δppm):0.71(3H,d,J=5.8Hz),0.74(3H, d,J=6.1Hz),1.08–1.32(3H,m),1.-35–1.70(8H,m),2.96(1H,dd, J=11.4Hz,13.2Hz),3.08–3.60(7H,m),3.-96–4.03(1H,m),4.40–4.60(1H,m),4.-58–4.70(1H,m),6.06(1H,d,J=7.1Hz),6.98(1H, t,J=7.5Hz),7.06(1H,t,J=7.5Hz),7.19(1H,s),7.25–7.50(4-H, m),7.51(1H,d,J=7.5Hz),7.84(1H,d,J=7.0Hz),7.93(1H,-d, J=7.0Hz),8.18(1H,d,J=7.5Hz),8.42(1H,d,J=5.6Hz),1-0.82 (1H,d,J=2.0Hz),12.28(1H,brs)

EXAMPLE 173

Synthesis of Compound 194

Compound 194 was prepared using D-3-(1,1-dioxo-3-benzo[b]thienyl)alanine methyl ester hydrochloride instead of DTrp-OMe·HCl in the same manner described in Example 45.

m.p.: 161°–168° C.

IR(KBr,cm$^{-1}$):3382,3058,2926,2860,1731,1632,1530,-1470, 1416,1389,1341,1305,1206,1188,1152,1125

High Resolution FAB-MS(m/e,(C$_{35}$H$_{43}$-N$_5$O$_7$S+H)$^+$): Calcd: 678.2961 Found: 678.2983

EXAMPLE 174

Synthesis of Compound 195, 196

Compounds 195 and 196 were prepared using DL-N-tert-butoxycarbonyl-3-(2-ethoxycarbonylphenyl)alanine instead of Boc-DTrp(CHO)-OH in the same manner described in Example 163.

Compound 195 m.p.: 123°–126° C.

IR(KBr,cm$^{-1}$):3370,2932,2866,1722,1638,1527,1449,-1416, 1371,1284,1200,1107,744

High Resolution FAB-MS(m/e,(C$_{36}$H$_{47}$-N$_5$O$_7$+H)$^+$): Calcd: 662.3554 Found: 662.3530

$^1$H-NMR(300MHz,DMSO-d$_6$,δppm):0.60–0.90(6H,m),1.05–1.64 (11H,m),1.28+1.30(3H,t×2,J=7.0Hz),2.86–3.60(8H,-m), 3.92–4.05(1H,m),4.26+4.28(2H,q×2,J=7.0Hz),4.-39–4.61 (2H,m),5.92–6.03(1H,m),6.-94–7.80(8H,m),7.55(1H,d,J=1.5Hz),7.62+8.17(1H,dX-2,J=8.8Hz),8.30–8.47(1H,m), 10.81(1H,d,J=1.5Hz)

Compound 196 m.p.: 145°–165° C.

IR(KBr,cm$^{-1}$):3352,3064,2932,2866,1641,1530,1458,-1407, 1248,1206,1107,744

FAB-MS(m/e,(C$_{34}$H$_{43}$N$_5$O$_7$+H)$^+$): 634

$^1$H-NMR(300MHz,DMSO-d$_6$,δppm):0.65–0.88(6H,m),1.05–1.64 (11H,m),2.85–3.60(5H,m),3.93–4.12(1H,m),4.-38–4.68(2H, m),5.96+6.00(1H,dX2,J=7.4Hz),6.97(1H,t,J=7.5Hz), 7.04(1H,t,J=7.5Hz),7.10–7.26(2H,m),7.27–7.92(4H,m), 7.30(1H,d,J=2.2Hz),7.40–7.48+8.10–8.23(1H,m×2), 8.36+8.41(1H,d×2,J=7.7Hz),10.82(1H,d,J=2.2Hz)

EXAMPLE 175

Synthesis of Compound 197, 198

Compounds 197 and 198 were prepared using DL-N-tert-butoxycarbonyl-3-(4-methoxycarbonylphenyl)alanine instead of Boc-DTrp(CHO)-OH in the same manner described in Example 163.

Compound 197 m.p.: 120°–125° C.

IR(KBr,cm$^{-1}$):3364,2932,2860,1725,1635,1527,1443,-1419, 1344,1284,1209,1185,1110,744

High Resolution FAB-MS(m/e,(C$_{35}$H$_{45}$-N$_5$O$_7$+H)$^+$): Calcd: 648.3397 Found: 648.3378

$^1$H-NMR(300MHz,DMSO-d$_6$,δppm):0.64–0.90(6H,m),1.10–1.67 (11H,m),2.82–3.50(8H,m),3.79+3.81(3H,sX2),3.92–4.14

(1H,m),4.35–4.50(1H,m),4.52–4.63(1H,m),6.00–6.06(1H,m),6.92–8.08(10H,m),8.30–8.42(1H,m),10.-79–10.87(1H,m)

Compound 198 m.p.: 145°–154° C.
IR(KBr,cm$^{-1}$):3412,2932,2872,1644,1530,1461,1443,-1422, 1344,1248,1182,1110,741
High Resolution FAB-MS(m/e,(C$_{34}$H$_{43}$-N$_5$O$_7$+H)$^+$): Calcd: 634.3241 Found: 634.3265
$^1$H-NMR(300MHz,DMSO-d$_6$,δppm):0.64–0.91(6H,m),1.04–1.63 (11H,m),2.58–3.50(5H,m),3.91–4.15(1H,m),4.-37–4.62(2H, m),5.98–6.09(1H,m),6.-88–8.09(10H,m),8.38(1H,d,J=6.8 Hz),10.78–10.90(1H,m),12.40–12.60(2H,m)

EXAMPLE 176

Synthesis of Compound 199

Boc-DTrp-DTrp-OMe was converted to the corresponding thioamide by treatment with the Lawesson's reagent. After removal of a Boc group, the thioamide derivative was converted to Compound 199 in the same manner described in Example 49.

m.p.: 148°–156° C.
IR(KBr,cm$^{-1}$):3418,2926,1635,1524,1461,1443,1407,-1344,741
High Resolution FAB-MS(m/e,(C$_{35}$H$_{44}$-N$_6$O$_4$$_1$S+H)$^+$): Calcd: 645.3223 Found: 645.3199
$^1$H-NMR(300MHz,DMSO-d$_6$,δppm):0.70(3H,d,J=5.7Hz),0.75(3H, d,J=5.7Hz),0.75–0.92(1H,m),1.-10–1.70(10H,m),2.80(1H, dd,J=9.7Hz,15.0Hz),3.10–3.60(7H,m),3.-98–4.16(1H,m), 4.70–5.03(2H,m),6.05(1H,d,J=6.8Hz),6.95(2H,t,J=7.7-Hz), 7.00–7.10(1H,m),7.03(2H,t,J=7.7Hz),7.06(1H,brs),7.12 (1H,brs),7.29(1H,d,J=7.7Hz),7.30(1H,d,J=7.7Hz),7.55 (1H,d,J=7.7Hz),7.58(1H,d,J=7.7Hz),8.04(1H,d,J=6.9-Hz), 10.76(1H,brs),10.78(1H,brs)

EXAMPLE 177

Synthesis of Compound 200

Compound 200 was prepared by reaction of cycloheptanecarboxylic acid with Leu-DTrp-DTrp-OBzl followed by catalytic hydrogenation in methanol.

m.p.: 218.5°–223° C.
IR(KBr,cm$^{-1}$):3418,2926,1653,1518,1464,1446,1101,-741
High Resolution FAB-MS(m/e,(C$_{36}$H$_{45}$-N$_5$O$_5$+H)$^+$): Calcd: 628.3499 Found: 628.3479
$^1$H-NMR(300MHz,DMSO-d$_6$,δppm):0.64–0.75(6H,m),1.04–1.71 (15H,m),2.21–2.34(1H,m),2.83(1H,dd,J=9.5Hz,-13–7Hz), 2.99–3.52(3H,m),4.13–4.25(1H,m),4.-37–4.58(2H,m),6.85–7.09(5H,m),7.13–7.20(1H,m),7.-23–7.31(2H,m),7.48–7.58 (2H,m),7.68(1H,d,J=7.5Hz),7.82–7.94(2H,m),10.-63–10.78 (2H,m)

EXAMPLE 178

Synthesis of Compound 201

Cycloheptanecarboxylic acid and L-leucic acid benzyl ester were refluxed in chloroform for 3 h in the presence of an equimolar amount of DMAP, HOBT·H$_2$O and EDCI·HCl to give an ester as a condensation product. Using the ester, Compound 201 was prepared in the same manner described in Example 162.

m.p.: 108°–111° C.
IR(KBr,cm$^{-1}$):3418,2932,2866,1728,1665,1524,1464,-1344, 1233,1188,741
High Resolution FAB-MS(m/e,(C$_{36}$H$_{44}$-N$_4$O$_6$+H)$^+$): Calcd: 629.3339 Found: 629.3353
$^1$H-NMR(300MHz,DMSO-d$_6$,δppm):0.72(3H,d,J=4.3Hz),0.74(3H, d,J=4.3Hz),1.10–1.80(15H,m),2.-34–2.70(1H,m),2.93(1H, dd,J=9.5Hz,14.5Hz),3.00–3.50(3H,m),4.-44–4.62(2H,m), 4.81–4.89(1H,m),6.-90–7.08(5H,m),7.11(1H,d,J=1.2Hz), 7.28(1H,d,J=7.4Hz),7.32(1H,d,J=7.4Hz),7.52(1H,d,J-=7.4Hz),7.54(1H,d,J=7.4Hz),7.97(1H,d,J=8.4Hz),8.1-6(1H, d,J=6.9Hz),10.78(1H,d,J=1.2Hz),10.83(1H,d,J=1.2H-z)

EXAMPLE 179

Synthesis of Compound 202

Compound 202 was prepared using O-perhydroazepin-1-ylcarbonyl-L-leucic acid benzyl ester prepared from perhydroazepine, CDI and L-leucic acid benzyl ester, in the same manner described in Example 171.

m.p.: 100°–110° C.
IR(KBr,cm$^{-1}$):3412,2932,1683,1524,1464,1437,1272,-1209, 1086,741
FAB-MS(m/e,(C$_{35}$H$_{43}$N$_5$O$_6$+H)$^+$):630
$^1$H-NMR(300MHz,DMSO-d$_6$,δppm):0.74(6H,d,J=5.8Hz),1.10–1.71 (11H,m),2.89(1H,dd,J=9.9Hz,14.7Hz),3.04–3.32(7H,m-), 4.40–4.59(2H,m),4.72–4.81(1H,m),6.-89–7.08(5H,m),7.16 (1H,d,J=1.6Hz),7.28(1H,d,J=7.9Hz),7.32(1H,d,J=7.9-Hz), 7.50(1H,d,J=7.9Hz),7.53(1H,d,J=7.9Hz),7.93(1H,d,J-=8.6Hz),8.13(1H,d,J=6.8Hz),10.78(1H,d,J=1.6Hz),1-0.81 (1H,d,J=1.6Hz)

EXAMPLE 180

Synthesis of Compound 203

Compound 203 was prepared using the corresponding C-terminal amino acid ethyl ester in the same manner described in Example 45.

m.p.: 130°–137° C.
IR(KBr,cm$^{-1}$):3412,2932,1665,4632,15331446,741
FAB-MS(m/e,(C$_{28}$H$_{39}$N$_5$O$_5$+H)$^+$): 526
$^1$H-NMR(300MHz,DMSO-d$_6$,δppm):0.68(3H,d,J=5.9Hz),0.76(3H, d,J=5.9Hz),1.10–1.70(14H,m),2.85(1H,dd,J=10.6Hz,1-4.4 Hz),3.00–3.50(6H,m),3.80–3.90(1H,m),4.-30–4.40(1H,m), 6.10–6.20(1H,m),6.95(1H,t,J=7.2Hz),7.04(1H,t,J=7.2-Hz), 7.06(1H,s),7.30(1H,d,J=7.2Hz),7.53(1H,d,J=7.2Hz),8.-10–8.30(2H,m),10.80(1H,s)

Compound 203 was a 1:1 mixture of two diastereomers. These diastereomers can be separated by HPLC( Shiseido, Capcell Pak C$_8$ SG120Å, 4.6 mmφ×250 mm, flow rate 1 ml/min) with acetonitrile/0.1% TFA in water=30/70.

Compound 203A: retention time 38.51 min.
Compound 203B: retention time 39.95 min.

EXAMPLE 181

Production of a transfusion solution for drip infusion

A sodium salt of Compound 50 obtained in Example 46 (1 g) was dissolved in 500 ml of a 5% glucose solution for transfusion. The resulting solution was filtered through a milipore filter (pore size, 0.22 μm) under aseptic conditions. A transfusion vial was filled with the filtrate to afford a transfusion solution for drip infusion.

EXAMPLE 182

Production of a solution for intravenous injection

A sodium salt of Compound 50 obtained in Example 46 (1 g) ws dissolved in 100 ml of an aqueous, isotonic sodium chloride solution. The resulting solution was filtered through a milipore filter (pore size, 0.22 μm) under aseptic conditions to afford a solution for intravenous injection.

EXAMPLE 183

| Production of tablets | |
|---|---|
| a sodium salt of Compound 50 | 7 parts |
| Hydroxypropylcellulose | 1 part |
| Lactose | 10.9 parts |
| Corn starch | 1 part |
| Magnesium stearate | 0.1 parts |

A sodium salt of Compound 50 obtained in Example 46 (7 parts), 10.9 parts of lactose and one part of corn starch, were blended thoroughly with 5 parts of a 60% aqueous ethanol solution containing one part of hydroxypropyl cellulose. the mixture was dried under reduced pressure, mixed with 0.1 parts of magnesium stearate and compressed by a conventional method into tablets.

REFERENTIAL EXAMPLE 1

Preparation of
D-(S)-(5-methyl-4-imidazolylmethyl)cysteine dihydrochlorides

D-Cysteine hydrochloride monohydrate (527 mg), and 4-hydroxymethyl-5-methylimidazole hydrochloride (490 mg) were dissolved in conc. HCl (10 ml). The reaction mixture was refluxed for 11 h and then concentrated under reduced pressure to give a pale yellow residual oil. The oil was triturated with isopropanol to give the title compound (699 mg) as pale brown crystals.

m.p.: 204° C.
$^1$H-NMR(90MHz,D$_2$O, δppm): 2.33(3H,s),2.90–3.20(2H,m),3.92 (3H,s),4.18(1H,dd,J=5.1Hz,6.6Hz),8.56(1H,s)

REFERENTIAL EXAMPLE 2

Preparation of (R)-2-amino-3-phenylpropanesulfonic acid (1) Preparation of
(R)-2-(N-tert-butoxycarbonylamino)-3-phenylpropyl methanesulfonate To a solution of N-tert-butoxycarbonyl-D-Phenylalaninol (754 mg) and TEA (0.5 ml) in dichloromethane was added methanesulfonyl chloride (0.28 ml) at 0°∼5 ° C. The reaction mixture was stirred at 0°∼5 ° C. for 30 min, quenched with water, and extracted with dichloromethane. The organic layer was washed with 10% citric acid and sat. NaHCO, dried over MgSO$_4$, filtered, and concentrated under reduced pressure. The residue was crystallized from ethyl acetate/hexane=1/2 to afford the product (931 mg).

m.p.: 119°–119.5° C.

(2) Preparation of
(R)-1-bromomethyl-N-tert-butoxycarbonylamino-3-phenylethylamine The compound obtained in (1) (659 mg) and lithium bromide monohydrate (1.05 g) were dissolved in acetone (5.0 ml). The mixture was stirred at room temperature for 16 h and then at 45° C. for 8 h, and concentrated under reduced pressure. The residue was partitioned between ethyl acetate and water. The organic layer was dried over MgSO$_4$, filtered, and concentrated under reduced pressure. The residue was purified by dry column flash chromatography (Merck, Kieselgel 60) with hexane/ethyl acetate=2/1 for elution to give the product (304 mg).

m.p.: 94°–100° C.
FAB-MS(m/e,(C$_{14}$H$_{20}$BrNO$_2$+H)$^+$): 314and 316

(3) Preparation of
(R)-1-bromomethyl-2-phenylethylamine hydrochloride

The compound obtained in (2) (265 mg) was dissolved in 2.9M HCl/1,4-dioxane (20 ml). The solution was stirred at 0°∼5 ° C. for 3 h and then at room temperature for 15 h, and concentrated under reduced pressure. The residue was triturated with ether to give the product (209 mg).

m.p.: 133°–138° C.
FAB-MS(m/e, (C$_9$H$_{12}$BrN+H)$^+$): 214 and 216

(4) Preparation of
(R)-2-amino-3-phenylpropanesulfonic acid

The compound obtained in (3) (206 mg) and sodium sulfite (207 mg) were dissolved in water (1.6 ml). The solution was stirred at room temperature for 69 h, diluted with water, and chromatographed over a cation exchange resin (Amberlite IR-120B:H$^+$-form) with water for elution and washing. The eluate and washing water were combined and concentrated under reduced pressure. The residue was triturated with ethanol to give the title compound (142 mg) as colorless crystals.

m.p.: >290° C.
FAB-MS(m/e,(C$_9$H$_{13}$NO$_3$S+H)$^+$): 216
$^1$H-NMR(90MHz,D$_2$O,
δppm):3.12(2H,d,J=7.0Hz),3.22(2H,d,J=4.4Hz),3.80–4.15(1H,m),7.20–7.60(5H,m)

REFERENTIAL EXAMPLE 3

Preparation of (1,3-dithiol-2-ylidene)malonic acid monomethyl ester (1,3-Dithiol-2-ylidene)malonic acid dimethyl ester (232 mg) prepared according to the procedure described in JP-76-48666, was suspended in methanol (0.1 ml) and iN KOH/methanol (3.0 ml) was added. The reaction mixture was refluxed for 1 h and then concentrated under reduced pressure. The residue was dissolved in water and the pH of the solution was adjusted to 2 with 1N HCl. The resulting precipitate was collected by filtration, washed with water, and dried in vacuo to give the title compound (196 mg) as a pale yellow powder.

m.p.: 48°–51° C.
$^1$H-NMR(90MHz,DMSO-d$_6$,δppm):3.80(3H,s),7.63(2H,s)

The peptide derivatives of the present invention have a potent antagonistic activity against endothelin which is an endogenous peptide with potent vasoconstrictor and other activities. Therefore, they are useful as drugs which exhibit antagonism against vascular and non-vascular smooth muscles contraction effects by endothelin. Particularly, they are useful as drugs for treating human hypertension, pulmonary hypertension, Raynaud's disease, asthma, acute renal failure, myocardial infarction, angina pectoris, arteriosclerosis, cerebral infarction or cerebral vasospasm. Further, they are useful also as drugs for treating endotoxin shock, or endotoxin-induced multiple organ failure or disseminated intravascular coagulation as well as cyclosporin-induced renal failure or hypertension.

We claim:

1. A peptide of the formula

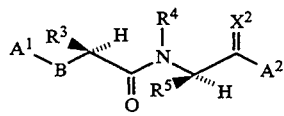

wherein $A^1$ is
(1) a group of the formula $R^{11}$—CO—, wherein $R^{11}$ is a lower alkyl group;
(2) a group of the formula $R^{12}O$—CO—, wherein $R^{12}$ is a lower alkyl group, or
(3) a group of the formula $R^{13}R^{14}N$—C(=O)—, wherein $R^{13}$ is a lower alkyl group, and $R^{14}$ is a hydrogen atom or a lower alkyl group or $R^{13}$ and $R^{14}$ form, together with the adjacent nitrogen atom, a 5- to 9-membered nitrogen-containing saturated heterocyclic ring having 4 to 8 carbon atoms, wherein among methylene groups forming the ring, one optional methylene group not adjacent to the above nitrogen atom may be replaced by an oxy group, a thio group or a group of the formula —NR$^{15}$— wherein $R^{15}$ is a lower alkyl group, and one to four optional hydrogen atoms on the carbon atoms of the heterocyclic ring may independently be replaced by a hydroxyl group or a lower alkyl group which may be substituted by a hydroxyl group;

B is —NR$^2$— wherein $R^2$ is hydrogen or a methyl group;

$R^3$ is a lower alkyl group having three to five carbon atoms;

$R^4$ is a hydrogen atom or a methyl group;

$R^5$ is a 3-indolylmethyl group, a (2,3-dihydro-2-oxo-3-indolyl)methyl group, a 3-indolylmethyl group wherein the indole ring is substituted at the 1-position by a group of the formula $R^{51}$—CO—(CH$_2$)$_s$ wherein $R^{51}$ is a hydrogen atom, a lower alkyl group, a hydroxyl group, a lower alkoxy group, s is an integer of from 0 to 6, provided that when s=0, $R^{51}$ is other than a hydroxyl group, a 3-benzothienylmethYl group, a (1-oxo-3-benzothienyl)-methyl group, or a (1,1-dioxo-3-benzothienyl)-methyl group;

$X^2$ is an oxygen atom;

$A^2$ is selected from the group consisting of groups of the formulas (III), (IV) and (VI)

 (III)

 (IV)

—NH—(CH$_2$)$_v$—Y (VI)

wherein Y is SO$_3$H or PO$_3$H$_2$, $R^{61}$ is a hydrogen atom or a lower alkyl group, $R^{71}$ is a hydrogen atom, a lower alkyl group, a phenyl group, a thienyl group, a phenyl lower alkyl group wherein an optional hydrogen atom on the benzene ring may be replaced by a hydroxyl group or a benzyloxy group, a thienyl lower alkyl group, a thiazolyl lower alkyl group, a 4-imidazolylmethyl group, a 3-indolylmethyl group, a carbamoyl lower alkyl group or an N-benzyloxycarbonyl-ω-amino lower linear alkyl group, provided than when $R^{61}$ is a lower alkyl group, said $R^{71}$ is not a hydrogen atom; $R^{62}$ is a hydrogen atom, a phenyl group, a benzyl group, or together with $R^8$ represents a single bond, $R^{72}$ is a hydrogen atom, a lower alkyl group, a phenyl group, a benzyl group, or a 3-indolylmethyl group, provided that when $R^{62}$ is a group other than a hydrogen atom, $R^{72}$ iS a hydrogen atom or a lower alkyl group; $R^8$ is a hydrogen atom or a lower alkyl group, or together with $R^{62}$ represents a single bond, and v is 3, 4 or 5;

or a pharmaceutically acceptable salt thereof.

2. The peptide of claim 1, wherein $A^1$ is a group of the formula $R^{11}$CO—.

3. The peptide of claim 1, wherein $A^1$ is a group of the formula $R^{12}O$—CO—.

4. The peptide of claim 1, wherein $R^{13}$ and $R^{14}$ form, together with the adjacent nitrogen atom, a 5–9 membered nitrogen-containing saturated heterocyclic ring having 4–8 carbon atoms 5. The peptide of claim 1, wherein $R^{13}$ and $R^{14}$ form, together with the adjacent nitrogen atom, a 7-membered nitrogen-containing saturated heterocyclic ring having 6 carbon atoms.

6. The peptide of claim 1, wherein B is a group of the formula -NR$^{2}$- wherein $R^2$ is a hydrogen atom or a methyl group 7. The compound of claim 4, wherein B is a group of the formula —NR$^2$—, wherein $R^2$ is a hydrogeniatom or a methyl group 8. The peptide of claim 1, wherein $R^5$ is a 3-indolylmethyl group.

9. The peptide of claim 1, wherein $R^5$ is a 3-indolylmethyl group substituted at the 1-position by a group of the formula $R^{51}$—CO(CH$_2$)$_s$— wherein $R^{51}$ is a hydrogen atom, a lower alkyl group, a hydroxy group, a lower alkoxy group, a benzyloxy group, an amino group or a mono lower alkyl amino group and s is an integer from 0 to 6, provided that when s=0, $R^{51}$ is other than a hydroxyl group.

10. The peptide of claim 1, wherein B is a group of the formula —NR$^2$— wherein $R^2$ is a hydrogen atom or a methyl group, and $R^5$ is a 3-indolylmethyl group or a 3-indolylmethyl group substituted a the 1-position by a group of the formula $R^{51}$—CO—(CH$_2$)$_s$— wherein $R^{51}$ is a hydrogen atom and s=0.

11. The peptide of claim 1, wherein Y is a SO$_3$H group.

12. The peptide of claim 1, wherein Y is a PO$_3$H$_2$ group.

13. A vasodilator or bronchodilator pharmaceutical composition, comprising the peptide of claim 1 or a pharmaceutically acceptable salt thereof and a pharmaceutically acceptable carrier.

14. A method of inhibiting the binding of endothelin to its receptor in a mammal producing or secreting excess endothelin, comprising parenterally administering to a mammal in need thereof, a pharmaceutically effective amount of the peptide of claim or a pharmaceutically acceptable salt thereof, wherein said administering is effective to inhibit the binding of said excess endothelin to its receptor thereby inhibiting vasoconstriction induced by the excess endothelin.

* * * * *